US012479899B2

(12) United States Patent
Wong

(10) Patent No.: US 12,479,899 B2
(45) Date of Patent: *Nov. 25, 2025

(54) MULTI-CHAIN CHIMERIC POLYPEPTIDES AND USES THEREOF

(71) Applicant: ImmunityBio, Inc., San Diego, CA (US)

(72) Inventor: Hing C. Wong, Miramar, FL (US)

(73) Assignee: ImmunityBio, Inc., San Diego, CA (US)

( * ) Notice: Subject to any disclaimer, the term of this patent is extended or adjusted under 35 U.S.C. 154(b) by 201 days.

This patent is subject to a terminal disclaimer.

(21) Appl. No.: 18/354,866

(22) Filed: Jul. 19, 2023

(65) Prior Publication Data

US 2023/0381238 A1 Nov. 30, 2023

Related U.S. Application Data

(63) Continuation of application No. 16/906,781, filed on Jun. 19, 2020, now Pat. No. 11,738,052.

(60) Provisional application No. 62/864,996, filed on Jun. 21, 2019.

(51) Int. Cl.

| | |
|---|---|
| ***C07K 14/54*** | (2006.01) |
| ***A61K 40/15*** | (2025.01) |
| ***A61K 40/42*** | (2025.01) |
| ***C07K 16/42*** | (2006.01) |
| ***C12N 5/0783*** | (2010.01) |

(52) U.S. Cl.

CPC .......... *C07K 14/5418* (2013.01); *A61K 40/15* (2025.01); *A61K 40/42* (2025.01); *C07K 14/5434* (2013.01); *C07K 14/5443* (2013.01); *C07K 16/4283* (2013.01); *C12N 5/0646* (2013.01); *A61K 2239/31* (2023.05); *A61K 2239/38* (2023.05); *C07K 2319/74* (2013.01)

(58) Field of Classification Search

CPC ................ A61K 40/15; C07K 14/5418; C07K 14/5434; C07K 14/5443

See application file for complete search history.

(56) References Cited

U.S. PATENT DOCUMENTS

| | | | |
|---|---|---|---|
| 6,117,980 | A | 9/2000 | Gonzalez et al. |
| 7,452,537 | B2 | 11/2008 | Bauer et al. |
| 7,482,436 | B2 | 1/2009 | Sugimura et al. |
| 7,488,802 | B2 | 2/2009 | Collins et al. |
| 7,521,051 | B2 | 4/2009 | Collins et al. |
| 7,612,181 | B2 | 11/2009 | Wu et al. |
| 7,691,380 | B2 | 4/2010 | Thorpe et al. |
| 7,723,482 | B2 | 5/2010 | Soulillou et al. |
| 7,968,094 | B2 | 6/2011 | Jiao et al. |
| 8,007,795 | B2 | 8/2011 | Jiao et al. |
| 8,133,485 | B2 | 3/2012 | Levi-Schaffer et al. |
| 8,217,149 | B2 | 7/2012 | Irving et al. |
| 8,258,268 | B2 | 9/2012 | Wu et al. |
| 8,475,792 | B2 | 7/2013 | Dall'Acqua et al. |
| 8,552,156 | B2 | 10/2013 | Takayanagi et al. |
| 8,586,714 | B2 | 11/2013 | Ghayur et al. |
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |
| 8,741,604 | B2 | 6/2014 | Campbell et al. |
| 8,753,640 | B2 | 6/2014 | Wu et al. |
| 8,759,494 | B2 | 6/2014 | Bachmann et al. |
| 8,822,645 | B2 | 9/2014 | Ghayur et al. |
| 9,035,026 | B2 | 5/2015 | Hoffmann et al. |
| 9,067,997 | B2 | 6/2015 | Romagne et al. |
| 9,085,623 | B2 | 7/2015 | Rother et al. |
| 9,090,684 | B2 | 7/2015 | Borras et al. |
| 9,226,962 | B2 | 1/2016 | Le Gall et al. |
| 9,238,084 | B2 | 1/2016 | Liu et al. |
| 9,273,136 | B2 | 3/2016 | Rader et al. |
| 9,371,395 | B2 | 6/2016 | Takahashi et al. |
| 9,441,034 | B2 | 9/2016 | Sivakumar et al. |
| 9,505,843 | B2 | 11/2016 | Kim et al. |
| 9,617,345 | B2 | 4/2017 | Berne et al. |
| 9,701,758 | B2 | 7/2017 | Cooper et al. |
| 11,401,324 | B2 | 8/2022 | Wong |
| 11,518,792 | B2 | 12/2022 | Wong |
| 11,672,826 | B2 | 6/2023 | Wong |
| 11,730,762 | B2 | 8/2023 | Wong |
| 11,738,052 | B2 | 8/2023 | Wong |
| 2001/0044427 | A1 | 11/2001 | Mazel et al. |
| 2003/0124678 | A1 | 7/2003 | Epstein et al. |
| 2003/0219441 | A1 | 11/2003 | Thorpe et al. |
| 2005/0014224 | A1 | 1/2005 | Collins et al. |
| 2006/0159655 | A1 | 7/2006 | Collins et al. |

(Continued)

FOREIGN PATENT DOCUMENTS

| | | |
|---|---|---|
| CN | 1844150 | 10/2006 |
| CN | 101653603 | 2/2010 |

(Continued)

OTHER PUBLICATIONS

Ng et al., "Stimulation of Natural Killer Cell-Mediated Tumor Immunity by an IL 15/TGFβ-Neutralizing Fusion Protein," Cancer Research, Oct. 1, 2016, vol. 76(19), pp. 5683-5695.

(Continued)

*Primary Examiner* — Prema M Mertz

(74) *Attorney, Agent, or Firm* — Sheridan Ross P.C.

(57) ABSTRACT

The present disclosure relates to methods that include the use of a first multi-chain chimeric polypeptide and a second multi-chain chimeric polypeptide for stimulating the NK cells, inducing or increasing proliferation of the NK cells, inducing differentiation of the NK cells, and treating a subject in need thereof using activated NK cells.

38 Claims, 32 Drawing Sheets

Specification includes a Sequence Listing.

(56) References Cited

U.S. PATENT DOCUMENTS

| | | | |
|---|---|---|---|
| 2007/0160579 | A1 | 7/2007 | Schmitz et al. |
| 2008/0025979 | A1 | 1/2008 | Honjo et al. |
| 2009/0148942 | A1 | 6/2009 | McDonagh et al. |
| 2012/0171197 | A1 | 7/2012 | Eriksson et al. |
| 2012/0264920 | A1 | 10/2012 | Wang et al. |
| 2013/0274446 | A1 | 10/2013 | Kumagai et al. |
| 2014/0242077 | A1 | 8/2014 | Choi |
| 2015/0218274 | A1 | 8/2015 | Sabatos-Peyton et al. |
| 2015/0259429 | A1 | 9/2015 | Benaroch et al. |
| 2016/0175397 | A1 | 6/2016 | Umana et al. |
| 2016/0340413 | A1 | 11/2016 | Duerner et al. |
| 2016/0367664 | A1 | 12/2016 | Wang et al. |
| 2017/0051063 | A1 | 2/2017 | Baum et al. |
| 2017/0198042 | A1 | 7/2017 | Williams et al. |
| 2017/0283499 | A1 | 10/2017 | Delhem et al. |
| 2018/0200366 | A1 | 7/2018 | Wong |
| 2019/0078082 | A1 | 3/2019 | Amorese et al. |
| 2019/0092846 | A1 | 3/2019 | Ibebunjo et al. |
| 2019/0177406 | A1 | 6/2019 | Ledbetter et al. |
| 2019/0315850 | A1 | 10/2019 | Bedinger et al. |
| 2020/0071374 | A1 | 3/2020 | Wong |
| 2020/0123607 | A1 | 4/2020 | Serrano Marugan et al. |
| 2020/0190174 | A1 | 6/2020 | Wong |
| 2020/0392221 | A1 | 12/2020 | Van Snick et al. |
| 2020/0399358 | A1 | 12/2020 | Shapiro et al. |
| 2021/0060064 | A1 | 3/2021 | Wong |
| 2021/0061897 | A1 | 3/2021 | Ledbetter et al. |
| 2021/0070825 | A1 | 3/2021 | Wong |
| 2021/0070826 | A1 | 3/2021 | Wong |
| 2021/0100840 | A1 | 4/2021 | Wong et al. |
| 2021/0137981 | A1 | 5/2021 | Wong |
| 2021/0268022 | A1 | 9/2021 | Wong et al. |
| 2021/0277054 | A1 | 9/2021 | Wong et al. |
| 2021/0338724 | A1 | 11/2021 | Wong |
| 2021/0355204 | A1 | 11/2021 | Bedinger et al. |
| 2021/0403545 | A1 | 12/2021 | Van Snick et al. |
| 2022/0073578 | A1 | 3/2022 | Wong et al. |
| 2023/0023389 | A1 | 1/2023 | Wong |
| 2023/0039157 | A1 | 2/2023 | Wong |
| 2023/0128292 | A1 | 4/2023 | Wong |
| 2023/0174666 | A1 | 6/2023 | Wong et al. |
| 2023/0272027 | A1 | 8/2023 | Wong |
| 2023/0372399 | A1 | 11/2023 | Wong |
| 2023/0372444 | A1 | 11/2023 | Wong et al. |
| 2023/0398151 | A1 | 12/2023 | Wong |
| 2024/0124543 | A1 | 4/2024 | Wong |
| 2024/0124544 | A1 | 4/2024 | Wong |
| 2024/0132561 | A1 | 4/2024 | Wong |

FOREIGN PATENT DOCUMENTS

| | | |
|---|---|---|
| CN | 101965364 | 2/2011 |
| CN | 102153653 | 8/2011 |
| CN | 106255703 | 12/2016 |
| CN | 109513003 | 3/2019 |
| EP | 1245676 | 10/2002 |
| EP | 1719528 | 11/2006 |
| EP | 2537933 | 12/2012 |
| EP | 3029069 | 6/2016 |
| EP | 3348276 | 7/2018 |
| JP | 2005-124568 | 5/2005 |
| JP | 2008-536487 | 9/2008 |
| JP | 2009-512433 | 3/2009 |
| JP | 4361133 | 8/2009 |
| KR | 2016/0127688 | 11/2016 |
| KR | 101778439 | 9/2017 |
| WO | WO 1995/015341 | 6/1995 |
| WO | WO 1996/001653 | 1/1996 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/097743 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/067825 | 4/2018 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/0047299 | 3/2020 |
| WO | WO 2020/047333 | 3/2020 |
| WO | WO 2020/047462 | 3/2020 |
| WO | WO 2020/047473 | 3/2020 |
| WO | WO 2021/163369 | 8/2021 |

OTHER PUBLICATIONS

Shen et al., "Engineering peptide linkers for scFv immunosensors," Anal Chem., Mar. 2008, 80(6):1910-1917.

U.S. Appl. No. 16/556,040, Wong, filed Aug. 29, 2019.

U.S. Appl. No. 16/557,822, Wong, filed Aug. 30, 2019.

[No Author Listed], "CN Br-activated Sepharose 4 Fast Flow," 1999, Affinity Chromatography, 4 pages.

Abbott et al., "Genomic organization, exact localization, and tissue expression of the human CD26 (dipeptidyl peptidase IV) gene," Immunogentics, Sep. 1994, 40(5):331-338.

Abdul-Aziz et al., "Acute myeloid leukemia induces protumoral p16INK4a-driven senescence in the bone marrow microenvironment," Blood, Jan. 31, 2019, 133(5):446-456.

Aertgeerts et al., "Crystal structure of human dipeptidyl peptidase IV in complex with a decapeptide reveals details on substrate specificity and tetrahedral intermediate formation," Protein Science, Feb. 2004, 13(2):412-421.

Ait-Oufella et al., "Natural regulatory T cells control the development of atherosclerosis in mice," Nature Medicine, Feb. 5, 2006, 12:178-180.

Akbari, et al., "Design, expression and evaluation of a novel humanized single chain antibody against epidermal growth factor receptor (EGFR)," Protein Expr. Purif., 2016, 127:8-15.

Ali et al., "Regulatory T cells in skin," Immunology, Jul. 12, 2017, 152(3):372-381.

Angevin et al., "First-in-human phase 1 of YS110, a monoclonal antibody directed against CD26 in advanced CD26-expressing cancers," British Journal of Cancer, Mar. 14, 2017, 116(9):1126-1134.

Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.

Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.

Baker et al., "Effects of conjugated linoleic acid (CLA) on tissue composition parameters in a murine cachexia model," The FASEB Journal, Mar. 2006, 20(4), 2 pages (Abstract Only).

(56) References Cited

OTHER PUBLICATIONS

Baker, et al., "Clearance of p16Ink4a-positive senescent cells delays ageing-associated disorders," Nature, 2011, 479(7372): 232-236.
Bartscht et al., "Dasatinib blocks transcriptional and promigratory responses to transforming growth factor-beta in pancreatic adenocarcinoma cells through inhibition of Smad signalling: implications for in vivo mode of action," Molecular Cancer, Dec. 2015, 14(199):1-12.
Bennett et al., "Erratum: Killing the old: cell senescence in atherosclerosis," Nature Reviews Cardiology, Jan. 12, 2017, 14(3):132.
Bennett et al., "Killing the old: cell senescence in atherosclerosis," Nature Reviews Cardiology, Dec. 12, 2016, 14(1):8-9, 2 pages.
Bentebibel et al., "A First-in-Human Study and Biomarker Analysis of NKTR-214, a Novel IL2Raf Biased Cytokine, in Patients with Advanced or Metastatic Solid Tumors," Cancer Discovery, Jun. 2019, 9(6):711-721.
Berry et al., "Cancer Anorexia and Cachexia: Screening in an Ambulatory Infusion Service and Nutrition Consultation," Clin J Oncol Nurs., 2018, 22(1):63-68.
Bhat et al., "Astrocyte Senescence as a Component of Alzheimer's Disease," PLoS One, Sep. 12, 2012, 7(9):e45069, 10 pages.
Biran et al., "Senescent cells communicate via intercellular protein transfer," Genes & Development, Apr. 8, 2015, 29(8):791-802, 13 pages.
Bird et al., "TGFβ inhibition restores a regenerative response in acute liver injury by suppressing paracrine senescence," Science translational medicine, Aug. 15, 2018, 10(454):eaan1230, 15 pages.
Borea et al., "Pharmacology of Adenosine Receptors: The State of the Art," Physiological Reviews, May 30, 2018, 98(3):1591-1625.
Borgerding et al., "B-lymphoma cells escape rituximab-triggered elimination by NK cells through increased HLA class I expression," Experimental Hematology, Mar. 1, 2010, 38(3):213-21.
Bork, "Powers and Pitfalls in Sequence Analysis: The 70% Hurdle," Genome Research, 2000, 10:398-400.
Bourgeois et al., "Regulation of cellular senescence via the FOXO4-p53 axis," FEBS Lett., 2018, 592(12): 2083-2097.
Bowie et al., "Deciphering the Message in Protein Sequences: Tolerance to Amino Acid Substitutions," Science, 1990, 247:1306-1310.
Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.
Boyman et al., "Selective Stimulation of T Cell Subsets with Antibody-Cytokine Immune Complexes," Science, Mar. 31, 2006, 311(5769):1924-1927.
Brämer et al., "Membrane adsorber for the fast purification of a monoclonal antibody using protein a chromatography," Membranes, Nov. 27, 2019, 9(12):159, 15 pages.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Broxmeyer et al., "Modulation of Hematopoietic Chemokine Effects In Vitro and In Vivo by DPP-4/CD26," Stem Cells and Development, Mar. 4, 2016, 25(8):575-585.
Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.
Brunstein et al., "Umbilical cord blood-derived T regulatory cells to prevent GVHD:kinetics, toxicity profile, and clinical effect," Blood, Feb. 25, 2016, 127(8):1044-1051.
Buhling et al., "Functional role of CD26 on human B lymphocytes," Immunology Letters, Feb. 1995, 45(1-2):47-51.
Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.
Bussian et al., "Clearance of senescent glial cells prevents tau-dependent pathology and cognitive decline," Nature, Sep. 19, 2018, 562(7728):578-582, 21 pages.
Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.
Cai et al., "Quercetin inhibits transforming growth factor β1-induced epithelial-mesenchymal transition in human retinal pigment epithelial cells via the Smad pathway," Drug design, development and therapy, Dec. 6, 2018, 12:4149-4161.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Cao, "Self-regulation and cross-regulation of pattern-recognition receptor signaling in health and disease," Nature Reviews Immunology, Dec. 29, 2015, 16(1):35-50.
Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.
Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin," Experimental Gerontology. Aug. 2017, 94:78-82.
Chabannon et al., "Manufacturing natural killer cells as medicinal products," Frontiers in Immunology, Nov. 15, 2016, 7(504): 1-9.
Chalan et al., "Expression of Lectin-Like Transcript 1, the Ligand for CD161, in Rheumatoid Arthritis," PLoS ONE, 2015, 10(7):e0132436.
Chambers et al., "Can blocking inflammation enhance immunity during aging?," Journal of Allergy and Clinical Immunology, May 2020, 145(5):1323-1331.
Chan et al., "Molecular mechanisms of natural killer cell activation in response to cellular stress," Cell Death & Differentiation, Jan. 2014, 21(1):5-14.
Chance et al., "A simple and rapid assay of oxidative phosphorylation," Nature, Jun. 1955, 175(4469):1120-1121.
Chandrudu et al., "Chemical methods for peptide and protein production," Molecules, 2013, 18(4):4373-4388.
Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.
Chang et al., "The dock and lock method: a novel platform technology for building multivalent, multifunctional structures of defined composition with retained bioactivity," Clinical cancer research, Sep. 15, 2007, 13(18):5586s-5591s.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chen et al., "Circulating levels of resistin and risk of type 2 diabetes in men and women: results from two prospective cohorts," Diabetes Care, Feb. 2009, 32(2):329-334.
Chen et al., "Sterile inflammation: sensing and reacting to damage," Nature Reviews Immunology, Nov. 19, 2010, 10(12):826-837.
Chichili et al., "Linkers in the structural biology of protein-protein interactions," Protein Science, Feb. 2013, 22(2):153-67.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.

(56) References Cited

OTHER PUBLICATIONS

Chinta, et al., "Cellular senescence is induced by the environmental neurotoxin paraquat and bontributes to neuropathology linked to Parkinson's Disease," Cell Rep., 2018, 22(4): 930-940.
Chong et al., "CD36 initiates the secretory phenotype during the establishment of cellular senescence," EMBO Rep., May 18, 2018, 19(6):e45274, 13 pages.
Ciaglia et al., "Recognition by natural killer cells of N6-isopentenyladensoine-treated human glioma cell lines," Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Cifaldi et al., "Boosting Natural Killer Cell-Based Immunotherapy with Anticancer Drugs: a Perspective," Trends Molecular Medicine, Dec. 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Clayton et al.,"Soluble T Cell Immunoglobulin Mucin Domain 3 Is Shed from CD8 T Cells by the Sheddase ADAM10, Is Increased in Plasma during Untreated HIV Infection, and Correlates with HIV Disease Progression," J Viral., 2015, 89(7):3723-3736.
Collado et al., "Senescence in tumours: evidence from mice and humans," Nature Reviews Cancer, Jan. 2010, 10(1):51-57.
Conarello et al., "Mice lacking dipeptidyl peptidase IV are protected against obesity and insulin resistance," Proc. Natl. Acad. Sci. U.S.A., May 27, 2003, 100(11):6825-6830.
Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl. ):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Cosgrove et al., "Usher protein functions in hair cells and photoreceptors," Int J Biochem Cell Biol., Jan. 2014, 46:80-89.
Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Crews et al., "Molecular mechanisms of neurodegeneration in Alzheimer's disease," Human Molecular Genetics, Apr. 22, 2010, 19(R1):R12-R20, 9 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.
Dall'Era et al., "Adoptive Regulatory T Cell Therapy in a Patient with Systemic Lupus Erythematosus," Arthritis Rheumatology, Mar. 2019, 71(3):431-440.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Demaria et al., "An Essential Role for Senescent Cellsin Optimal Wound Healing through Secretion of PDGF-AA," Developmental Cell, Dec. 22, 2014, 31(6):722-733.
Deyev et al., "Design of multivalent complexes using the barnase• barstar module," Nature Biotechnology, Dec. 2003, 21(12):1486-92.
Di Ianni et al., "Tregs prevent GVHD and promote immune reconstitution inHLA-haploidentical transplantation," Blood, Apr. 7, 2011, 117(14):3921-3928.
Dietel et al., "Decreased Nos. of regulatory T cells are associated with human atherosclerotic lesion vulnerability and inversely correlate with infiltrated mature dendritic cells," Atherosclerosis, Sep. 2013, 230:92-99.
DiGiammarino et al., "Design and generation of DVD-Ig™ molecules for dual- specific targeting," Therapeutic Proteins: Methods and Protocols, Methods in Molecular Biology, 2012, Humana Press, Totowa, NJ., 899:145-516.
Dikov et al., "New fluorescent method for the histochemical detection of tripeptidyl peptidase I using glycyl-l-prolyl-l-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.
Dinarello, "Interleukin 1 and interleukin 18 as mediators of inflammation and the aging process," The American Journal of Clinical Nutrition, Feb. 1, 2006, 83(2):447S-455S.
Docagne et al., "A soluble transforming growth factor-β (TGF-β) type I receptor mimics TGF-β responses," Journal of Biological Chemistry, Dec. 7, 2001, 276(49):46243-50.
Dong et al., "Characterization of adenosine deaminase binding to human CD26 on T cells and its biologic role in immune response," Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.
Dong et al., "Loss of methylation at theIFNGpromoter and CNS-1 is associated with the development of functional IFN-γ memory in human CD4+T lymphocytes," European Journal of Immunology, 2013, 43(3), 793-804.
Dou et al., "Cytoplasmic chromatin triggers inflammation in senescence and cancer," Nature, Oct. 4, 2017, 550(7676):402-406, 21 pages.
Drees et al., "Soluble production of a biologically active single-chain antibody against murine PD-L1 in *Escherichia coli*," Protein Express. Purif., 2014, 94:60-66.
Dubois et al., "Preassociation of IL-15 with IL-15Rα-IgG1-Fc Enhances Its Activity on Proliferation of NK and CD8+/CD44high T Cells and Its Antitumor Action," The Journal of Immunology, Feb. 15, 2008, 180:2099-2106.
Edwardraja et al., "Redesigning of anti-c-met single chain Fv antibody for the cytoplasmic folding and its structural analysis," Biotechnology and Bioengineering, Jun. 15, 2010, 106(3):367-75.
Eisenhut et al., "Ion Channels in Inflammation," Pflugers Archive, Jan. 29, 2011, 461(4):401-421.
Elgueta et al., "Molecular mechanism and function of CD40/CD40L engagement in the immune system," Immunological Reviews, 2009, 229(1):152-172 doi.org/10.1111/j.1600-065X.2009.00782.x.
Elpek et al., "Mature natural killer cells with phenotypic and functional alterations accumulate upon sustained stimulation with

(56) References Cited

OTHER PUBLICATIONS

IL-15/IL-15Rα complexes," Proceedings of the National Academy of Science, Dec. 14, 2010, 107: 21647-21652.
Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Farr et al., "Targeting cellular senescence prevents age-related bone loss in mice," Nat. Med., 2017, 23(9): 1072-1079.
Fehniger et al., "A Phase 1 Trial of CNDO-109-Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Fernando et al., "Targeting tumor endothelial marker 8 in the tumor vasculature of colorectal carcinomas in mice," Cancer research, Jun. 15, 2009, 69(12):5126-5132.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151:1235-1244.
Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunol. Res. 62(3):377-385, 2015.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gibbs et al., "Identification of the factor VIIa binding site on tissue factor by homologous loop swap and alanine scanning mutagenesis," Biochemistry, Nov. 1, 1994, 33(47):14003-10.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Greenspan et al., "Defining epitopes: Its not as easy as it seems," Nature Biotechnology, 1999, 17:936-937.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Guha et al., "Affinity purification of human tissue factor: interaction of factor VII and tissue factor in detergent micelles," Proceedings of the National Academy of Sciences, Jan. 1986, 83(2):299-302.
Guo et al., "Immunobiology of the IL-15-IL-15R complex as an antitumor and antiviral agent," 2017, Cytokine & Growth Factor Reviews, 38:10-21.
Gutschmidt et al., "A quantitative histochemical study of dipeptidyl peptidase IV (DPP IV)," Histochemistry, 1981, 73(2):285-304.
Haile et al., "Soluble CD80 Restores T Cell Activation and Overcomes Tumor Cell Programmed Death Ligand 1-Mediated Immune Suppression," J. Immunol., 2013, 191(5):2829-2836.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Hebbar et al., "Detection of circulating soluble CD28 in patients with systemic lupus erythematosus, primary Sjögren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145.
Hélie et al., "Application of the Protein Maker as a platform purification system for therapeutic antibody research and development," Computational and Structural Biotechnology Journal, Jan. 1, 2016, 14:238-244.
Helman et al., "Effects of ageing and senescence on pancreatic β-cell function," Diabetes Obes Metab., Sep. 2016, 18(Suppl. 1):58-62.
Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice," Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Heng et al., "Multiple soluble TGF-β receptors in addition to soluble endoglin are elevated in preeclamptic serum and they synergistically inhibit TGF-β signalling." Placenta, 2017 57: 320 (1 page).
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hombach et al., "Generation of the single chain antibody fragment conserves the idiotypic profile of the anti-CD30 monoclonal antibody HRS3," Scandinavian Journal of Immunology, Nov. 1998, 48(5):497-501.

(56) References Cited

OTHER PUBLICATIONS

Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Huang et al., "Targeting the vasculature of colorectal carcinoma with a fused protein of (RGD) 3-tTF" The Scientific World Journal, 2013(637086): 1-11, 2013.
Hudak et al., "Glycocalyx engineering reveals a Siglec-based mechanism for NK cell immunoevasion," Nature Chemical Biology, Jan. 2014, 10(1), 20 pages.
Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hughes et al., "Transfer of a TCR gene derived from a patient with a marked antitumor response conveys highly active T-cell effector functions," Hum. Gene Ther., 2005, 16:457-72.
Hui et al., "Butyrate inhibit collagen-induced arthritis via Treg/IL-10/Th17 axis," International immunopharmacology, Mar. 1, 2019, 68: Abstract 1 page.
Hynes et al., "In vitro analysis of cell metabolism using a long-decay pH-sensitive lanthanide probe and extracellular acidification assay," Analytical biochemistry, Jul. 1, 2009, 390(1):21-28.
Iannello et al., "p53-dependent chemokine production by senescent tumor cells supports NKG2D-dependent tumor elimination by natural killer cells," Journal of Experimental Medicine, Sep. 23, 2013, 210(10):2057-69.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.
info.gbiosciences.com [Online], "G-Biosciences, The Basics of Affinity Purification/Affinity Chromatography," Jul. 31, 2018, retrieved on Apr. 18, 2023, retrieved from URL<https://info.gbiosciences.com/blog/the-basics-of-affinity-purification/affinity-chromatography?utm_campaign=G-Bio+Search+Ads&utm_term=&utm_source=adwords&utm_medium=ppc&hsa_src=g&hsa_ver-3&hsa_cam=737902488&hsa_kw=&hsa_ad=621736020174&hsa_tgt=dsa-460355902483&hsa_mt-&hsa_acc-6752996364&hsa_grp=92226101427&hsa_net-adwords&gclid=CjwKCAjw_ihBhADEiwAXEazJvXifVFgeRGV_W99XbY72eRROhWnHtdd695ydPgyh8qdvTwd9ikGIRoCdecQAvDBwE >, 5 pages.
International Preliminary Report on Patentability in International Appln. No. PCT/US2019/048881, dated Mar. 11, 2021, 7 pages.
International Preliminary Report on Patentability in International Appln. No. PCT/US2019/048930, dated Mar. 11, 2021, 9 pages.
International Preliminary Report on Patentability in International Appln. No. PCT/US2019/049142, dated Mar. 11, 2021, 11 pages.
International Preliminary Report on Patentability in International Appln. No. PCT/US2019/049158, dated Mar. 11, 2021, 8 pages.
International Preliminary Report on Patentability in International Appln. No. PCT/US2020/035598, mailed Dec. 6, 2022, 7 pages.
International Preliminary Report on Patentability in International Appln. No. PCT/US2020/038717, dated Dec. 30, 2021, 9 pages.
International Preliminary Report on Patentability in International Appln. No. PCT/US2021/017620, dated Aug. 25, 2022, 12 pages.
International Preliminary Report on Patentability in International Appln. No. PCT/US2021/017621, dated Aug. 25, 2022, 8 pages.
International Preliminary Report on Patentability in International Appln. No. PCT/US2021/017714, dated Aug. 25, 2022, 12 pages.
International Preliminary Report on Patentability in International Appln. No. PCT/US2021/029920, dated Nov. 10, 2022, 11 pages.
International Preliminary Report on Patentability in International Appln. No. PCT/US2021/035285, mailed Dec. 15, 2022, 7 pages.
International Search Report and Written Opinion in International Appln. No. PCT/US2019/048881, dated Nov. 9, 2019, 16 pages.
International Search Report and Written Opinion in International Appln. No. PCT/US2019/048930, dated Nov. 20, 2019, 18 pages.
International Search Report and Written Opinion in International Appln. No. PCT/US2019/049142, dated Jun. 23, 2020, 20 pages.
International Search Report and Written Opinion in International Appln. No. PCT/US2019/049158, dated Jan. 20, 2020, 17 pages.
International Search Report and Written Opinion in International Appln. No. PCT/US2020/035598, dated Feb. 18, 2021, 12 pages.
International Search Report and Written Opinion in International Appln. No. PCT/US2020/038717, dated Oct. 16, 2020, 17 pages.
International Search Report and Written Opinion in International Appln. No. PCT/US2021/017620, dated Aug. 6, 2021, 22 pages.
International Search Report and Written Opinion in International Appln. No. PCT/US2021/017621, dated Jun. 9, 2021, 15 pages.
International Search Report and Written Opinion in International Appln. No. PCT/US2021/017714, dated Aug. 27, 2021, 22 pages.
International Search Report and Written Opinion in International Appln. No. PCT/US2021/029920, dated Oct. 6, 2021, 21 pages.
International Search Report and Written Opinion in International Appln. No. PCT/US2021/035285, dated Oct. 18, 2021, 14 pages.
Inzucchi et al., "New Drugs for the Treatment of Diabetes, Part II: Incretin-Based Therapy and Beyond," Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Jakob et al., "Structure reveals function of the dual variable domain immunoglobulin (DVD-Ig™) molecule," Mabs, May 1, 2013, Taylor & Francis, 5(3):358-63.
Janeway, "Approaching the Asymptote? Evolution and Revolution in Immunology," Cold Spring Harbor Symposia on Quantitative Biology, 1989, 54 Pt 1:1-13.
Jeannin et al., "Soluble CD86 Is a Costimulatory Moleculefor Human T Lymphocytes," Immunity, 2000, 13(3):303-312.
Jeon et al., "Local clearance of senescent cells attenuates the development of post-traumatic osteoarthritis and creates a pro-regenerative environment," Nat Med., Jun. 2017, 23(6):775-781.
Jin et al., "Novel Insights Into the NLRP3 Inflammasome in Atherosclerosis," Journal of the American Heart Association, Jun. 11, 2019, 8(12):e012219, 12 pages.
Justice et al., "Senolytics in idiopathic pulmonary fibrosis: Results from a first-in-human, open-label, pilot study," EBioMedicine, Feb. 2019, 40:554-563.
Kain et al., "The identification of the endogenous ligands of natural killer T cells reveals the presence of mammalian α-linked glycosylceramides," Immunity, Oct. 16, 2014, 41(4):543-54.
Karin et al., "Senescent cell turnover slows with age providing an explanation for the Gompertz law," Nature Communications, 10:5495, 9 pages.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, 5:18, 13 pages.
Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.
Kijanka et al., "Nanobody-based cancer therapy of solid tumors," Nanomedicine, Jan. 2015, 10(1):161-74.
Kim et al., "Experimental malaria infection triggers early expansion of natural killer cells," Infection and Immunity, Dec. 1, 2008, 76(12):5873-82.
Kim et al., "Identification of senescent cell surface targetable protein DPP4," Genes & Development, 2017, 31(15):1529-1534.

(56) References Cited

OTHER PUBLICATIONS

Kim et al., "Insulin resistance, inflammation, and nonalcoholic fatty liver disease in non-obese adults without metabolic syndrome components," Hepatol Int., Jun. 2013, 7(2):586-591.
Kim et al., "SCAMP4 enhances the senescent cell secretome," Genes & Development, 2018, 32(13-14):909-914.
Kirchhofer et al., "The tissue factor region that interacts with substrates factor IX and factor X," Biochemistry, Jun. 27, 2000, 39(25):7380-7.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.
Klein et al., "Design and characterization of structured protein linkers with differing flexibilities," Protein Engineering, Design & Selection, 2014, 27(10):325-30.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Klingemann et al., "Natural killer cells for immunotherapy-advantages of the NK-92 cell line over blood NK cells," Frontiers in immunology, Mar. 14, 2016, 7(91): 1-7.
Klingenberg et al., "Depletion of FOXP3+ regulatory T cells promotes hypercholesterolemia and atherosclerosis," The Journal of Clinical Investigation, Feb. 15, 2013, 123:1323-1334.
Kondo et al., "Requirements for the functional expression of OX40 ligand on human activated CD4+ and CD8+ T cells," Human Immunology, 2007, 68(7):563-571.
Kovaleva et al., "Shark variable new antigen receptor biologics—a novel technology platform for therapeutic drug development," Expert Opinion on Biological Therapy, Oct. 1, 2014, 14(10):1527-39.
Kozlowska et al., "Adoptive transfer of osteoclast-expanded natural killer cells for immunotherapy targeting cancer stem-like cells in humanized mice," Cancer Immunology, Immunotherapy, Jul. 2016, 65:835-845.
Krah et al., "Single-domain antibodies for biomedical applications," Immunopharmacology and Immunotoxicology, Jan. 2, 2016, 38(1):21-8.
Kritsilis et al., "Ageing, Cellular Senescence and Neurodegenerative Disease," International Journal of Molecular Sciences, Sep. 27, 2018, 19(10):2937, 37 pages.
Krizhanovsky et al., "Senescence of activated stellate cells limits liver fibrosis," Cell, Aug. 22, 2008, 134(4):657-67.
Kumagai et al., "Monitoring of glutamate-induced excitotoxicity by mitochondrial oxygen consumption," Synapse, Jan. 2019, 73(1):e22067, 24 Pages.
Kuyinu et al., "Animal models of osteoarthritis: classification, update, and measurement of outcomes," J Orthop Surg Res., Feb. 2, 2016, 11:19, 27 pages.
Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lamkanfi et al., "Mechanisms and Functions of Inflammasomes," Cell, May 22, 2014, 157(5):1013-1022.
Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lau et al., "RNA-associated autoantigens activate B cells by combined B cell antigen receptor/Toll-like receptor 7 engagement," The Journal of Experimental Medicine, Oct. 31, 2005, 202(9):1171-1177.
Lazar et al., "Transforming Growth Factor Alpha: Mutation of Aspartic Acid 47 and Leucine 48 Results in Different Biological Activities," Mol. Cell. Biol., 1988, 8:1247-1252.
Li et al., "A Novel I L2-based Irrmunotherapeutic Protein Prevents the Development of Atherosclerosis in ApoE−/mice and LDLR−/− mice," Journal of Immunology, May 1, 2020, 204(1):Supplement (Abstract Only), 2 pages.
Li et al., "Adoptive transfer of natural killer cells in combination with chemotherapy improves outcomes of patients with locally advanced colon carcinoma," Cytotherapy, Jan. 2018, 20(1):134-148, 15 pages.
Li et al., "Lipid metabolism fuels cancer's spread," Cell metabolism, Feb. 7, 2017, 25(2):228-230.
Li et al., "The cGAS-cGAMP-STING pathway connects DNA damage to inflammation, senescence, and cancer," Journal of Experimental Medicine, Apr. 5, 2018, 215(5):1287-1299.
Li et al., "Transforming Growth Factor-β Regulation of Immune Responses," Annu. Rev. Immunol., 2006, 24:99-146.
Liton et al., "Cellular senescence in the glaucomatous outflow pathway," Experimental Gerontology, Aug.-Sep. 2005, 40(8-9):745-748.
Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.
Liu et al., "Evaluation of the biological activities of the IL-15 superagonist complex, ALT-803, following intravenous versus subcutaneous administration in murine models," Cytokine, Jul. 2018, 107: 105-112, 8 pages.
Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.
Lu et al., "Molecular basis of binding between novel human coronavirus MERS-CoV and its receptor CD26," Nature, Jul. 7, 2013, 500(7461):227-231.
Lujambio et al., "Non-Cell-Autonomous Tumor Suppression by p53," Cell, Apr. 11, 2013, 153(2):449-460.
Maeda et al., "Original Ligand for LTβR Is LIGHT: Insight into Evolution of the LT/LTβR System," J Immunol., 2018, 201(1):202-214.
Maganto-García et al., "Dynamic Changes in Regulatory T Cells Are Linked to Levels of Diet-Induced Hypercholesterolemia," Circulation, Jun. 20, 2011, 124:185-195.
Mandelboim et al., "Recognition of haemagglutinins on virus-infected cells by NKp46 activates lysis by human NK cells," Nature, Feb. 2001, 409(6823):1055.
Marguet et al., "Enhanced insulin secretion and improved glucose tolerance in mice lacking CD26," Proc. Natl. Acad. Sci. U.S.A., Jun. 6, 2000, 97(12):6874-6879.
Martelli et al., "HLA-haploidentical transplantation with regulatory and conventionalT-cell adoptive immunotherapy prevents acute leukemia relapse," Blood, Jul. 24, 2014, 124(4):638-644.
Masoumi et al., "The role of hypoxia as the driving force for non-erythroid production of globin chains in preeclamptic placentas," Placenta. 2017;57:320.
McCarron et al., "TGF-β prevents T follicular helper cell accumulation and B cell autoreactivity," J Clin Invest., 2014, 124(10):4375-4386.
McHugh et al., "Senescence and aging: Causes, consequences, and therapeutic avenues," Journal of Cellular Biology, Nov. 7, 2017, 217(1):65-77.
Mehta et al., "Why do trials for Alzheimer's disease drugs keep failing? A discontinued drug perspective for 2010-2015," Expert Opinion on Investigational Drugs, May 2017, 26(6):735-739.
Melk et al., "Expression of p16INK4a and other cell cycle regulator and senescence associated genes in aging human kidney," Kidney Int., Feb. 2004, 65(2):510-520.
Melk et al., "Senescence of renal cells: molecular basis and clinical implications," Nephrology Dialysis Transplantation, Dec. 2003, 18(12):2474-2478.

(56) References Cited

OTHER PUBLICATIONS

Menshawy et al., "CD58; leucocyte function adhesion-3 (LFA-3) could be used as a differentiating marker between immune and non-immune thyroid disorders," Comparative Clinical Pathology, 2018, 27(3), 721-727.
Mentlein et al., "Dipeptidyl-peptidase IV (CD26)-role in the inactivation of regulatory peptides," Regulatory Peptides, Nov. 30, 1999, 85(1):9-24.
Miah et al., "KIR2DL4 differentially signals downstream functions in human NK cells through distinct structural modules," The Journal of Immunology, Mar. 1, 2008, 180(5):2922-32.
Michelet et al., "Metabolic reprogramming of natural killer cells in obesity limits antitumor responses," Nature Immunology, Nov. 12, 2018, 19(12):1330-1340.
Mikayama et al., "Molecular cloning and functional expression of a cDNA encoding glycosylation-inhibiting factor," Proc. Natl. Acad. Sci. USA, Nov. 1, 1993, 90(21):10056-10060.
Milanovic et al., "Senescence-associated reprogramming promotes cancer stemness," Nature, Dec. 20, 2017, 553(7686):96-100.
Milanovic et al., "The Senescence-Stemness Alliance—A Cancer-Hijacked Regeneration Principle," Trends in Cellular Biology, Dec. 2018, 28(12):1049-1061, 13 pages.
Miller et al., "Soluble CD70: a novel immunotherapeutic agent for experimental glioblastoma," J Neurosurg., 2010, 113(2):280-285.
Miller et al., "Successful adoptive transfer and in vivo expansion of human haploidentical NK cells in patients with cancer," Blood, Apr. 15, 2005, 105(8):3051-3057.
Minamino et al., "A crucial role for adipose tissue p53 in the regulation of insulin resistance," Nature Medicine, Aug. 30, 2009, 15(9):1082-1087.
Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.
Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.
Moesta et al., "Targeting CD39 in cancer," Nature Reviews Immunology, Jul. 29, 2020, 20(12):739-755, 17 pages.
Moiseeva et al., "Metformin inhibits the senescence-associated secretory phenotype by interfering with IKK/NF-κB activation," Aging Cell, Mar. 23, 2013, 12(3):489-498.
Molema et al., "The use of bispecific antibodies in tumor cell and tumor vasculature directed immunotherapy," Journal of Controlled Release, 2000, 64(1-3):229-239.
Molgora et al., "Regulatory role of IL-1R8 in immunity and disease," Frontiers in Immunology, Apr. 20, 2016, 7:149.
Mookerjee et al., "Measurement and Analysis of Extracellular Acid Production to Determine Glycolytic Rate," Journal of Visualized Experiments : Jove, Dec. 2015, (106):e53464, 9 Pages.
Moore et al., "Macrophages in atherosclerosis: a dynamic balance," Nature Reviews Immunology, Sep. 2, 2013, 13:709-721, 13 pages.
Moreno et al., "Molecular Evidence of Adenosine Deaminase Linking Adenosine A2A Receptor and CD26 Proteins," Frontiers in Pharmacology, Feb. 15, 2018, 9:106, 18 pages.
Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.
Mortier et al., "Soluble interleukin-15 receptor α (IL-15Rα)-sushi as a selective and potent agonist of IL-15 action through IL-15Rβ/γ: hyperagonist IL-15. IL-15Rα fusion proteins," Journal of Biological Chemistry, Jan. 20, 2006, 281(3):1612-1619.
Mujić-Delić et al., "GPCR-targeting nanobodies: attractive research tools, diagnostics, and therapeutics," Trends in Pharmacological Sciences, May 1, 2014, 35(5):247-55.
Muller et al., "Antibody fusions with immunomodulatory proteins for cancer therapy," Pharmacology and Therapeutics, 2015, 154:57-66.
Mulvihill et al., "Pharmacology, Physiology, and Mechanisms of Action of Dipeptidyl Peptidase-4 Inhibitors," Endocrine Reviews, Dec. 1, 2014, 35(6):992-1019.
Munoz-Espin et al., "Cellular senescence: from physiology to pathology," Nature Reviews Molecular Cellular Biology, Jun. 23, 2014, 15(7):482-496.
Munoz-Espin et al., "Programmed Cell Senescence during Mammalian Embryonic Development," Cell, Nov. 21, 2013, 155(5):1104-1118.
Musi et al., "Tau protein aggregation is associated with cellular senescence in the brain," Aging Cell, Aug. 20, 2018, 17(6):e12840, 13 pages.
Must et al., "The Disease Burden Associated with Overweight and Obesity," Endotext, Feingold et al. (eds.), South Dartmouth, MA, 2000, 35 pages.
Muyldermans et al., "Recognition of antigens by single-domain antibody fragments: the superfluous luxury of paired domains," Trends in Biochemical Sciences, Apr. 1, 2001, 26(4):230-5.
Muyldermans, "Nanobodies: natural single-domain antibodies," Annual Review of Biochemistry, Jun. 2, 2013, 82:775-97.
Muyldermans, "Single domain camel antibodies: current status," Reviews in Molecular Biotechnology, Jun. 1, 2001, 74(4):277-302.
Myung et al., "Evidence of DNA damage in Alzheimer disease: phosphorylation of histone H2AX in astrocytes," Age, Apr. 23, 2008, 30(4):209-215.
Nag et al., "Soluble MHC II-peptide complexes induce antigen-specific apoptosis in T cells," Cellular Immunology, May 25, 1996, 170(1):25-33.
Nayyar et al., "Overcoming Resistance to Natural Killer Cell Based Immunotherapies for Solid Tumors," Frontiers in Oncology, 2019, 9: 28 pages.
Nelson et al., "A senescent cell bystander effect: senescence-induced senescence," Aging Cell, Feb. 9, 2012, 11(2):345-349.
Nilsson et al., "Targeted delivery of tissue factor to the ED-B domain of fibronectin, a marker of angiogenesis, mediates the infarction of solid tumors in mice," Cancer Research, American Association for Cancer Researc, Proceddings: AACR 107th Annual Meeting, 2016, Apr. 16-20, 2016, New Orleans, LA 61(2):711-716.
Nishida et al., "CD26 is a potential therapeutic target by humanized monoclonal antibody for the treatment of multiple myeloma," Blood Cancer Journal, Oct. 22, 2018, 8(11):99, 17 pages.
O'Sullivan et al., "Natural Killer Cell Memory," Immunity, Oct. 20, 2015, 43(4):634-645.
Oberle et al., "Rapid Suppression of Cytokine Transcription in Human CD4+CD25-T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.
Ogrodnik et al., "Cellular senescence drives age-dependent hepatic steatosis," Nat Commun. Jun. 13, 2017;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.
Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.

(56) References Cited

OTHER PUBLICATIONS

Ovadya et al., "Strategies targeting cellular senescence," The Journal of Clinical Investigation, Apr. 2, 2018, 128(4):1247-54.
Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Pittayapruek et al., "Role of Matrix Metalloproteinases in Photoaging and Photocarcinogenesis," International Journal of Molecular Sciences, 2016, 17(6):868, 20 pages.
Price et al., "Comparison of collagenase-cleaved articular cartilage collagen in mice in the naturally occurring STR/ort model of osteoarthritis and in collagen-induced arthritis," Osteoarthritis Cartilage, Mar. 2002, 10(3):172-179.
Priyanka et al., "Linkers in the structural biology of protein-protein interactions," Protein Sci., 2013, 22(2):153-167.
Purohit et al., "Smad3-dependent regulation of type I collagen in human dermal fibroblasts: Impact on human skin connective tissue aging," Journal of Dermatological Science, Jul. 2016, 83(1):80-83.
Putnam et al., "Clinical grade manufacturing of human alloantigen-reactive regulatory T cells for use in transplantation," American journal of transplantation, Nov. 1, 2013, 13(11):3010-3020.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf virus specific T-cells for therapy of adenovirus disease in immunosuppressed patients," Journal of Clinical Oncology, May 26, 2019, 37(15 Suppl.):7008, 2 pages.
Rahbarizadeh et al., "Nanobody; an old concept and new vehicle for immunotargeting," Immunological Investigations, Jan. 1, 2011, 40(3):299-338.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Ranganathan et al., "Pinpointing the putative heparin/sialic acid-binding residues in the 'sushi' domain 7 of factor H: a molecular modeling study," Biocomputing 2000, 1999, 155-67.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.
Resta et al., "Ecto-enzyme and signaling functions of lymphocyte CD 7 3," Immunological Reviews, 1998, 161:95-109.
Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.
Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.
Rittie et al., "Natural and Sun-Induced Aging of Human Skin," Cold Spring Harbor Perspective in Medicine, 2015, 5(1):a015370, 15 pages.
Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.
Rodier et al., "Persistent DNA damage signaling triggers senescence-associated inflammatory cytokine secretion," Nature Cell Biology, Jul. 13, 2009, 11(8): 15 pages.
Rogge et al., "Antibodies to the IL-12 receptor β2 chain mark human Th1 but not Th2 cells in vitro and in vivo," The Journal of Immunology, Apr. 1, 1999, 162(7):3926-32.
Roh et al., "Damage-Associated Molecular Patterns in Inflammatory Diseases," Immune Network, Aug. 2018, 18(4):e27, 14 pages.
Romano et al., "Past, Present, and Future of Regulatory T Cell Therapy in Transplantation and Autoimmunity," Frontiers in Immunology, Jan. 1, 2019, 10:43, 14 pages.
Romee et al., "Cytokine activation induces human memory-like NK cells," Blood, Dec. 6, 2012, 120(24):4751-4760.
Rossi et al., "Complex and defined biostructures with the dock-and-lock method," Trends in Pharmacological Sciences, Sep. 1, 2012, 33(9):474-81.
Rossi et al., "Stably tethered multifunctional structures of defined composition made by the dock and lock method for use in cancer targeting," Proceedings of the National Academy of Sciences, May 2, 2006, 103(18):6841-6.
Rubinstein et al., "Converting IL-15 to a superagonist by binding to soluble IL-15Rα," Proceedings of the National Academy of Sciences U.S.A., Jun. 13, 2006, 103(24):9166-9171.
Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.
Ruf et al., "Tissue factor residues 157-167 are required for efficient proteolytic activation of factor X and factor VII," Journal of Biological Chemistry, Nov. 5, 1992, 267(31):22206-10.
Ruscetti et al., "NK cell-mediated cytotoxicity contributes to tumor control by a cytostatic drug combination," Science, Dec. 21, 2018, 362(6421):1416-1422, 8 pages.
Sagiv et al., "Granule exocytosis mediates immune surveillance of senescent cells," Oncogene, 2013, 32(15):1971-1977.
Sakaguchi et al., "Regulatory T Cells and Human Disease," Annual Review of Immunology, Apr. 26, 2020, 38:541-566.
Sakaguchi et al., "Regulatory T Cells and Immune Tolerance," Cell, May 30, 2008, 133(5):775-787.
Sakaguchi et al., "Regulatory T cells: how do they suppress immune responses?" International Immunology, Sep. 7, 2009, 21(10):1105-1111.
Sakamoto et al., "Phase I clinical trial of autologous NK cell therapy using novel expansion method in patients with advanced digestive cancer," Journal of Translational Medicine, Aug. 25, 2015, 13:277, 13 pages.
Sakamuri et al., "Measurement of respiratory function in isolated cardiac mitochondria using Seahorse XFe24 Analyzer: applications for aging research," Geroscience, Jun. 1, 2018, 40(3):347-356.
Salminen et al., "Emerging role of NF-κB signaling in the induction of senescence-associated secretory phenotype (SASP)," Cellular Signaling, Apr. 2012, 24(4):835-845.
Sandusky et al., "Regulation of 2B4 (CD244)-mediated NK cell activation by ligand-induced receptor modulation," European Journal of Immunology, Dec. 2006, 36(12):3268-76.
Sato et al., "Recombinant soluble murine IL-4 receptor can inhibit or enhance IgE responses in vivo," The Journal of Immunology, Apr. 1, 1993, 150:2717-2723.
Schafer et al., "Cellular senescence mediates fibrotic pulmonary disease," Nat Commun., Feb. 2017, 8:14532, 11 pages.
Schullek et al., "Key ligand interface residues in tissue factor contribute independently to factor VIIa binding," Journal of Biological Chemistry, Jul. 29, 1994, 269(30):19399-403.
Schwoppe et al., "Tissue-factor fusion proteins induce occlusion of tumor vessels," Thrombosis Research, Apr. 1, 2010, 125:S143-S150.

(56) References Cited

OTHER PUBLICATIONS

Seo et al., "Positive Feedback Loop between Plasminogen Activator Inhibitor-1 and Transforming Growth Factor-Betal during Renal Fibrosis in Diabetes," American Journal of Nephrology, Sep. 25, 2009, 30:481-490.
Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.
Sharma et al., "Regulatory T Cells License Macrophage Pro Resolving Functions During Atherosclerosis Regression," Circulation Research, Apr. 27, 2020, 127:335-353.
Smith et al., "Antigen Nature and Complexity Influence Human Antibody Light Chain Usage and Specificity," Vaccine, 2016, 34(25): 2813-2820.
Smith et al., "Development and evaluation of an optimal human single-chain variable fragment-derived BCMA-targeted CAR T cell vector," Molecular Therapy, Jun. 6, 2018, 26(6):1447-56.
Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.
Sondel et al., "Combination Therapy with Interleukin-2 and Anti-tumor Monoclonal Antibodies," Cancer Journal from Scientific American, Jan. 1, 1997, 3(Suppl. 1):S121-S127.
Sone et al., "Pancreatic beta cell senescence contributes to the pathogenesis of type 2 diabetes in high-fat diet-induced diabetic mice," Diabetologia, 2005, 48(1):58-67.
Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.
Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.
Sousa-Victor et al., "Geroconversion of aged muscle stem cells under regenerative pressure," Cell Cycle, Oct. 15, 2014, 13(20):3183-3190.
Spiess et al., "Alternative molecular formats and therapeutic applications for bispecific antibodies," Molecular Immunology, Oct. 1, 2015, 67(2):95-106.
Stoklasek et al., "Combined IL-15/IL-15Rα Immunotherapy Maximizes IL-15 Activity In Vivo," The Journal of Immunology, Nov. 1, 2006, 177(9):6072-6080.
Storer et al., "Senescence Is a Developmental Mechanism that Contributes to Embryonic Growth and Patterning," Cell, Nov. 21, 2013, 155(5):1119-1130.
Stryer, Biochemistry Fourth Edition, W. H. Freeman and Company, New York, 1995, pp. 18-23, 8 pages.
Swanson et al., "The NLRP3 inflammasome: molecular activation and regulation to therapeutics," Nature Reviews Immunology, Apr. 29, 2019, 19(8):477-489, 13 pages.
Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.
Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.
Takahashi et al., "Downregulation of cytoplasmic DNases is implicated in cytoplasmic DNA accumulation and SASP in senescent cells," Nature Communications, Mar. 28, 2018, 9:1249, 12 pages.
Takahashi et al., "Simple and inexpensive technique for measuring oxygen consumption rate in adherent cultured cells," The Journal of Physiological Sciences, Nov. 2017, 67(6):731-737.
Takeda et al., "Phase I study of YS110, a recombinant humanized monoclonal antibody to CD26, in Japanese patients with advanced malignant pleural mesothelioma," Lung Cancer, Nov. 2019, 137:64-70.
Tam et al., "Methods and strategies of peptide ligation," Peptide Science: Original Research on Biomolecules, 2001, 60(3):194-205.
Tanaka et al., "Cloning and functional expression of the T cell activation antigen CD26," Journal of Immunology, Jul. 15, 1992, 149(2):481-486.
Tang et al., "The Foxp3+ regulatory T cell: a jack of all trades, master of regulation," Nature Immunology, Feb. 19, 2008, 9(3):239-244.
Teissier et al., "The receptor for advanced glycation end-products (RAGE) is an important pattern recognition receptor (PRR) for inflammaging," Biogerontology, Apr. 9, 2019, 20(3):279-301, 23 pages.
Teng et al., "Structural assessment of the effects of amino acid substitutions on protein stability and protein proteininteraction," International journal of computational biology and drug design, Feb. 7, 2011, 3(4):334-349.
Theil et al., "Adoptive transfer of allogeneic regulatory T cells into patients with chronic graft-versus-host disease," Cytotherapy, Apr. 2015, 17(4):473-486, 14 pages.
ThermoFisher.com [Online], "Covalent Immobilization of Affinity Ligands," 2018, retrieved on Apr. 18, 2023, retrieved from <URLhttps://www.thermofisher.com/us/en/home/life-science/protein-biology/protein-biology-learning-center/protein-biology-resource-library/pierce-protein-methods/covalent-immobilization-affinity-ligands.html>, 13 pages.
Thonhoff et al., "Expanded autologous regulatory T-lymphocyte infusions in ALS," Neurology Neuroimmunology Neuroinflammation, May 18, 2018, 5(4):e465, 8 pages.
Tobin et al., "NK cells in childhood obesity are activated, metabolically stressed, and functionally deficient," JCI Insight, Dec. 21, 2017, 2(24):e94939, 9 pages.
Tomala et al., "In Vivo Expansion of Activated Naive CD8+ T Cells and NK Cells Driven by Complexes of IL-2 and Anti-IL-2 Monoclonal Antibody As Novel Approach of Cancer Immunotherapy," The Journal of Immunology, Oct. 15, 2009, 183:4904-4912.
Tominaga et al., "TGF-β Signaling in Cellular Senescence and Aging-Related Pathology," International Journal of Molecular Sciences, Oct. 10, 2019, 20(20):5002, 18 pages.
Trevani et al., "Extracellular acidification induces human neutrophil activation," The Journal of Immunology, Apr. 15, 1999, 162(8):4849-4857.
Tse et al., "ABT-263: A Potent and Orally Bioavailable Bcl-2 Family Inhibitor," Cancer Research, May 2008, 68(9):3421-3428.
Uppendahl et al., "Natural killer cell-based immunotherapy in gynecologic malignancy: a review," Frontiers in immunology, Jan. 5, 2018, 8(1825): 1-15.
Urh et al., "Affinity chromatography: general methods," Methods in enzymology, Jan. 1, 2009, 463: 23 pages.
Uryga et al., "Ageing induced vascular smooth muscle cell senescence in atherosclerosis," Journal of Physiology, Apr. 15, 2016, 594(8):2115-2124.
Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Van Deursen, "The role of senescent cells in ageing," Nature, May 21, 2014, 509(7501):439-446.
Vankadari et al., "Emerging COVID-19 coronavirus: glycan shield and structure prediction of spike glycoprotein and its interaction with human CD26," Emerging Microbes and Infection, Mar. 17, 2020, 9(1):601-604.

(56) References Cited

OTHER PUBLICATIONS

Veluchamy et al., "The rise of allogeneic natural killer cells as a platform for cancer immunotherapy: recent innovations and future developments," Frontiers in immunology, May 31, 2017, 8(631): 1-20.
Vidarsson et al., "IgG subclasses and allotypes: from structure to effector functions," Frontiers in immunology, Oct. 20, 2014, 5:520, 17 Pages.
Vincke et al., "Introduction to heavy chain antibodies and derived Nanobodies," Single Domain Antibodies, Humana Press, Totowa, NJ, 2012, pp. 15-26.
Voelker et al., "Anti-TGF-β1 Antibody Therapy in Patients with Diabetic Nephropathy," J Am Soc Nephrol., 2017, 28:953-962.
Voet et al., Biochemistry, John Wiley & Sons, Inc., 1990, pp. 126-128 and 228-234, 12 pages.
Von Kobbe, "Cellular senescence: a view throughout organismal life," Cellular and Molecular Life Sciences, Jul. 20, 2018, 75:3553-3567, 15 pages.
Waaijer et al., "Do senescence markers correlate in vitro and in situ within individual human donors?," Aging Feb. 2018, 10(2):278-289.
Wallace et al., "B lymphocytes confer immune tolerance via cell surface GARP-TGF-β complex," JCI Insight., 2018, 3(7):e99863, 19 pages.
Walsh et al., "Inflammasomes in the CNS," Nature Reviews Neuroscience, Jan. 8, 2014, 15(2):84-97, 14 pages.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565.
Wang et al., "Biomarkers of Cellular Senescence and Skin Aging," Frontiers in Genetics, Aug. 23, 2018, 9:247, 14 pages.
Wang et al., "Loss of lamin B1 is a biomarker to quantify cellular senescence in photoaged skin," Scientific Reports, Nov. 15, 2017, 7(1):15678, 8 pages.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weihermann et al., "Elastin structure and its involvement in skin photoageing," International Journal of Cosmetic Science, Jun. 2017, 39(3):241-247.
Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.
Weiner et al., "Antibody-based immunotherapy of cancer," Cell, Mar. 16, 2012, 148(6):1081-4.
Weiss et al., "Formyl-Peptide Receptors in Infection, Inflammation, and Cancer," Trends in Immunology, Oct. 2018, 39(10):815-829, 15 pages.
Wesolowski et al., "Single domain antibodies: promising experimental and therapeutic tools in infection and immunity," Medical Microbiology and Immunology. Aug. 1, 2009, 198(3):157-74.
Wiemann et al., "Hepatocyte telomere shortening and senescence are general markers of human liver cirrhosis," The FASEB Journal, Jul. 2002, 16(9):935-942.
Wilchek et al., "Essentials of biorecognition: The (strept) avidin-biotin system as a model for protein-protein and protein-ligand interaction," Immunology letters, Feb. 28, 2006, 103(1): Abstract 2 pages.
Wiley et al., "Mitochondrial Dysfunction Induces Senescence with a Distinct Secretory Phenotype," Cell Metabolism, Feb. 9, 2016, 23(2):303-314.
Witkowsa et al., "Soluble intercellular adhesion molecule-1 (sICAM-1): an overview," Eur Cytokine Netw. 2004, 15(2):91-98.
Wong et al., "Interleukin-15: Interleukin-15 receptor a scaffold for creation of multivalent targeted immune molecules," Protein Engineering, Design & Selection, Apr. 1, 2011, 24(4):373-383.
Xiong et al., "Maternal uterine NK cell-activating receptor KIR2DS1 enhances placentation," The Journal of Clinical Investigation, Oct. 1, 2013, 123(10):4264-72.
Xu et al., "Celecoxib attenuates cachectic events in mice by modulating the expression of vascular endothelial growth factor," Mol Med Rep., Jan. 2015, 11(1):289-294.
Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.
Xu et al., "Senolytics improve physical function and increase lifespan in old age," Nature Medicine, Aug. 2018, 24(8):1246, 15 pages.
Xu et al., "Transplanted senescent cells induce an osteoarthritis-like condition in mice," The Journals of Gerontology: Series A, Jun. 1, 2017, 72(6):780-5.
Yamamoto et al., "Measurement of glucose uptake in cultured cells," Curr Protoc Pharmacol, Dec. 2011, Chapter 12:12.14.1-12.14.22.
Yamazaki et al., "Vascular Cell Senescence Contributes to Blood-Brain Barrier Breakdown," Stroke, Feb. 16, 2016, 47(4):1068-1077, 15 pages.
Yan et al., "Obesity- and aging-induced excess of central transforming growth factor-β potentiates diabetic development via an RNA stress response," Nature Medicine, Aug. 3, 2014, 20:1001-1008, 9 pages.
Yanai et al., "Cellular senescence-like features of lung fibroblasts derived from idiopathic pulmonary fibrosis patients," Aging (Albany NY), Sep. 2015, 7(9):664-672.
Yigit et al., "A combination of an anti-SLAMF6 antibody and ibrutinib efficiently abrogates expansion of chronic lymphocytic leukemia cells," Oncotarget, May 3, 2016, 7(18):26346.
Yousefzadeh et al., "An aged immune system drives senescence and ageing of solid organs," Nature, May 12, 2021, 594:100-105, 34 pages.
Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.
Yu et al., "The dipeptidyl peptidase IV family in cancer and cell biology," FEBS Journal, Feb. 5, 2010, 277(5):1126-1144.
Yun et al., "Recurrent turnover of senescent cells during regeneration of a complex structure," Elife, May 5, 2015, 4:e05505, 16 pages.
Yung et al., "A selective transforming growth factor-β ligand trap attenuates pulmonary hypertension," American Journal of Respiratory and Critical Care Medicine, Nov. 1, 2016, 194(9):1140-51.
Zhang et al., "AAED1 modulates proliferation and glycolysis in gastric cancer," Oncology Reports, Aug. 1, 2018, 40(2):1156-1164.
Zhang et al., "Depletion of NK cells improves cognitive function in the Alzheimer disease mouse model," The Journal of Immunology, Jul. 15, 2020, 205(2): 10pages.
Zhang et al., "The bone anabolic effects of irisin are through preferential stimulation of aerobic glycolysis," Bone, Sep. 1, 2018, 114:150-160.
Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.
Zheng et al., "Acquisition of Suppressive Function by Activated Human CD4+CD25-T Cells Is Associated with the Expression of CTLA-4 Not FoxP3," The Journal of Immunology, Aug. 1, 2008, 181(3):1683-1691.
Zhong et al., "A Potential Role for Dendritic Cell/Macrophage-Expressing DPP4 in Obesity-Induced Visceral Inflammation," Diabetes, Jan. 2013, 62(1):149-157.
Zhou et al., "A novel chimeric antigen receptor redirecting T-cell specificity towards CD26cancer cells," Leukemia, Apr. 2020, 35(1):119-129, 11 pages.

(56) References Cited

OTHER PUBLICATIONS

Zhou, "Emerging mechanisms and applications of low-dose IL-2 therapy in autoimmunity," Cytokine & Growth Factor Reviews, Jun. 30, 2022, 67: 80-88.

Zhu et al., "New agents that target senescent cells: the flavone, fisetin, and the BCL-XL inhibitors, A1331852 and A1155463," Aging (Albany NY), Mar. 2017, 9(3):955-963.

Zhu et al., "Novel Human Interleukin-15 Agonists," The Journal of Immunology, Sep. 15, 2009, 183(6):3598-3607.

Zou et al., "2-NBDG as a fluorescent indicator for direct glucose uptake measurement," Journal of biochemical and biophysical methods, Sep. 30, 2005, 64(3):207-215.

Zwaagstra et al., "Engineering and therapeutic application of single-chain bivalent TGF-β family traps," Molecular Cancer Therapeutics, Jul. 1, 2012, 11(7):1477-87.

Chen et al., "A novel idea for establishing Parkinson's disease mouse model by intranasal administration of paraquat" Neurological Research, 43(4):267-277, 2021.

Igarashi et al., "VEGF-C and TGF-β reciprocally regulate mesenchymal stem cell commitment to differentiation into lymphatic endothelial or osteoblastic phenotypes," International journal of molecular medicine, 37(4):1005-1013, Apr. 1, 2016.

Infante-Duarte et al., "New developments in understanding and treating neuroinflammation" Journal of Molecular Medicine, 86:975-985, Sep. 2008.

International Search Report and Written Opinion in International Appln. No. PCT/US2023/065745, mailed on Jun. 26, 2023, 14 pages.

Janeway et al., "The interaction of the antibody molecule with specific antigen" In Immunobiology: The Immune System in Health and Disease, 5th edition, 5 pages, 2001.

Matsuura et al., "Pole test is a useful method for evaluating the mouse movement disorder caused by striatal dopamine depletion" Journal of neuroscience methods, 73(1):45-48, 1997.

Reddy et al., "Linkers in the structural biology of protein-protein interactions" Protein science, 22(2):153-167, 2013.

Ross et al., "Signaling and function of interleukin-2 in T lymphocytes" Annual review of immunology, 36:411-433, 2018.

Van Bockstaele et al., "The development of nanobodies for therapeutic applications" Current opinion in investigational drugs, 10(11):1212-1224, 2009.

Kick

18t15-12s for
Cytokine Induced Memory Like (CIML) NK Cells

Expand

7t15-21s with αTF for
Expansion of NK Cells

SEQUENCE LISTING

```
Sequence total quantity: 84
SEQ ID NO: 1            moltype = AA  length = 220
FEATURE                 Location/Qualifiers
source                  1..220
                        mol_type = protein
                        organism = Homo sapiens
SEQUENCE: 1
PCPAPELLGG PSVFLFPPKP KDTLMISRTP EVTCVVVDVS HEDPEVKFNW YVDGVEVHNA  60
KTKPREEQYN STYRVVSVLT VLHQDWLNGK EYKCKVSNKA LPAPIEKTIS KAKGQPREPQ  120
VYTLPPSRDE LTKNQVSLTC LVKGFYPSDI AVEWESNGQP ENNYKTTPPV LDSDGSFFLY  180
SKLTVDKSRW QQGNVFSCSV MHEALHNHYT QKSLSLSPGK                        220

SEQ ID NO: 2            moltype = AA  length = 138
FEATURE                 Location/Qualifiers
source                  1..138
                        mol_type = protein
                        organism = Homo sapiens
SEQUENCE: 2
HQDWLNGKEY KCKVSNKGLP APIEKTISKT KGQPREPQVY TLPPSREEMT KNQVSLTCLV  60
KGFYPSDISV EWESNGQPEN NYKTTPPMLD SDGSFFLYSK LTVDKSRWQQ GNVFSCSVMH  120
EALHNHYTQK SLSLSPGK                                                138

SEQ ID NO: 3            moltype = AA  length = 217
FEATURE                 Location/Qualifiers
source                  1..217
                        mol_type = protein
                        organism = Homo sapiens
SEQUENCE: 3
APELLGGPSV FLFPPKPKDT LMISRTPEVT CVVVDVSHED PEVQFKWYVD GVEVHNAKTK  60
PREEQYNSTF RVVSVLTVLH QDWLNGKEYK CKVSNKALPA PIEKTISKTK GQPREPQVYT  120
LPPSREEMTK NQVSLTCLVK GFYPSDIAVE WESSGQPENN YNTTPPMLDS DGSFFLYSKL  180
TVDKSRWQQG NIFSCSVMHE ALHNRFTQKS LSLSPGK                           217

SEQ ID NO: 4            moltype = AA  length = 217
FEATURE                 Location/Qualifiers
source                  1..217
                        mol_type = protein
                        organism = Homo sapiens
SEQUENCE: 4
APEFLGGPSV FLFPPKPKDT LMISRTPEVT CVVVDVSQED PEVQFNWYVD GVEVHNAKTK  60
PREEQFNSTY RVVSVLTVLH QDWLNGKEYK CKVSNKGLPS SIEKTISKAK GQPREPQVYT  120
LPPSQEEMTK NQVSLTCLVK GFYPSDIAVE WESNGQPENN YKTTPPVLDS DGSFFLYSRL  180
TVDKSRWQEG NVFSCSVMHE ALHNHYTQKS LSLSLGK                           217

SEQ ID NO: 5            moltype = AA  length = 219
FEATURE                 Location/Qualifiers
source                  1..219
                        mol_type = protein
                        organism = Homo sapiens
SEQUENCE: 5
SGTTNTVAAY NLTWKSTNFK TILEWEPKPV NQVYTVQIST KSGDWKSKCF YTTDTECDLT  60
DEIVKDVKQT YLARVFSYPA GNVESTGSAG EPLYENSPEF TPYLETNLGQ PTIQSFEQVG  120
TKVNVTVEDE RTLVRRNNTF LSLRDVFGKD LIYTLYYWKS SSSGKKTAKT NTNEFLIDVD  180
KGENYCFSVQ AVIPSRTVNR KSTDSPVECM GQEKGEFRE                         219

SEQ ID NO: 6            moltype = DNA  length = 657
FEATURE                 Location/Qualifiers
source                  1..657
                        mol_type = genomic DNA
                        organism = Homo sapiens
SEQUENCE: 6
agcggcacaa ccaacacagt cgctgcctat aacctcactt ggaagagcac caacttcaaa  60
accatcctcg aatgggaacc caaacccgtt aaccaagttt acaccgtgca gatcagcacc  120
aagtccggcg actggaagtc caaatgtttc tataccaccg acaccgagtg cgatctcacc  180
gatgagatcg tgaaagatgt gaaacagacc tacctcgccc gggtgtttag ctacccgcc  240
ggcaatgtgg agagcactgg ttccgctggc gagcctttat acgagaacag ccccgaattt  300
accccttacc tcgagaccaa tttaggacag cccaccatcc aaagctttga gcaagttggc  360
acaaaggtga atgtgacagt ggaggacgag cggactttag tgcggcggaa caacaccttt  420
```

```
ctcagcctcc gggatgtgtt cggcaaagat ttaatctaca cactgtatta ctggaagtcc  480
tcttcctccg gcaagaagac agctaaaacc aacacaaacg agtttttaat cgacgtggat  540
aaaggcgaaa actactgttt cagcgtgcaa gctgtgatcc cctcccggac cgtgaatagg  600
aaaagcaccg atagccccgt tgagtgcatg ggccaagaaa agggcgagtt ccgggag     657

SEQ ID NO: 7           moltype = AA  length = 223
FEATURE                Location/Qualifiers
source                 1..223
                       mol_type = protein
                       organism = Mus musculus
SEQUENCE: 7
AGIPEKAFNL TWISTDFKTI LEWQPKPTNY TYTVQISDRS RNWKNKCFST TDTECDLTDE  60
IVKDVTWAYE AKVLSVPRRN SVHGDGDQLV IHGEEPPFTN APKFLPYRDT NLGQPVIQQF  120
EQDGRKLNVV VKDSLTLVRK NGTFLTLRQV FGKDLGYIIT YRKGSSTGKK TNITNTNEFS  180
IDVEEGVSYC FFVQAMIFSR KTNQNSPGSS TVCTEQWKSF LGE                   223

SEQ ID NO: 8           moltype = AA  length = 224
FEATURE                Location/Qualifiers
source                 1..224
                       mol_type = protein
                       organism = Rattus rattus
SEQUENCE: 8
AGTPPGKAFN LTWISTDFKT ILEWQPKPTN YTYTVQISDR SRNWKYKCTG TTDTECDLTD  60
EIVKDVNWTY EARVLSVPWR NSTHGKETLF GTHGEEPPFT NARKFLPYRD TKIGQPVIQK  120
YEQGGTKLKV TVKDSFTLVR KNGTFLTLRQ VFGNDLGYIL TYRKDSSTGR KTNTTHTNEF  180
LIDVEKGVSY CFFAQAVIFS RKTNHKSPES ITKCTEQWKS VLGE                  224

SEQ ID NO: 9           moltype = AA  length = 219
FEATURE                Location/Qualifiers
source                 1..219
                       mol_type = protein
                       organism = Homo sapiens
SEQUENCE: 9
SGTTNTVAAY NLTWKSTNFA TALEWEPKPV NQVYTVQIST KSGDWKSKCF YTTDTECALT  60
DEIVKDVKQT YLARVFSYPA GNVESTGSAG EPLYENSPEF TPYLETNLGQ PTIQSFEQVG  120
TKVNVTVEDE RTLVARNNTA LSLRDVFGKD LIYTLYYWKS SSSGKKTAKT NTNEFLIDVD  180
KGENYCFSVQ AVIPSRTVNR KSTDSPVECM GQEKGEFRE                        219

SEQ ID NO: 10          moltype = AA  length = 219
FEATURE                Location/Qualifiers
source                 1..219
                       mol_type = protein
                       organism = Homo sapiens
SEQUENCE: 10
SGTTNTVAAY NLTWKSTNFA TALEWEPKPV NQVYTVQIST KSGDAKSKCF YTTDTECALT  60
DEIVKDVKQT YLARVFSYPA GNVESTGSAG EPLAENSPEF TPYLETNLGQ PTIQSFEQVG  120
TKVNVTVEDE RTLVARNNTA LSLRDVFGKD LIYTLYYWKS SSSGKKTAKT NTNEFLIDVD  180
KGENYCFSVQ AVIPSRTVNR KSTDSPVECM GQEKGEFRE                        219

SEQ ID NO: 11          moltype = AA  length = 15
FEATURE                Location/Qualifiers
source                 1..15
                       mol_type = protein
                       organism = Synthetic construct
SEQUENCE: 11
GGGGSGGGGS GGGGS                                                  15

SEQ ID NO: 12          moltype = DNA  length = 45
FEATURE                Location/Qualifiers
source                 1..45
                       mol_type = other DNA
                       organism = Synthetic construct
SEQUENCE: 12
ggcggtggag gatccggagg aggtggctcc ggcggcggag gatct                 45

SEQ ID NO: 13          moltype = AA  length = 8
FEATURE                Location/Qualifiers
source                 1..8
                       mol_type = protein
                       organism = Synthetic construct
SEQUENCE: 13
GGGSGGGS                                                          8

SEQ ID NO: 14          moltype = AA  length = 306
FEATURE                Location/Qualifiers
source                 1..306
                       mol_type = protein
                       organism = Homo sapiens
SEQUENCE: 14
```

```
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                             306

SEQ ID NO: 15           moltype = DNA  length = 918
FEATURE                 Location/Qualifiers
source                  1..918
                        mol_type = genomic DNA
                        organism = Homo sapiens
SEQUENCE: 15
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agaccttttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacacccc acagctactt ctctttaacc ttttgtgtgc aagttcaagg taaaagcaag  780
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttcc                                                918

SEQ ID NO: 16           moltype = AA  length = 197
FEATURE                 Location/Qualifiers
source                  1..197
                        mol_type = protein
                        organism = Homo sapiens
SEQUENCE: 16
RNLPVATPDP GMFPCLHHSQ NLLRAVSNML QKARQTLEFY PCTSEEIDHE DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNAS                                                 197

SEQ ID NO: 17           moltype = DNA  length = 591
FEATURE                 Location/Qualifiers
source                  1..591
                        mol_type = genomic DNA
                        organism = Homo sapiens
SEQUENCE: 17
cgtaacctcc ccgtggctac ccccgatccc ggaatgttcc cttgtttaca ccacagccag  60
aatttactga gggccgtgag caacatgctg cagaaagcta ggcagacttt agaattttac  120
ccttgcacca gcgaggagat cgaccatgaa gatatcacca aggacaagac atccaccgtg  180
gaggcttgtt tacctctgga gctgacaaag aacgagtctt gtctcaactc tcgtgaaacc  240
agcttcatca caaatggctc ttgtttagct tcccggaaga cctcctttat gatggcttta  300
tgcctcagct ccatctacga ggatttaaag atgtaccaag tggagttcaa gaccatgaac  360
gccaagctgc tcatggaccc taaacggcag atctttttag accagaacat gctggctgtg  420
attgatgagc tgatgcaagc tttaaacttc aactccgaga ccgtccctca gaagtcctcc  480
ctcgaggagc ccgattttta caagacaaag atcaaactgt gcattttact ccacgccttt  540
aggatccggg ccgtgaccat tgaccgggtc atgagctatt taaacgccag c           591

SEQ ID NO: 18           moltype = AA  length = 518
FEATURE                 Location/Qualifiers
source                  1..518
                        mol_type = protein
                        organism = Homo sapiens
SEQUENCE: 18
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNAS                          518

SEQ ID NO: 19           moltype = DNA  length = 1554
FEATURE                 Location/Qualifiers
source                  1..1554
                        mol_type = genomic DNA
                        organism = Homo sapiens
```

SEQUENCE: 19
atttgggaac tgaagaagga cgtctacgtg gtcgaactgg actggtatcc cgatgctccc 60
ggcgaaatgg tggtgctcac ttgtgacacc cccgaagaag acggcatcac ttggaccctc 120
gatcagagca gcgaggtgct gggctccgga aagaccctca caatccaagt taaggagttc 180
ggagacgctg gccaatacac atgccacaag ggaggcgagg tgctcagcca ttccttatta 240
ttattacaca agaaggaaga cggaatctgg tccaccgaca ttttaaaaga tcagaaggag 300
cccaagaata agaccttttt aaggtgtgag gccaaaaact acagcggtcg tttcacttgt 360
tggtggctga ccaccatttc caccgattta accttctccg tgaaaagcag ccggggaagc 420
tccgaccctc aaggtgtgac atgtggagcc gctaccctca gcgctgagag ggttcgtggc 480
gataacaagg aatacgagta cagcgtggag tgccaagaag atagcgcttg tcccgctgcc 540
gaagaatctt tacccattga ggtgatggtg gacgccgtgc acaaactcaa gtacgagaac 600
tacacctcct ccttctttat ccgggacatc attaagcccg atcctcctaa gaatttacag 660
ctgaagcctc tcaaaaatag ccggcaagtt gaggtctctt gggaatatcc cgacacttgg 720
agcacacccc acagctactt ctctttaacc ttttgtgtgc aagttcaagg taaaagcaag 780
cgggagaaga aagaccgggt gtttaccgac aaaaccagcg ccaccgtcat ctgtcggaag 840
aacgcctcca tcagcgtgag ggctcaagat cgttattact ccagcagctg gtccgagtgg 900
gccagcgtgc cttgttccgg cggtggagga tccggaggag gtggctccgg cggcggagga 960
tctcgtaacc tccccgtggc tacccccgat cccggaatgt tcccttgttt acaccacagc 1020
cagaatttac tgagggccgt gagcaacatg ctgcagaaag ctaggcagac tttagaattt 1080
tacccttgca ccagcgagga gatcgaccat gaagatatca ccaaggacaa gacatccacc 1140
gtggaggctt gtttacctct ggagctgaca aagaacgagt cttgtctcaa ctctcgtgaa 1200
accagcttca tcacaaatgg ctcttgttta gcttcccgga agacctcctt tatgatggct 1260
ttatgcctca gctccatcta cgaggattta aagatgtacc aagtggagtt caagaccatg 1320
aacgccaagc tgctcatgga ccctaaacgg cagatctttt tagaccagaa catgctggct 1380
gtgattgatg agctgatgca agctttaaac ttcaactccg agaccgtccc tcagaagtcc 1440
tccctcgagg agcccgattt ttacaagaca aagatcaaac tgtgcatttt actccacgcc 1500
tttaggatcc gggccgtgac cattgaccgg gtcatgagct atttaaacgc cagc 1554

SEQ ID NO: 20 moltype = AA length = 157
FEATURE Location/Qualifiers
source 1..157
mol_type = protein
organism = Homo sapiens
SEQUENCE: 20
YFGKLESKLS VIRNLNDQVL FIDQGNRPLF EDMTDSDCRD NAPRTIFIIS MYKDSQPRGM 60
AVTISVKCEK ISTLSCENKI ISFKEMNPPD NIKDTKSDII FFQRSVPGHD NKMQFESSSY 120
EGYFLACEKE RDLFKLILKK EDELGDRSIM FTVQNED 157

SEQ ID NO: 21 moltype = DNA length = 471
FEATURE Location/Qualifiers
source 1..471
mol_type = genomic DNA
organism = Homo sapiens
SEQUENCE: 21
tacttcggca aactggaatc caagctgagc gtgatccgga atttaaacga ccaagttctg 60
tttatcgatc aaggtaaccg gcctctgttc gaggacatga ccgactccga ttgccgggac 120
aatgcccccc ggaccatctt cattatctcc atgtacaagg acagccagcc ccggggcatg 180
gctgtgacaa ttagcgtgaa gtgtgagaaa atcagcactt tatcttgtga gaacaagatc 240
atctccttta aggaaatgaa cccccccgat aacatcaagg acaccaagtc cgatatcatc 300
ttcttccagc ggtccgtgcc cggtcacgat aacaagatgc agttcgaatc ctcctcctac 360
gagggctact ttttagcttg tgaaaaggag agggatttat tcaagctgat cctcaagaag 420
gaggacgagc tgggcgatcg ttccatcatg ttcaccgtcc aaaacgagga t 471

SEQ ID NO: 22 moltype = AA length = 133
FEATURE Location/Qualifiers
source 1..133
mol_type = protein
organism = Homo sapiens
SEQUENCE: 22
QGQDRHMIRM RQLIDIVDQL KNYVNDLVPE FLPAPEDVET NCEWSAFSCF QKAQLKSANT 60
GNNERIINVS IKKLKRKPPS TNAGRRQKHR LTCPSCDSYE KKPPKEFLER FKSLLQKMIH 120
QHLSSRTHGS EDS 133

SEQ ID NO: 23 moltype = AA length = 152
FEATURE Location/Qualifiers
source 1..152
mol_type = protein
organism = Homo sapiens
SEQUENCE: 23
DCDIEGKDGK QYESVLMVSI DQLLDSMKEI GSNCLNNEFN FFKRHICDAN KEGMFLFRAA 60
RKLRQFLKMN STGDFDLHLL KVSEGTTILL NCTGQVKGRK PAALGEAQPT KSLEENKSLK 120
EQKKLNDLCF LKRLLQEIKT CWNKILMGTK EH 152

SEQ ID NO: 24 moltype = AA length = 65
FEATURE Location/Qualifiers
source 1..65
mol_type = protein
organism = Homo sapiens
SEQUENCE: 24

```
ITCPPPMSVE HADIWVKSYS LYSRERYICN SGFKRKAGTS SLTECVLNKA TNVAHWTTPS  60
LKCIR                                                             65

SEQ ID NO: 25          moltype = DNA  length = 195
FEATURE                Location/Qualifiers
source                 1..195
                       mol_type = genomic DNA
                       organism = Homo sapiens
SEQUENCE: 25
attacatgcc cccctcccat gagcgtggag cacgccgaca tctgggtgaa gagctatagc  60
ctctacagcc gggagaggta tatctgtaac agcggcttca agaggaaggc cggcaccagc  120
agcctcaccg agtgcgtgct gaataaggct accaacgtgg ctcactggac aacaccctct  180
ttaaagtgca tccgg                                                  195

SEQ ID NO: 26          moltype = AA  length = 114
FEATURE                Location/Qualifiers
source                 1..114
                       mol_type = protein
                       organism = Homo sapiens
SEQUENCE: 26
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 27          moltype = DNA  length = 342
FEATURE                Location/Qualifiers
source                 1..342
                       mol_type = genomic DNA
                       organism = Homo sapiens
SEQUENCE: 27
aactgggtga acgtcatcag cgatttaaag aagatcgaag atttaattca gtccatgcat  60
atcgacgcca ctttatacac agaatccgac gtgcacccct cttgtaaggt gaccgccatg  120
aaatgttttt tactggagct gcaagttatc tctttagaga gcggagacgc tagcatccac  180
gacaccgtgg agaatttaat cattttagcc aataactctt tatccagcaa cggcaacgtg  240
acagagtccg gctgcaagga gtgcgaagag ctggaggaga agaacatcaa ggagtttctg  300
caatcctttg tgcacattgt ccagatgttc atcaatacct cc                    342

SEQ ID NO: 28          moltype = AA  length = 18
FEATURE                Location/Qualifiers
source                 1..18
                       mol_type = protein
                       organism = Homo sapiens
SEQUENCE: 28
MKWVTFISLL FLFSSAYS                                                18

SEQ ID NO: 29          moltype = DNA  length = 54
FEATURE                Location/Qualifiers
source                 1..54
                       mol_type = other DNA
                       organism = Synthetic construct
SEQUENCE: 29
atgaaatggg tgacctttat ttctttactg ttcctcttta gcagcgccta ctcc        54

SEQ ID NO: 30          moltype = DNA  length = 54
FEATURE                Location/Qualifiers
source                 1..54
                       mol_type = other DNA
                       organism = Synthetic construct
SEQUENCE: 30
atgaagtggg tcacatttat ctctttactg ttcctcttct ccagcgccta cagc        54

SEQ ID NO: 31          moltype = DNA  length = 54
FEATURE                Location/Qualifiers
source                 1..54
                       mol_type = other DNA
                       organism = Synthetic construct
SEQUENCE: 31
atgaaatggg tgacctttat ttctttactg ttcctcttta gcagcgccta ctcc        54

SEQ ID NO: 32          moltype = AA  length = 16
FEATURE                Location/Qualifiers
source                 1..16
                       mol_type = protein
                       organism = Homo sapiens
SEQUENCE: 32
MKCLLYLAFL FLGVNC                                                  16

SEQ ID NO: 33          moltype = AA  length = 58
FEATURE                Location/Qualifiers
source                 1..58
```

```
                         mol_type = protein
                         organism = Homo sapiens
SEQUENCE: 33
MGQIVTMFEA LPHIIDEVIN IVIIVLIIIT SIKAVYNFAT CGILALVSFL FLAGRSCG    58

SEQ ID NO: 34            moltype = AA  length = 97
FEATURE                  Location/Qualifiers
source                   1..97
                         mol_type = protein
                         organism = Homo sapiens
SEQUENCE: 34
MPNHQSGSPT GSSDLLLSGK KQRPHLALRR KRRREMRKIN RKVRRMNLAP IKEKTAWQHL  60
QALISEAEEV LKTSQTPQNS LTLFLALLSV LGPPVTG                           97

SEQ ID NO: 35            moltype = AA  length = 30
FEATURE                  Location/Qualifiers
source                   1..30
                         mol_type = protein
                         organism = Homo sapiens
SEQUENCE: 35
MDSKGSSQKG SRLLLLLVVS NLLLCQGVVS                                   30

SEQ ID NO: 36            moltype = AA  length = 58
FEATURE                  Location/Qualifiers
source                   1..58
                         mol_type = protein
                         organism = Homo sapiens
SEQUENCE: 36
MGQIVTMFEA LPHIIDEVIN IVIIVLIIIT SIKAVYNFAT CGILALVSFL FLAGRSCG    58

SEQ ID NO: 37            moltype = AA  length = 97
FEATURE                  Location/Qualifiers
source                   1..97
                         mol_type = protein
                         organism = Homo sapiens
SEQUENCE: 37
MPNHQSGSPT GSSDLLLSGK KQRPHLALRR KRRREMRKIN RKVRRMNLAP IKEKTAWQHL  60
QALISEAEEV LKTSQTPQNS LTLFLALLSV LGPPVTG                           97

SEQ ID NO: 38            moltype = AA  length = 30
FEATURE                  Location/Qualifiers
source                   1..30
                         mol_type = protein
                         organism = Homo sapiens
SEQUENCE: 38
MDSKGSSQKG SRLLLLLVVS NLLLCQGVVS                                   30

SEQ ID NO: 39            moltype = AA  length = 5
FEATURE                  Location/Qualifiers
source                   1..5
                         mol_type = protein
                         organism = Synthetic construct
SEQUENCE: 39
HHHHH                                                              5

SEQ ID NO: 40            moltype = AA  length = 6
FEATURE                  Location/Qualifiers
source                   1..6
                         mol_type = protein
                         organism = Synthetic construct
SEQUENCE: 40
HHHHHH                                                             6

SEQ ID NO: 41            moltype = AA  length = 7
FEATURE                  Location/Qualifiers
source                   1..7
                         mol_type = protein
                         organism = Synthetic construct
SEQUENCE: 41
HHHHHHH                                                            7

SEQ ID NO: 42            moltype = AA  length = 8
FEATURE                  Location/Qualifiers
source                   1..8
                         mol_type = protein
                         organism = Synthetic construct
SEQUENCE: 42
HHHHHHHH                                                           8
```

```
SEQ ID NO: 43           moltype = AA  length = 9
FEATURE                 Location/Qualifiers
source                  1..9
                        mol_type = protein
                        organism = Synthetic construct
SEQUENCE: 43
HHHHHHHHH                                                     9

SEQ ID NO: 44           moltype = AA  length = 10
FEATURE                 Location/Qualifiers
source                  1..10
                        mol_type = protein
                        organism = Synthetic construct
SEQUENCE: 44
HHHHHHHHHH                                                    10

SEQ ID NO: 45           moltype = AA  length = 10
FEATURE                 Location/Qualifiers
source                  1..10
                        mol_type = protein
                        organism = Synthetic construct
SEQUENCE: 45
EQKLISEEDL                                                    10

SEQ ID NO: 46           moltype = AA  length = 18
FEATURE                 Location/Qualifiers
source                  1..18
                        mol_type = protein
                        organism = Synthetic construct
SEQUENCE: 46
TKENPRSNQE ESYDDNES                                           18

SEQ ID NO: 47           moltype = AA  length = 15
FEATURE                 Location/Qualifiers
source                  1..15
                        mol_type = protein
                        organism = Synthetic construct
SEQUENCE: 47
KETAAAKFER QHMDS                                              15

SEQ ID NO: 48           moltype = AA  length = 38
FEATURE                 Location/Qualifiers
source                  1..38
                        mol_type = protein
                        organism = Synthetic construct
SEQUENCE: 48
MDEKTTGWRG GHVVEGLAGE LEQLRARLEH HPQGQREP                     38

SEQ ID NO: 49           moltype = AA  length = 13
FEATURE                 Location/Qualifiers
source                  1..13
                        mol_type = protein
                        organism = Synthetic construct
SEQUENCE: 49
SLAELLNAGL GGS                                                13

SEQ ID NO: 50           moltype = AA  length = 8
FEATURE                 Location/Qualifiers
source                  1..8
                        mol_type = protein
                        organism = Synthetic construct
SEQUENCE: 50
TQDPSRVG                                                      8

SEQ ID NO: 51           moltype = AA  length = 12
FEATURE                 Location/Qualifiers
source                  1..12
                        mol_type = protein
                        organism = Synthetic construct
SEQUENCE: 51
PDRVRAVSHW SS                                                 12

SEQ ID NO: 52           moltype = AA  length = 8
FEATURE                 Location/Qualifiers
source                  1..8
                        mol_type = protein
                        organism = Synthetic construct
SEQUENCE: 52
WSHPQFEK                                                      8
```

```
SEQ ID NO: 53           moltype = AA  length = 6
FEATURE                 Location/Qualifiers
source                  1..6
                        mol_type = protein
                        organism = Synthetic construct
SEQUENCE: 53
CCPGCC                                                              6

SEQ ID NO: 54           moltype = AA  length = 10
FEATURE                 Location/Qualifiers
source                  1..10
                        mol_type = protein
                        organism = Synthetic construct
SEQUENCE: 54
EVHTNQDPLD                                                          10

SEQ ID NO: 55           moltype = AA  length = 14
FEATURE                 Location/Qualifiers
source                  1..14
                        mol_type = protein
                        organism = Synthetic construct
SEQUENCE: 55
GKPIPNPLLG LDST                                                     14

SEQ ID NO: 56           moltype = AA  length = 11
FEATURE                 Location/Qualifiers
source                  1..11
                        mol_type = protein
                        organism = Synthetic construct
SEQUENCE: 56
YTDIEMNRLG K                                                        11

SEQ ID NO: 57           moltype = AA  length = 8
FEATURE                 Location/Qualifiers
source                  1..8
                        mol_type = protein
                        organism = Synthetic construct
SEQUENCE: 57
DLYDDDDK                                                            8

SEQ ID NO: 58           moltype = AA  length = 10
FEATURE                 Location/Qualifiers
source                  1..10
                        mol_type = protein
                        organism = Synthetic construct
SEQUENCE: 58
EQKLISEEDL                                                          10

SEQ ID NO: 59           moltype = DNA  length = 1803
FEATURE                 Location/Qualifiers
source                  1..1803
                        mol_type = other DNA
                        organism = Synthetic construct
SEQUENCE: 59
atgaaatggg tgacctttat ttctttactg ttcctcttta gcagcgccta ctccatttgg  60
gaactgaaga aggacgtcta cgtggtcgaa ctggactggt atcccgatgc tcccggcgaa  120
atggtggtgc tcacttgtga cacccccgaa gaagacggca tcacttggac cctcgatcag  180
agcagcgagg tgctgggctc cggaaagacc ctcacaatcc aagttaagga gttcggagac  240
gctggccaat acacatgcca caagggaggc gaggtgctca gccattcctt attattatta  300
cacaagaagg aagacggaat ctggtccacc gacattttaa aagatcagaa ggagcccaag  360
aataagacct ttttaaggtg tgaggccaaa aactacagcg gtcgtttcac ttgttggtgg  420
ctgaccacca tttccaccga tttaaccttc tccgtgaaaa gcagccgggg aagctccgac  480
cctcaaggtg tgacatgtgg agccgctacc ctcagcgctg agagggttcg tggcgataac  540
aaggaatacg agtacagcgt ggagtgccaa gaagatagcg cttgtcccgc tgccgaagaa  600
tctttaccca ttgaggtgat ggtggacgcc gtgcacaaac tcaagtacga gaactacacc  660
tcctccttct ttatccggga catcattaag cccgatcctc ctaagaattt acagctgaag  720
cctctcaaaa atagccggca agttgaggtc tcttgggaat atcccgacac ttggagcaca  780
ccccacagct acttctcttt aaccttttgt gtgcaagttc aaggtaaaag caagcgggag  840
aagaaagacc gggtgtttac cgacaaaacc agcgccaccg tcatctgtcg gaagaacgcc  900
tccatcagcg tgagggctca agatcgttat tactccagca gctggtccga gtgggccagc  960
gtgccttgtt ccggcggtgg aggatccgga ggaggtggct ccggcggcgg aggatctcgt  1020
aacctccccg tggctacccc cgatcccgga atgttccctt gtttacacca cagccagaat  1080
ttactgaggg ccgtgagcaa catgctgcag aaagctaggc agactttaga attttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
```

```
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcat tacatgcccc  1620
cctcccatga gcgtggagca cgccgacatc tgggtgaaga gctatagcct ctacagccgg  1680
gagaggtata tctgtaacag cggcttcaag aggaaggccg gcaccagcag cctcaccgag  1740
tgcgtgctga ataaggctac caacgtggct cactggacaa caccctcttt aaagtgcatc  1800
cgg                                                                1803

SEQ ID NO: 60          moltype = DNA  length = 1524
FEATURE                Location/Qualifiers
source                 1..1524
                       mol_type = other DNA
                       organism = Synthetic construct
SEQUENCE: 60
atgaagtggg tcacatttat ctctttactg ttcctcttct ccagcgccta cagctacttc  60
ggcaaactgg aatccaagct gagcgtgatc cggaatttaa acgaccaagt tctgtttatc  120
gatcaaggta accggcctct gttcgaggac atgaccgact ccgattgccg ggacaatgcc  180
ccccggacca tcttcattat ctccatgtac aaggacagcc agccccgggg catggctgtg  240
acaattagcg tgaagtgtga gaaaatcagc actttatctt gtgagaacaa gatcatctcc  300
tttaaggaaa tgaacccccc cgataacatc aaggacacca agtccgatat catcttcttc  360
cagcggtccg tgcccggtca cgataacaag atgcagttcg aatcctcctc ctacgagggc  420
tactttttag cttgtgaaaa ggagagggat ttattcaagc tgatcctcaa gaaggaggac  480
gagctgggcg atcgttccat catgttcacc gtccaaaacg aggatagcgg cacaaccaac  540
acagtcgctg cctataacct cacttggaag agcaccaact tcaaaaccat cctcgaatgg  600
gaacccaaac ccgttaacca agtttacacc gtgcagatca gcaccaagtc cggcgactgg  660
aagtccaaat gtttctatac caccgacacc gagtgcgatc tcaccgatga gatcgtgaaa  720
gatgtgaaac agacctacct cgcccgggtg tttagctacc ccgccggcaa tgtggagagc  780
actggttccg ctggcgagcc tttatacgag aacagccccg aatttacccc ttacctcgag  840
accaatttag gacagcccac catccaaagc tttgagcaag ttggcacaaa ggtgaatgtg  900
acagtggagg acgagcggac tttagtgcgg cggaacaaca cctttctcag cctccgggat  960
gtgttcggca aagatttaat ctacacactg tattactgga agtcctcttc ctccggcaag  1020
aagacagcta aaaccaacac aaacgagttt ttaatcgacg tggataaagg cgaaaactac  1080
tgtttcagcg tgcaagctgt gatcccctcc cggaccgtga ataggaaaag caccgatagc  1140
cccgttgagt gcatgggcca agaaaagggc gagttccggg agaactgggt gaacgtcatc  1200
agcgatttaa agaagatcga agatttaatt cagtccatgc atatcgacgc cactttatac  1260
acagaatccg acgtgcaccc ctcttgtaag gtgaccgcca tgaaatgttt tttactggag  1320
ctgcaagtta tctctttaga gagcggagac gctagcatcc acgacaccgt ggagaattta  1380
atcattttag ccaataactc tttatccagc aacggcaacg tgacagagtc cggctgcaag  1440
gagtgcgaag agctggagga gaagaacatc aaggagtttc tgcaatcctt tgtgcacatt  1500
gtccagatgt tcatcaatac ctcc                                         1524

SEQ ID NO: 61          moltype = AA  length = 601
FEATURE                Location/Qualifiers
source                 1..601
                       mol_type = protein
                       organism = Synthetic construct
SEQUENCE: 61
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASITCP  540
PPMSVEHADI WVKSYSLYSR ERYICNSGFK RKAGTSSLTE CVLNKATNVA HWTTPSLKCI  600
R                                                                  601

SEQ ID NO: 62          moltype = AA  length = 508
FEATURE                Location/Qualifiers
source                 1..508
                       mol_type = protein
                       organism = Synthetic construct
SEQUENCE: 62
MKWVTFISLL FLFSSAYSYF GKLESKLSVI RNLNDQVLFI DQGNRPLFED MTDSDCRDNA  60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDSGTTN  180
TVAAYNLTWK STNFKTILEW EPKPVNQVYT VQISTKSGDW KSKCFYTTDT ECDLTDEIVK  240
DVKQTYLARV FSYPAGNVES TGSAGEPLYE NSPEFTPYLE TNLGQPTIQS FEQVGTKVNV  300
TVEDERTLVR RNNTFLSLRD VFGKDLIYTL YYWKSSSSGK KTAKTNTNEF LIDVDKGENY  360
CFSVQAVIPS RTVNRKSTDS PVECMGQEKG EFRENWVNVI SDLKKIEDLI QSMHIDATLY  420
TESDVHPSCK VTAMKCFLLE LQVISLESGD ASIHDTVENL IILANNSLSS NGNVTESGCK  480
ECEELEEKNI KEFLQSFVHI VQMFINTS                                     508

SEQ ID NO: 63          moltype = AA  length = 490
FEATURE                Location/Qualifiers
source                 1..490
                       mol_type = protein
```

```
                         organism = Synthetic construct
SEQUENCE: 63
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNEDSGT TNTVAAYNLT WKSTNFKTIL  180
EWEPKPVNQV YTVQISTKSG DWKSKCFYTT DTECDLTDEI VKDVKQTYLA RVFSYPAGNV  240
ESTGSAGEPL YENSPEFTPY LETNLGQPTI QSFEQVGTKV NVTVEDERTL VRRNNTFLSL  300
RDVFGKDLIY TLYYWKSSSS GKKTAKTNTN EFLIDVDKGE NYCFSVQAVI PSRTVNRKST  360
DSPVECMGQE KGEFRENWVN VISDLKKIED LIQSMHIDAT LYTESDVHPS CKVTAMKCFL  420
LELQVISLES GDASIHDTVE NLIILANNSL SSNGNVTESG CKECEELEEK NIKEFLQSFV  480
HIVQMFINTS                                                        490

SEQ ID NO: 64            moltype = AA  length = 508
FEATURE                  Location/Qualifiers
source                   1..508
                         mol_type = protein
                         organism = Synthetic construct
SEQUENCE: 64
MKWVTFISLL FLFSSAYSYF GKLESKLSVI RNLNDQVLFI DQGNRPLFED MTDSDCRDNA  60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDSGTTN  180
TVAAYNLTWK STNFKTILEW EPKPVNQVYT VQISTKSGDW KSKCFYTTDT ECDLTDEIVK  240
DVKQTYLARV FSYPAGNVES TGSAGEPLYE NSPEFTPYLE TNLGQPTIQS FEQVGTKVNV  300
TVEDERTLVR RNNTFLSLRD VFGKDLIYTL YYWKSSSSGK KTAKTNTNEF LIDVDKGENY  360
CFSVQAVIPS RTVNRKSTDS PVECMGQEKG EFRENWVNVI SDLKKIEDLI QSMHIDATLY  420
TESDVHPSCK VTAMKCFLLE LQVISLESGD ASIHDTVENL IILANNSLSS NGNVTESGCK  480
ECEELEEKNI KEFLQSFVHI VQMFINTS                                    508

SEQ ID NO: 65            moltype = AA  length = 583
FEATURE                  Location/Qualifiers
source                   1..583
                         mol_type = protein
                         organism = Synthetic construct
SEQUENCE: 65
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASIT CPPPMSVEHA DIWVKSYSLY  540
SRERYICNSG FKRKAGTSSL TECVLNKATN VAHWTTPSLK CIR                   583

SEQ ID NO: 66            moltype = AA  length = 601
FEATURE                  Location/Qualifiers
source                   1..601
                         mol_type = protein
                         organism = Synthetic construct
SEQUENCE: 66
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASITCP  540
PPMSVEHADI WVKSYSLYSR ERYICNSGFK RKAGTSSLTE CVLNKATNVA HWTTPSLKCI  600
R                                                                 601

SEQ ID NO: 67            moltype = AA  length = 485
FEATURE                  Location/Qualifiers
source                   1..485
                         mol_type = protein
                         organism = Synthetic construct
SEQUENCE: 67
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHSGTTNTVA AYNLTWKSTN FKTILEWEPK  180
PVNQVYTVQI STKSGDWKSK CFYTTDTECD LTDEIVKDVK QTYLARVFSY PAGNVESTGS  240
AGEPLYENSP EFTPYLETNL GQPTIQSFEQ VGTKVNVTVE DERTLVRRNN TFLSLRDVFG  300
KDLIYTLYYW KSSSSGKKTA KTNTNEFLID VDKGENYCFS VQAVIPSRTV NRKSTDSPVE  360
CMGQEKGEFR ENWVNVISDL KKIEDLIQSM HIDATLYTES DVHPSCKVTA MKCFLLELQV  420
ISLESGDASI HDTVENLIIL ANNSLSSNGN VTESGCKECE ELEEKNIKEF LQSFVHIVQM  480
FINTS                                                             485
```

```
SEQ ID NO: 68          moltype = AA  length = 503
FEATURE                Location/Qualifiers
source                 1..503
                       mol_type = protein
                       organism = Synthetic construct
SEQUENCE: 68
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH SGTTNTVAAY  180
NLTWKSTNFK TILEWEPKPV NQVYTVQIST KSGDWKSKCF YTTDTECDLT DEIVKDVKQT  240
YLARVFSYPA GNVESTGSAG EPLYENSPEF TPYLETNLGQ PTIQSFEQVG TKVNVTVEDE  300
RTLVRRNNTF LSLRDVFGKD LIYTLYYWKS SSSGKKTAKT NTNEFLIDVD KGENYCFSVQ  360
AVIPSRTVNR KSTDSPVECM GQEKGEFREN WVNVISDLKK IEDLIQSMHI DATLYTESDV  420
HPSCKVTAMK CFLLELQVIS LESGDASIHD TVENLIILAN NSLSSNGNVT ESGCKECEEL  480
EEKNIKEFLQ SFVHIVQMFI NTS                                         503

SEQ ID NO: 69          moltype = AA  length = 198
FEATURE                Location/Qualifiers
source                 1..198
                       mol_type = protein
                       organism = Synthetic construct
SEQUENCE: 69
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIR                                               198

SEQ ID NO: 70          moltype = AA  length = 216
FEATURE                Location/Qualifiers
source                 1..216
                       mol_type = protein
                       organism = Synthetic construct
SEQUENCE: 70
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIR                            216

SEQ ID NO: 71          moltype = AA  length = 466
FEATURE                Location/Qualifiers
source                 1..466
                       mol_type = protein
                       organism = Synthetic construct
SEQUENCE: 71
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSSGTTNTV AAYNLTWKST NFKTILEWEP KPVNQVYTVQ ISTKSGDWKS  180
KCFYTTDTEC DLTDEIVKDV KQTYLARVFS YPAGNVESTG SAGEPLYENS PEFTPYLETN  240
LGQPTIQSFE QVGTKVNVTV EDERTLVRRN NTFLSLRDVF GKDLIYTLYY WKSSSSGKKT  300
AKTNTNEFLI DVDKGENYCF SVQAVIPSRT VNRKSTDSPV ECMGQEKGEF RENWVNVISD  360
LKKIEDLIQS MHIDATLYTE SDVHPSCKVT AMKCFLLELQ VISLESGDAS IHDTVENLII  420
LANNSLSSNG NVTESGCKEC EELEEKNIKE FLQSFVHIVQ MFINTS                466

SEQ ID NO: 72          moltype = AA  length = 483
FEATURE                Location/Qualifiers
source                 1..483
                       mol_type = protein
                       organism = Synthetic construct
SEQUENCE: 72
MGVKVLFALI CIAVAEAQGQ DRHMIRMRQL IDIVDQLKNY VNDLVPEFLP APEDVETNCE  60
WSAFSCFQKA QLKSANTGNN ERIINVSIKK LKRKPPSTNA GRRQKHRLTC PSCDSYEKKP  120
PKEFLERFKS LLQKMIHQHL SSRTHGSEDS SGTTNTVAAY NLTWKSTNFK TILEWEPKPV  180
NQVYTVQIST KSGDWKSKCF YTTDTECDLT DEIVKDVKQT YLARVFSYPA GNVESTGSAG  240
EPLYENSPEF TPYLETNLGQ PTIQSFEQVG TKVNVTVEDE RTLVRRNNTF LSLRDVFGKD  300
LIYTLYYWKS SSSGKKTAKT NTNEFLIDVD KGENYCFSVQ AVIPSRTVNR KSTDSPVECM  360
GQEKGEFREN WVNVISDLKK IEDLIQSMHI DATLYTESDV HPSCKVTAMK CFLLELQVIS  420
LESGDASIHD TVENLIILAN NSLSSNGNVT ESGCKECEEL EEKNIKEFLQ SFVHIVQMFI  480
NTS                                                               483

SEQ ID NO: 73          moltype = AA  length = 217
FEATURE                Location/Qualifiers
source                 1..217
                       mol_type = protein
                       organism = Synthetic construct
SEQUENCE: 73
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHITCPPPMS VEHADIWVKS YSLYSRERYI  180
CNSGFKRKAG TSSLTECVLN KATNVAHWTT PSLKCIR                           217
```

```
SEQ ID NO: 74           moltype = AA  length = 234
FEATURE                 Location/Qualifiers
source                  1..234
                        mol_type = protein
                        organism = Synthetic construct
SEQUENCE: 74
MGVKVLFALI CIAVAEADCD IEGKDGKQYE SVLMVSIDQL LDSMKEIGSN CLNNEFNFFK  60
RHICDANKEG MFLFRAARKL RQFLKMNSTG DFDLHLLKVS EGTTILLNCT GQVKGRKPAA  120
LGEAQPTKSL EENKSLKEQK KLNDLCFLKR LLQEIKTCWN KILMGTKEHI TCPPPMSVEH  180
ADIWVKSYSL YSRERYICNS GFKRKAGTSS LTECVLNKAT NVAHWTTPSL KCIR        234

SEQ ID NO: 75           moltype = AA  length = 15
FEATURE                 Location/Qualifiers
source                  1..15
                        mol_type = protein
                        organism = Synthetic construct
SEQUENCE: 75
GLNDIFEAQK IEWHE                                                   15

SEQ ID NO: 76           moltype = AA  length = 26
FEATURE                 Location/Qualifiers
source                  1..26
                        mol_type = protein
                        organism = Synthetic construct
SEQUENCE: 76
KRRWKKNFIA VSAANRFKKI SSSGAL                                       26

SEQ ID NO: 77           moltype = AA  length = 6
FEATURE                 Location/Qualifiers
source                  1..6
                        mol_type = protein
                        organism = Synthetic construct
SEQUENCE: 77
EEEEEE                                                             6

SEQ ID NO: 78           moltype = AA  length = 13
FEATURE                 Location/Qualifiers
source                  1..13
                        mol_type = protein
                        organism = Synthetic construct
SEQUENCE: 78
GAPVPYPDPL EPR                                                     13

SEQ ID NO: 79           moltype = AA  length = 8
FEATURE                 Location/Qualifiers
source                  1..8
                        mol_type = protein
                        organism = Synthetic construct
SEQUENCE: 79
DYKDDDDK                                                           8

SEQ ID NO: 80           moltype = AA  length = 9
FEATURE                 Location/Qualifiers
source                  1..9
                        mol_type = protein
                        organism = Synthetic construct
SEQUENCE: 80
YPYDVPDYA                                                          9

SEQ ID NO: 81           moltype = DNA  length = 17
FEATURE                 Location/Qualifiers
source                  1..17
                        mol_type = other DNA
                        organism = Synthetic construct
SEQUENCE: 81
agaaaagggg ggattta                                                 17

SEQ ID NO: 82           moltype = DNA  length = 22
FEATURE                 Location/Qualifiers
source                  1..22
                        mol_type = other DNA
                        organism = Synthetic construct
SEQUENCE: 82
taacactcac aaccaaatta tc                                           22

SEQ ID NO: 83           moltype = DNA  length = 16
FEATURE                 Location/Qualifiers
source                  1..16
```

-continued

```
                          mol_type = other DNA
                          organism = Synthetic construct
SEQUENCE: 83
ggggatttag aaaaat                                                     16

SEQ ID NO: 84             moltype = DNA  length = 19
FEATURE                   Location/Qualifiers
source                    1..19
                          mol_type = other DNA
                          organism = Synthetic construct
SEQUENCE: 84
tgtatgatgt taggagttt                                                  19
```

MULTI-CHAIN CHIMERIC POLYPEPTIDES AND USES THEREOF

CROSS-REFERENCE TO RELATED APPLICATIONS

This application is a continuation of U.S. patent application Ser. No. 16/906,781, filed on Jun. 19, 2020, now U.S. Pat. No. 11,738,052, which claims priority to U.S. Provisional Patent Application Ser. No. 62/864,996, filed on Jun. 21, 2019; the entire contents of which are herein incorporated by reference.

SEQUENCE LISTING

This application contains a Sequence Listing that has been submitted electronically as an XML, file named 47039-0017002_SL_ST26.xml. The XML file, created on Jul. 11, 2023, is 91,445 bytes in size. The material in the XML file is hereby incorporated by reference in its entirety.

TECHNICAL FIELD

The present disclosure relates to the field of biotechnology, and more specifically, to the use of a combination of two multi-chain chimeric polypeptides, each having a linker domain positioned between two target-binding domains.

BACKGROUND

Adoptive immunotherapy or cellular therapy requires the culture of immune cells obtained from a subject in vivo (and optionally genetic manipulation of the immune cells to express a T-cell or a chimeric antigen receptor) before administration back into the subject. A sufficient number of immune cells is necessary in order to provide a therapeutic effect in the subject. In many examples, immune cells obtained from a subject need to be cultured for three or more weeks before a therapeutically effective number of immune cells can be obtained. In addition, many methods of culturing immune cells obtained from a subject in vitro require a layer of feeder cells, which requires subsequent purification or isolation of the immune cells before administration back to the subject.

SUMMARY

The present invention is based on the discovery that a specific two-step method of contacting NK cells results in a significant expansion of NK cells in vitro and the expanded NK cells are highly activated with a long persistence and a high degree of cytotoxicity against diseased cells in a recipient host.

In one aspect, provided herein is a method of promoting the activation and proliferation of a natural killer cell, the method includes: (a) contacting a natural killer cell in a liquid culture medium that includes an effective amount of a first multi-chain chimeric polypeptide for a first period of time under conditions that allow for the differentiation of the natural killer cell; and (b) contacting the natural killer cell in a liquid culture medium that includes an effective amount of (i) a second multi-chain chimeric polypeptide, and (ii) an IgG1 antibody construct, for a second period of time under conditions that allow for the activation and proliferation of the natural killer cell, wherein the first multi-chain chimeric polypeptide includes: a first chimeric polypeptide that includes a first target-binding domain, a soluble tissue factor domain, and a first domain of a pair of affinity domains, and a second chimeric polypeptide that includes a second domain of a pair of affinity domains and a second target-binding domain, wherein the first chimeric polypeptide and the second chimeric polypeptide in the first multi-chain chimeric polypeptide associate through the binding of the first domain and the second domain of the pair of affinity domains in the first multi-chain chimeric polypeptide, and the first target-binding domain and the second target-binding domain in the first multi-chain chimeric polypeptide each independently bind specifically to a receptor of IL-18 or a receptor of IL-12; and wherein the second multi-chain chimeric polypeptide includes: a first chimeric polypeptide that includes a first target-binding domain, a linker domain, a first domain of a pair of affinity domains, and a second chimeric polypeptide that includes a second domain of a pair of affinity domains, and a second target-binding domain, wherein the first chimeric polypeptide and the second chimeric polypeptide in the second multi-chain chimeric polypeptide associate through the binding of the first domain and the second domain of the pair of affinity domains in the second multi-chain chimeric polypeptide; the first target-binding domain and the second target-binding domain in the second multi-chain chimeric polypeptide each independently bind specifically to a receptor for IL-7 or a receptor for IL-21, and the IgG1 antibody construct includes at least one antigen-binding domain that binds specifically to the linker domain.

In some embodiments, the first target-binding domain and the soluble tissue factor domain directly abut each other in the first chimeric polypeptide in the first multi-chain chimeric polypeptide. In some embodiments, the first chimeric polypeptide in the first multi-chain chimeric polypeptide further includes a linker sequence between the first target-binding domain and the soluble tissue factor domain in the first chimeric polypeptide. In some embodiments, the soluble tissue factor domain and the first domain of the pair of affinity domains in the first chimeric polypeptide in the first multi-chain chimeric polypeptide directly abut each other in the first chimeric polypeptide. In some embodiments, the first chimeric polypeptide in the first multi-chain chimeric polypeptide further includes a linker sequence between the soluble tissue factor domain and the first domain of the pair of affinity domains in the first chimeric polypeptide. In some embodiments, the second domain of the pair of affinity domains and the second target-binding domain in the second chimeric polypeptide in the first multi-chain chimeric polypeptide directly abut each other in the second chimeric polypeptide. In some embodiments, the second chimeric polypeptide in the first multi-chain chimeric polypeptide further includes a linker sequence between the second domain of the pair of affinity domains and the second target-binding domain in the second chimeric polypeptide. In some embodiments, the soluble tissue factor domain is a soluble human tissue factor domain. In some embodiments, the soluble human tissue factor domain includes a sequence that is at least 80% identical to SEQ ID NO: 5. In some embodiments, the soluble human tissue factor domain includes a sequence that is at least 90% identical to SEQ ID NO: 5. In some embodiments, the soluble human tissue factor domain includes a sequence that is at least 95% identical to SEQ ID NO: 5. In some embodiments, the soluble human tissue factor domain includes SEQ ID NO: 5. In some embodiments, the soluble human tissue factor domain includes a sequence that is at least 80% identical to SEQ ID NO: 9. In some embodiments, the soluble human tissue factor domain includes a sequence that is at least 90% identical to SEQ ID NO: 9. In some embodiments, the soluble human tissue factor domain includes a sequence that is at least 95% identical to SEQ ID NO: 9. In some embodiments, the soluble human tissue factor domain includes SEQ ID NO: 9. In some embodiments, the soluble human tissue factor domain includes a sequence that is at least 80% identical to SEQ ID NO: 10. In some embodiments, the soluble human tissue factor domain includes a sequence that is at least 90% identical to SEQ ID NO: 10. In some embodiments, the soluble human tissue factor domain includes a sequence that is at least 95% identical to SEQ ID NO: 10. In some embodiments, the soluble human tissue factor domain includes SEQ ID NO: 10. In some embodiments, the soluble human tissue factor domain does not comprise one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the first multi-chain chimeric polypeptide does not stimulate coagulation in a mammal. In some embodiments, the first chimeric polypeptide and/or the second chimeric polypeptide in the first multi-chain chimeric polypeptide further includes a signal sequence at its N-terminal end. In some embodiments, the signal sequence includes SEQ ID NO: 28. In some embodiments, the signal sequence is SEQ ID NO: 28. In some embodiments, the pair of affinity domains in the first multi-chain chimeric polypeptide is a sushi domain from an alpha chain of human IL-15 receptor (IL15Rα) and a soluble IL-15. In some embodiments, the soluble IL-15 has a D8N or D8A amino acid substitution. In some embodiments, the soluble IL-15 includes a sequence that is 80% identical to SEQ ID NO: 26. In some embodiments, the soluble IL-15 includes a sequence that is 90% identical to SEQ ID NO: 26. In some embodiments, the soluble IL-15 includes a sequence that is 95% identical to SEQ ID NO: 26. In some embodiments, the soluble IL-15 includes SEQ ID NO: 26. In some embodiments, the sushi domain of IL15Rα includes a sushi domain from human IL15Rα. In some embodiments, the sushi domain from human IL15Rα includes a sequence that is 80% identical to SEQ ID NO: 24. In some embodiments, the sushi domain from human IL15Rα includes a sequence that is 90% identical to SEQ ID NO: 24. In some embodiments, the sushi domain from human IL15Rα includes a sequence that is 95% identical to SEQ ID NO: 24. In some embodiments, the sushi domain from human IL15Rα includes SEQ ID NO: 24. In some embodiments, the sushi domain from human IL15Rα is a mature full-length IL15Rα.

In some embodiments, the pair of affinity domains in the first multi-chain chimeric polypeptide is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first target-binding domain and the second target-binding domain in the first multi-chain chimeric polypeptide are each independently a soluble IL-15 or a soluble IL-18 In some embodiments, the first target-binding domain in the first multi-chain chimeric polypeptide binds specifically to a receptor for IL-12, and the second target-binding domain in the first multi-chain chimeric polypeptide binds specifically to a receptor for IL-18. In some embodiments, the first target-binding domain in the first multi-chain chimeric polypeptide binds specifically to a receptor for IL-18, and the second target-binding domain in the first multi-chain chimeric polypeptide binds specifically to a receptor for IL-12. In some embodiments, the first target-binding domain in the first multi-chain chimeric polypeptide includes a soluble IL-18. In some embodiments, the soluble IL-18 is a soluble human IL-18. In some embodiments, the soluble human IL-18 includes a sequence at least 80% identical to SEQ ID NO: 20. In some embodiments, the soluble human IL-18 includes a sequence at least 90% identical to SEQ ID NO: 20. In some embodiments, the soluble human IL-18 includes a sequence at least 95% identical to SEQ ID NO: 20. In some embodiments, the soluble human IL-18 includes a sequence of SEQ ID NO: 20. In some embodiments, the second target-binding domain in the first multi-chain chimeric polypeptide includes a soluble IL-12. In some embodiments, the soluble IL-12 is a soluble human IL-12. In some embodiments, the soluble human IL-12 includes a sequence of soluble human IL-12β (p40) and a sequence of soluble human IL-12α (p35). In some embodiments, the soluble human IL-15 further includes a linker sequence between the sequence of soluble IL-12β (p40) and the sequence of soluble human IL-12α (p35). In some embodiments, the linker sequence includes SEQ ID NO: 11. In some embodiments, the sequence of soluble human IL-12β (p40) includes a sequence that is at least 80% identical to SEQ ID NO: 14. In some embodiments, the sequence of soluble human IL-12β (p40) includes a sequence that is at least 90% identical to SEQ ID NO: 14. In some embodiments, the sequence of soluble human IL-12β (p40) includes a sequence that is at least 95% identical to SEQ ID NO: 14. In some embodiments, the sequence of soluble human IL-12β (p40) includes SEQ ID NO: 14. In some embodiments, the sequence of soluble human IL-12α (p35) includes a sequence that is at least 80% identical to SEQ ID NO: 16. In some embodiments, the sequence of soluble human IL-12α (p35) includes a sequence that is at least 90% identical to SEQ ID NO: 16. In some embodiments, the sequence of soluble human IL-12α (p35) includes a sequence that is at least 95% identical to SEQ ID NO: 16. In some embodiments, the sequence of soluble human IL-12α (p35) includes SEQ ID NO: 16. In some embodiments, the first chimeric polypeptide in the first multi-chain chimeric polypeptide includes a sequence that is at least 80% identical to YFGKLESKLSVIRNLNDQVL-FIDQGNRPLFEDMTDSDCRDNAPRTIFIISMYKDSQ PRGMAVTISVKCEKISTLSCENKIISFKEMNPPD-NIKDTKSDIIFFQRSVPGHDNKM QFESSSYEGY-FLACEKERDLFKLILKKEDELGDRSIMFTVQNED-SGTTNTVAAYN LTWKSTNFKTILEWEPKPVNQVYTVQISTKSGDWK-SKCFYTTDTECDLTDEIVKD VKQTYLARVFSYPAG-NVESTGSAGEPLYENSPEFTPYLETNLGQPTIQS-FEQVGT KVNVTVEDERTLVRRNNTFLSLRDVFGKDLIYT-LYYWKSSSSGKKTAKTNTNEF LIDVDKG-ENYCFSVQAVIPSRTVNRKSTDSPVECMGQEKGE-FRENWVNVISDLK KIEDLIQSMHIDATLYTESDVHPSCKVTAMKCFL-LELQVISLESGDASIHDTVENLI ILANNSLSSNG-NVTESGCKECEELEEKNIKEFLQSFVHIVQMFINTS (SEQ ID NO: 63). In some embodiments, the first chimeric polypeptide in the first multi-chain chimeric polypeptide includes a sequence that is at least 90% identical to SEQ ID NO: 63. In some embodiments, the first chimeric polypeptide in the first multi-chain chimeric polypeptide includes a sequence that is at least 95% identical to SEQ ID NO: 63. In some embodiments, the first chimeric polypeptide in the first multi-chain chimeric polypeptide includes SEQ ID NO: 63. In some embodiments, the first chimeric polypeptide in the first multi-chain chimeric polypeptide includes MKWVTFISLLFLFSSAYSYFGKLESKLS-VIRNLNDQVLFIDQGNRPLFEDMTDSD CRDNAPRTI-FIISMYKDSQPRGMAVTISVKCEKISTLSCENKIIS-FKEMNPPDNIKD TKSDIIFFQRSVPGHDNKMQFESSSYEGYFLACEKER-DLFKLILKKEDELGDRSIM FTVQNED-SGTTNTVAAYNLTWK-STNFKTILEWEPKPVNQVYTVQISTKSGDWKS KCFYTTDTECDLTDEIVKDVKQTYLARVFSYPAG-NVESTGSAGEPLYENSPEFTP YLETNLGQPTIQS-FEQVGTKVNVTVEDERTLVRRNNT-FLSLRDVFGKDLIYTLYY WKSSSSGKKTAKTNTNEFLIDVDKG-ENYCFSVQAVIPSRTVNRKSTDSPVECMG QEKGE-FRENWVNVISDLKKIEDLIQSMHIDATLYTESDVHP-SCKVTAMKCFLLEL QVISLESGDASIHDTVENLIILANNSLSSNG-NVTESGCKECEELEEKNIKEFLQSFV HIVQMFINTS (SEQ ID NO: 64). In some embodiments, the second chimeric polypeptide includes a sequence that is at least 80% identical to IWELKKDVYVVELDWYP-DAPGEMVVLTCDTPEEDGITWTLDQSSEV-LGSGKTLT IQVKEFGDAGQYTCHKG-GEVLSHSLLLLHKKEDGIWSTDILKDQKEPKNKTFLR CEAKNYSGRFTCWWLT-TISTDLTFSVKSSRGSSDPQGVTCGAATL-SAERVRGDN KEYEYSVECQEDSACPAAEE-SLPIEVMVDAVHKLKYENYTSSFFIRDIIKPDPPKN LQLKPLKNSRQVEVSWEYPDTW-STPHSYFSLTFCVQVQGKSKREKKDRVFTDKT SAT-VICRKNASISVRAQDRYYSSSWSE-WASVPCSGGGGSGGGGSGGGGSRNLPV ATPDPGMFPCLHEISQNLLRAVSNMLQKAR-QTLEFYPCTSEEIDHEDITKDKTSTV EACLPLELTK-NESCLNSRETSFITNGSCLASRKTSFMMALCLSSI-YEDLKMYQVEF KTMNAKLLMDPKRQIFLDQNMLAVIDELMQALNFN-SETVPQKSSLEEPDFYKTK IKLCILLHAFRI-RAVTIDRVMSYLNASITCPPPMSVEHADIWVKSYS-LYSRERYICN SGFKRKAGTSSLTECVLNKATNVAHWTTPSLKCIR (SEQ ID NO: 65). In some embodiments, the second chimeric polypeptide includes a sequence that is at least 90% identical to SEQ ID NO: 65. In some embodiments, the second chimeric polypeptide includes a sequence that is at least 95% identical to SEQ ID NO: 65. In some embodiments, the second chimeric polypeptide includes SEQ ID NO: 65. In some embodiments, the second chimeric polypeptide includes MKWVTFISLLFLFSSAYSI-WELKKDVYVVELDWYPDAPGEMVVLTCDTPEEDGI TWTLDQSSEVLGSGKTLTIQVKEFGDAGQYTCHKG-GEVLSHSLLLLHKKEDGIW STDILKDQKEPKNKT-FLRCEAKNYSGRFTCWWLT-TISTDLTFSVKSSRGSSDPQG VTCGAATLSAERVRGDNKEYEYSVECQED-SACPAAEESLPIEVMVDAVHKLKYE NYTSSFFIR-DIIKPDPPKNLQLKPLKNSRQVEVSWEYPDTW-STPHSYFSLTFCVQV QGKSKREKKDRVFTDKTSATVICRKNA-SISVRAQDRYYSSSWSEWASVPCSGGG GSGGGGSGGGGSRNLPVATPDPGMFPCLHHSQNLL-RAVSNMLQKARQTLEFYP CTSEEIDHEDITKDKT-STVEACLPLELTKNESCLNSRETSFITNGSCLAS-RKTSFMM ALCLSSIYEDLKMYQVEFKTMNAKLLMDPKRQI-FLDQNMLAVIDELMQALNFNS ETVPQKSSLEEPDFYKTKIKLCILLHAFRI-RAVTIDRVMSYLNASITCPPPMSVEHA DIWVKSYS-LYSRERYICNSGFKRKAGTSSLTECVLNKATN-VAHWTTPSLKCIR (SEQ ID NO: 66). In some embodiments, the first target-binding domain and the linker domain in the first chimeric polypeptide in the second multi-chain chimeric polypeptide directly abut each other in the first chimeric polypeptide. In some embodiments, the first chimeric polypeptide in the second multi-chain chimeric polypeptide further includes a linker sequence between the first target-binding domain and the linker domain in the first chimeric polypeptide. In some embodiments, the linker domain and the first domain of the pair of affinity domains directly abut each other in the first chimeric polypeptide in the second multi-chain chimeric polypeptide. In some embodiments, the first chimeric polypeptide in the second multi-chain chimeric polypeptide further includes a linker sequence between the linker domain and the first domain of the pair of affinity domains in the first chimeric polypeptide. In some embodiments, the second domain of the pair of affinity domains and the second target-binding domain in the second chimeric polypeptide of the second multi-chain chimeric polypeptide directly abut each other in the second chimeric polypeptide. In some embodiments, the second chimeric polypeptide in the second multi-chain chimeric polypeptide further includes a linker sequence between the second domain of the pair of affinity domains and the second target-binding domain in the second chimeric polypeptide. In some embodiments, the linker domain is a soluble tissue factor domain. In some embodiments, the soluble tissue factor domain is a soluble human tissue factor domain. In some embodiments, the soluble human tissue factor domain includes a sequence that is at least 80% identical to SEQ ID NO: 5 In some embodiments, the soluble human tissue factor domain includes a sequence that is at least 90% identical to SEQ ID NO: 5. In some embodiments, the soluble human tissue factor domain includes a sequence that is at least 95% identical to SEQ ID NO: 5. In some embodiments, the soluble human tissue factor domain includes SEQ ID NO: 5. In some embodiments, the soluble human tissue factor domain includes a sequence that is at least 80% identical to SEQ ID NO: 9. In some embodiments, the soluble human tissue factor domain includes a sequence that is at least 90% identical to SEQ ID NO: 9. In some embodiments, the soluble human tissue factor domain includes a sequence that is at least 95% identical to SEQ ID NO: 9. In some embodiments, the soluble human tissue factor domain includes SEQ ID NO: 9. In some embodiments, the soluble human tissue factor domain includes a sequence that is at least 80% identical to SEQ ID NO: 10. In some embodiments, the soluble human tissue factor domain includes a sequence that is at least 90% identical to SEQ ID NO: 10. In some embodiments, the soluble human tissue factor domain includes a sequence that is at least 95% identical to SEQ ID NO: 10. In some embodiments, the soluble human tissue factor domain includes SEQ ID NO: 10.

In some embodiments, the soluble human tissue factor domain does not comprise one or more of: a lysine at an amino acid position that corresponds to amino acid position of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the second multi-chain chimeric polypeptide does not stimulate coagulation in a mammal. In some embodiments, the first chimeric polypeptide and/or the second chimeric polypeptide in the second multi-chain chimeric polypeptide further includes a signal sequence at its N-terminal end. In some embodiments, the signal sequence includes SEQ ID NO: 28. In some embodiments, the signal sequence is SEQ ID NO: 28. In some embodiments, the pair of affinity domains in the second multi-chain chimeric polypeptide is a sushi domain from an alpha chain of human IL-15 receptor (IL15Rα) and a soluble IL-15. In some embodiments, the soluble IL-15 has a D8N or D8A amino acid substitution. In some embodiments, the soluble IL-15 includes a sequence that is 80% identical to SEQ ID NO: 26. In some embodiments, the soluble IL-15 includes a sequence that is 90% identical to SEQ ID NO: 26. In some embodiments, the soluble IL-15 includes a sequence that is 95% identical to SEQ ID NO: 26. In some embodiments, the soluble IL-15 includes SEQ ID NO: 26. In some embodiments, the sushi domain of IL15Rα includes a sushi domain from human IL15Rα. In some embodiments, the sushi domain from human IL15Rα includes a sequence that is 80% identical to SEQ ID NO: 24. In some embodiments, the sushi domain from human IL15Rα includes a sequence that is 90% identical to SEQ ID NO: 24. In some embodiments, the sushi domain from human IL15Rα includes a sequence that is 95% identical to SEQ ID NO: 24. In some embodiments, the sushi domain from human IL15Rα includes SEQ ID NO: 24. In some embodiments, the sushi domain from human IL15Rα is a mature full-length IL15Rα. In some embodiments, the pair of affinity domains in the second multi-chain chimeric polypeptide is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first target-binding domain and the second target-binding domain in the second multi-chain chimeric polypeptide are each independently a soluble IL-7 or a soluble IL-21. In some embodiments, the first target-binding domain in the second multi-chain chimeric polypeptide binds specifically to a receptor for IL-21, and the second target-binding domain in the second multi-chain chimeric polypeptide binds specifically to a receptor for IL-7. In some embodiments, the first target-binding domain in the second multi-chain chimeric polypeptide binds specifically to a receptor for IL-7, and the second target-binding domain in the second multi-chain chimeric polypeptide binds specifically to a receptor for IL-21. In some embodiments, the first target-binding domain in the second multi-chain chimeric polypeptide includes a soluble IL-21. In some embodiments, the soluble IL-21 is a soluble human IL-21. In some embodiments, the soluble human IL-21 includes a sequence at least 80% identical to SEQ ID NO: 22. In some embodiments, the soluble human IL-21 includes a sequence at least 90% identical to SEQ ID NO: 22. In some embodiments, the soluble human IL-21 includes a sequence at least 95% identical to SEQ ID NO: 22. In some embodiments, the soluble human IL-21 includes a sequence of SEQ ID NO: 22. In some embodiments, the second target-binding domain includes a soluble IL-7. In some embodiments, the soluble IL-7 is a soluble human IL-7. In some embodiments, the soluble human IL-7 includes a sequence at least 80% identical to SEQ ID NO: 23. In some embodiments, the soluble human IL-7 includes a sequence at least 90% identical to SEQ ID NO: 23. In some embodiments, the soluble human IL-7 includes a sequence at least 95% identical to SEQ ID NO: 23. In some embodiments, the soluble human IL-7 includes a sequence of SEQ ID NO: 23.

In some embodiments, the first chimeric polypeptide in the second multi-chain chimeric polypeptide includes a sequence that is at least 80% identical to DCDI-EGKDGKQYESVLMVSIDQLLDSMKEIGSN-CLNNEFNEFKRHICDANKEGM FLFRAARKLRQFLKMNSTGDFDLHLLKVSEGT-TILLNCTGQVKGRKPAALGEAQ PTKSLEENKSLKEQKKLNDLCFLKRLLQEIKTC-WNKILMGTKEHSGTTNTVAAY NLTWK-STNFKTILEWEPKPVNQVYTVQISTKSGDWK-SKCFYTTDTECDLTDEIVK DVKQTYLARVF SYPAG-NVESTGSAGEPLYENSPEFTPYLETNLGQPTIQ-SFEQVG TKVNVTVEDERTLVRRNNTELSLRDVEG-KDLIYTLYYWKSSSSGKKTAKTNTNE FLIDVDKG-ENYCFSVQAVIPSRTVNRKSTDSPVECMGQEKGE-FRENWVNVISDL KKIEDLIQSMHIDATLYTESDVHPSCKVTAMKCFL-LELQVISLESGDASIHDTVEN LIILANNSLSSNG-NVTESGCKECEELEEKNIKEFLQSFVHIVQMFINTS (SEQ ID NO: 67). In some embodiments, the first chimeric polypeptide in the second multi-chain chimeric polypeptide includes a sequence that is at least 90% identical to SEQ ID NO: 67. In some embodiments, the first chimeric polypeptide in the second multi-chain chimeric polypeptide includes a sequence that is at least 95% identical to SEQ ID NO: 67. In some embodiments, the first chimeric polypeptide in the second multi-chain chimeric polypeptide includes SEQ ID NO: 67. In some embodiments, the first chimeric polypeptide in the second multi-chain chimeric polypeptide includes MKWVTFISLLFLFSSAYSDCDI-EGKDGKQYESVLMVSIDQLLDSMKEIGSNCLNN EFNEFKRHICDANKEGMFLFRAARKLRQFLKMN-STGDFDLHLLKVSEGTTILLNC TGQVKGRKPAAL-GEA-QPTKSLEENKSLKEQKKLNDLCFLKRLLQEIKTC-WNKIL MGTKEHSGTTNTVAAYNLTWK-STNFKTILEWEPKPVNQVYTVQISTKSGDWKS KCFYTTDTECDLTDEIVKDVKQTYLARVFSYPAG-NVESTGSAGEPLYENSPEFTP YLETNLGQPTIQS-FEQVGTKVNVTVEDERTLVRRNNTELSLRDVEG-KDLIYTLYY WKSSSSGKKTAKTNTNEFLIDVDKG-ENYCFSVQAVIPSRTVNRKSTDSPVECMG QEKGE-FRENWVNVISDLKKIEDLIQSMHIDATLYTESDVHP-SCKVTAMKCELLEL QVISLESGDASIHDTVENLIILANNSLSSNG-NVTESGCKECEELEEKNIKEFLQSFV HIVQMFINTS (SEQ ID NO: 68). In some embodiments, the second chimeric polypeptide in the second multi-chain chimeric polypeptide includes a sequence that is at least 80% identical to QGQDRHMIRMRQLIDIVDQLKNYVNDLVPEFLPAPE-DVETNCEWSAFSCFQKAQ LKSANTGNNERIINVSIK-KLKRKPPSTNAGRRQKHRLTCPSCDSYEKKPPKE-FLER FKSLLQKMIHQHLSSRTHGSEDSITCPPPMSVEHAD-IWVKSYSLYSRERYICNSGF KRK-AGTSSLTECVLNKATNVAHWTTPSLKCIR (SEQ ID NO: 69). In some embodiments, the second chimeric polypeptide in the second multi-chain chimeric polypeptide includes a sequence that is at least 90% identical to SEQ ID NO: 69. In some embodiments, the second chimeric polypeptide in the second multi-chain chimeric polypeptide includes a sequence that is at least 95% identical to SEQ ID NO: 69. In some embodiments, the second chimeric polypeptide in the second multi-chain chimeric polypeptide includes SEQ ID NO: 69. In some embodiments, the second chimeric polypeptide in the second multi-chain chimeric polypeptide includes MKWVTFISLLFLFSSAY-SQGQDRHMIRMRQLIDIVDQLKNYVNDLVPEFL-PAPED VETNCEWSAFSCFQKAQLKSANTGNNERI-INVSIKKLKRKPPSTNAGRRQKHRLT CPSCDSYEKKPPKEFLERFKSLLQK-MIHQHLSSRTHGSEDSITCPPPMSVEHADIW VKSYS-LYSRERYICNSGFKRKAGTSSLTECVLNKATN-VAHWTTPSLKCIR (SEQ ID NO: 70). In some embodiments, the first chimeric polypeptide in the second multi-chain chimeric polypeptide includes a sequence that is at least 80% identical to QGQDRHMIRMRQLIDI-VDQLKNYVNDLVPEFLPAPEDVETNCEWS-AFSCFQKAQ LKSANTGNNERIINVSIKKLKRKPPST-NAGRRQKHRLTCPSCDSYEKKPPKEFLER FKSLLQKMIHQHLSSRTHGSED-SSGTTNTVAAYNLTWKSTNEKTILEWEPKPVNQ VYTVQISTKSGDWKSKCEYTTDTECDLT-DEIVKDVKQTYLARVESYPAGNVEST GSAGEPLYEN-SPEFTPYLETNLGQPTIQSFEQVGTKVNVTVED-ERTLVRRNNTFLS LRDVEGKDLIYTLYYWKSSSSGKKTAKTNTNE-FLIDVDKGENYCFSVQAVIPSRT VNRKSTD-SPVECMGQEKGEFRENWVNVISDLKKIEDLIQSMHI-DATLYTESDVHP SCKVTAMKCFLLELQVISLESGDASIHDTVEN-LIILANNSLSSNGNVTESGCKECE ELEEKNIKE-FLQSFVHIVQMFINTS (SEQ ID NO: 71). In some embodiments, the first chimeric polypeptide in the second multi-chain chimeric polypeptide includes a sequence that is at least 90% identical to SEQ ID NO: 71. In some embodiments, the first chimeric polypeptide in the second multi-chain chimeric polypeptide includes a sequence that is at least 95% identical to SEQ ID NO: 71. In some embodiments, the first chimeric polypeptide in the second multi-chain chimeric polypeptide includes SEQ ID NO: 71. In some embodiments, the first chimeric polypeptide in the second multi-chain chimeric polypeptide includes

```
                                       (SEQ ID NO: 72)
MGVKVLFALICIAVAEAQGQDRHMIRMRQLIDIVDQLKNY

VNDLVPEFLPAPEDVETNCEWSAFSCFQKAQLKSANTGNN

ERIINVSIKKLKRKPPSTNAGRRQKHRLTCPSCDSYEKKP

PKEFLERFKSLLQKMIHQHLSSRTHGSEDSSGTTNTVAAY

NLTWKSTNFKTILEWEPKPVNQVYTVQISTKSGDWKSKCF

YTTDTECDLTDEIVKDVKQTYLARVFSYPAGNVESTGSAG

EPLYENSPEFTPYLETNLGQPTIQSFEQVGTKVNVTVEDE

RTLVRRNNTFLSLRDVFGKDLIYTLYYWKSSSSGKKTAKT

NTNEFLIDVDKGENYCFSVQAVIPSRTVNRKSTDSPVECM

GQEKGEFRENWVNVISDLKKIEDLIQSMHIDATLYTESDV

HPSCKVTAMKCFLLELQVISLESGDASIHDTVENLIILAN

NSLSSNGNVTESGCKECEELEEKNIKEFLQSFVHIVQMFI

NTS.
```

In some embodiments, the second chimeric polypeptide in the second multi-chain chimeric polypeptide includes a sequence that is at least 80% identical to DCDI-EGKDGKQYESVLMVSIDQLLDSMKEIGSN-CLNNEFNFFKRHICDANKEGM FLFRAARKLRQFLKMNSTGDFDLHLLKVSEGT-TILLNCTGQVKGRKPAALGEAQ PTKSLEENKSLKEQKKLNDLCFLKRLLQEIKT- CWNKILMGTKEHITCPPPMSVEH ADIWVKSYSLYSR-ERYICNSGFKRKAGTSSLTECVLNKATN-VAHWTTPSLKCIR (SEQ ID NO: 73). In some embodiments, the second chimeric polypeptide in the second multi-chain chimeric polypeptide includes a sequence that is at least 90% identical to SEQ ID NO: 73. In some embodiments, the second chimeric polypeptide in the second multi-chain chimeric polypeptide includes a sequence that is at least 95% identical to SEQ ID NO: 73. In some embodiments, the second chimeric polypeptide in the second multi-chain chimeric polypeptide includes SEQ ID NO: 73. In some embodiments, the second chimeric polypeptide in the second multi-chain chimeric polypeptide includes MGVKVLFALICIAVAEADCDI-EGKDGKQYESVLMVSIDQLLDSMKEIGSNCLNN EFNFFKRHICDANKEGMFLFRAARKLRQFLKMN-STGDFDLHLLKVSEGTTILLNC TGQVKGRKPAAL-GEAQPTKSLEENKSLKEQKKLND-LCFLKRLLQEIKTCWNKIL MGTKEHITCPPPMSVE-HADIWVKSYSLYSRERYICNSGFKRK-AGTSSLTECVLNK ATNVAHWTTPSLKCIR (SEQ ID NO: 74). In some embodiments, the IgG1 antibody construct is a monoclonal IgG1 antibody, where both antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain. In some embodiments, the first period of time is about 15 minutes to about 4 hours. In some embodiments, the first period of time is about 30 minutes to about 3.5 hours. In some embodiments, the first period of time is about 1 hour to about 3.5 hours. In some embodiments, the first period of time is about 2 hours to about 3.5 hours. In some embodiments, the liquid culture medium in step (a) and/or step (b) is a serum-containing liquid culture medium.

In some embodiments, the NK cells are in the liquid culture medium in step (a) at a density of about $4.0\times10^{7}$ cells/mL to about $1.5\times10^{8}$ cells/mL. In some embodiments, the NK cells are in the liquid culture medium in step (a) at a density of about $5.0\times10^{7}$ cells/mL to about $2.0\times10^{8}$ cells/mL. In some embodiments, the second period of time is about 1 day to about 30 days. In some embodiments, the second period of time is about 7 days to about 30 days. In some embodiments, the second period of time is about 14 days to about 21 days. In some embodiments, the liquid culture medium in step (b) includes the second multi-chain chimeric polypeptide and the IgG1 antibody construct at a molar ratio of about 0.5:1 to about 2:1. In some embodiments, the liquid culture medium in step (b) includes the second multi-chain chimeric polypeptide and the IgG1 antibody construct at a molar ratio of about 0.8:1 to about 1.2:1. In some embodiments, the NK cells are in the liquid culture medium in step (b) are maintained at a density of about $0.5\times10^{6}$ cells/mL to about $2.0\times10^{6}$ cells/mL. In some embodiments, the NK cells are in the liquid culture medium in step (b) are maintained at a density of about $1.0\times10^{6}$ cells/mL to about $2.0\times10^{6}$ cells/mL. In some embodiments, the NK cell was previously obtained from a subject. In some embodiments, the NK cell was previously obtained from umbilical cord blood or induced pluripotent stem cells. In some embodiments, the method further includes obtaining the NK cell from the subject prior to step (a). In some embodiments, the NK cell has previously been genetically modified to express a chimeric antigen receptor or a recombinant T-cell receptor. In some embodiments, the method further includes, between step (a) and step (b), introducing into the NK cell a nucleic acid encoding a chimeric antigen-receptor or a recombinant T-cell receptor. In some embodiments, the method further includes, prior to step (a), introducing into the NK cell a nucleic acid encoding a chimeric antigen-receptor or a recombinant T-cell receptor. In some embodiments, the method further includes, during step (b), introducing into the NK cell a nucleic acid encoding a chimeric antigen-receptor or a recombinant T-cell receptor. In some embodiments, the method further includes, after step (b), isolating the NK cell. In some embodiments, after step (b), the NK cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, TRAIL, FasL, CXCR3, CXCR4, LTB, MX1, BAX, TNF-α, and IFN-γ as compared to the level of expression or secretion of the one or more proteins prior to step (a). In some embodiments, the method further includes, after the contacting step, administering the NK cell to a subject in need thereof. In some embodiments, the subject has been identified or diagnosed as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is an activated NK cell produced by the method of any of the above embodiments. Also provided is a pharmaceutical composition comprising the activated NK cell of the above embodiment. Also provided is a kit that includes a pharmaceutical composition that includes the activated NK cell of any of the above embodiments. In another aspect, provided herein is a method of killing a cancer cell, an infected cell, or a senescent cell in a subject in need thereof, the method includes administering to the subject a therapeutically effective amount of the activated NK cell of any of the above embodiments or the pharmaceutical composition of any of the above embodiments. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In some embodiments, provided herein is a method of treating a subject in need thereof, the method comprising administering to the subject a therapeutically effective amount of the activated NK cell or the activated T cell of any of the above embodiments or the pharmaceutical composition of any of the above embodiment. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In another aspect, provided herein is a kit comprising: (a) a first multi-chain chimeric polypeptide comprises: a first chimeric polypeptide comprising a first target-binding domain, a soluble tissue factor domain, and a first domain of a pair of affinity domains, and a second chimeric polypeptide comprising a second domain of a pair of affinity domains and a second target-binding domain, wherein the first chimeric polypeptide and the second chimeric polypeptide in the first multi-chain chimeric polypeptide associate through the binding of the first domain and the second domain of the pair of affinity domains in the first multi-chain chimeric polypeptide, and the first target-binding domain and the second target-binding domain in the first multi-chain chimeric polypeptide each independently bind specifically to a receptor of IL-18 or a receptor of IL-12; a second multi-chain chimeric polypeptide comprises: a first chimeric polypeptide comprising a first target-binding domain, a linker domain, a first domain of a pair of affinity domains, and a second chimeric polypeptide comprising a second domain of a pair of affinity domains, and a second target-binding domain, wherein the first chimeric polypeptide and the second chimeric polypeptide in the second multi-chain chimeric polypeptide associate through the binding of the first domain and the second domain of the pair of affinity domains in the second multi-chain chimeric polypeptide; and the first target-binding domain and the second target-binding domain in the second multi-chain chimeric polypeptide each independently bind specifically to a receptor for IL-7 or a receptor for IL-21; and (c) an IgG1 antibody that comprises at least one antigen-binding domain that binds specifically to the linker domain. In some embodiments, the first target-binding domain and the soluble tissue factor domain directly abut each other in the first chimeric polypeptide in the first multi-chain chimeric polypeptide. In some embodiments, the first chimeric polypeptide in the first multi-chain chimeric polypeptide further comprises a linker sequence between the first target-binding domain and the soluble tissue factor domain in the first chimeric polypeptide. In some embodiments, the soluble tissue factor domain and the first domain of the pair of affinity domains in the first chimeric polypeptide in the first multi-chain chimeric polypeptide directly abut each other in the first chimeric polypeptide. In some embodiments, the first chimeric polypeptide in the first multi-chain chimeric polypeptide further comprises a linker sequence between the soluble tissue factor domain and the first domain of the pair of affinity domains in the first chimeric polypeptide. In some embodiments, the second domain of the pair of affinity domains and the second target-binding domain in the second chimeric polypeptide in the first multi-chain chimeric polypeptide directly abut each other in the second chimeric polypeptide. In some embodiments, the second chimeric polypeptide in the first multi-chain chimeric polypeptide further comprises a linker sequence between the second domain of the pair of affinity domains and the second target-binding domain in the second chimeric polypeptide. In some embodiments, the soluble tissue factor domain is a soluble human tissue factor domain. In some embodiments, the soluble human tissue factor domain comprises a sequence that is at least 80% identical to SEQ ID NO: 5. In some embodiments, the soluble human tissue factor domain comprises a sequence that is at least 90% identical to SEQ ID NO: 5. In some embodiments, the soluble human tissue factor domain comprises a sequence that is at least 95% identical to SEQ ID NO: 5. In some embodiments, the soluble human tissue factor domain comprises SEQ ID NO: 5. In some embodiments, the soluble human tissue factor domain comprises a sequence that is at least 80% identical to SEQ ID NO: 9. In some embodiments, the soluble human tissue factor domain comprises a sequence that is at least 90% identical to SEQ ID NO: 9. In some embodiments, the soluble human tissue factor domain comprises a sequence that is at least 95% identical to SEQ ID NO: 9. In some embodiments, the soluble human tissue factor domain comprises SEQ ID NO: 9. In some embodiments, the soluble human tissue factor domain comprises a sequence that is at least 80% identical to SEQ ID NO: 10. In some embodiments, the soluble human tissue factor domain comprises a sequence that is at least 90% identical to SEQ ID NO: In some embodiments, the soluble human tissue factor domain comprises a sequence that is at least 95% identical to SEQ ID NO: 10. In some embodiments, the soluble human tissue factor domain comprises SEQ ID NO: 10. In some embodiments, the soluble human tissue factor domain does not comprise one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the first multi-chain chimeric polypeptide does not stimulate coagulation in a mammal. In some embodiments, the first chimeric polypeptide and/or the second chimeric polypeptide in the first multi-chain chimeric polypeptide further comprises a signal sequence at its N-terminal end. In some embodiments, the signal sequence comprises SEQ ID NO: 28. In some embodiments, the signal sequence is SEQ ID NO: 28. In some embodiments, the pair of affinity domains in the first multi-chain chimeric polypeptide is a sushi domain from an alpha chain of human IL-15 receptor (IL15Rα) and a soluble IL-15. In some embodiments, the soluble IL-15 has a D8N or D8A amino acid substitution In some embodiments, the soluble IL-comprises a sequence that is 80% identical to SEQ ID NO: 26. In some embodiments, the soluble IL-15 comprises a sequence that is 90% identical to SEQ ID NO: 26. In some embodiments, the soluble IL-15 comprises a sequence that is 95% identical to SEQ ID NO: 26. In some embodiments, the soluble IL-15 comprises SEQ ID NO: 26. In some embodiments, the sushi domain of IL15Rα comprises a sushi domain from human IL15Rα. In some embodiments, the sushi domain from human IL15Rα comprises a sequence that is 80% identical to SEQ ID NO: 24. In some embodiments, the sushi domain from human IL15Rα comprises a sequence that is 90% identical to SEQ ID NO: 24. In some embodiments, the sushi domain from human IL15Rα comprises a sequence that is 95% identical to SEQ ID NO: 24. In some embodiments, the sushi domain from human IL15Rα comprises SEQ ID NO: 24. In some embodiments, the sushi domain from human IL15Rα is a mature full-length IL15Rα. In some embodiments, the pair of affinity domains in the first multi-chain chimeric polypeptide is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first target-binding domain and the second target-binding domain in the first multi-chain chimeric polypeptide are each independently a soluble IL-15 or a soluble IL-18. In some embodiments, the first target-binding domain in the first multi-chain chimeric polypeptide binds specifically to a receptor for IL-12, and the second target-binding domain in the first multi-chain chimeric polypeptide binds specifically to a receptor for IL-18. In some embodiments, the first target-binding domain in the first multi-chain chimeric polypeptide binds specifically to a receptor for IL-18, and the second target-binding domain in the first multi-chain chimeric polypeptide binds specifically to a receptor for IL-12. In some embodiments, the first target-binding domain in the first multi-chain chimeric polypeptide comprises a soluble IL-18. In some embodiments, the soluble IL-18 is a soluble human IL-18. In some embodiments, the soluble human IL-18 comprises a sequence at least 80% identical to SEQ ID NO: 20. In some embodiments, the soluble human IL-18 comprises a sequence at least 90% identical to SEQ ID NO: 20. In some embodiments, the soluble human IL-18 comprises a sequence at least 95% identical to SEQ ID NO: 20. In some embodiments, the soluble human IL-18 comprises a sequence of SEQ ID NO: 20. In some embodiments, the second target-binding domain in the first multi-chain chimeric polypeptide comprises a soluble IL-12. In some embodiments, the soluble IL-12 is a soluble human IL-12. In some embodiments, the soluble human IL-12 comprises a sequence of soluble human IL-12β (p40) and a sequence of soluble human IL-12α (p35). In some embodiments, the soluble human IL-further comprises a linker sequence between the sequence of soluble IL-12β (p40) and the sequence of soluble human IL-12α (p35). In some embodiments, the linker sequence comprises SEQ ID NO: 11. In some embodiments, the sequence of soluble human IL-12β (p40) comprises a sequence that is at least 80% identical to SEQ ID NO: 14. In some embodiments, the sequence of soluble human IL-12β (p40) comprises a sequence that is at least 90% identical to SEQ ID NO: 14. In some embodiments, the sequence of soluble human IL-12β (p40) comprises a sequence that is at least 95% identical to SEQ ID NO: 14. In some embodiments, the sequence of soluble human IL-12β (p40) comprises SEQ ID NO: 14. In some embodiments, the sequence of soluble human IL-12α (p35) comprises a sequence that is at least 80% identical to SEQ ID NO: 16. In some embodiments, the sequence of soluble human IL-12α (p35) comprises a sequence that is at least 90% identical to SEQ ID NO: 16. In some embodiments, the sequence of soluble human IL-12α (p35) comprises a sequence that is at least 95% identical to SEQ ID NO: 16. In some embodiments, the sequence of soluble human IL-12α (p35) comprises SEQ ID NO: 16. In some embodiments, the first chimeric polypeptide in the first multi-chain chimeric polypeptide comprises a sequence that is at least 80% identical to SEQ ID NO: 63. In some embodiments, the first chimeric polypeptide in the first multi-chain chimeric polypeptide comprises a sequence that is at least 90% identical to SEQ ID NO: 63. In some embodiments, the first chimeric polypeptide in the first multi-chain chimeric polypeptide comprises a sequence that is at least 95% identical to SEQ ID NO: 63. In some embodiments, the first chimeric polypeptide in the first multi-chain chimeric polypeptide comprises SEQ ID NO: 63. In some embodiments, the first chimeric polypeptide in the first multi-chain chimeric polypeptide comprises SEQ ID NO: 64. In some embodiments, the second chimeric polypeptide comprises a sequence that is at least 80% identical to SEQ ID NO: 65. In some embodiments, the second chimeric polypeptide comprises a sequence that is at least 90% identical to SEQ ID NO: 65. In some embodiments, the second chimeric polypeptide comprises a sequence that is at least 95% identical to SEQ ID NO: 65. In some embodiments, the second chimeric polypeptide comprises SEQ ID NO: 65. In some embodiments, the second chimeric polypeptide comprises SEQ ID NO: 66. In some embodiments, the first target-binding domain and the linker domain in the first chimeric polypeptide in the second multi-chain chimeric polypeptide directly abut each other in the first chimeric polypeptide. In some embodiments, the first chimeric polypeptide in the second multi-chain chimeric polypeptide further comprises a linker sequence between the first target-binding domain and the linker domain in the first chimeric polypeptide. In some embodiments, the linker domain and the first domain of the pair of affinity domains directly abut each other in the first chimeric polypeptide in the second multi-chain chimeric polypeptide. In some embodiments, the first chimeric polypeptide in the second multi-chain chimeric polypeptide further comprises a linker sequence between the linker domain and the first domain of the pair of affinity domains in the first chimeric polypeptide. In some embodiments, the second domain of the pair of affinity domains and the second target-binding domain in the second chimeric polypeptide of the second multi-chain chimeric polypeptide directly abut each other in the second chimeric polypeptide. In some embodiments, the second chimeric polypeptide in the second multi-chain chimeric polypeptide further comprises a linker sequence between the second domain of the pair of affinity domains and the second target-binding domain in the second chimeric polypeptide. In some embodiments, the linker domain is a soluble tissue factor domain. In some embodiments, the soluble tissue factor domain is a soluble human tissue factor domain. In some embodiments, the soluble human tissue factor domain comprises a sequence that is at least 80% identical to SEQ ID NO: 5. In some embodiments, the soluble human tissue factor domain comprises a sequence that is at least 90% identical to SEQ ID NO: 5. In some embodiments, the soluble human tissue factor domain comprises a sequence that is at least 95% identical to SEQ ID NO: 5. In some embodiments, the soluble human tissue factor domain comprises SEQ ID NO: 5. In some embodiments, the soluble human tissue factor domain comprises a sequence that is at least 80% identical to SEQ ID NO: 9. In some embodiments, the soluble human tissue factor domain comprises a sequence that is at least 90% identical to SEQ ID NO: 9. In some embodiments, the soluble human tissue factor domain comprises a sequence that is at least 95% identical to SEQ ID NO: 9. In some embodiments, the soluble human tissue factor domain comprises SEQ ID NO: 9. In some embodiments, the soluble human tissue factor domain comprises a sequence that is at least 80% identical to SEQ ID NO: 10. In some embodiments, the soluble human tissue factor domain comprises a sequence that is at least 90% identical to SEQ ID NO: 10. In some embodiments, the soluble human tissue factor domain comprises a sequence that is at least 95% identical to SEQ ID NO: 3. In some embodiments, the soluble human tissue factor domain comprises SEQ ID NO: 10. In some embodiments, the soluble human tissue factor domain does not comprise one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not comprise any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the second multi-chain chimeric polypeptide does not stimulate coagulation in a mammal. In some embodiments, the first chimeric polypeptide and/or the second chimeric polypeptide in the second multi-chain chimeric polypeptide further comprises a signal sequence at its N-terminal end. In some embodiments, the signal sequence comprises SEQ ID NO: 28. In some embodiments, the signal sequence is SEQ ID NO: 28. In some embodiments, the pair of affinity domains in the second multi-chain chimeric polypeptide is a sushi domain from an alpha chain of human IL-15 receptor (IL15Rα) and a soluble IL-15. In some embodiments, the soluble IL-15 has a D8N or D8A amino acid substitution. In some embodiments, the soluble IL-15 comprises a sequence that is 80% identical to SEQ ID NO: 26. In some embodiments, the soluble IL-15 comprises a sequence that is 90% identical to SEQ ID NO: 26. In some embodiments, the soluble IL-15 comprises a sequence that is 95% identical to SEQ ID NO: 26. In some embodiments, the soluble IL-comprises SEQ ID NO: 26. In some embodiments, the sushi domain of IL15Rα comprises a sushi domain from human IL15Rα. In some embodiments, the sushi domain from human IL15Rα comprises a sequence that is 80% identical to SEQ ID NO: 24. In some embodiments, the sushi domain from human IL15Rα comprises a sequence that is 90% identical to SEQ ID NO: 24. In some embodiments, the sushi domain from human IL15Rα comprises a sequence that is 95% identical to SEQ ID NO: 24. In some embodiments, the sushi domain from human IL15Rα comprises SEQ ID NO: 24. In some embodiments, the sushi domain from human IL15Rα is a mature full-length IL15Rα. In some embodiments, the pair of affinity domains in the second multi-chain chimeric polypeptide is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first target-binding domain and the second target-binding domain in the second multi-chain chimeric polypeptide are each independently a soluble IL-7 or a soluble IL-21. In some embodiments, the first target-binding domain in the second multi-chain chimeric polypeptide binds specifically to a receptor for IL-21, and the second target-binding domain in the second multi-chain chimeric polypeptide binds specifically to a receptor for IL-7. In some embodiments, the first target-binding domain in the second multi-chain chimeric polypeptide binds specifically to a receptor for IL-7, and the second target-binding domain in the second multi-chain chimeric polypeptide binds specifically to a receptor for IL-21. In some embodiments, the first target-binding domain in the second multi-chain chimeric polypeptide comprises a soluble IL-21. In some embodiments, the soluble IL-21 is a soluble human IL-21. In some embodiments, the soluble human IL-21 comprises a sequence at least 80% identical to SEQ ID NO: 22. In some embodiments, the soluble human IL-21 comprises a sequence at least 90% identical to SEQ ID NO: 22. In some embodiments, the soluble human IL-21 comprises a sequence at least 95% identical to SEQ ID NO: 22. In some embodiments, the soluble human IL-21 comprises a sequence of SEQ ID NO: 22. In some embodiments, the second target-binding domain comprises a soluble IL-7. 323. In some embodiments, the soluble IL-7 is a soluble human IL-7. In some embodiments, the soluble human IL-7 comprises a sequence at least 80% identical to SEQ ID NO: 23. In some embodiments, the soluble human IL-7 comprises a sequence at least 90% identical to SEQ ID NO: 23. In some embodiments, the soluble human IL-7 comprises a sequence at least 95% identical to SEQ ID NO: 23. In some embodiments, the soluble human IL-7 comprises a sequence of SEQ ID NO: 23. In some embodiments, the first chimeric polypeptide in the second multi-chain chimeric polypeptide comprises a sequence that is at least 80% identical to SEQ ID NO: 67. In some embodiments, the first chimeric polypeptide in the second multi-chain chimeric polypeptide comprises a sequence that is at least 90% identical to SEQ ID NO: 67. In some embodiments, the first chimeric polypeptide in the second multi-chain chimeric polypeptide comprises a sequence that is at least 95% identical to SEQ ID NO: 67. In some embodiments, the first chimeric polypeptide in the second multi-chain chimeric polypeptide comprises SEQ ID NO: 67. In some embodiments, the first chimeric polypeptide in the second multi-chain chimeric polypeptide comprises SEQ ID NO: 68. In some embodiments, the second chimeric polypeptide in the second multi-chain chimeric polypeptide comprises a sequence that is at least 80% identical to SEQ ID NO: 69. In some embodiments, the second chimeric polypeptide in the second multi-chain chimeric polypeptide comprises a sequence that is at least 90% identical to SEQ ID NO: 69. In some embodiments, the second chimeric polypeptide in the second multi-chain chimeric polypeptide comprises a sequence that is at least 95% identical to SEQ ID NO: 69. In some embodiments, the second chimeric polypeptide in the second multi-chain chimeric polypeptide comprises SEQ ID NO: 69. In some embodiments, the second chimeric polypeptide in the second multi-chain chimeric polypeptide comprises SEQ ID NO: 70. In some embodiments, the first chimeric polypeptide in the second multi-chain chimeric polypeptide comprises a sequence that is at least 80% identical to SEQ ID NO: 71. In some embodiments, the first chimeric polypeptide in the second multi-chain chimeric polypeptide comprises a sequence that is at least 90% identical to SEQ ID NO: 71. In some embodiments, the first chimeric polypeptide in the second multi-chain chimeric polypeptide comprises a sequence that is at least 95% identical to SEQ ID NO: 71. In some embodiments, the first chimeric polypeptide in the second multi-chain chimeric polypeptide comprises SEQ ID NO: 71. In some embodiments, the first chimeric polypeptide in the second multi-chain chimeric polypeptide comprises SEQ ID NO: 72. In some embodiments, the second chimeric polypeptide in the second multi-chain chimeric polypeptide comprises a sequence that is at least 80% identical to SEQ ID NO: 73. In some embodiments, the second chimeric polypeptide in the second multi-chain chimeric polypeptide comprises a sequence that is at least 90% identical to SEQ ID NO: 73. In some embodiments, the second chimeric polypeptide in the second multi-chain chimeric polypeptide comprises a sequence that is at least 95% identical to SEQ ID NO: 73. In some embodiments, the second chimeric polypeptide in the second multi-chain chimeric polypeptide comprises SEQ ID NO: 73. In some embodiments, the second chimeric polypeptide in the second multi-chain chimeric polypeptide comprises SEQ ID NO: 74. In some embodiments, the IgG1 antibody construct is a monoclonal IgG1 antibody, where both antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., a scFv) and a domain that is derived from a naturally-occurring protein (e.g., a naturally-occurring human protein). In some embodiments, a chimeric polypeptide can include at least two different domains that are synthetic sequences (e.g., two different scFvs).

A "multi-chain chimeric polypeptide" means a complex of two or more chimeric polypeptides.

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin protein" is used herein to refer to a mature and secreted interleukin protein or a biologically active fragment thereof. In some examples, a soluble interleukin protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble interleukin proteins are described herein.

The term "soluble cytokine protein" is used herein to refer to a mature and secreted cytokine protein or a biologically active fragment thereof. In some examples, a soluble cytokine protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble cytokine proteins are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "ligand of a co-stimulatory molecule" is used herein in the broadest sense to refer to a polypeptide that is capable of binding and activating a co-stimulatory receptor molecule on an immune cell (e.g., under physiological conditions, e.g., in phosphate buffered saline at room temperature). For example, a ligand of a co-stimulatory molecule can include a sequence that is at least 70% identical (e.g., at least 75% identical, at least 80% identical, at least 85% identical, at least 90% identical, at least 95% identical, at least 99% identical, or 100% identical) to a ligand of a co-stimulatory molecule that retains its ability to specifically bind to one or more of its natural receptors. Non-limiting examples of ligands of co-stimulatory molecules are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant (KD). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

The term "pair of affinity domains" is two different protein domain(s) that bind specifically to each other with a $K_D$ of less than of less than $1\times10^{-7}$ M (e.g., less than $1\times10^{-8}$ M, less than $1\times10^{-9}$ M, less than $1\times10^{-10}$ M, or less than $1\times10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

An "immune effector cell" refers to a cell of the immune system of a mammal that is capable, directly or indirectly, of recognizing and/or causing cytostasis or cell death of a pathogenic cell (e.g., a cancer cell) in the mammal. Non-limiting examples of immune effector cells include macrophages, natural killer cells, T-lymphocytes (e.g., cytotoxic T-lymphocytes and T-helper cells), neutrophils, monocytes, and eosinophils. Additional examples of immune effector cells are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of composition that reduces at least one symptom of a disorder to a subject who is in need of, or who has been determined to be in need of such treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Provided herein are a specific combination of two multi-chain chimeric polypeptides, uses of the same, and kits including the same. The multi-chain chimeric polypeptides include a linker domain positioned between two target-binding domains. In some embodiments, the linker domain is or includes a soluble tissue factor domain. In some embodiments, the linker domain can be recognized by a cognate IgG1 antibody (e.g., a monoclonal antibody). In some embodiments, a combination of two of the multi-chain chimeric polypeptides described herein can be used to stimulate a NK cell, induce or increase proliferation of a NK cell, and/or induce differentiation of a NK cell, and the NK cells can thereafter be used to treat a subject.

Figure 30:
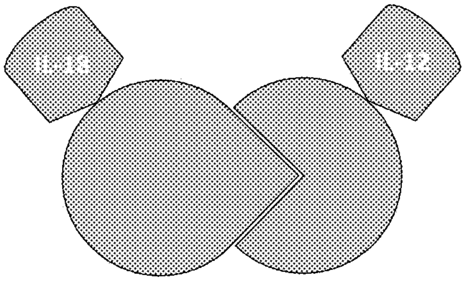
FIG. 30 is an exemplary illustration showing the multi-chain chimeric polypeptides that can be used in the methods described herein.
Figure 30:
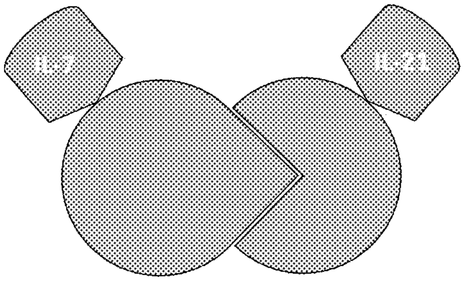
Figure 31:
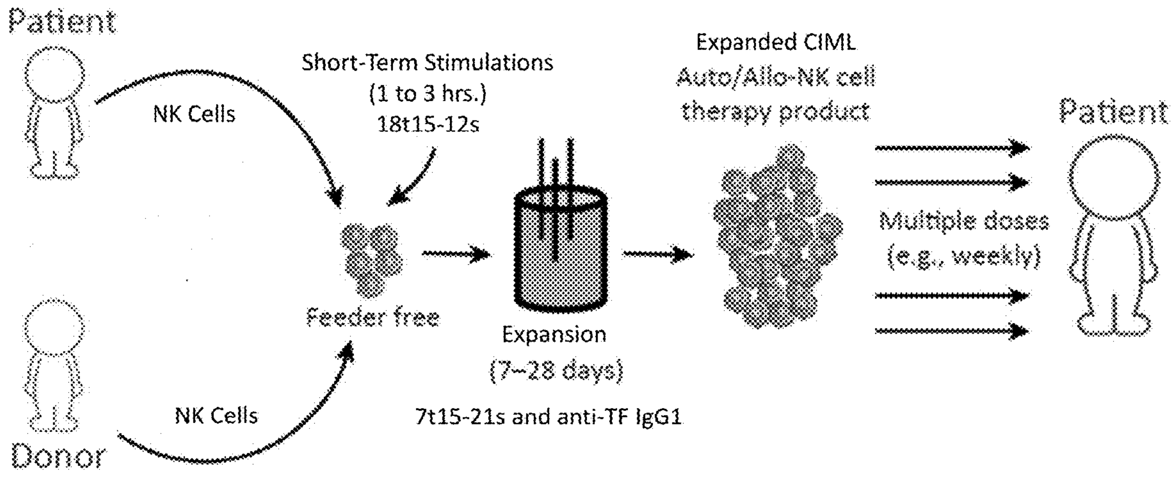
FIG. 31 is a schematic of an exemplary embodiment of the presently claimed methods.
Figure 32:
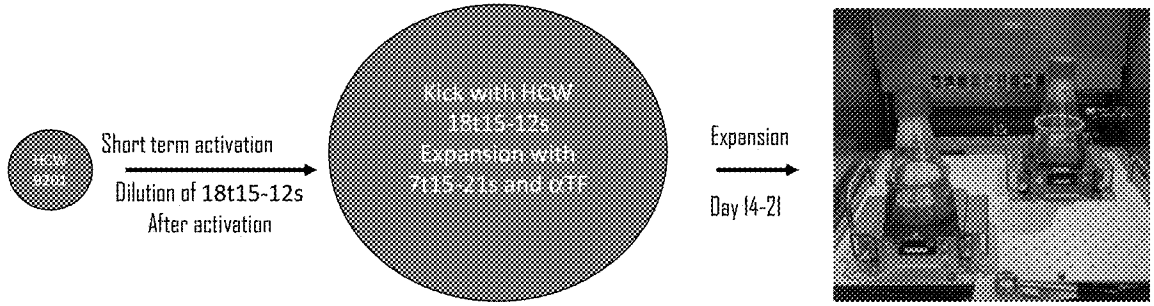
FIG. 32 is a schematic of an exemplary embodiment of the presently claimed methods.

Provided herein are methods of promoting the activation and proliferation of a natural killer cell that include: (a) contacting a natural killer cell in a liquid culture medium (e.g., any of the liquid culture media described herein) including an effective amount of a first multi-chain chimeric polypeptide for a first period of time under conditions that allow for the differentiation of the natural killer cell, and (b) contacting the natural killer cell in a liquid culture medium comprising an effective amount of (i) a second multi-chain chimeric polypeptide, and (ii) an IgG1 antibody construct that includes at least one antigen-binding domain that binds specifically to the linker domain (e.g., any of the exemplary IgG1 antibody constructs described herein), for a second period of time, under conditions that allow for activation and proliferation of the NK cell. Also provided are NK cells produced by any of these methods, and methods of using these NK cells to treat a subject. Also provided herein are compositions that include any of the NK cells generated using these methods. Also provided are kits that include (a) a first multi-chain chimeric polypeptide that includes a first and a second chimeric polypeptide (e.g., any of the exemplary first multi-chain chimeric polypeptides described herein), (b) a second multi-chain chimeric polypeptide that includes a first and a second chimeric polypeptide (e.g., any of the exemplary second multi-chain chimeric polypeptides described herein), and (c) an IgG1 antibody construct that includes at least one antigen-binding domain that binds specifically to the linker domain (e.g., any of the IgG1 antibody constructs described herein). Exemplary embodiments of the methods provided herein are depicted in FIGS. 30-32.

Current ex vivo NK expansion methods may include feeder-cell-based expansion methods and cytokine-based expansion methods. Exemplary disadvantages of feeder-cell-based expansion methods include, the development and maintenance of GMP-grade feeder cells and methods showing effective irradiation of the feeder cells, the final product must be depleted of all feeder-cell contaminants, including DNA, before administration to the patient, and the manufacturing process can be tedious and expensive. Exemplary disadvantages of cytokine-based expansion methods include, suboptimal purity of final NK cell product, low final NK cell number compared to feeder-cell expansion, and the expense of recombinant cytokines and the lack of commercially available GMP-grade cytokines, except IL-2. The methods described herein provide advantages such as, generation of highly activated NK cells from patients, large-scale expansion being comparable or similar to feeder-cell methods, cost effective expansion and activation with limited processing requirements, and the cells can be injected into subjects, thereby allowing expansion of cells in vivo.

In some embodiments, the methods described herein can induce the generation and proliferation of NK cells that are highly activated with a long persistence and a high degree of cytotoxicity against diseased cells in a recipient host (e.g., a cell having any of the exemplary aspects of a memory-like natural killer cell described herein). In some embodiments of any of the methods described herein, the contacting step that includes contacting a NK cell with a first multi-chain chimeric polypeptide results in less than 50% cell death (e.g., apoptosis) (e.g., less than 48% cell death, less than 46% cell death, less than 44% cell death, less than 42% cell death, less than 40% cell death, less than 38% cell death, less than 36% cell death, less than 34% cell death, less than 32% cell death, less than 30% cell death, less than 28% cell death, less than 26% cell death, less than 24% cell death, less than 22% cell death, less than 20% cell death, less than 18% cell death, less than 16% cell death, less than 14% cell death, less than 12% cell death, less than 10% cell death, less than 8% cell death, less than 6% cell death, less than 4% cell death, or less than 2% cell death).

In some embodiments, any of the methods described herein can result in an increase (e.g., about a 1% to about a 5,000% increase, about a 1% to about a 4,000% increase, about a 1% to about a 3,000% increase, about a 1% to about a 2,000% increase, about a 1% to about a 1,000% increase, about a 1% to about a 800% increase, about a 1% to about a 600% increase, about a 1% to about a 500% increase, about a 1% to about a 400% increase, about a 1% to about a 300% increase, about a 1% to about a 200% increase, about a 1% to about a 180% increase, about a 1% to about a 160% increase, about a 1% to about a 140% increase, about a 1% to about a 120% increase, about a 1% to about a 100% increase, about a 1% to about a 80% increase, about a 1% to about a 60% increase, about a 1% to about a 40% increase, about a 1% to about a 30% increase, about a 1% to about a 20% increase, about a 1% to about a 15% increase, about a 1% to about a 10% increase, about a 1% to about a 5% increase, about a 5% to about a 5,000% increase, about a 5% to about a 4,000% increase, about a 5% to about a 3,000% increase, about a 5% to about a 2,000% increase, about a 5% to about a 1,000% increase, about a 5% to about a 800% increase, about a 5% to about a 600% increase, about a 5% to about a 500% increase, about a 5% to about a 400% increase, about a 5% to about a 300% increase, about a 5% to about a 200% increase, about a 5% to about a 180% increase, about a 5% to about a 160% increase, about a 5% to about a 140% increase, about a 5% to about a 120% increase, about a 5% to about a 100% increase, about a 5% to about a 80% increase, about a 5% to about a 60% increase, about a 5% to about a 40% increase, about a 5% to about a 30% increase, about a 5% to about a 20% increase, about a 5% to about a 15% increase, about a 5% to about a 10% increase, about a 10% to about a increase, about a 10% to about a 4,000% increase, about a 10% to about a 3,000% increase, about a 10% to about a 2,000% increase, about a 10% to about a 1,000% increase, about a 10% to about a 800% increase, about a 10% to about a 600% increase, about a 10% to about a 500% increase, about a 10% to about a 400% increase, about a 10% to about a 300% increase, about a 10% to about a 200% increase, about a 10% to about a 180% increase, about a 10% to about a 160% increase, about a 10% to about a 140% increase, about a 10% to about a 120% increase, about a 10% to about a 100% increase, about a 10% to about a 80% increase, about a 10% to about a 60% increase, about a 10% to about a 40% increase, about a 10% to about a 30% increase, about a 10% to about a 20% increase, about a 10% to about a 15% increase, about a 15% to about a 5,000% increase, about a 15% to about a 4,000% increase, about a 15% to about a 3,000% increase, about a 15% to about a 2,000% increase, about a 15% to about a 1,000% increase, about a 15% to about a 800% increase, about a 15% to about a 600% increase, about a 15% to about a 500% increase, about a 15% to about a 400% increase, about a 15% to about a 300% increase, about a 15% to about a 200% increase, about a 15% to about a 180% increase, about a 15% to about a 160% increase, about a 15% to about a 140% increase, about a 15% to about a 120% increase, about a 15% to about a 100% increase, about a 15% to about a 80% increase, about a 15% to about a 60% increase, about a 15% to about a 40% increase, about a 15% to about a 30% increase, about a 15% to about a 20% increase, about a 20% to about a 5,000% increase, about a 20% to about a 4,000% increase, about a 20% to about a 3,000% increase, about a 20% to about a 2,000% increase, about a 20% to about a 1,000% increase, about a 20% to about a 800% increase, about a 20% to about a 600% increase, about a 20% to about a 500% increase, about a 20% to about a 400% increase, about a 20% to about a 300% increase, about a 20% to about a 200% increase, about a 20% to about a 180% increase, about a 20% to about a 160% increase, about a 20% to about a 140% increase, about a 20% to about a 120% increase, about a 20% to about a 100% increase, about a 20% to about a 80% increase, about a 20% to about a 60% increase, about a 20% to about a 40% increase, about a 20% to about a 30% increase, about a 30% to about a 5,000% increase, about a 30% to about a 4,000% increase, about a 30% to about a 3,000% increase, about a 30% to about a 2,000% increase, about a 30% to about a 1,000% increase, about a 30% to about a 800% increase, about a 30% to about a 600% increase, about a 30% to about a 500% increase, about a 30% to about a 400% increase, about a 30% to about a 300% increase, about a 30% to about a 200% increase, about a 30% to about a 180% increase, about a 30% to about a 160% increase, about a 30% to about a 140% increase, about a 30% to about a 120% increase, about a 30% to about a 100% increase, about a 30% to about a 80% increase, about a 30% to about a 60% increase, about a 30% to about a 40% increase, about a 40% to about a 5,000% increase, about a 40% to about a 4,000% increase, about a 40% to about a 3,000% increase, about a 40% to about a 2,000% increase, about a 40% to about a 1,000% increase, about a 40% to about a 800% increase, about a 40% to about a 600% increase, about a 40% to about a 500% increase, about a 40% to about a 400% increase, about a 40% to about a 300% increase, about a 40% to about a 200% increase, about a 40% to about a 180% increase, about a 40% to about a 160% increase, about a 40% to about a 140% increase, about a 40% to about a 120% increase, about a 40% to about a 100% increase, about a 40% to about a 80% increase, about a 40% to about a 60% increase, about a 60% to about a 5,000% increase, about a 60% to about a 4,000% increase, about a 60% to about a 3,000% increase, about a 60% to about a 2,000% increase, about a 60% to about a 1,000% increase, about a 60% to about a 800% increase, about a 60% to about a 600% increase, about a 60% to about a 500% increase, about a 60% to about a 400% increase, about a 60% to about a 300% increase, about a 60% to about a 200% increase, about a 60% to about a 180% increase, about a 60% to about a 160% increase, about a 60% to about a 140% increase, about a 60% to about a 120% increase, about a 60% to about a 100% increase, about a 60% to about a 80% increase, about a 80% to about a 5,000% increase, about a 80% to about a 4,000% increase, about a 80% to about a 3,000% increase, about a 80% to about a 2,000% increase, about a 80% to about a 1,000% increase, about a 80% to about a 800% increase, about a 80% to about a 600% increase, about a 80% to about a 500% increase, about a 80% to about a 400% increase, about a 80% to about a 300% increase, about a 80% to about a 200% increase, about a 80% to about a 180% increase, about a 80% to about a 160% increase, about a 80% to about a 140% increase, about a 80% to about a 120% increase, about a 80% to about a 100% increase, about a 100% to about a 5,000% increase, about a 100% to about a 4,000% increase, about a 100% to about a 3,000% increase, about a 100% to about a 2,000% increase, about a 100% to about a 1,000% increase, about a 100% to about a 800% increase, about a 100% to about a 600% increase, about a 100% to about a 500% increase, about a 100% to about a 400% increase, about a 100% to about a 300% increase, about a 100% to about a 200% increase, about a 100% to about a 180% increase, about a 100% to about a 160% increase, about a 100% to about a 140% increase, about a 100% to about a 120% increase, about a 120% to about a 5,000% increase, about a 120% to about a 4,000% increase, about a 120% to about a 3,000% increase, about a 120% to about a 2,000% increase, about a 120% to about a 1,000% increase, about a 120% to about a 800% increase, about a 120% to about a 600% increase, about a 120% to about a 500% increase, about a 120% to about a 400% increase, about a 120% to about a 300% increase, about a 120% to about a 200% increase, about a 120% to about a 180% increase, about a 120% to about a 160% increase, about a 120% to about a 140% increase, about a 140% to about a 5,000% increase, about a 140% to about a 4,000% increase, about a 140% to about a 3,000% increase, about a 140% to about a 2,000% increase, about a 140% to about a 1,000% increase, about a 140% to about a 800% increase, about a 140% to about a 600% increase, about a 140% to about a 500% increase, about a 140% to about a 400% increase, about a 140% to about a 300% increase, about a 140% to about a 200% increase, about a 140% to about a 180% increase, about a 140% to about a 160% increase, about a 160% to about a 5,000% increase, about a 160% to about a 4,000% increase, about a 160% to about a 3,000% increase, about a 160% to about a 2,000% increase, about a 160% to about a 1,000% increase, about a 160% to about a 800% increase, about a 160% to about a 600% increase, about a 160% to about a 500% increase, about a 160% to about a 400% increase, about a 160% to about a 300% increase, about a 160% to about a 200% increase, about a 160% to about a 180% increase, about a 180% to about a 5,000% increase, about a 180% to about a 4,000% increase, about a 180% to about a 3,000% increase, about a 180% to about a 2,000% increase, about a 180% to about a 1,000% increase, about a 180% to about a 800% increase, about a 180% to about a 600% increase, about a 180% to about a 500% increase, about a 180% to about a 400% increase, about a 180% to about a 300% increase, about a 180% to about a 200% increase, about a 200% to about a 5,000% increase, about a 200% to about a 4,000% increase, about a 200% to about a 3,000% increase, about a 200% to about a 2,000% increase, about a 200% to about a 1,000% increase, about a 200% to about a 800% increase, about a 200% to about a 600% increase, about a 200% to about a 500% increase, about a 200% to about a 400% increase, about a 200% to about a 300% increase, about a 300% to about a 5,000% increase, about a 300% to about a 4,000% increase, about a 300% to about a 3,000% increase, about a 300% to about a 2,000% increase, about a 300% to about a 1,000% increase, about a 300% to about a 800% increase, about a 300% to about a 600% increase, about a 300% to about a 500% increase, about a 300% to about a 400% increase, about a 400% to about a 5,000% increase, about a 400% to about a 4,000% increase, about a 400% to about a 3,000% increase, about a 400% to about a 2,000% increase, about a 400% to about a 1,000% increase, about a 400% to about a 800% increase, about a 400% to about a 600% increase, about a 400% to about a 500% increase, about a 500% to about a 5,000% increase, about a 500% to about a 4,000% increase, about a 500% to about a 3,000% increase, about a 500% to about a 2,000% increase, about a 500% to about a 1,000% increase, about a 500% to about a 800% increase, about a 500% to about a 600% increase, about a 600% to about a 5,000% increase, about a 600% to about a 4,000% increase, about a 600% to about a 3,000% increase, about a 600% to about a 2,000% increase, about a 600% to about a 1,000% increase, about a 600% to about a 800% increase, about a 800% to about a 5,000% increase, about a 800% to about a 4,000% increase, about a 800% to about a 3,000% increase, about a 800% to about a 2,000% increase, about a 800% to about a 1,000% increase, about a 1,000% to about a 5,000% increase, about a 1,000% to about a 4,000% increase, about a 1,000% to about a 3,000% increase, about a 1,000% to about a 2,000% increase, about a 2,000% to about a 5,000% increase, about a 2,000% to about a 4,000% increase, about a 2,000% to about a 3,000% increase, about a 3,000% to about a 5,000% increase, about a 3,000% to about a 4,000% increase, or about a 4,000% to about a 5,000% increase, in one or more of glycolysis, aerobic metabolism, oxidative phosphorylation, glucose consumption, and extracellular acidification rate (ECAR) as compared to the NK cell prior to performance of any of methods described herein (e.g., prior to contacting the NK cell with any of the exemplary first multi-chain chimeric polypeptides described herein).

In some embodiments of any of the methods described herein, the method results in, e.g., about a 5-fold to about a 5,000-fold, about a 5-fold to about a 4,500-fold, about a 5-fold to about a 4,000-fold, about a 5-fold to about a 3,500-fold, about a 5-fold to about a 3,000-fold, about a 5-fold to about a 2,500-fold, about a 5-fold to about a 2,000-fold, about a 5-fold to about a 1,500-fold, about a 5-fold to about a 1,000-fold, about a 5-fold to about a 800-fold, about a 5-fold to about a 600-fold, about a 5-fold to about a 500-fold, about a 5-fold to about 450-fold, about a 5-fold to about a 400-fold, about a 5-fold to about a 350-fold, about a 5-fold to about a 300-fold, about a 5-fold to about a 250-fold, about a 5-fold to about a 200-fold, about a 5-fold to about a 150-fold, about a 5-fold to about a 100-fold, about a 5-fold to about a 80-fold, about a 5-fold to about a 60-fold, about a 5-fold to about a 40-fold, about a 5-fold to about a 20-fold, about a 5-fold to about a 10-fold, about a 10-fold to about a 5,000-fold, about a 10-fold to about a 4,500-fold, about a 10-fold to about a 4,000-fold, about a 10-fold to about a 3,500-fold, about a to about a 3,000-fold, about a 10-fold to about a 2,500-fold, about a 10-fold to about a 2,000-fold, about a 10-fold to about a 1,500-fold, about a 10-fold to about a 1,000-fold, about a 10-fold to about a 800-fold, about a 10-fold to about a 600-fold, about a 10-fold to about a 500-fold, about a 10-fold to about 450-fold, about a 10-fold to about a 400-fold, about a 10-fold to about a 350-fold, about a 10-fold to about a 300-fold, about a 10-fold to about a 250-fold, about a 10-fold to about a 200-fold, about a 10-fold to about a 150-fold, about a 10-fold to about a 100-fold, about a 10-fold to about a 80-fold, about a 10-fold to about a 60-fold, about a 10-fold to about a 40-fold, about a 10-fold to about a 20-fold, about a 20-fold to about a 5,000-fold, about a 20-fold to about a 4,500-fold, about a 20-fold to about a 4,000-fold, about a 20-fold to about a 3,500-fold, about a 20-fold to about a 3,000-fold, about a 20-fold to about a 2,500-fold, about a 20-fold to about a 2,000-fold, about a 20-fold to about a 1,500-fold, about a 20-fold to about a 1,000-fold, about a 20-fold to about a 800-fold, about a 20-fold to about a 600-fold, about a 20-fold to about a 500-fold, about a 20-fold to about 450-fold, about a 20-fold to about a 400-fold, about a 20-fold to about a 350-fold, about a 20-fold to about a 300-fold, about a 20-fold to about a 250-fold, about a 20-fold to about a 200-fold, about a 20-fold to about a 150-fold, about a 20-fold to about a 100-fold, about a 20-fold to about a 80-fold, about a 20-fold to about a 60-fold, about a 20-fold to about a 40-fold, about a 40-fold to about a 5,000-fold, about a 40-fold to about a 4,500-fold, about a 40-fold to about a 4,000-fold, about a 40-fold to about a 3,500-fold, about a 40-fold to about a 3,000-fold, about a 40-fold to about a 2,500-fold, about a 40-fold to about a 2,000-fold, about a 40-fold to about a 1,500-fold, about a 40-fold to about a 1,000-fold, about a 40-fold to about a 800-fold, about a 40-fold to about a 600-fold, about a 40-fold to about a 500-fold, about a 40-fold to about 450-fold, about a 40-fold to about a 400-fold, about a 40-fold to about a 350-fold, about a 40-fold to about a 300-fold, about a 40-fold to about a 250-fold, about a 40-fold to about a 200-fold, about a 40-fold to about a 150-fold, about a 40-fold to about a 100-fold, about a 40-fold to about a 80-fold, about a 40-fold to about a 60-fold, about a 60-fold to about a 5,000-fold, about a 60-fold to about a 4,500-fold, about a 60-fold to about a 4,000-fold, about a 60-fold to about a 3,500-fold, about a 60-fold to about a 3,000-fold, about a 60-fold to about a 2,500-fold, about a 60-fold to about a 2,000-fold, about a 60-fold to about a 1,500-fold, about a 60-fold to about a 1,000-fold, about a 60-fold to about a 800-fold, about a 60-fold to about a 600-fold, about a 60-fold to about a 500-fold, about a 60-fold to about 450-fold, about a 60-fold to about a 400-fold, about a to about a 350-fold, about a 60-fold to about a 300-fold, about a 60-fold to about a 250-fold, about a 60-fold to about a 200-fold, about a 60-fold to about a 150-fold, about a 60-fold to about a 100-fold, about a 60-fold to about a 80-fold, about a 80-fold to about a 5,000-fold, about a 80-fold to about a 4,500-fold, about a 80-fold to about a 4,000-fold, about a 80-fold to about a 3,500-fold, about a 80-fold to about a 3,000-fold, about a 80-fold to about a 2,500-fold, about a 80-fold to about a 2,000-fold, about a 80-fold to about a 1,500-fold, about a 80-fold to about a 1,000-fold, about a 80-fold to about a 800-fold, about a 80-fold to about a 600-fold, about a 80-fold to about a 500-fold, about a 80-fold to about 450-fold, about a 80-fold to about a 400-fold, about a 80-fold to about a 350-fold, about a 80-fold to about a 300-fold, about a 80-fold to about a 250-fold, about a 80-fold to about a 200-fold, about a 80-fold to about a 150-fold, about a 80-fold to about a 100-fold, about a 100-fold to about a 5,000-fold, about a 100-fold to about a 4,500-fold, about a 100-fold to about a 4,000-fold, about a 100-fold to about a 3,500-fold, about a 100-fold to about a 3,000-fold, about a 100-fold to about a 2,500-fold, about a 100-fold to about a 2,000-fold, about a 100-fold to about a 1,500-fold, about a 100-fold to about a 1,000-fold, about a 100-fold to about a 800-fold, about a 100-fold to about a 600-fold, about a 100-fold to about a 500-fold, about a 100-fold to about 450-fold, about a 100-fold to about a 400-fold, about a 100-fold to about a 350-fold, about a 100-fold to about a 300-fold, about a 100-fold to about a 250-fold, about a 100-fold to about a 200-fold, about a 100-fold to about a 150-fold, about a 150-fold to about a 5,000-fold, about a 150-fold to about a 4,500-fold, about a 150-fold to about a 4,000-fold, about a 150-fold to about a 3,500-fold, about a 150-fold to about a 3,000-fold, about a 150-fold to about a 2,500-fold, about a 150-fold to about a 2,000-fold, about a 150-fold to about a 1,500-fold, about a 150-fold to about a 1,000-fold, about a 150-fold to about a 800-fold, about a 150-fold to about a 600-fold, about a 150-fold to about a 500-fold, about a 150-fold to about 450-fold, about a 150-fold to about a 400-fold, about a 150-fold to about a 350-fold, about a 150-fold to about a 300-fold, about a 150-fold to about a 250-fold, about a 150-fold to about a 200-fold, about a 200-fold to about a 5,000-fold, about a 200-fold to about a 4,500-fold, about a 200-fold to about a 4,000-fold, about a 200-fold to about a 3,500-fold, about a 200-fold to about a 3,000-fold, about a 200-fold to about a 2,500-fold, about a 200-fold to about a 2,000-fold, about a 200-fold to about a 1,500-fold, about a 200-fold to about a 1,000-fold, about a 200-fold to about a 800-fold, about a 200-fold to about a 600-fold, about a 200-fold to about a 500-fold, about a 200-fold to about 450-fold, about a 200-fold to about a 400-fold, about a 200-fold to about a 350-fold, about a 200-fold to about a 300-fold, about a 200-fold to about a 250-fold, about a 250-fold to about a 5,000-fold, about a 250-fold to about a 4,500-fold, about a 250-fold to about a 4,000-fold, about a 250-fold to about a 3,500-fold, about a 250-fold to about a 3,000-fold, about a 250-fold to about a 2,500-fold, about a 250-fold to about a 2,000-fold, about a 250-fold to about a 1,500-fold, about a 250-fold to about a 1,000-fold, about a 250-fold to about a 800-fold, about a 250-fold to about a 600-fold, about a 250-fold to about a 500-fold, about a 250-fold to about 450-fold, about a 250-fold to about a 400-fold, about a 250-fold to about a 350-fold, about a 250-fold to about a 300-fold, about a 300-fold to about a 5,000-fold, about a 300-fold to about a 4,500-fold, about a 300-fold to about a 4,000-fold, about a 300-fold to about a 3,500-fold, about a 300-fold to about a 3,000-fold, about a 300-fold to about a 2,500-fold, about a 300-fold to about a 2,000-fold, about a 300-fold to about a 1,500-fold, about a 300-fold to about a 1,000-fold, about a 300-fold to about a 800-fold, about a 300-fold to about a 600-fold, about a 300-fold to about a 500-fold, about a 300-fold to about 450-fold, about a 300-fold to about a 400-fold, about a 300-fold to about a 350-fold, about a 350-fold to about a 5,000-fold, about a 350-fold to about a 4,500-fold, about a 350-fold to about a 4,000-fold, about a 350-fold to about a 3,500-fold, about a 350-fold to about a 3,000-fold, about a 350-fold to about a 2,500-fold, about a 350-fold to about a 2,000-fold, about a 350-fold to about a 1,500-fold, about a 350-fold to about a 1,000-fold, about a 350-fold to about a 800-fold, about a 350-fold to about a 600-fold, about a 350-fold to about a 500-fold, about a 350-fold to about 450-fold, about a 350-fold to about a 400-fold, about a 400-fold to about a 5,000-fold, about a 400-fold to about a 4,500-fold, about a 400-fold to about a 4,000-fold, about a 400-fold to about a 3,500-fold, about a 400-fold to about a 3,000-fold, about a 400-fold to about a 2,500-fold, about a 400-fold to about a 2,000-fold, about a 400-fold to about a 1,500-fold, about a 400-fold to about a 1,000-fold, about a 400-fold to about a 800-fold, about a 400-fold to about a 600-fold, about a 400-fold to about a 500-fold, about a 400-fold to about 450-fold, about a 450-fold to about a 5,000-fold, about a 450-fold to about a 4,500-fold, about a 450-fold to about a 4,000-fold, about a 450-fold to about a 3,500-fold, about a 450-fold to about a 3,000-fold, about a 450-fold to about a 2,500-fold, about a 450-fold to about a 2,000-fold, about a 450-fold to about a 1,500-fold, about a 450-fold to about a 1,000-fold, about a 450-fold to about a 800-fold, about a 450-fold to about a 600-fold, about a 450-fold to about a 500-fold, about a 500-fold to about a 5,000-fold, about a 500-fold to about a 4,500-fold, about a 500-fold to about a 4,000-fold, about a 500-fold to about a 3,500-fold, about a 500-fold to about a 3,000-fold, about a 500-fold to about a 2,500-fold, about a 500-fold to about a 2,000-fold, about a 500-fold to about a 1,500-fold, about a 500-fold to about a 1,000-fold, about a 500-fold to about a 800-fold, about a 500-fold to about a 600-fold, about a 600-fold to about a 5,000-fold, about a 600-fold to about a 4,500-fold, about a 600-fold to about a 4,000-fold, about a 600-fold to about a 3,500-fold, about a 600-fold to about a 3,000-fold, about a 600-fold to about a 2,500-fold, about a 600-fold to about a 2,000-fold, about a 600-fold to about a 1,500-fold, about a 600-fold to about a 1,000-fold, about a 600-fold to about a 800-fold, about a 800-fold to about a 5,000-fold, about a 800-fold to about a 4,500-fold, about a 800-fold to about a 4,000-fold, about a 800-fold to about a 3,500-fold, about a 800-fold to about a 3,000-fold, about a 800-fold to about a 2,500-fold, about a 800-fold to about a 2,000-fold, about a 800-fold to about a 1,500-fold, about a 800-fold to about a 1,000-fold, about a 1,000-fold to about a 5,000-fold, about a 1,000-fold to about a 4,500-fold, about a 1,000-fold to about a 4,000-fold, about a 1,000-fold to about a 3,500-fold, about a 1,000-fold to about a 3,000-fold, about a 1,000-fold to about a 2,500-fold, about a 1,000-fold to about a 2,000-fold, about a 1,000-fold to about a 1,500-fold, about a 1,500-fold to about a 5,000-fold, about a 1,500-fold to about a 4,500-fold, about a 1,500-fold to about a 4,000-fold, about a 1,500-fold to about a 3,500-fold, about a 1,500-fold to about a 3,000-fold, about a 1,500-fold to about a 2,500-fold, about a 1,500-fold to about a 2,000-fold, about a 2,000-fold to about a 5,000-fold, about a 2,000-fold to about a 4,500-fold, about a 2,000-fold to about a 4,000-fold, about a 2,000-fold to about a 3,500-fold, about a 2,000-fold to about a 3,000-fold, about a 2,000-fold to about a 2,500-fold, about a 2,500-fold to about a 5,000-fold, about a 2,500-fold to about a 4,500-fold, about a 2,500-fold to about a 4,000-fold, about a 2,500-fold to about a 3,500-fold, about a 2,500-fold to about a 3,000-fold, about a 3,000-fold to about a 5,000-fold, about a 3,000-fold to about a 4,500-fold, about a 3,000-fold to about a 4,000-fold, about a 3,000-fold to about a 3,500-fold, about a 3,500-fold to about a 5,000-fold, about a 3,500-fold to about a 4,500-fold, about a 3,500-fold to about a 4,000-fold, about a 4,000-fold to about a about a 4,000-fold to about a 4,500-fold, or about a 4,500-fold to about a expansion in the number of viable NK cells as compared to the number of NK cells prior to the step of contacting the NK cells with any of the exemplary first multi-chain chimeric polypeptides described herein.

In some embodiments, the methods provide NK cells that have improved persistence and cytotoxicity against diseased cells in a subject as compared to untreated control NK cells.

Multi-Chain Chimeric Polypeptides

The methods described herein include the use of two different the multi-chain chimeric polypeptides.

The first multi-chain chimeric polypeptides provided herein include: (a) a first chimeric polypeptide including: a first target-binding domain; a soluble tissue factor domain; and a first domain of a pair of affinity domains; and (b) a second chimeric polypeptide including: a second domain of a pair of affinity domains; and a second target-binding domain, where the first chimeric polypeptide and the second chimeric polypeptide associate through the binding of the first domain and the second domain of the pair of affinity domains, and the first target-binding domain and the second target-binding domain each independently bind specifically to a receptor of IL-18 or a receptor of IL-12.

The second multi-chain chimeric polypeptides provided herein include: (a) first chimeric polypeptide including: a first target-binding domain, a linker domain, a first domain of a pair of affinity domains; and (b) a second chimeric polypeptide including a second domain of a pair of affinity domains, and a second target-binding domain, where the first chimeric polypeptide and the second chimeric polypeptide associate through the binding of the first domain and the second domain of the pair of affinity domains, and the first target-binding domain and the second target-binding domain each independently bind specifically to a receptor for IL-7 or a receptor for IL-21.

In some examples of any of the first and second multi-chain chimeric polypeptides described herein the total length of first chimeric polypeptide and/or the second chimeric polypeptide can each independently be about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids. Diagrams of exemplary first multi-chain chimeric polypeptides provided herein are depicted in FIGS. 1-4. Diagrams of exemplary second multi-chain chimeric polypeptides are depicted in FIG. 5-12.

In some embodiments of any of the first and second multi-chain chimeric polypeptides described herein, the first target-binding domain (e.g., any of the first target-binding domains described herein) and the linker domain (e.g., any of the exemplary linker domains described herein) directly abut each other in the first chimeric polypeptide. In some embodiments of any of the first and second multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the linker domain (e.g., any of the exemplary linker domains described herein) in the first chimeric polypeptide.

In some embodiments of any of the first and second multi-chain chimeric polypeptides described herein, the linker domain (e.g., any of the exemplary linker domains described herein) and the first domain of the pair of affinity domains (e.g., any of the exemplary first domains of any of the exemplary pairs of affinity domains described herein) directly abut each other in the first chimeric polypeptide. In some embodiments of any of the first and second multi-chain chimeric polypeptides described herein, the first chimeric polypeptide further comprises a linker sequence (e.g., any of the exemplary linker sequences described herein or known in the art) between the linker domain (e.g., any of the exemplary linker domains described herein) and the first domain of the pair of affinity domains (e.g., any of the exemplary first domains of any of the exemplary pairs of affinity domains described herein) in the first chimeric polypeptide.

In some embodiments of any of the first and second multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the first and second multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at $Ser^{253}$ and $Ser^{258}$, and one S-palmitoylation site at $Cys^{245}$. Deletion or mutation of the cytoplasmic domain was not found to affect tissue factor coagulation activity. Tissue factor has one S-palmitoylation site in the intracellular domain of the protein at $Cys^{245}$. The $Cys^{245}$ is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand βA and βB, βC and βD, and βE and βF, all of which are conserved in conformation in the two modules. There are three short α-helix segments connecting the β-strands. A unique feature of tissue is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue-FVIIa complex on phospholipid bilayer (i.e., upon exposure of phosphatidyl-L-serine on membrane surfaces) increases the rate of FIX or FX activation, in a Ca'-dependent manner, an additional 1,000-fold. The roughly million-fold overall increase in FX activation by tissue-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the $Ile^{-154}$-$Arg^{152}$ bond in the short linker region between the EGF2 and the protease domain. This cleavage results in the light and heavy chains being held together by a single disulfide bond of Cys 135 and $Cys^{262}$. FVIIa binds phospholipid membrane in a Ca'-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of $His^{193}$, $Asp^{242}$, and $Ser^{344}$, and binding of a single $Ca^{2+}$ ion within the FVIIa protease domain is critical for its catalytic activity. Proteolytic activation of FVII to FVIIa frees the newly formed amino terminus at $Ile^{153}$ to fold back and be inserted into the activation pocket forming a salt bridge with the carboxylate of $Asp^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues $Arg^{135}$ and $Phe^{140}$ located on the protruding B-C loop provide an independent contact with FVIIa. $Leu^{133}$ is located at the base of the fingerlike structure and packed into the cleft between the two modules. This provides continuity to a major cluster of important binding residues consisting of $Lys^{20}$, $Thr^{60}$, $Asp^{58}$, and $Ile^{22}$. $Thr^{60}$ is only partially solvent-exposed and may play a local structural role rather than making a significant contact with ligand. The binding site extends onto the concave side of the intermodule angle involving $Glu^{24}$ and $Gln_{110}$, and potentially the more distant residue $Val^{207}$. The binding region extends from $Asp^{58}$ onto a convex surface area formed by $Lys^{48}$, $Lys^{46}$, $Gln^{37}$, $Asp^{44}$, and $Trp^{45}$. $Trp^{45}$ and $Asp^{44}$ do not interact independently with FVIIa, indicating that the mutational effect at the $Trp^{45}$ position may reflect a structural importance of this side chain for the local packing of the adjacent $Asp^{44}$ and $Gln^{37}$ side chain. The interactive area further includes two surface-exposed aromatic residues, $Phe^{76}$ and $Tyr^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues $Lys^{165}$ and $Lys^{166}$ have also been demonstrated to be important for substrate recognition and binding. Mutation of either of these residues to alanine results in a significant decrease in the tissue factor co-factor function. $Lys^{165}$ and $Lys^{166}$ face away from each other, with $Lys^{165}$ pointing towards FVIIa in most tissue factor-FVIIa structures, and $Lys^{166}$ pointing into the substrate binding exosite region in the crystal structure. Putative salt bridge formation between $Lys^{165}$ of and $Gla^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Exemplary Linker Domains and IgG1 Antibody Constructs

In some examples of any of the methods, compositions, or kits described herein, the linker domain in the second multi-chain chimeric polypeptide can be or include any antigen that is recognized by a cognate IgG1 antibody (e.g., a monoclonal antibody). IgG1 antibodies are distinguished from other IgG classes of antibodies by their constant region, particularly in hinge regions and upper CH2 domains (see, e.g., Vadarsson et al., IgG Subclasses and Allotypes: From Structure to Effector Functions, Front Immunol., 5, Article 520, 2014). Human IgG1 is the only known IgG subclass which binds to human CD16a and activates the signaling of human CD16a.

Any of a variety of linker domains can be used in the second multi-chain chimeric polypeptides provided herein. In certain embodiments, a linker domain is recognized by an antibody (e.g., an IgG1 antibody) or antibody fragment. In some embodiments, the linker domain is a kappa light chain of an antibody that is recognized by a cognate anti-kappa light chain IgG1 antibody. In some embodiments, the linker domain is a lambda light chain of an antibody that is recognized by a cognate anti-lambda light chain human IgG1 antibody. A variety of kappa light chains and lambda light chains are known in the art (see, e.g., Smith et al., Antigen Nature and Complexity Influence Human Antibody Light Chain Usage and Specificity, Vaccine, 34(25): 2813-2820, 2016). In some embodiments, the linker domain is or comprises a human polypeptide (e.g., a human kappa light chain of an antibody or a human lambda light chain of an antibody) that is recognized by a cognate human IgG1 antibody (e.g., a monoclonal antibody). In some embodiments, the cognate human IgG1 antibody includes at least two antigen-binding domains, and each antigen-binding domain binds specifically to the linker domain. In some embodiments, the cognate human IgG1 antibody includes at least two antigen-binding domains, and only a subset (e.g., one) of the antigen-binding domains bind specifically to the linker domain in the second multi-chain chimeric polypeptide. In some embodiments, a linker domain can be any of the soluble tissue factor domains described herein.

In some embodiments of any of the methods, compositions, and kits described herein, an IgG1 antibody construct can be an IgG1 antibody (e.g., a monoclonal or a polyclonal IgG1 antibody that binds specifically to the linker domain). In some embodiments of any of the methods, compositions, and kits described herein, an IgG1 antibody construct can be an antibody or an antibody fragment that includes an IgG1 Fc region (e.g., a human IgG1 Fc region) and that binds specifically to the linker domain in the second multi-chain chimeric polypeptide. As is known in the art, the IgG1 Fc region binds to CD16a (FcRgammaIII) (e.g., human CD16a) and induces its intracellular signaling. In some embodiments, an IgG1 antibody construct can be a single chain or a multi-chain polypeptide that includes an Fc region that is capable of binding specifically to CD16a (FcRgammaIII) (e.g., human CD16a) and is capable of inducing its intracellular signaling in a natural killer cell (e.g., a human natural killer cell), and specifically binds to the linker domain. In some embodiments, an IgG1 antibody construct can be a single chain or a multi-chain polypeptide that includes an Fc region that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, or at least 99% identical) to a wildtype IgG1 Fc domain (e.g., a wildtype human IgG1 Fc domain, e.g., SEQ ID NO: 1) and is capable of binding specifically to CD16a (FcRgammaIII) (e.g., human CD16a), and is capable of inducing its intracellular signaling in a natural killer cell (e.g., a human natural killer cell), and specifically binds to the linker domain. In some embodiments of any of the methods, compositions, or kits described herein, the IgG1 antibody construct can be an antibody or antibody fragment that specifically binds to the linker domain and includes a non-IgG1 Fc region (e.g., an IgG2, IgG3, or IgG4 Fc region) that has been altered (e.g., by substituting 1, 2, 3, 4, 5, 6, 7, 8, 9, 10, 11, 12, 13, 14, 15, 16, 17, 18, 19, or 20 amino acids in the wildtype non-IgG1 Fc region) such that the non-IgG1 Fc region is capable of binding to CD16a (FcRgammaIII) (e.g., human CD16a) and inducing its intracellular signaling in a natural killer cell (e.g., a human natural killer cell). In some embodiments of any of the methods, compositions, or kits described herein, the IgG1 antibody construct binds specifically to the linker domain in the second multi-chain chimeric polypeptide and includes a non-human Fc region (e.g., a Fc region from a non-human antibody) that has been altered (e.g., by substituting 1, 2, 3, 4, 5, 6, 7, 8, 9, 10, 11, 12, 13, 14, 15, 16, 17, 18, 19, or 20 amino acids in the wildtype non-human Fc region) such that the non-human Fc region is capable of binding to human CD16a (human FcRgammaIII) and inducing its intracellular signaling in a natural killer cell (e.g., a human natural killer cell).

```
Wildtype Human IgG1 Fc Region
                                    (SEQ ID NO: 1)
PCPAPELLGGPSVFLFPPKPKDTIMISRTPEVTCVVVDVS

HEDPEVKENWYVDGVEVHNAKTKPREEQYNSTYRVVSVLT

VLHQDWLNGKEYKCKVSNKALPAPIEKTISKAKGQPREPQ

VYTLPPSRDELTKNQVSLTCLVKGFYPSDIAVEWESNGQP

ENNYKTTPPVLDSDGSFFLYSKLTVDKSRWQQGNVFSCSV

MHEALHNHYTQKSLSLSPGK

Wildtype Human IgG2 Fc Region
                                    (SEQ ID NO: 2)
APPVAGPSVELFPPKPKDTIMISRTPEVTCVVVDVSHEDP

EVQFNWYVDGVEVHNAKTKPREEQFNSTFRVVSVLIVVHO

DWINGKEYKCKVSNKGLPAPIEKTISKTKGQPREPQVYTI

PPSREEMTKNQVSLTCLVKGFYPSDISVEWESNGQPENNY

KTTPPMLDSDGSFFLYSKLTVDKSRWQQGNVFSCSVMHEA

LHNHYTQKSLSLSPGK

Wildtype Human IgG3 Fc Region
                                    (SEQ ID NO: 3)
APELLGGPSVFLFPPKPKDTIMISRTPEVTCVVVDVSHED

PEVQFKWYVDGVEVHNAKTKPREEQYNSTFRVVSVLTVLH

QDWINGKEYKCKVSNKALPAPIEKTISKTKGOPREPQVYT

LPPSREEMTKNQVSLTCLVKGFYPSDIAVEWESSGQPENN

YNTTPPMLDSDGSFFLYSKITVDKSRWQQGNIFSCSVMHE

ALHNRFTQKSLSLSPGK

Wildtype Human IgG4 Fc Region
                                    (SEQ ID NO: 4)
APEFLGGPSVFLFPPKPKDTLMISRTPEVTCVVVDVSQED

PEVQFNWYVDGVEVHNAKTKPREEQENSTYRVVSVLTVLH

QDWINGKEYKCKVSNKGLPSSIEKTISKAKGQPREPQVYT

IPPSQEEMTKNQVSLTCLVKGFYPSDIAVEWESNGQPENN

YKTTPPVLDSDGSFFLYSRLTVDKSRWQEGNVFSCSVMHE

ALHNHYTQKSLSLSLGK
```

In some embodiments, the linker domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Soluble Tissue Factor Domain

In some examples of any of the methods, compositions, or kits described herein, the linker domain can be a soluble tissue factor domain. In some embodiments, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

```
Exemplary Soluble Human Tissue Factor Domain
                                    (SEQ ID NO: 5)
SGTTNTVAAYNLTWKSTNFKTILEWEPKPVNQVYTVQIST

KSGDWKSKCFYTTDTECDLTDEIVKDVKQTYLARVFSYPA

GNVESTGSAGEPLYENSPEFTPYLETNLGQPTIQSFEQVG

TKVNVTVEDERTLVRRNNTFLSLRDVFGKDLIYTLYYWKS

SSSGKKTAKTNTNEFLIDVDKGENYCFSVQAVIPSRTVNR

KSTDSPVECMGQEKGEFRE

Exemplary Nucleic Acid Encoding Soluble
Human Tissue Factor Domain
                                    (SEQ ID NO: 6)
AGCGGCACAACCAACACAGTCGCTGCCTATAACCTCACTT

GGAAGAGCACCAACTTCAAAACCATCCTCGAATGGGAACC

CAAACCCGTTAACCAAGTTTACACCGTGCAGATCAGCACC

AAGTCCGGCGACTGGAAGTCCAAATGTTTCTATACCACCG
```

-continued

ACACCGAGTGCGATCTCACCGATGAGATCGTGAAAGATGT

GAAACAGACCTACCTCGCCCGGGTGTTTAGCTACCCCGCC

GGCAATGTGGAGAGCACTGGTTCCGCTGGCGAGCCTTTAT

ACGAGAACAGCCCCGAATTTACCCCTTACCTCGAGACCAA

TTTAGGACAGCCCACCATCCAAAGCTTTGAGCAAGTTGGC

ACAAAGGTGAATGTGACAGTGGAGGACGAGCGGACTTTAG

TGCGGCGGAACAACACCTTTCTCAGCCTCCGGGATGTGTT

CGGCAAAGATTTAATCTACACACTGTATTACTGGAAGTCC

TCTTCCTCCGGCAAGAAGACAGCTAAAACCAACACAAACG

AGTTTTTAATCGACGTGGATAAAGGCGAAAACTACTGTTT

CAGCGTGCAAGCTGTGATCCCCTCCCGGACCGTGAATAGG

AAAAGCACCGATAGCCCCGTTGAGTGCATGGGCCAAGAAA

AGGGCGAGTTCCGGGAG

Exemplary Soluble Mouse Tissue Factor Domain (SEQ ID NO: 7)

agipekafnltwistdfktilewqpkptnytytvqisdrs rnwknkcfsttdtecdltdeivkdvtwayeakvlsvprrn svhgdgdqlvihgeeppftnapkflpyrdtnlgqpviqqf eqdgrklnvvvkdsltlvrkngtfltlrqvfgkdlgyiit yrkgsstgkktnitntnefsidveegvsycffvqamifsr ktnqnspgsstvcteqwksflge Exemplary Soluble Rat Tissue Factor Domain (SEQ ID NO: 8)

Agtppgkafnltwistdfktilewqpkptnytytvqisdr srnwkykctgttdtecdltdeivkdvnwtyearvlsvpwi nsthgketlfgthgeeppftnarkflpyrdtkigqpviqk yeqggtklkvtvkdsftlvrkngtfltlrqvfgndlgyil tyrkdsstgrktntthtneflidvekgvsycffaqavifs rktnhkspesitkcteqwksvlge Exemplary Mutant Soluble Human Tissue Factor Domain (SEQ ID NO: 9)

SGTTNTVAAYNLTWKSTNFATALEWEPKPVNQVYTVQIST

KSGDWKSKCFYTTDTECALTDEIVKDVKQTYLARVFSYPA

GNVESTGSAGEPLYENSPEFTPYLETNLGQPTIQSFEQVG

TKVNVTVEDERTLVARNNTALSLRDVFGKDLIYTLYYWKS

SSSGKKTAKTNTNEFLIDVDKGENYCFSVQAVIPSRTVNR

KSTDSPVECMGQEKGEFRE

Exemplary Mutant Soluble Human Tissue Factor Domain (SEQ ID NO: 10)

SGTTNTVAAYNLTWKSTNFATALEWEPKPVNQVYTVQIST

KSGDAKSKCFYTTDTECALTDEIVKDVKQTYLARVFSYPA

GNVESTGSAGEPLAENSPEFTPYLETNLGQPTIQSFEQVG

TKVNVTVEDERTLVARNNTALSLRDVFGKDLIYTLYYWKS

-continued

SSSGKKTAKTNTNEFLIDVDKGENYCFSVQAVIPSRTVNR

KSTDSPVECMGQEKGEFRE

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 5, 7, 8, 9, or 10. In some embodiments, a soluble tissue factor domain can include a sequence of SEQ ID NO: 5, 7, 8, 9, or 10 with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As will be appreciated by those of skill in the art, mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples, the soluble tissue factor domain is not capable of binding to Factor VIIa. In some examples, the soluble tissue factor domain does not convert inactive Factor X into Factor Xa. In some embodiments, the single-chain chimeric polypeptide does not stimulate blood coagulation in a mammal.

In some examples, the soluble tissue domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 9 or SEQ ID NO: 10.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 6.

In some embodiments, the soluble tissue factor domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Linker Sequences

In some embodiments, the linker sequence can be a flexible linker sequence. Non-limiting examples of linker sequences that can be used are described in Klein et al., Protein Engineering, Design & Selection Vol. 27, No. 10, pp. 325-330, 2014; Priyanka et al., Protein Sci., 2013 February; 22(2):153-167. In some examples, the linker sequence is a synthetic linker sequence.

In some embodiments of any of the multi-chain chimeric polypeptides described herein, the first and/or second polypeptide(s) can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker sequence is rich in glycine (Gly or G) residues. In some embodiments, the linker sequence is rich in serine (Ser or S) residues. In some embodiments, the linker sequence is rich in glycine and serine residues. In some embodiments, the linker sequence has one or more glycine-serine residue pairs (GS), e.g., 1, 2, 3, 4, 5, 6, 7, 8, 9, or 10 or more GS pairs. In some embodiments, the linker sequence has one or more Gly-Gly-Gly-Ser (GGGS) sequences, e.g., 1, 2, 3, 4, 5, 6, 7, 8, 9, or 10 or more GGGS sequences. In some embodiments, the linker sequence has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker sequence has one or more Gly-Gly-Ser-Gly (GGSG) sequences, e.g., 1, 2, 3, 4, 5, 6, 7, 8, 9, or 10 or more GGSG sequences.

In some embodiments, the linker sequence can comprise or consist of GGGGSGGGGSGGGGS (SEQ ID NO: 11). In some embodiments, the linker sequence can be encoded by a nucleic acid comprising or consisting of: GGCGGTGGAGGATCCGGAGGAGGTGGCTCCGGCGGCGGAGGATCT (SEQ ID NO: 12). In some embodiments, the linker sequence can comprise or consist of:

```
                    (SEQ ID NO: 13)
GGGSGGGS.
```

Target-Binding Domains

In some embodiments of any of the first multi-chain chimeric polypeptides or any of the second multi-chain chimeric polypeptides described herein, the first and second target-binding domains can be an antigen-binding domain (e.g., any of the exemplary antigen-binding domains described herein or known in the art, e.g., an agonistic antigen-binding domain), or a soluble interleukin or cytokine protein (e.g., any of the exemplary soluble interleukin proteins or soluble cytokine proteins described herein or known in the art).

In some embodiments of any of the first multi-chain chimeric polypeptides described herein, the first target-binding domain and the second target-binding domain each independently bind specifically to a receptor of IL-18 and a receptor of IL-12.

In some embodiments of any of the second multi-chain chimeric polypeptides described herein, the first target-binding domain and the second target-binding domain each independently bind specifically to a receptor of IL-7 and a receptor of IL-21.

In some embodiments of any of the first multi-chain chimeric polypeptides or any of the second multi-chain chimeric polypeptides described herein, the first target-binding domain and/or the second target-binding domain can be a soluble interleukin or soluble cytokine protein. In some examples, the soluble interleukin or soluble cytokine protein is selected from the group of: IL-7, IL-12, IL-18, and IL-21.

In some embodiments of any of the first multi-chain chimeric polypeptides or any of the second multi-chain chimeric polypeptides described herein, the first and second target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids, about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids, about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to its target with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the antigen-binding protein constructs provided herein can bind to an identifying antigen with a $K_D$ of about $1\times10^{-3}$ M to about $1\times10^{-5}$ M, about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 30 nM, about 5 pM to about nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about pM, about 20 pM to about 70 pM, about 20 pM to about 60 pM, about 20 pM to about pM, about 20 pM to about 40 pM, about 20 pM to about 30 pM, about 30 pM to about nM, about 30 pM to about 25 nM, about 30 pM to about 30 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about pM, about 30 pM to about 80 pM, about 30 pM to about 70 pM, about 30 pM to about pM, about 30 pM to about 50 pM, about 30 pM to about 40 pM, about 40 pM to about nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about pM, about 40 pM to about 80 pM, about 40 pM to about 70 pM, about 40 pM to about pM, about 40 pM to about 50 pM, about 50 pM to about 30 nM, about 50 pM to about 25 nM, about 50 pM to about 30 nM, about 50 pM to about 15 nM, about 50 pM to about nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about pM, about 50 pM to about 70 pM, about 50 pM to about 60 pM, about 60 pM to about 30 nM, about 60 pM to about 25 nM, about 60 pM to about 30 nM, about 60 pM to about nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about pM, about 60 pM to about 80 pM, about 60 pM to about 70 pM, about 70 pM to about nM, about 70 pM to about 25 nM, about 70 pM to about 30 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about pM, about 70 pM to about 80 pM, about 80 pM to about 30 nM, about 80 pM to about nM, about 80 pM to about 30 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about nM, about 90 pM to about 25 nM, about 90 pM to about 30 nM, about 90 pM to about nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about 30 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 30 nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about 20 nM to about 30 nM, and about 20 nM to about 25 nM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the target-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the first multi-chain chimeric polypeptides and/or any of the second multi-chain chimeric polypeptides described herein, one or both of the first target-binding domain and the second target-binding domain can be an antigen-binding domain. In some embodiments of any of the first multi-chain chimeric polypeptides or any of the second multi-chain chimeric polypeptides described herein, the first target-binding domain and the second target-binding domain can each be an antigen-binding domain. In some embodiments of any of the first multi-chain chimeric polypeptides and/or any of the second multi-chain chimeric polypeptides described herein, the first target-binding domain and the second target-binding domain can bind specifically to different antigens. In some embodiments, the first target-binding domain and/or the second target-binding domain can be an agonistic antigen-binding domain.

In some embodiments of any of the first multi-chain chimeric polypeptides or any of the second multi-chain chimeric polypeptides described herein, the antigen-binding domain can include or is a scFv or a single domain antibody (e.g., a VHH or a VNAR domain). The antigen-binding domain present in any of the multi-chain polypeptides described herein are each independently selected from the group of: a VHH domain, a VNAR domain, and a scFv. In some examples, an antigen-binding domain (e.g., any of the antigen-binding domain described herein) can bind specifically to a receptor of IL-7, a receptor of IL-12, a receptor of IL-18, or a receptor for IL-21.

In some embodiments, any of the antigen-binding domains described herein is a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the multi-chain chimeric polypeptides (e.g., a first multi-chain chimeric polypeptide and a second multi-chain chimeric polypeptide) described herein are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments of any of the first multi-chain chimeric polypeptides described herein, the first target-binding domain and the second target-binding domain are both VHH domains, or at least one antigen-binding domain is a VHH domain. In some embodiments of any of the first multi-chain chimeric polypeptides described herein, the first target-binding domain and the second target-binding domain are both VNAR domains, or at least one antigen-binding domain is a VNAR domain. In some embodiments of any of the first multi-chain chimeric polypeptides described herein, the first target-binding domain and the second target-binding domain are both scFv domains, or at least one antigen-binding domain is a scFv domain.

In some embodiments of any of the second multi-chain chimeric polypeptides described herein, the first target-binding domain and the second target-binding domain are both VHH domains, or at least one antigen-binding domain is a VHH domain. In some embodiments of any of the second multi-chain chimeric polypeptides described herein, the first target-binding domain and the second target-binding domain are both VNAR domains, or at least one antigen-binding domain is a VNAR domain. In some embodiments of any of the second multi-chain chimeric polypeptides described herein, the first target-binding domain and the second target-binding domain are both scFv domains, or at least one antigen-binding domain is a scFv domain. DARTs are described in, e.g., Garber, *Nature Reviews Drug Discovery* 13:799-801, 2014.

In some embodiments of any of the antigen-binding domains described herein, the antigen-binding domain can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the first multi-chain chimeric polypeptides and/or the second multi-chain chimeric polypeptides described herein, one or both of the first target-binding domain and the second target-binding domain can be a soluble interleukin protein or soluble cytokine protein. In some embodiments, the soluble interleukin or soluble cytokine protein is selected from the group of: IL-7, IL-12, IL-18, and IL-21. Non-limiting examples of soluble IL-7, IL-12. IL-18, and IL-21 are provided below.

Human Soluble IL-12β (p40)

(SEQ ID NO: 14)

IWELKKDVYVVELDWYPDAPGEMVVLTCDTPEEDGITWTL

DQSSEVLGSGKTLTIQVKEFGDAGQYTCHKGGEVLSHSLL

LLHKKEDGIWSTDILKDQKEPKNKTFLRCEAKNYSGRFTC

-continued

WWLTTISTDLTFSVKSSRGSSDPQGVTCGAATLSAERVRG

DNKEYEYSVECQEDSACPAAEESLPIEVMVDAVHKLKYEN

YTSSFFIRDIIKPDPPKNLQLKPLKNSRQVEVSWEYPDTW

STPHSYFSLTFCVQVQGKSKREKKDRVFTDKTSATVICRK

NASISVRAQDRYYSSSWSEWASVPCS

Nucleic Acid Encoding Human Soluble IL-12β (p40)

(SEQ ID NO: 15)

ATTTGGGAACTGAAGAAGGACGTCTACGTGGTCGAACTGG

ACTGGTATCCCGATGCTCCCGGCGAAATGGTGGTGCTCAC

TTGTGACACCCCCGAAGAAGACGGCATCACTTGGACCCTC

GATCAGAGCAGCGAGGTGCTGGGCTCCGGAAAGACCCTCA

CAATCCAAGTTAAGGAGTTCGGAGACGCTGGCCAATACAC

ATGCCACAAGGGAGGCGAGGTGCTCAGCCATTCCTTATTA

TTATTACACAAGAAGGAAGACGGAATCTGGTCCACCGACA

TTTTAAAAGATCAGAAGGAGCCCAAGAATAAGACCTTTTT

AAGGTGTGAGGCCAAAAACTACAGCGGTCGTTTCACTTGT

TGGTGGCTGACCACCATTTCCACCGATTTAACCTTCTCCG

TGAAAAGCAGCCGGGGAAGCTCCGACCCTCAAGGTGTGAC

ATGTGGAGCCGCTACCCTCAGCGCTGAGAGGGTTCGTGGC

GATAACAAGGAATACGAGTACAGCGTGGAGTGCCAAGAAG

ATAGCGCTTGTCCCGCTGCCGAAGAATCTTTACCCATTGA

GGTGATGGTGGACGCCGTGCACAAACTCAAGTACGAGAAC

TACACCTCCTCCTTCTTTATCCGGGACATCATTAAGCCCG

ATCCTCCTAAGAATTTACAGCTGAAGCCTCTCAAAAATAG

CCGGCAAGTTGAGGTCTCTTGGGAATATCCCGACACTTGG

AGCACACCCCACAGCTACTTCTCTTTAACCTTTTGTGTGC

AAGTTCAAGGTAAAAGCAAGCGGGAGAAGAAAGACCGGGT

GTTTACCGACAAAACCAGCGCCACCGTCATCTGTCGGAAG

AACGCCTCCATCAGCGTGAGGGCTCAAGATCGTTATTACT

CCAGCAGCTGGTCCGAGTGGGCCAGCGTGCCTTGTTCC

Human Soluble IL-12α (p35)

(SEQ ID NO: 16)

RNLPVATPDPGMFPCLHHSQNLLRAVSNMLQKARQTLEFY

PCTSEEIDHEDITKDKTSTVEACLPLELTKNESCLNSRET

SFITNGSCLASRKTSFMMALCLSSIYEDLKMYQVEFKTMN

AKLLMDPKRQIFLDQNMLAVIDELMQALNFNSETVPQKSS

LEEPDFYKTKIKLCILLHAFRIRAVTIDRVMSYLNAS

Nucleic Acid Encoding Human Soluble IL-12α (p35)

(SEQ ID NO: 17)

CGTAACCTCCCCGTGGCTACCCCCGATCCCGGAATGTTCC

CTTGTTTACACCACAGCCAGAATTTACTGAGGGCCGTGAG

CAACATGCTGCAGAAAGCTAGGCAGACTTTAGAATTTTAC

CCTTGCACCAGCGAGGAGATCGACCATGAAGATATCACCA

-continued

AGGACAAGACATCCACCGTGGAGGCTTGTTTACCTCTGGA
GCTGACAAAGAACGAGTCTTGTCTCAACTCTCGTGAAACC
AGCTTCATCACAAATGGCTCTTGTTTAGCTTCCCGGAAGA
CCTCCTTTATGATGGCTTTATGCCTCAGCTCCATCTACGA
GGATTTAAAGATGTACCAAGTGGAGTTCAAGACCATGAAC
GCCAAGCTGCTCATGGACCCTAAACGGCAGATCTTTTTAG
ACCAGAACATGCTGGCTGTGATTGATGAGCTGATGCAAGC
TTTAAACTTCAACTCCGAGACCGTCCCTCAGAAGTCCTCC
CTCGAGGAGCCCGATTTTTACAAGACAAAGATCAAACTGT
GCATTTTACTCCACGCCTTTAGGATCCGGGCCGTGACCAT
TGACCGGGTCATGAGCTATTTAAACGCCAGC

Exemplary Human Soluble IL-12

(SEQ ID NO: 18)

IWELKKDVYVVELDWYPDAPGEMVVLTCDTPEEDGITWTL
DQSSEVLGSGKTLTIQVKEFGDAGQYTCHKGGEVLSHSLL
LLHKKEDGIWSTDILKDQKEPKNKTFLRCEAKNYSGRFTC
WWLTTISTDLTFSVKSSRGSSDPQGVTCGAATLSAERVRG
DNKEYEYSVECQEDSACPAAEESLPIEVMVDAVHKLKYEN
YTSSFFIRDIIKPDPPKNLQLKPLKNSRQVEVSWEYPDTW
STPHSYFSLTFCVQVQGKSKREKKDRVFTDKTSATVICRK
NASISVRAQDRYYSSSWSEWASVPCSGGGGSGGGGSGGGG
SRNLPVATPDPGMFPCLHHSQNLLRAVSNMLQKARQTLEF
YPCTSEEIDHEDITKDKTSTVEACLPLELTKNESCLNSRE
TSFITNGSCLASRKTSFMMALCLSSIYEDLKMYQVEFKTM
NAKLLMDPKRQIFLDQNMLAVIDELMQALNFNSETVPQKS
SLEEPDFYKTKIKLCILLHAFRIRAVTIDRVMSYLNAS

Nucleic Acid Encoding Exemplary Human Soluble IL-12

(SEQ ID NO: 19)

ATTTGGGAACTGAAGAAGGACGTCTACGTGGTCGAACTGG
ACTGGTATCCCGATGCTCCCGGCGAAATGGTGGTGCTCAC
TTGTGACACCCCCGAAGAAGACGGCATCACTTGGACCCTC
GATCAGAGCAGCGAGGTGCTGGGCTCCGGAAAGACCCTCA
CAATCCAAGTTAAGGAGTTCGGAGACGCTGGCCAATACAC
ATGCCACAAGGGAGGCGAGGTGCTCAGCCATTCCTTATTA
TTATTACACAAGAAGGAAGACGGAATCTGGTCCACCGACA
TTTTAAAAGATCAGAAGGAGCCCAAGAATAAGACCTTTTT
AAGGTGTGAGGCCAAAAACTACAGCGGTCGTTTCACTTGT
TGGTGGCTGACCACCATTTCCACCGATTTAACCTTCTCCG
TGAAAAGCAGCCGGGGAAGCTCCGACCCTCAAGGTGTGAC
ATGTGGAGCCGCTACCCTCAGCGCTGAGAGGGTTCGTGGC
GATAACAAGGAATACGAGTACAGCGTGGAGTGCCAAGAAG
ATAGCGCTTGTCCCGCTGCCGAAGAATCTTTACCCATTGA

-continued

GGTGATGGTGGACGCCGTGCACAAACTCAAGTACGAGAAC
TACACCTCCTCCTTCTTTATCCGGGACATCATTAAGCCCG
ATCCTCCTAAGAATTTACAGCTGAAGCCTCTCAAAAATAG
CCGGCAAGTTGAGGTCTCTTGGGAATATCCCGACACTTGG
AGCACACCCCACAGCTACTTCTCTTTAACCTTTTGTGTGC
AAGTTCAAGGTAAAAGCAAGCGGGAGAAGAAAGACCGGGT
GTTTACCGACAAAACCAGCGCCACCGTCATCTGTCGGAAG
AACGCCTCCATCAGCGTGAGGGCTCAAGATCGTTATTACT
CCAGCAGCTGGTCCGAGTGGGCCAGCGTGCCTTGTTCCGG
CGGTGGAGGATCCGGAGGAGGTGGCTCCGGCGGCGGAGGA
TCTCGTAACCTCCCCGTGGCTACCCCCGATCCCGGAATGT
TCCCTTGTTTACACCACAGCCAGAATTTACTGAGGGCCGT
GAGCAACATGCTGCAGAAAGCTAGGCAGACTTTAGAATTT
TACCCTTGCACCAGCGAGGAGATCGACCATGAAGATATCA
CCAAGGACAAGACATCCACCGTGGAGGCTTGTTTACCTCT
GGAGCTGACAAAGAACGAGTCTTGTCTCAACTCTCGTGAA
ACCAGCTTCATCACAAATGGCTCTTGTTTAGCTTCCCGGA
AGACCTCCTTTATGATGGCTTTATGCCTCAGCTCCATCTA
CGAGGATTTAAAGATGTACCAAGTGGAGTTCAAGACCATG
AACGCCAAGCTGCTCATGGACCCTAAACGGCAGATCTTTT
TAGACCAGAACATGCTGGCTGTGATTGATGAGCTGATGCA
AGCTTTAAACTTCAACTCCGAGACCGTCCCTCAGAAGTCC
TCCCTCGAGGAGCCCGATTTTTACAAGACAAAGATCAAAC
TGTGCATTTTACTCCACGCCTTTAGGATCCGGGCCGTGAC
CATTGACCGGGTCATGAGCTATTTAAACGCCAGC

Human Soluble IL-18

(SEQ ID NO: 20)

YFGKLESKLSVIRNLNDQVLFIDQGNRPLFEDMTDSDCRD
NAPRTIFIISMYKDSQPRGMAVTISVKCEKISTLSCENKI
ISFKEMNPPDNIKDTKSDIIFFQRSVPGHDNKMQFESSSY
EGYFLACEKERDLFKLILKKEDELGDRSIMFTVQNED

Nucleic Acid Encoding Human Soluble IL-18

(SEQ ID NO: 21)

TACTTCGGCAAACTGGAATCCAAGCTGAGCGTGATCCGGA
ATTTAAACGACCAAGTTCTGTTTATCGATCAAGGTAACCG
GCCTCTGTTCGAGGACATGACCGACTCCGATTGCCGGGAC
AATGCCCCCCGGACCATCTTCATTATCTCCATGTACAAGG
ACAGCCAGCCCCGGGGCATGGCTGTGACAATTAGCGTGAA
GTGTGAGAAAATCAGCACTTTATCTTGTGAGAACAAGATC
ATCTCCTTTAAGGAAATGAACCCCCCCGATAACATCAAGG
ACACCAAGTCCGATATCATCTTCTTCCAGCGGTCCGTGCC
CGGTCACGATAACAAGATGCAGTTCGAATCCTCCTCCTAC

-continued

```
GAGGGCTACTTTTTAGCTTGTGAAAAGGAGAGGGATTTAT

TCAAGCTGATCCTCAAGAAGGAGGACGAGCTGGGCGATCG

TTCCATCATGTTCACCGTCCAAAACGAGGAT
```

In some embodiments, a soluble IL-12 protein can include a first sequence that is at least 70% identical (e.g., at least 75% identical, at least 80% identical, at least 85% identical, at least 90% identical, at least 95% identical, at least 99% identical, or 100% identical) to SEQ ID NO: 14, and a second sequence that is at least 70% identical (e.g., at least 75% identical, at least 80% identical, at least 85% identical, at least 90% identical, at least 95% identical, at least 99% identical, or 100% identical) to SEQ ID NO: 16. In some embodiments, the soluble IL-12 can further include a linker sequence (e.g., any of the exemplary linker sequences described herein or known in the art) between the first sequence and the second sequence.

In some embodiments, a soluble IL-12 protein is encoded by a first nucleic acid encoding a first sequence at least 70% identical (e.g., at least 75% identical, at least 80% identical, at least 85% identical, at least 90% identical, at least 95% identical, at least 99% identical, or 100% identical) to SEQ ID NO: 15, and a second nucleic acid sequence encoding a second sequence that is at least 70% identical (e.g., at least 75% identical, at least 80% identical, at least 85% identical, at least 90% identical, at least 95% identical, at least 99% identical, or 100% identical) to SEQ ID NO: 17. In some embodiments, the nucleic acid encoding a soluble IL-12 protein further includes a nucleic acid sequence encoding a linker sequence (e.g., any of the exemplary linker sequences described herein or known in the art) between the first nucleic acid and the second nucleic acid.

In some embodiments, a soluble IL-12 protein includes a sequence that is at least 70% identical (e.g., at least 75% identical, at least 80% identical, at least 85% identical, at least 90% identical, at least 95% identical, at least 99% identical, or 100% identical) to SEQ ID NO: 18. In some embodiments, a soluble IL-12 protein is encoded by a nucleic acid including a sequence at least 70% identical (e.g., at least 75% identical, at least 80% identical, at least 85% identical, at least 90% identical, at least 95% identical, at least 99% identical, or 100% identical) to SEQ ID NO: 19.

In some embodiments, a soluble IL-18 protein can include a sequence that is at least 70% identical (e.g., at least 75% identical, at least 80% identical, at least 85% identical, at least 90% identical, at least 95% identical, at least 99% identical, or 100% identical) to SEQ ID NO: 20. In some embodiments, a soluble IL-18 protein is encoded by a nucleic acid including a sequence at least 70% identical (e.g., at least 75% identical, at least 80% identical, at least 85% identical, at least 90% identical, at least 95% identical, at least 99% identical, or 100% identical) to SEQ ID NO: 21.

In some embodiments of any of the multi-chain chimeric polypeptides described herein, one or both of the first target-binding domain and the second target-binding domain can be a soluble IL-21 (e.g., a soluble human IL-21). For example, one or both of the first target-binding domain and the second target-binding domain can be a human soluble IL-21 including an amino acid sequence of QGQDRH-MIRMRQLIDIVDQLKNYVNDLVPEFLPAPED-VETNCEWSAFSCFQKAQ LKSANTGNNERIINVSIK-KLKRKPPSTNAGRRQKHRLTCPSCDSYEKKP-PKEFLER FKSLLQKMIHQHLSSRTHGSEDS (SEQ ID NO: 22). In some embodiments, one or both of the first target-binding domain and the second target-binding domain can include a sequence that is at least 80%, at least 85%, at least 90%, at least 95%, at least 96%, at least 97%, at least 98%, or at least 99% identical to SEQ ID NO: 22.

In some embodiments of any of the multi-chain chimeric polypeptides described herein, one or both of the first target-binding domain and the second target-binding domain can be a soluble IL-7 (a soluble human IL-7). For example, one or both of the first target-binding domain and the second target-binding domain can be a human IL-7 including an amino acid sequence of DCDI-EGKDGKQYESVLMVSIDQLLDSMKEIGSN-CLNNEFNFFKRHICDANKEGM FLFRAARKLRQFLKMNSTGDFDLHLLKVSEGT-TILLNCTGQVKGRKPAALGEAQ PTKSLEENKSLKEQKKLNDLCFLKRLLQEIKTCW-NKILMGTKEH (SEQ ID NO: 23). In some embodiments, one or both of the first target-binding domain and the second target-binding domain can include a sequence that is at least 80%, at least 85%, at least 90%, at least 95%, at least 96%, at least 97%, at least 98%, or at least 99% identical to SEQ ID NO: 23.

Additional examples of soluble interleukin proteins and soluble cytokine proteins are known in the art.

Pairs of Affinity Domains

The first and second multi-chain chimeric polypeptides include: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of an IL-15 receptor (IL15Rα) (e.g., a human IL-15 receptor (IL15Rα)) and a soluble IL-15 (e.g., a human soluble IL-15). A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL15 has a D8N or D8A amino acid substitution. In some embodiments in which one member of the pair of affinity domains is an alpha chain of human IL-15 receptor (IL15Rα), the human IL15Rα is a mature full-length IL15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA.* 103:6841-6846, 2006; Sharkey et al., *Cancer Res.* 68:5282-5290, 2008; Rossi et al., *Trends Pharmacol Sci.* 33:474-481, 2012) or SNARE modules based on interactions of the proteins syntaxin, synaptotagmin, synaptobrevin, and SNAP25 (Deyev et al., *Nat Biotechnol.* 1486-1492, 2003).

In some embodiments, a first chimeric polypeptide of a first and second multi-chain chimeric polypeptide includes a first domain of a pair of affinity domains and a second chimeric polypeptide of the first and second multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the first domain of the pair of affinity domains and the second domain of the pair of affinity domains bind to each other with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, about $1\times10^{-9}$ M to about $1\times10^{-11}$ M, about $1\times10^{-10}$ M to about $1\times10^{-12}$ M, about $1\times10^{-11}$ M to about $1\times10^{-13}$ M, about $1\times10^{-4}$ M to about $1\times10^{-5}$ M, about $1\times10^{-5}$ M to about $1\times10^{-6}$ M, about $1\times10^{-6}$ M to about $1\times10^{-7}$ M, about $1\times10^{-7}$ M to about $1\times10^{-8}$ M, about $1\times10^{-8}$ M to about $1\times10^{-9}$ M, about $1\times10^{-9}$ M to about $1\times10^{-10}$ M, about $1\times10^{-10}$ M to about $1\times10^{-11}$ M, about $1\times10^{-11}$ M to about $1\times10^{-12}$ M, or about $1\times10^{-12}$ M to about $1\times10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a first and second multi-chain chimeric polypeptides includes a first domain of a pair of affinity domains and a second chimeric polypeptide of the first and second multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about to 80 amino acids in length, about 40 to 70 amino acids in length, about 50 to 60 amino acids in length, or any range in between. In some embodiments, a first domain of a pair of affinity domains, a second domain of a pair of affinity domains, or both is about 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL15Rα).

A non-limiting example of a sushi domain from an alpha chain of IL-15 receptor alpha (IL15Rα) can include a sequence that is at least 70% identical, at least 75% identical, at least 80% identical, at least 85% identical, at least 90% identical, at least 95% identical, at least 99% identical, or 100% identical to ITCPPPMSVEHADIWVKSYSLYSR-ERYICNSGFKRKAGTSSLTECVLNKATNVAH WTTPSLKCIR (SEQ ID NO: 24). In some embodiments, a sushi domain from an alpha chain of IL15Rα can be encoded by a nucleic acid including

```
                                    (SEQ ID NO: 25)
ATTACATGCCCCCCTCCCATGAGCGTGGAGCACGCCGACA

TCTGGGTGAAGAGCTATAGCCTCTACAGCCGGGAGAGGTA

TATCTGTAACAGCGGCTTCAAGAGGAAGGCCGGCACCAGC

AGCCTCACCGAGTGCGTGCTGAATAAGGCTACCAACGTGG

CTCACTGGACAACACCCTCTTTAAAGTGCATCCGG.
```

In some embodiments, a soluble IL-15 can include a sequence that is at least 70% identical, at least 75% identical, at least 80% identical, at least 85% identical, at least 90% identical, at least 95% identical, at least 99% identical, or 100% identical to NWVNVISDLKKIEDLIQSMIIIDAT-LYTESDVHPSCKVTAMKCFLLELQVISLESGD ASIHDTVENLIILANNSLSSNGNVTESGCKE-CEELEEKNIKEFLQSFVHIVQMFINTS (SEQ ID NO: 26). In some embodiments, a soluble IL-15 can be encoded by a nucleic acid including the sequence of

```
                                    (SEQ ID NO: 27)
AACTGGGTGAACGTCATCAGCGATTTAAAGAAGATCGAAG

ATTTAATTCAGTCCATGCATATCGACGCCACTTTATACAC

AGAATCCGACGTGCACCCCTCTTGTAAGGTGACCGCCATG

AAATGTTTTTTACTGGAGCTGCAAGTTATCTCTTTAGAGA

GCGGAGACGCTAGCATCCACGACACCGTGGAGAATTTAAT

CATTTTAGCCAATAACTCTTTATCCAGCAACGGCAACGTG
```

-continued

```
ACAGAGTCCGGCTGCAAGGAGTGCGAAGAGCTGGAGGAGA

AGAACATCAAGGAGTTTCTGCAATCCTTTGTGCACATTGT

CCAGATGTTCATCAATACCTCC.
```

Signal Sequence

In some embodiments, any of the first and second polypeptides described herein includes a signal sequence at its N-terminal end. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a first and/or second polypeptide includes a signal sequence having an amino acid sequence MKWVTFISLLFLFSSAYS (SEQ ID NO: 28). In some embodiments, a single chain chimeric polypeptide includes a signal sequence encoded by the nucleic acid sequence

```
                                    (SEQ ID NO: 29)
ATGAAATGGGTGACCTTTATTTCTTTACTGTTCCTCTTTA

GCAGCGCCTACTCC,

                                    (SEQ ID NO: 30)
ATGAAGTGGGTCACATTTATCTCTTTACTGTTCCTCTTCT

CCAGCGCCTACAGC,

or
                                    (SEQ ID NO: 31)
ATGAAATGGGTGACCTTTATTTCTTTACTGTTCCTCTTTA

GCAGCGCCTACTCC.
```

In some embodiments, a first and/or second polypeptide includes a signal sequence having an amino acid sequence MKCLLYLAFLFLGVNC (SEQ ID NO: 32). In some embodiments, a first and/or second polypeptide includes a signal sequence having an amino acid sequence MGQIVTMFEALPHIIDEVINIVIIVLIIITSIKAVYNFATCGILALVSFLFLAGRSCG (SEQ ID NO: 33). In some embodiments, a first and/or second polypeptide includes a signal sequence having an amino acid sequence

```
                                    (SEQ ID NO: 34)
MPNHQSGSPTGSSDLLLSGKKQRPHLALRRKRRREMRKIN

RKVRRMNLAPIKEKTAWQHLQALISEAEEVLKTSQTPQNS

LTLFLALLSVLGPPVTG.
```

In some embodiments, a first and/or second polypeptide includes a signal sequence having an amino acid sequence MDSKGSSQKGSRLLLLLVVSNLLLCQGVVS (SEQ ID NO: 35). Those of ordinary skill in the art will be aware of other appropriate signal sequences for use in a single-chain chimeric polypeptide.

In some embodiments, a first and/or second polypeptide includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKWVTFISLLFLFSSAYS (SEQ ID NO: 28) can include one or more additional amino acids at the N-terminus or C-terminus, while still retaining the ability to direct the single-chain chimeric polypeptide to the secretory pathway.

In some embodiments, a first and/or second polypeptide includes a signal sequence that directs the single-chain chimeric polypeptide into the extracellular space. Such embodiments are useful in producing first and/or second polypeptides that are relatively easy to be isolated and/or purified.

In some embodiments, a first and/or second multi-chain chimeric polypeptide includes a first chimeric polypeptide that includes a signal sequence at its N-terminal end. In some embodiments, a first and/or second multi-chain chimeric polypeptide includes a second chimeric polypeptide that includes a signal sequence at its N-terminal end. In some embodiments, both the first chimeric polypeptide of a first and/or second multi-chain chimeric polypeptide and a second chimeric polypeptide of the first and/or second multi-chain chimeric polypeptide include a signal sequence. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a first chimeric polypeptide of a first and/or second multi-chain chimeric polypeptide, a second chimeric polypeptide of the first and/or second multi-chain chimeric polypeptide, or both includes a signal sequence having an amino acid sequence MKWVTFISLLFLFSSAYS (SEQ ID NO: 28). In some embodiments, a first chimeric polypeptide of a first and/or second multi-chain chimeric polypeptide, a second chimeric polypeptide of the first and/or second multi-chain chimeric polypeptide, or both includes a signal sequence encoded by the nucleic acid sequence

```
                                      (SEQ ID NO: 29)
ATGAAATGGGTGACCTTTATTTCTTTACTGTTCCTCTTTA

GCAGCGCCTACTCC,

                                      (SEQ ID NO: 30)
ATGAAGTGGGTCACATTTATCTCTTTACTGTTCCTCTTCT

CCAGCGCCTACAGC,

or
                                      (SEQ ID NO: 31)
ATGAAATGGGTGACCTTTATTTCTTTACTGTTCCTCTTTA

GCAGCGCCTACTCC.
```

In some embodiments, a first chimeric polypeptide of a first and/or second multi-chain chimeric polypeptide, a second chimeric polypeptide of the first and/or second multi-chain chimeric polypeptide, or both includes a signal sequence having an amino acid sequence MKCLLYLAFLFLGVNC (SEQ ID NO: 32). In some embodiments, a first chimeric polypeptide of a first and/or second multi-chain chimeric polypeptide, a second chimeric polypeptide of the first and/or second multi-chain chimeric polypeptide, or both includes a signal sequence having an amino acid sequence MGQIVTWIFEALPHIIDEVINIVIIVLIIITSIKAVYNFATCGILALVSFLFLAGRSCG (SEQ ID NO: 36). In some embodiments, a first chimeric polypeptide of a first and/or second multi-chain chimeric polypeptide, a second chimeric polypeptide of the first and/or second multi-chain chimeric polypeptide, or both includes a signal sequence having an amino acid sequence

```
                                      (SEQ ID NO: 37)
MPNHQSGSPTGSSDLLLSGKKQRPHLALRRKRRREMRKIN

RKVRRMNLAPIKEKTAWQHLQALISEAEEVLKTSQTPQNS

LTLFLALLSVLGPPVTG.
```

In some embodiments, a first chimeric polypeptide of a first and/or second multi-chain chimeric polypeptide, a second chimeric polypeptide of the first and/or second multi-chain chimeric polypeptide, or both includes a signal sequence having an amino acid sequence MDSKGSSQKGSRLLLLLVVSNLLLCQGVVS (SEQ ID NO: 38). Those of ordinary skill in the art will be aware of other appropriate signal sequences for use in a first chimeric polypeptide and/or a second chimeric polypeptide of the first and/or second multi-chain chimeric polypeptides described herein.

In some embodiments, a first chimeric polypeptide of a first and/or second multi-chain chimeric polypeptide, a second chimeric polypeptide of the first and/or second multi-chain chimeric polypeptide, or both includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKCLLYLAFLFLGVNC (SEQ ID NO: 32) can include one or more additional amino acids at the N-terminus or C-terminus, while still retaining the ability to direct the a first chimeric polypeptide of a first and/or second multi-chain chimeric polypeptide, a second chimeric polypeptide of the first and/or second multi-chain chimeric polypeptide, or both to the secretory pathway.

In some embodiments, a first chimeric polypeptide of a first and/or second multi-chain chimeric polypeptide, a second chimeric polypeptide of the first and/or second multi-chain chimeric polypeptide, or both includes a signal sequence that directs the multi-chain chimeric polypeptide into the extracellular space. Such embodiments are useful in producing first and/or second multi-chain chimeric polypeptides that are relatively easy to be isolated and/or purified.

Peptide Tags

In some embodiments, a first and/or second multi-chain chimeric polypeptide includes a first chimeric polypeptide that includes a peptide tag (e.g., at the N-terminal end or the C-terminal end of the first chimeric polypeptide). In some embodiments, a first and/or second multi-chain chimeric polypeptide includes a second chimeric polypeptide that includes a peptide tag (e.g., at the N-terminal end or the C-terminal end of the second chimeric polypeptide). In some embodiments, both the first chimeric polypeptide of a first and/or second multi-chain chimeric polypeptide and a second chimeric polypeptide of the first and/or second multi-chain chimeric polypeptide include a peptide tag. In some embodiments, a first chimeric polypeptide of a first and/or second multi-chain chimeric polypeptide, a second chimeric polypeptide of the first and/or second multi-chain chimeric polypeptide, or both include two or more peptide tags.

Exemplary peptide tags that can be included in a first chimeric polypeptide of a first and/or second multi-chain chimeric polypeptide, a second chimeric polypeptide of the first and/or second multi-chain chimeric polypeptide, or both include, without limitation, AviTag (GLNDIFEAQKIEWHE; SEQ ID NO: 75), a calmodulin-tag (KRRWKKNFIAVSAANRFKKISSSGAL; SEQ ID NO: 76), a polyglutamate tag (EEEEEE; SEQ ID NO: 77), an E-tag (GAPVPYPDPLEPR; SEQ ID NO: 78), a FLAG-tag (DYKDDDDK; SEQ ID NO: 79), an HA-tag, a peptide from hemagglutinin (YPYDVPDYA; SEQ ID NO: 80), a his-tag (HHEIHH (SEQ ID NO: 39); HEIHHHH (SEQ ID NO: 40); HEIHHHHH (SEQ ID NO: 41); HHHHHHHH (SEQ ID NO: 42); HEIHHHHHHH (SEQ ID NO: 43); or HEIHHHEIHHHH (SEQ ID NO: 44)), a myc-tag (EQKLISEEDL; SEQ ID NO: 45), NE-tag (TKENPRSNQEESYDDNES; SEQ ID NO: 46), S-tag, (KETAAAKFERQHMDS; SEQ ID NO: 47), SBP-tag (MDEKTTGWRGGHVVEGLAGELEQLRARLEHHPQGQREP; SEQ ID NO: 48), Softag 1 (SLAELLNAGLGGS; SEQ ID NO: 49), Softag 3 (TQDPSRVG; SEQ ID NO: Spot-tag (PDRVRAVSHWSS; SEQ ID NO: 51), Strep-tag (WSHPQFEK; SEQ ID NO: 52), TC tag (CCPGCC; SEQ ID NO: 53), Ty tag (EVHTNQDPLD; SEQ ID NO: 54), V5 tag (GKPIPNPLLGLDST; SEQ ID NO: 55), VSV-tag (YTDIEMNRLGK; SEQ ID NO: 56), and Xpress tag (DLYDDDDK; SEQ ID NO: 57). In some embodiments, tissue factor protein is a peptide tag.

Peptide tags that can be included in a first chimeric polypeptide of a first and/or second multi-chain chimeric polypeptide, a second chimeric polypeptide of the first and/or second multi-chain chimeric polypeptide, or both can be used in any of a variety of applications related to the multi-chain chimeric polypeptide. For example, a peptide tag can be used in the purification of a first and/or second multi-chain chimeric polypeptide. As one non-limiting example, a first chimeric polypeptide of a first and/or second multi-chain chimeric polypeptide (e.g., a recombinantly expressed first chimeric polypeptide), a second chimeric polypeptide of the first and/or second multi-chain chimeric polypeptide (e.g., a recombinantly expressed second chimeric polypeptide), or both can include a myc tag; the first and/or second multi-chain chimeric polypeptide that includes the myc-tagged first chimeric polypeptide, the myc-tagged second chimeric polypeptide, or both can be purified using an antibody that recognizes the myc tag(s). One non-limiting example of an antibody that recognizes a myc tag is 9E10, available from the non-commercial Developmental Studies Hybridoma Bank. As another non-limiting example, a first chimeric polypeptide of a first and/or second multi-chain chimeric polypeptide (e.g., a recombinantly expressed first chimeric polypeptide), a second chimeric polypeptide of the first and/or second multi-chain chimeric polypeptide (e.g., a recombinantly expressed second chimeric polypeptide), or both can include a histidine tag; the first and/or second multi-chain chimeric polypeptide that includes the histidine-tagged first chimeric polypeptide, the histidine-tagged second chimeric polypeptide, or both can be purified using a nickel or cobalt chelate. Those of ordinary skill in the art will be aware of other suitable tags and agent that bind those tags for use in purifying a first and/or second multi-chain chimeric polypeptide. In some embodiments, a peptide tag is removed from the first chimeric polypeptide and/or the second chimeric polypeptide of the first and/or second multi-chain chimeric polypeptide after purification. In some embodiments, a peptide tag is not removed from the first chimeric polypeptide and/or the second chimeric polypeptide of the first and/or second multi-chain chimeric polypeptide after purification.

Peptide tags that can be included in a first chimeric polypeptide of a first and/or second multi-chain chimeric polypeptide, a second chimeric polypeptide of the first and/or second multi-chain chimeric polypeptide, or both can be used, for example, in immunoprecipitation of the first and/or second multi-chain chimeric polypeptide, imaging of the first and/or second multi-chain chimeric polypeptide (e.g., via Western blotting, ELISA, flow cytometry, and/or immunocytochemistry), and/or solubilization of the first and/or second multi-chain chimeric polypeptide.

In some embodiments, a first chimeric polypeptide of a first and/or second multi-chain chimeric polypeptide, a second chimeric polypeptide of the first and/or second multi-chain chimeric polypeptide, or both includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about 10 to 30 amino acids in length, about 10 to 25 amino acids in length, about 10 to 20 amino acids in length, about 10 to 15 amino acids in length, about to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 30, 35, 40, 45, 50, 55, 60, 65, 70, 75, 80, 85, 90, 95, or 100 amino acids in length.

Peptide tags included in a first chimeric polypeptide of a first and/or second multi-chain chimeric polypeptide, a second chimeric polypeptide of the first and/or second multi-chain chimeric polypeptide, or both can be of any suitable length. For example, peptide tags can be 5, 6, 7, 8, 9, 10, 11, 12, 13, 14, 15, 16, 17, 18, 19, 20, or more amino acids in length. In embodiments in which a first and/or second multi-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 58) can include one or more additional amino acids (e.g., at the N-terminus and/or the C-terminus of the peptide tag), while still retaining the ability to be bound by an antibody (e.g., 9E10).

Compositions/Kits

Also provided herein are compositions (e.g., pharmaceutical compositions) that include at least one of any of the single-chain chimeric polypeptides, multi-chain chimeric polypeptides, IgG1 antibody constructs, any of the cells, or any of the nucleic acids described herein. In some embodiments, the compositions include at least one of any of the single-chain chimeric polypeptides described herein. In some embodiments, the compositions include at least one of any of the multi-chain chimeric polypeptides described herein (e.g., a first multi-chain chimeric polypeptide and/or a second multi-chain chimeric polypeptide). In some embodiments, the compositions include at least one of any of the multi-chain chimeric polypeptides and any of the IgG1 antibodies described herein. In some embodiments, the compositions include any of the NK cells (e.g., any of the NK cells described herein, e.g., any of the NK cells produced using any of the methods described herein).

In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Single or multiple administrations of pharmaceutical compositions can be given to a subject in need thereof depending on for example: the dosage and frequency as required and tolerated by the subject. The formulation should provide a sufficient quantity of active agent to effectively treat, prevent or ameliorate conditions, diseases or symptoms.

Also provided herein are kits that include any of multi-chain chimeric polypeptides (e.g., any of the first multi-chain chimeric polypeptides and second multi-chain polypeptides described herein), IgG1 antibody constructs (e.g., any of the IgG1 antibody constructs described herein), compositions, nucleic acids, and/or cells (e.g., NK cells) described herein. In some embodiments, the kits can include instructions for performing any of the methods described herein. In some embodiments, the kits can include at least one dose of any of the pharmaceutical compositions described herein.

Also provided herein is an NK cell (e.g., an activated NK cell) produced by any of the methods described herein. Also provided herein are pharmaceutical compositions that include any of the activated NK cells produced by any of the methods described herein. Also provided herein are kits that include any of the pharmaceutical compositions described herein that include any of the activated NK cells (e.g., an activated NK cell) produced by any of the methods described herein.

Also provided herein are kits that include any of the IgG1 antibody constructs described herein and any of the multi-chain chimeric polypeptides described herein (e.g., any of the exemplary first multi-chain chimeric polypeptides described herein and/or any of the exemplary second multi-chain chimeric polypeptides described herein). In some embodiments of any of the kits described herein, the kits further include instructions for performing any of the methods described herein.

Nucleic Acids/Vectors

Also provided herein are nucleic acids that encode any of the first and/or second polypeptides of any of the first multi-chain chimeric polypeptides described herein. Also provided herein are vectors that include any of the nucleic acids encoding any of the first and/or second polypeptides of any of the second multi-chain chimeric polypeptides described herein.

Also provided herein are vectors that include any of the nucleic acids encoding any of the multi-chain chimeric polypeptides described herein. In some embodiments, a first vector can include a nucleic acid encoding the first chimeric polypeptide of the first multi-chain chimeric polypeptide and a second vector can include a nucleic acid encoding the second chimeric polypeptide of the first multi-chain chimeric polypeptide. In some embodiments, a single vector can include a first nucleic acid encoding the first chimeric polypeptide of the first multi-chain chimeric polypeptide and a second nucleic acid encoding the second chimeric polypeptide of the first multi-chain chimeric polypeptide.

In some embodiments, a first vector can include a nucleic acid encoding the first chimeric polypeptide of the second multi-chain chimeric polypeptide and a second vector can include a nucleic acid encoding the second chimeric polypeptide of the second multi-chain chimeric polypeptide. In some embodiments, a single vector can include a nucleic acid encoding the first chimeric polypeptide of the second multi-chain chimeric polypeptide and a second nucleic acid encoding the second chimeric polypeptide of the second multi-chain chimeric polypeptide.

Also provided herein is a single nucleic acid sequence that encode the first and second multi-chain chimeric polypeptides. In some embodiments, a single nucleic acid can encode both the both of the first and second chimeric polypeptides of the first multi-chain chimeric polypeptide, and the first and second chimeric polypeptides of the second multi-chain chimeric polypeptide.

Also provided herein are the vectors that include the single nucleic acid sequences that encode both the first and second multi-chain chimeric polypeptides (e.g., the first and second chimeric polypeptides of each the first and second multi-chain chimeric polypeptides).

Also provided herein are nucleic acids that encode any of the IgG1 antibody constructs described herein.

Any of the vectors described herein can be an expression vector. For example, an expression vector can include a promoter sequence operably linked to the sequence encoding the single-chain chimeric polypeptide, or the first chimeric polypeptide and the second chimeric polypeptide of a multi-chain chimeric polypeptide. In another example, an expression vector can include a promoter sequence operably linked to the sequence encoding any of the first polypeptides and/or second polypeptides described herein.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, e.g., include sufficient cis-acting elements for expression; other elements for expression can be supplied by the host mammalian cell or in an in vitro expression system. Skilled practitioners will be capable of selecting suitable vectors and mammalian cells for making any of the single-chain chimeric polypeptides or multi-chain chimeric polypeptides described herein.

Cells

Also provided herein are cells (e.g., any of the exemplary cells described herein or known in the art) comprising any of the nucleic acids described herein that encode any of the exemplary first polypeptides and/or second polypeptides of any of the first multi-chain chimeric polypeptides described herein.

Also provided herein are cells (e.g., any of the exemplary cells described herein or known in the art) that include any of the vectors described herein that encode any of the first polypeptides and/or second polypeptides of any of the first multi-chain chimeric polypeptides described herein.

Also provided herein are cells (e.g., any of the exemplary cells described herein or known in the art) comprising any of the nucleic acids described herein that encode any of the first polypeptides and/or second polypeptides of any of the second multi-chain chimeric polypeptides described herein.

Also provided herein are cells (e.g., any of the exemplary cells described herein or known in the art) that include any of the vectors described herein that encode any of the first polypeptides and/or second polypeptides of any of the second multi-chain chimeric polypeptides described herein.

Also provided herein are cells (e.g., any of the exemplary cells described herein or known in the art) comprising any of the nucleic acids described herein that encode any of the multi-chain chimeric polypeptides described herein (e.g., encoding both the first and second chimeric polypeptides of the first multi-chain chimeric polypeptide and/or the second multi-chain chimeric polypeptide). Also provided herein are cells (e.g., any of the exemplary cells described herein or known in the art) that include any of the vectors described herein that encode any of the multi-chain chimeric polypeptides described herein (e.g., encoding both the first and second chimeric polypeptides of the first multi-chain chimeric polypeptide and/or the second multi-chain chimeric polypeptide).

Also provided herein are cells (e.g., any of the exemplary cells described herein or known in the art) that include (i) any of the nucleic acids described herein that encode a first multi-chain chimeric polypeptide, (ii) any of the nucleic acids described herein that encode a second multi-chain chimeric polypeptide, and (iii) any of the nucleic acids described herein that encode an IgG1 antibody construct.

Also provided herein are cells (e.g., any of the exemplary cells described herein or known in the art) that include (i) any of the vectors described herein that encode a first multi-chain chimeric polypeptide, (ii) any of the vectors that encode a second multi-chain chimeric polypeptide, and (iii) any of the vectors that encode an IgG1 antibody construct.

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary cells and human embryonic kidney cells (e.g., HEK293 cells).

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection.

Methods of Producing Single-Chain and Multi-Chain Chimeric Polypeptides

Also provided herein are methods of producing any of the single-chain chimeric polypeptides described herein that include culturing any of the cells described herein in a culture medium under conditions sufficient to result in the production of the single-chain chimeric polypeptide; and recovering the single-chain chimeric polypeptide from the cell and/or the culture medium.

The recovery of the single-chain chimeric polypeptide from a culture medium or a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Also provided herein are single-chain chimeric polypeptides (e.g., any of the single-chain chimeric polypeptides described herein) produced by any of the methods described herein.

Also provided herein are methods of producing any of the multi-chain chimeric polypeptides described herein that include culturing any of the cells described herein in a culture medium under conditions sufficient to result in the production of the multi-chain chimeric polypeptide; and recovering the multi-chain chimeric polypeptide from the cell and/or the culture medium.

Also provided herein are methods of producing any of the multi-chain chimeric polypeptides described herein that include: culturing any of cells described herein in a first culture medium under conditions sufficient to result in the production of the first chimeric polypeptide; recovering the first chimeric polypeptide from the cell and/or the first culture medium; culturing any of the cells described herein in a second culture medium under conditions sufficient to result in the production of the second chimeric polypeptide; recovering the second chimeric polypeptide from the cell and/or the second culture medium; and combining (e.g., mixing) the recovered first chimeric polypeptide and the recovered second chimeric polypeptide to form the multi-chain chimeric polypeptide (e.g., any of the multi-chain chimeric polypeptides described herein).

The recovery of the multi-chain chimeric polypeptide, the first chimeric polypeptide, or the second chimeric polypeptide from a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Also provided herein are multi-chain chimeric polypeptides (e.g., any of the multi-chain chimeric polypeptides described herein), first chimeric polypeptides (e.g., any of the first chimeric polypeptides), or second chimeric polypeptides (e.g., any of the second chimeric polypeptides described herein) produced by any of the methods described herein.

Methods of culturing cells are well known in the art. Cells can be maintained in vitro under conditions that favor proliferation, differentiation and growth. Briefly, cells can be cultured by contacting a cell (e.g., any cell) with a cell culture medium that includes the necessary growth factors and supplements to support cell viability and growth.

Methods of Promoting the Activation and Proliferation of an Immune Cell

Also provided herein are methods of promoting the activation and proliferation of a NK cell (e.g., an any of the exemplary NK cells described herein or known in the art) that include contacting a NK cell in a liquid culture medium including an effective amount of a first multi-chain chimeric polypeptide described herein for a first period of time under conditions that allow for differentiation of the NK cell, and contacting the NK cell in a liquid culture medium including an effective amount of (i) a second multi-chain chimeric polypeptides described herein, and (ii) an IgG1 antibody construct, that comprises at least one antigen-binding domain that binds specifically to the linker domain (e.g., a monoclonal or polyclonal human, mouse, rabbit, or goat IgG1 antibody that binds specifically to a linker domain or any of the other exemplary IgG1 antibody constructs described herein), for a second period of time under conditions that allow for the activation and proliferation of the NK cell.

In some embodiments of these methods, the IgG1 antibody construct includes at least one antigen-binding domain that binds specifically to the linker domain in the second multi-chain chimeric polypeptide. In some embodiments of these methods, the IgG1 antibody construct is a monoclonal IgG1 antibody, where both of the antigen-binding domains in the monoclonal IgG1 antibody bind specifically to the linker domain. In some embodiments of these methods, the IgG1 antibody construct is a bispecific IgG1 antibody, where one of the two antigen-binding domains in the bispecific IgG1 antibody binds specifically to the linker domain.

In some embodiments of these methods, the first period of time is about 15 minutes to about 4 hours (e.g., about 15 minutes to about 3.75 hours, about 15 minutes to about 3.5 hours, about 15 minutes to about 3.25 hours, about 15 minutes to about 3 hours, about 15 minutes to about 2.75 hours, about 15 minutes to about 2.5 hours, about 15 minutes to about 2.25 hours, about 15 minutes to about 2 hours, about 15 minutes to about 1.75 hours, about 15 minutes to about 1.5 hours, about 15 minutes to about 1.25 hours, about 15 minutes to about 1 hour, about 15 minutes to about 45 minutes, about 15 minutes to about 30 minutes, about 30 minutes to about 3.75 hours, about 30 minutes to about 3.5 hours, about 30 minutes to about 3.25 hours, about 30 minutes to about 3 hours, about 30 minutes to about 2.75 hours, about 30 minutes to about 2.5 hours, about 30 minutes to about 2.25 hours, about 30 minutes to about 2 hours, about 30 minutes to about 1.75 hours, about 30 minutes to about 1.5 hours, about 30 minutes to about 1.25 hours, about 30 minutes to about 1 hour, about 30 minutes to about 45 minutes, about 45 minutes to about 3.75 hours, about 45 minutes to about 3.5 hours, about 45 minutes to about 3.25 hours, about 45 minutes to about 3 hours, about 45 minutes to about 2.75 hours, about 45 minutes to about 2.5 hours, about 45 minutes to about 2.25 hours, about 45 minutes to about 2 hours, about 45 minutes to about 1.75 hours, about 45 minutes to about 1.5 hours, about 45 minutes to about 1.25 hours, about 45 minutes to 1 hour, about 1 hour to about 3.75 hours, about 1 hour to about 3.5 hours, about 1 hour to about 3.25 hours, about 1 hour to about 3 hours, about 1 hour to about 2.75 hours, about 1 hour to about 2.5 hours, about 1 hour to about 2.5 hours, about 1 hour to about 2.25 hours, about 1 hour to about 2 hours, about 1 hour to about 1.75 hours, about 1 hour to about 1.5 hours, about 1 hour to about 1.25 hours, about to 1.25 hours to about 3.75 hours, about 1.25 hours to about 3.5 hours, about 1.25 hours to about 3.25 hours, about 1.25 hours to about 3 hours, about 1.25 hours to about 2.75 hours, about 1.25 hours to about 2.75 hours, about 1.25 hours to about 2.5 hours, about 1.25 hours to about 2.25 hours, about 1.25 hours to about 2 hours, about 1.25 hours to about 1.75 hours, about 1.25 hours to about 1.5 hours, about 1.5 hours to about 3.75 hours, about 1.5 hours to about 3.5 hours, about 1.5 hours to about 3.25 hours, about 1.5 hours to about 3 hours, about 1.5 hours to about 2.75 hours, about 1.5 hours to about 2.5 hours, about 1.5 hours to about 2.25 hours, about 1.5 hours to about 2 hours, about 1.5 hours to about 1.75 hours, about 1.75 hours to about 3.75 hours, about 1.75 hours to about 3.5 hours, about 1.75 hours to about 3.25 hours, about 1.75 hours to about 3 hours, about 1.75 hours to about 2.75 hours, about 1.75 hours to about 2.5 hours, about 1.75 hours to about 2.25 hours, or about 1.75 hours to 2 hours).

In some embodiments of these methods, the second period is about 1 day to about days (e.g., about 1 day to about 28 days, about 1 day to about 26 days, about 1 day to about 24 days, about 1 day to about 22 days, about 1 day to about 20 days, about 1 day to about 18 days, about 1 day to about 16 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 28 days, about 2 days to about 26 days, about 2 days to about 24 days, about 2 days to about 22 days, about 2 days to about 20 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 28 days, about 3 days to about 26 days, about 3 days to about 24 days, about 3 days to about 22 days, about 3 days to about days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 28 days, about 4 days to about 26 days, about 4 days to about 24 days, about 4 days to about 22 days, about 4 days to about 20 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 28 days, about 5 days to about 26 days, about 5 days to about 24 days, about 5 days to about 22 days, about 5 days to about 20 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 28 days, about 6 days to about 26 days, about 6 days to about 24 days, about 6 days to about 22 days, about 6 days to about 20 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 28 days, about 7 days to about 26 days, about 7 days to about 24 days, about 7 days to about 22 days, about 7 days to about 20 days, about 7 days to about 18 days, about 7 days to about 16 days, about 7 days to about 14 days, about 7 days to about 12 days, about 7 days to about 10 days, about 7 days to about 8 days, about 8 days to about 28 days, about 8 days to about 26 days, about 8 days to about 24 days, about 8 days to about 22 days, about 8 days to about 20 days, about 8 days to about 18 days, about 8 days to about 16 days, about 8 days to about 14 days, about 8 days to about 12 days, about 8 days to about 10 days, about 8 days to about 9 days, about 9 days to about 28 days, about 9 days to about 26 days, about 9 days to about 24 days, about 9 days to about 22 days, about 9 days to about 20 days, about 9 days to about 18 days, about 9 days to about 16 days, about 9 days to about 14 days, about 9 days to about 12 days, about 9 days to about 10 days, about 10 days to about 28 days, about 10 days to about 26 days, about 10 days to about 24 days, about 10 days to about 22 days, about 10 days to about 20 days, about 10 days to about 18 days, about 10 days to about 16 days, about 10 days to about 14 days, about 10 days to about 12 days, about 12 days to about 28 days, about 12 days to about 26 days, about 12 days to about 24 days, about 12 days to about 22 days, about 12 days to about 20 days, about 12 days to about 18 days, about 12 days to about 16 days, about 12 days to about 14 days, about 14 days to about 28 days, about 14 days to about 26 days, about 14 days to about 24 days, about 14 days to about 22 days, about 14 days to about 20 days, about 14 days to about 18 days, about 14 days to about 16 days, about 16 days to about 28 days, about 16 days to about 26 days, about 16 days to about 24 hours, about 16 days to about 22 days, about 16 days to about 20 days, about 16 days to about 18 days, about 18 days to about 28 days, about 18 days to about 26 days, about 18 days to about 24 days, about 18 days to about 22 days, about 18 days to about 20 days, about 20 days to about 28 days, about 20 days to about 26 days, about 20 days to about 24 days, about 20 days to about 22 days, 22 days to about 28 days, about 22 days to about 26 days, about 22 days to about 24 days, about 24 days to about 28 days, about 24 days to about 26 days, or about 26 to about 28 days.

In some embodiments of any of the methods described herein, the liquid culture medium is a serum-free liquid culture medium. In some embodiments of any of the methods described herein, the liquid culture medium is a chemically-defined liquid culture medium.

In some embodiments of any of the methods described herein, the liquid culture medium includes the second multi-chain chimeric polypeptide and the IgG1 antibody construct at a molar ratio of about 0.5:0.5:1 to about 2:2:1 (e.g., about 0.8:0.8:1 to about 1.2:1.2:1).

In some embodiments of any of the methods described herein, the NK cell was previously obtained from a subject. Some embodiments of any of the methods described herein further include obtaining the NK cell from the subject prior to the contacting step.

In some embodiments, the NK cell was previously obtained from umbilical cord blood or induced pluripotent stem cells. Some embodiments of any of the methods described herein further include obtaining the NK cell from umbilical cord blood. Some embodiments further include generating the NK cell from an induced pluripotent stem cell.

In some embodiments of any of the methods described herein, the NK cell has previously been genetically modified to express a chimeric antigen receptor or a recombinant T-cell receptor.

Some embodiments of any of the methods described herein further includes, after the contacting step, introducing into the NK cell a nucleic acid encoding a chimeric antigen-receptor or a recombinant T-cell receptor.

Some embodiments of any of the methods described herein further include, before the contacting step, introducing into the NK cell a nucleic acid encoding a chimeric antigen-receptor or a recombinant T-cell receptor.

Some embodiments of any of the methods described herein further include, after the contacting step, isolating the NK cell.

In some embodiments of any of the methods described herein, after the first and/or second period of time, the NK cell is a chemokine-induced memory NK cell. In some examples, after the first and/or second period of time, the NK cell has an increased level of expression, secretion, and or activity of one or more proteins selected from the group consisting of: 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, TRAIL, FasL, CXCR3, CXCR4, LTB, MX1, BAX, TNF-α, STAT5, and IFN-γ as compared to the level of expression or secretion of the one or more proteins prior to the first period of time.

Some embodiments of any of the methods described herein further include, after the contacting step, administering the NK cell to a subject in need thereof. In some embodiments of any of the methods described herein, the subject has been identified or diagnosed as having an age-related disease or condition. In some embodiments of any of the methods described herein, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is an activated NK produced by any of the methods described herein. Also provided herein are pharmaceutical compositions that include any of the NK cells produced by any of the methods described herein. Also provided herein are kits that include any of the pharmaceutical compositions including any of the activated NK cells produced by any of the methods described herein.

Methods of Stimulating an NK Cell

Also provided herein are methods of stimulating a NK cell (e.g., any of the exemplary NK cells described herein or known in the art) that include contacting a NK cell in a liquid culture medium including an effective amount of a first multi-chain chimeric polypeptide described herein for a first period of time under conditions that allow for differentiation of the NK cell, and contacting the NK cell in a liquid culture medium including an effective amount of (i) a second multi-chain chimeric polypeptides described herein, and (ii) an IgG1 antibody construct that comprises at least one antigen-binding domain that binds specifically to the linker domain (e.g., a monoclonal or polyclonal human, mouse, rabbit, or goat IgG1 antibody that binds specifically to a linker domain or any of the other exemplary IgG1 antibody constructs described herein), for a second period of time under conditions that allow for stimulation of the NK cell. In some examples, the NK cell is contacted in vitro (e.g., in a suitable liquid culture medium under conditions sufficient to result in stimulation of the NK cell). In some examples, the contacting further includes contacting the NK cell with an effective amount of any of the IgG1 antibody constructs described herein.

In some examples, the NK cell has been previously obtained from a subject (e.g., a mammal, e.g., a human). Some embodiments of these methods further include obtaining the NK cell from the subject prior to the contacting step.

In some examples, the NK cell is contacted in vivo. In such embodiments, the first multi-chain chimeric polypeptide, the second multi-chain chimeric polypeptide, and the IgG1 antibody construct is administered to a subject (e.g., a mammal, e.g., a human) in an amount sufficient to result in stimulation of an immune cell in the subject. In some embodiments of any of the methods, compositions, and kits described herein, the IgG1 antibody construct (e.g., any of the exemplary IgG1 antibody constructs described herein is administered to the subject in combination (e.g., simultaneously or sequentially) with administration of the first and second multi-chain chimeric polypeptides (e.g., any of the first and second multi-chain chimeric polypeptides described herein)).

In some examples, the NK cell has previously been genetically-modified to express a chimeric antigen receptor or a recombinant T-cell receptor.

Some embodiments of these methods can further include, after the contacting step, introducing into the NK cell (e.g., any of the NK cells described herein) a nucleic acid encoding a chimeric antigen-receptor or a recombinant T-cell receptor. Some embodiments of these methods can further include administering a therapeutically effective amount of the NK cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Activation of an NK cell can be determined using methods known in the art. For example, activation of an immune cell can be determined by detecting the levels of cytokines, chemokines, and activating receptors that are secreted or upregulated upon activation of an immune cell. Non-limiting examples of cytokines, chemokines and activating receptors that are secreted or upregulated upon activation of an immune cell include: IL-2, interferon-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, perforin, TGFβ, STAT3, RORγT, FOXP3, STATE, GATA3, granzyme A, granzyme B, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, TRAIL, FasL, CXCR3, CXCR4, LTB, MX1, BAX, TNF-α, and IFN-γ. The detection of these cytokines and chemokines can be performed using an immunoassay (e.g., an enzyme-linked immunosorbent assay). For example, activation of an immune cell can result in an increase of about 1% to about 800% (e.g., about 1% to about 750%, about 1% to about 700%, about 1% to about 650%, about 1% to about 600%, about 1% to about 550%, about 1% to about 500%, about 1% to about 450%, about 1% to about 400%, about 1% to about 350%, about 1% to about 300%, about 1% to about 280%, about 1% to about 260%, about 1% to about 240%, about 1% to about 220%, about 1% to about 200%, about 1% to about 180%, about 1% to about 160%, about 1% to about 140%, about 1% to about 120%, about 1% to about 100%, about 1% to about 90%, about 1% to about 80%, about 1% to about 70%, about 1% to about 60%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 800%, about 5% to about 750%, about 5% to about 700%, about 5% to about 650%, about 5% to about 600%, about 5% to about 550%, about 5% to about 500%, about 5% to about 450%, about 5% to about 400%, about 5% to about 350%, about 5% to about 300%, about 5% to about 280%, about 5% to about 260%, about 5% to about 240%, about 5% to about 220%, about 5% to about 200%, about 5% to about 180%, about 5% to about 160%, about 5% to about 140%, about 5% to about 120%, about 5% to about 100%, about 5% to about 90%, about 5% to about 80%, about 5% to about 70%, about 5% to about 60%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 800%, about 10% to about 750%, about 10% to about 700%, about 10% to about 650%, about 10% to about 600%, about 10% to about 550%, about 10% to about 500%, about 10% to about 450%, about 10% to about 400%, about 10% to about 350%, about 10% to about 300%, about 10% to about 280%, about 10% to about 260%, about 10% to about 240%, about 10% to about 220%, about 10% to about 200%, about 10% to about 180%, about 10% to about 160%, about 10% to about 140%, about 10% to about 120%, about 10% to about 100%, about 10% to about 90%, about 10% to about 80%, about 10% to about 70%, about 10% to about 60%, about 10% to about 50%, about 10% to about 45%, about 10% to about 40%, about 10% to about 35%, about 10% to about 30%, about 10% to about 25%, about 10% to about 20%, about 10% to about 15%, about 15% to about 800%, about 15% to about 750%, about 15% to about 700%, about 15% to about 650%, about 15% to about 600%, about 15% to about 550%, about 15% to about 500%, about 15% to about 450%, about 15% to about 400%, about 15% to about 350%, about 15% to about 300%, about 15% to about 280%, about 15% to about 260%, about 15% to about 240%, about 15% to about 220%, about 15% to about 200%, about 15% to about 180%, about 15% to about 160%, about 15% to about 140%, about 15% to about 120%, about 15% to about 100%, about 15% to about 90%, about 15% to about 80%, about 15% to about 70%, about 15% to about 60%, about 15% to about 50%, about 15% to about 45%, about 15% to about 40%, about 15% to about 35%, about 15% to about 30%, about 15% to about 25%, about 15% to about 20%, about 20% to about 800%, about 20% to about 750%, about 20% to about 700%, about 20% to about 650%, about 20% to about 600%, about 20% to about 550%, about 20% to about 500%, about 20% to about 450%, about 20% to about 400%, about 20% to about 350%, about 20% to about 300%, about 20% to about 280%, about 20% to about 260%, about 20% to about 240%, about 20% to about 220%, about 20% to about 200%, about 20% to about 180%, about 20% to about 160%, about 20% to about 140%, about 20% to about 120%, about 20% to about 100%, about 20% to about 90%, about 20% to about 80%, about 20% to about 70%, about 20% to about 60%, about 20% to about 50%, about 20% to about 45%, about 20% to about 40%, about 20% to about 35%, about 20% to about 30%, about 20% to about 25%, about 25% to about 800%, about 25% to about 750%, about 25% to about 700%, about 25% to about 650%, about 25% to about 600%, about 25% to about 550%, about 25% to about 500%, about 25% to about 450%, about 25% to about 400%, about 25% to about 350%, about 25% to about 300%, about 25% to about 280%, about 25% to about 260%, about 25% to about 240%, about 25% to about 220%, about 25% to about 200%, about 25% to about 180%, about 25% to about 160%, about 25% to about 140%, about 25% to about 120%, about 25% to about 100%, about 25% to about 90%, about 25% to about 80%, about 25% to about 70%, about 25% to about 60%, about 25% to about 50%, about 25% to about 45%, about 25% to about 40%, about 25% to about 35%, about 35% to about 800%, about 35% to about 750%, about 35% to about 700%, about 35% to about 650%, about 35% to about 600%, about 35% to about 550%, about 35% to about 500%, about 35% to about 450%, about 35% to about 400%, about 35% to about 350%, about 35% to about 300%, about 35% to about 280%, about 35% to about 260%, about 35% to about 240%, about 35% to about 220%, about 35% to about 200%, about 35% to about 180%, about 35% to about 160%, about 35% to about 140%, about 35% to about 120%, about 35% to about 100%, about 35% to about 90%, about 35% to about 80%, about 35% to about 70%, about 35% to about 60%, about 35% to about 50%, about 35% to about 45%, about 35% to about 40%, about 40% to about 800%, about 40% to about 750%, about 40% to about 700%, about 40% to about 650%, about 40% to about 600%, about 40% to about 550%, about 40% to about 500%, about 40% to about 450%, about 40% to about 400%, about 40% to about 350%, about 40% to about 300%, about 40% to about 280%, about 40% to about 260%, about 40% to about 240%, about 40% to about 220%, about 40% to about 200%, about 40% to about 180%, about 40% to about 160%, about 40% to about 140%, about 40% to about 120%, about 40% to about 100%, about 40% to about 90%, about 40% to about 80%, about 40% to about 70%, about 40% to about 60%, about 40% to about 50%, about 40% to about 45%, about 45% to about 800%, about 45% to about 750%, about 45% to about 700%, about 45% to about 650%, about 45% to about 600%, about 45% to about 550%, about 45% to about 500%, about 45% to about 450%, about 45% to about 400%, about 45% to about 350%, about 45% to about 300%, about 45% to about 280%, about 45% to about 260%, about 45% to about 240%, about 45% to about 220%, about 45% to about 200%, about 45% to about 180%, about 45% to about 160%, about 45% to about 140%, about 45% to about 120%, about 45% to about 100%, about 45% to about 90%, about 45% to about 80%, about 45% to about 70%, about 45% to about 60%, about 45% to about 50%, about 50% to about 800%, about 50% to about 750%, about 50% to about 700%, about 50% to about 650%, about 50% to about 600%, about 50% to about 550%, about 50% to about 500%, about 50% to about 450%, about 50% to about 400%, about 50% to about 350%, about 50% to about 300%, about 50% to about 280%, about 50% to about 260%, about 50% to about 240%, about 50% to about 220%, about 50% to about 200%, about 50% to about 180%, about 50% to about 160%, about 50% to about 140%, about 50% to about 120%, about 50% to about 100%, about 50% to about 90%, about 50% to about 80%, about 50% to about 70%, about 50% to about 60%, about 60% to about 800%, about 60% to about 750%, about 60% to about 700%, about 60% to about 650%, about 60% to about 600%, about 60% to about 550%, about 60% to about 500%, about 60% to about 450%, about 60% to about 400%, about 60% to about 350%, about 60% to about 300%, about 60% to about 280%, about 60% to about 260%, about 60% to about 240%, about 60% to about 220%, about 60% to about 200%, about 60% to about 180%, about 60% to about 160%, about 60% to about 140%, about 60% to about 120%, about 60% to about 100%, about 60% to about 90%, about 60% to about 80%, about 60% to about 70%, about 70% to about 800%, about 70% to about 750%, about 70% to about 700%, about 70% to about 650%, about 70% to about 600%, about 70% to about 550%, about 70% to about 500%, about 70% to about 450%, about 70% to about 400%, about 70% to about 350%, about 70% to about 300%, about 70% to about 280%, about 70% to about 260%, about 70% to about 240%, about 70% to about 220%, about 70% to about 200%, about 70% to about 180%, about 70% to about 160%, about 70% to about 140%, about 70% to about 120%, about 70% to about 100%, about 70% to about 90%, about 70% to about 80%, about 80% to about 800%, about 80% to about 750%, about 80% to about 700%, about 80% to about 650%, about 80% to about 600%, about 80% to about 550%, about 80% to about 500%, about 80% to about 450%, about 80% to about 400%, about 80% to about 350%, about 80% to about 300%, about 80% to about 280%, about 80% to about 260%, about 80% to about 240%, about 80% to about 220%, about 80% to about 200%, about 80% to about 180%, about 80% to about 160%, about 80% to about 140%, about 80% to about 120%, about 80% to about 100%, about 80% to about 90%, about 90% to about 800%, about 90% to about 750%, about 90% to about 700%, about 90% to about 650%, about 90% to about 600%, about 90% to about 550%, about 90% to about 500%, about 90% to about 450%, about 90% to about 400%, about 90% to about 350%, about 90% to about 300%, about 90% to about 280%, about 90% to about 260%, about 90% to about 240%, about 90% to about 220%, about 90% to about 200%, about 90% to about 180%, about 90% to about 160%, about 90% to about 140%, about 90% to about 120%, about 90% to about 100%, about 100% to about 800%, about 100% to about 750%, about 100% to about 700%, about 100% to about 650%, about 100% to about 600%, about 100% to about 550%, about 100% to about 500%, about 100% to about 450%, about 100% to about 400%, about 100% to about 350%, about 100% to about 300%, about 100% to about 280%, about 100% to about 260%, about 100% to about 240%, about 100% to about 220%, about 100% to about 200%, about 100% to about 180%, about 100% to about 160%, about 100% to about 140%, about 100% to about 120%, about 120% to about 800%, about 120% to about 750%, about 120% to about 700%, about 120% to about 650%, about 120% to about 600%, about 120% to about 550%, about 120% to about 500%, about 120% to about 450%, about 120% to about 400%, about 120% to about 350%, about 120% to about 300%, about 120% to about 280%, about 120% to about 260%, about 120% to about 240%, about 120% to about 220%, about 120% to about 200%, about 120% to about 180%, about 120% to about 160%, about 120% to about 140%, about 140% to about 800%, about 140% to about 750%, about 140% to about 700%, about 140% to about 650%, about 140% to about 600%, about 140% to about 550%, about 140% to about 500%, about 140% to about 450%, about 140% to about 400%, about 140% to about 350%, about 140% to about 300%, about 140% to about 280%, about 140% to about 260%, about 140% to about 240%, about 140% to about 220%, about 140% to about 200%, about 140% to about 180%, about 140% to about 160%, about 160% to about 800%, about 160% to about 750%, about 160% to about 700%, about 160% to about 650%, about 160% to about 600%, about 160% to about 550%, about 160% to about 500%, about 160% to about 450%, about 160% to about 400%, about 160% to about 350%, about 160% to about 300%, about 160% to about 280%, about 160% to about 260%, about 160% to about 240%, about 160% to about 220%, about 160% to about 200%, about 160% to about 180%, about 180% to about 800%, about 180% to about 750%, about 180% to about 700%, about 180% to about 650%, about 180% to about 600%, about 180% to about 550%, about 180% to about 500%, about 180% to about 450%, about 180% to about 400%, about 180% to about 350%, about 180% to about 300%, about 180% to about 280%, about 180% to about 260%, about 180% to about 240%, about 180% to about 220%, about 180% to about 200%, about 200% to about 800%, about 200% to about 750%, about 200% to about 700%, about 200% to about 650%, about 200% to about 600%, about 200% to about 550%, about 200% to about 500%, about 200% to about 450%, about 200% to about 400%, about 200% to about 350%, about 200% to about 300%, about 200% to about 280%, about 200% to about 260%, about 200% to about 240%, about 200% to about 220%, about 220% to about 800%, about 220% to about 750%, about 220% to about 700%, about 220% to about 650%, about 220% to about 600%, about 220% to about 550%, about 220% to about 500%, about 220% to about 450%, about 220% to about 400%, about 220% to about 350%, about 220% to about 300%, about 220% to about 280%, about 220% to about 260%, about 220% to about 240%, about 240% to about 800%, about 240% to about 750%, about 240% to about 700%, about 240% to about 650%, about 240% to about 600%, about 240% to about 550%, about 240% to about 500%, about 240% to about 450%, about 240% to about 400%, about 240% to about 350%, about 240% to about 300%, about 240% to about 280%, about 240% to about 260%, about 260% to about 800%, about 260% to about 750%, about 260% to about 700%, about 260% to about 650%, about 260% to about 600%, about 260% to about 550%, about 260% to about 500%, about 260% to about 450%, about 260% to about 400%, about 260% to about 350%, about 260% to about 300%, about 260% to about 280%, about 280% to about 800%, about 280% to about 750%, about 280% to about 700%, about 280% to about 650%, about 280% to about 600%, about 280% to about 550%, about 280% to about 500%, about 280% to about 450%, about 280% to about 400%, about 280% to about 350%, about 280% to about 300%, about 300% to about 800%, about 300% to about 750%, about 300% to about 700%, about 300% to about 650%, about 300% to about 600%, about 300% to about 550%, about 300% to about 500%, about 300% to about 450%, about 300% to about 400%, about 300% to about 350%, about 350% to about 800%, about 350% to about 750%, about 350% to about 700%, about 350% to about 650%, about 350% to about 600%, about 350% to about 550%, about 350% to about 500%, about 350% to about 450%, about 350% to about 400%, about 400% to about 800%, about 400% to about 750%, about 400% to about 700%, about 400% to about 650%, about 400% to about 600%, about 400% to about 550%, about 400% to about 500%, about 400% to about 450%, about 450% to about 800%, about 450% to about 750%, about 450% to about 700%, about 450% to about 650%, about 450% to about 600%, about 450% to about 550%, about 450% to about 500%, about 500% to about 800%, about 500% to about 750%, about 500% to about 700%, about 500% to about 650%, about 500% to about 600%, about 500% to about 550%, about 550% to about 800%, about 550% to about 750%, about 550% to about 700%, about 550% to about 650%, about 550% to about 600%, about 600% to about 800%, about 600% to about 750%, about 600% to about 700%, about 600% to about 650%, about 650% to about 800%, about 650% to about 750%, about 650% to about 700%, about 700% to about 800%, about 700% to about 750%, or about 750% to about 800%) of one or more of any of the cytokines or chemokines described herein (e.g., one or more of any of IL-2, interferon-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, granzymes, perforin, TGFβ, STAT3, RORγT, FOXP3, STATE, and GATA3) (e.g., as compared to the level of the one or more cytokines and chemokines in a control not contacted with any of the single-chain chimeric polypeptides or any of the multi-chain chimeric polypeptides described herein).

Methods of Inducing or Increasing Proliferation of a NK Cell

Also provided herein are methods of inducing or increasing proliferation of an NK cell (e.g., any of the exemplary NK cells described herein or known in the art) that include contacting a NK cell in a liquid culture medium including an effective amount of a first multi-chain chimeric polypeptide described herein for a first period of time under conditions that allow for differentiation of the NK cell, and contacting the NK cell in a liquid culture medium including an effective amount of (i) a second multi-chain chimeric polypeptides described herein, and (ii) an IgG1 antibody construct that comprises at least one antigen-binding domain that binds specifically to the linker domain (e.g., a monoclonal or polyclonal human, mouse, rabbit, or goat IgG1 antibody that binds specifically to a linker domain or any of the other exemplary IgG1 antibody constructs described herein), for a second period of time under conditions that allow for the inducing or increasing proliferation of the NK cell.

In some examples, the NK cell is contacted in vitro (e.g., in a suitable liquid culture medium under conditions sufficient to result in stimulation of the immune cell)). In some examples, the NK cell is further contacted in vitro with any of the IgG1 antibody constructs described herein in combination (e.g., simultaneously or sequentially) with contacting the immune cell in vitro with the multi-chain chimeric polypeptides (e.g., any of the first and/or second multi-chain chimeric polypeptides described herein).

In some examples, the NK cell has been previously obtained from a subject (e.g., a mammal, e.g., a human). Some embodiments of these methods further include obtaining the NK cell from the subject prior to the contacting step.

In some examples, the NK cell is contacted in vivo. In such embodiments, any of the first multi-chain chimeric polypeptides, any of the second multi-chain chimeric polypeptides, and any of the IgG1 antibody constructs are administered to a subject (e.g., a mammal, e.g., a human) in an amount sufficient to result in stimulation of a NK cell in the subject.

In some examples, the NK cell has previously been genetically-modified to express a chimeric antigen receptor or a recombinant T-cell receptor.

Some embodiments of these methods can further include, after the contacting step, introducing into the NK cell (e.g., any of the NK cells described herein) a nucleic acid encoding a chimeric antigen-receptor or a recombinant T-cell receptor.

Some embodiments of these methods can further include administering a therapeutically effective amount of the NK cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Detection of the proliferation of an immune cell can be performed using methods known in the art, e.g., cytometry (e.g., fluorescence-assisted flow cytometry), microscopy, and immunofluorescence microscopy, e.g., by comparing the rate of increase in the concentration of the immune cell in a sample not contacted with a single-chain chimeric polypeptide or a multi-chain chimeric polypeptide to the rate of increase in the concentration of the immune cell in a similar sample contacted with any of the single-chain chimeric polypeptides described herein or any of the multi-chain chimeric polypeptides described herein).

In other examples, the proliferation of an NK cell can be indirectly detected by detecting an increase in the level of one or more cytokines, chemokines and proliferation biomarkers secreted or upregulated on the surface by proliferating immune cells (e.g., one or more of IL-2, interferon-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, TGFβ, TNF-α, IFN-γ, and Ki67) (e.g., as compared to the level of the one or more cytokines and chemokines in a control not contacted with any of the single-chain chimeric polypeptides described herein).

In some embodiments, the methods provided herein can result in an increase (e.g., about 1% to about 800% increase, or any of the subranges of this range described herein) in the rate of increase in the concentration of the NK in a sample contacted with any of the first and second multi-chain chimeric polypeptides described herein and the IgG1 antibody constructs described herein (as set forth in the methods described herein) as compared to the rate of increase in a similar control sample before the first period of time.

Methods of Inducing Differentiation of an NK Cell

Also provided herein are methods of inducing differentiation of a NK cell (e.g., any of the exemplary immune cells described herein or known in the art) that include contacting a NK cell in a liquid culture medium including an effective amount of a first multi-chain chimeric polypeptide described herein for a first period of time under conditions that allow for differentiation of the NK cell, and contacting the NK cell in a liquid culture medium including an effective amount of (i) a second multi-chain chimeric polypeptides described herein, and (ii) an IgG1 antibody construct that comprises at least one antigen-binding domain that binds specifically to the linker domain (e.g., a monoclonal or polyclonal human, mouse, rabbit, or goat IgG1 antibody that binds specifically to a linker domain or any of the other exemplary IgG1 antibody constructs described herein), for a second period of time under conditions that allow for the activation and proliferation of the NK cell. In some examples, the NK cell is contacted in vitro (e.g., in a suitable liquid culture medium under conditions sufficient to result in stimulation of the NK cell).

In some examples, the NK cell has been previously obtained from a subject (e.g., a mammal, e.g., a human). Some embodiments of these methods further include obtaining the NK cell from the subject prior to the contacting step.

In some examples, the immune cell is contacted in vivo. In such embodiments, any of the first multi-chain chimeric polypeptide, any of the second multi-chain chimeric polypeptides, and any of the IgG1 antibody constructs described herein can be administered to a subject (e.g., a mammal, e.g., a human) in an amount sufficient to result in stimulation of an NK cell in the subject.

In some examples, the NK cell has previously been genetically-modified to express a chimeric antigen receptor or a recombinant T-cell receptor. Some embodiments of these methods can further include, after the contacting step, introducing into the NK cell (e.g., any of the immune cells described herein) a nucleic acid encoding a chimeric antigen-receptor or a recombinant T-cell receptor.

Some embodiments of these methods can further include administering a therapeutically effective amount of the NK cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

In some examples, the immune cell is a NK cell, and the detection of NK cells that are highly activated with a long persistence and a high degree of cytotoxicity against diseased cells in a recipient host (e.g., a memory NK cell) can include, e.g., the detection of the level of one or more of IL-12, IL-18, IL-33, STAT4, Zbtb32, DNAM-1, BIM, Noxa, SOCS1, BNIP3, BNIP3L, interferon-γ, TNFα, CXCL16, CXCR6, NKG2D, TRAIL, CD49, Ly49D, CD49b, and Ly79H. A description of NK memory cells and methods of detecting the same is described in O'Sullivan et al., Immunity 43:634-645, 2015.

Methods of Treatment

Also provided herein are methods of treating a subject in need thereof (e.g., any of the exemplary subjects described herein or known in the art) that include administering to the subject a therapeutically effective amount of any of the NK cells produced by any of the methods described herein or any of the compositions (e.g., pharmaceutical compositions) described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, these methods can result in a reduction in the number, severity, or frequency of one or more symptoms of the cancer in the subject (e.g., as compared to the number, severity, or frequency of the one or more symptoms of the cancer in the subject prior to treatment). In some embodiments, these methods can result in a reduction (e.g., about 1% reduction to about 99% reduction, about 1% reduction to about 95% reduction, about 1% reduction to about 90% reduction, about 1% reduction to about 85% reduction, ab out 1% reduction to about 80% reduction, about 1% reduction to about 75% reduction, about 1% reduction to about 70% reduction, about 1% reduction to about 65% reduction, about 1% reduction to about 60% reduction, about 1% reduction to about 55% reduction, ab out 1% reduction to about 50% reduction, about 1% reduction to about 45% reduction, about 1% reduction to about 40% reduction, about 1% reduction to about 35% reduction, about 1% reduction to about 30% reduction, about 1% reduction to about 25% reduction, about 1% reduction to about 20% reduction, about 1% reduction to about 15% reduction, about 1% reduction to about 10% reduction, about 1% reduction to about 5% reduction, about 5% reduction to about 99% reduction, about 5% reduction to about 95% reduction, about 5% reduction to about 90% reduction, about 5% reduction to about 85% reduction, ab out 5% reduction to about 80% reduction, about 5% reduction to about 75% reduction, about 5% reduction to about 70% reduction, about 5% reduction to about 65% reduction, about 5% reduction to about 60% reduction, about 5% reduction to about 55% reduction, ab out 5% reduction to about 50% reduction, about 5% reduction to about 45% reduction, about 5% reduction to about 40% reduction, about 5% reduction to about 35% reduction, about 5% reduction to about 30% reduction, about 5% reduction to about 25% reduction, about 5% reduction to about 20% reduction, about 5% reduction to about 15% reduction, about 5% reduction to about 10% reduction, about 10% reduction to about 99% reduction, about 10% reduction to about 95% reduction, about 10% reduction to about 90% reduction, about 10% reduction to about 85% reduction, about 10% reduction to about 80% reduction, about 10% reduction to about 75% reduction, about 10% reduction to about 70% reduction, about 10% reduction to about 65% reduction, about 10% reduction to about 60% reduction, about 10% reduction to about 55% reduction, about 10% reduction to about 50% reduction, about 10% reduction to about 45% reduction, about 10% reduction to about 40% reduction, about 10% reduction to about 35% reduction, about 10% reduction to about 30% reduction, about 10% reduction to about 25% reduction, about 10% reduction to about 20% reduction, about 10% reduction to about 15% reduction, about 15% reduction to about 99% reduction, about 15% reduction to about 95% reduction, about 15% reduction to about 90% reduction, about 15% reduction to about 85% reduction, about 15% reduction to about 80% reduction, about 15% reduction to about 75% reduction, about 15% reduction to about 70% reduction, about 15% reduction to about 65% reduction, about 15% reduction to about 60% reduction, about 15% reduction to about 55% reduction, about 15% reduction to about 50% reduction, about 15% reduction to about 45% reduction, about 15% reduction to about 40% reduction, about 15% reduction to about 35% reduction, about 15% reduction to about 30% reduction, about 15% reduction to about 25% reduction, about 15% reduction to about 20% reduction, about 20% reduction to about 99% reduction, about 20% reduction to about 95% reduction, about 20% reduction to about 90% reduction, about 20% reduction to about 85% reduction, about 20% reduction to about 80% reduction, about 20% reduction to about 75% reduction, about 20% reduction to about 70% reduction, about 20% reduction to about 65% reduction, about 20% reduction to about 60% reduction, about 20% reduction to about 55% reduction, about 20% reduction to about 50% reduction, about 20% reduction to about 45% reduction, about 20% reduction to about 40% reduction, about 20% reduction to about 35% reduction, about 20% reduction to about 30% reduction, about 20% reduction to about 25% reduction, about 25% reduction to about 99% reduction, about 25% reduction to about 95% reduction, about 25% reduction to about 90% reduction, about 25% reduction to about 85% reduction, about 25% reduction to about 80% reduction, about 25% reduction to about 75% reduction, about 25% reduction to about 70% reduction, about 25% reduction to about 65% reduction, about 25% reduction to about 60% reduction, about 25% reduction to about 55% reduction, about 25% reduction to about 50% reduction, about 25% reduction to about 45% reduction, about 25% reduction to about 40% reduction, about 25% reduction to about 35% reduction, about 25% reduction to about 30% reduction, about 30% reduction to about 99% reduction, about 30% reduction to about 95% reduction, about 30% reduction to about 90% reduction, about 30% reduction to about 85% reduction, about 30% reduction to about 80% reduction, about 30% reduction to about 75% reduction, about 30% reduction to about 70% reduction, about 30% reduction to about 65% reduction, about 30% reduction to about 60% reduction, about 30% reduction to about 55% reduction, about 30% reduction to about 50% reduction, about 30% reduction to about 45% reduction, about 30% reduction to about 40% reduction, about 30% reduction to about 35% reduction, about 35% reduction to about 99% reduction, about 35% reduction to about 95% reduction, about 35% reduction to about 90% reduction, about 35% reduction to about 85% reduction, about 35% reduction to about 80% reduction, about 35% reduction to about 75% reduction, about 35% reduction to about 70% reduction, about 35% reduction to about 65% reduction, about 35% reduction to about 60% reduction, about 35% reduction to about 55% reduction, about 35% reduction to about 50% reduction, about 35% reduction to about 45% reduction, about 35% reduction to about 40% reduction, about 40% reduction to about 99% reduction, about 40% reduction to about 95% reduction, about 40% reduction to about 90% reduction, about 40% reduction to about 85% reduction, about 40% reduction to about 80% reduction, about 40% reduction to about 75% reduction, about 40% reduction to about 70% reduction, about 40% reduction to about 65% reduction, about 40% reduction to about 60% reduction, about 40% reduction to about 55% reduction, about 40% reduction to about 50% reduction, about 40% reduction to about 45% reduction, about 45% reduction to about 99% reduction, about 45% reduction to about 95% reduction, about 45% reduction to about 90% reduction, about 45% reduction to about 85% reduction, about 45% reduction to about 80% reduction, about 45% reduction to about 75% reduction, about 45% reduction to about 70% reduction, about 45% reduction to about 65% reduction, about 45% reduction to about 60% reduction, about 45% reduction to about 55% reduction, about 45% reduction to about 50% reduction, about 50% reduction to about 99% reduction, about 50% reduction to about 95% reduction, about 50% reduction to about 90% reduction, about 50% reduction to about 85% reduction, about 50% reduction to about 80% reduction, about 50% reduction to about 75% reduction, about 50% reduction to about 70% reduction, about 50% reduction to about 65% reduction, about 50% reduction to about 60% reduction, about 50% reduction to about 55% reduction, about 55% reduction to about 99% reduction, about 55% reduction to about 95% reduction, about 55% reduction to about 90% reduction, about 55% reduction to about 85% reduction, about 55% reduction to about 80% reduction, about 55% reduction to about 75% reduction, about 55% reduction to about 70% reduction, about 55% reduction to about 65% reduction, about 55% reduction to about 60% reduction, about 60% reduction to about 99% reduction, about 60% reduction to about 95% reduction, about 60% reduction to about 90% reduction, about 60% reduction to about 85% reduction, about 60% reduction to about 80% reduction, about 60% reduction to about 75% reduction, about 60% reduction to about 70% reduction, about 60% reduction to about 65% reduction, about 65% reduction to about 99% reduction, about 65% reduction to about 95% reduction, about 65% reduction to about 90% reduction, about 65% reduction to about 85% reduction, about 65% reduction to about 80% reduction, about 65% reduction to about 75% reduction, about 65% reduction to about 70% reduction, about 70% reduction to about 99% reduction, about 70% reduction to about 95% reduction, about 70% reduction to about 90% reduction, about 70% reduction to about 85% reduction, about 70% reduction to about 80% reduction, about 70% reduction to about 75% reduction, about 75% reduction to about 99% reduction, about 75% reduction to about 95% reduction, about 75% reduction to about 90% reduction, about 75% reduction to about 85% reduction, about 75% reduction to about 80% reduction, about 80% reduction to about 99% reduction, about 80% reduction to about 95% reduction, about 80% reduction to about 90% reduction, about 80% reduction to about 85% reduction, about 85% reduction to about 99% reduction, about 85% reduction to about 95% reduction, about 85% reduction to about 90% reduction, about 90% reduction to about 99% reduction, about 90% reduction to about 95% reduction, or about 95% reduction to about 99% reduction) in the volume of one or more solid tumors in the subject (e.g., as compared to the volume of the one or more solid tumors prior to treatment or at the start of treatment). In some embodiments, the these methods can reduce (e.g., about 1% reduction to about 99% reduction, or any of the subranges of this range described herein) the risk of developing a metastasis or developing one or more additional metastasis in a subject (e.g., as compared to the risk of developing a metastasis or developing one or more additional metastasis in a subject prior to treatment or in a similar subject or a population of subjects administered a different treatment).

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples, these methods can result in a reduction in the number, severity, or frequency of one or more symptoms of the aging-related disease or condition in the subject (e.g., as compared to the number, severity, or frequency of the one or more symptoms of the aging-related disease or condition in the subject prior to treatment). In some examples, the methods can result in a decrease (e.g., about 1% decrease to about 99% decrease, an about 1% decrease to about 95% decrease, about 1% decrease to about 90% decrease, about 1% decrease to about 85% decrease, about 1% decrease to about 80% decrease, about 1% decrease to about 75% decrease, about 1% to about 70% decrease, about 1% decrease to about 65% decrease, about 1% decrease to about 60% decrease, about 1% decrease to about 55% decrease, about 1% decrease to about 50% decrease, about 1% decrease to about 45% decrease, about 1% decrease to about 40% decrease, about 1% decrease to about 35% decrease, about 1% decrease to about 30% decrease, about 1% decrease to about 25% decrease, about 1% decrease to about 20% decrease, about 1% decrease to about 15% decrease, about 1% decrease to about 10% decrease, about 1% decrease to about 5% decrease, about 5% decrease to about 99% decrease, an about 5% decrease to about 95% decrease, about 5% decrease to about 90% decrease, about 5% decrease to about 85% decrease, about 5% decrease to about 80% decrease, about 5% decrease to about 75% decrease, about 5% to about 70% decrease, about 5% decrease to about 65% decrease, about 5% decrease to about 60% decrease, about 5% decrease to about 55% decrease, about 5% decrease to about 50% decrease, about 5% decrease to about 45% decrease, about 5% decrease to about 40% decrease, about 5% decrease to about 35% decrease, about 5% decrease to about 30% decrease, about 5% decrease to about 25% decrease, about 5% decrease to about 20% decrease, about 5% decrease to about 15% decrease, about 5% decrease to about 10% decrease, about 10% decrease to about 99% decrease, an about 10% decrease to about 95% decrease, about 10% decrease to about 90% decrease, about 10% decrease to about 85% decrease, about 10% decrease to about 80% decrease, about 10% decrease to about 75% decrease, about 10% to about 70% decrease, about 10% decrease to about 65% decrease, about 10% decrease to about 60% decrease, about 10% decrease to about 55% decrease, about 10% decrease to about 50% decrease, about 10% decrease to about 45% decrease, about 10% decrease to about 40% decrease, about 10% decrease to about 35% decrease, about 10% decrease to about 30% decrease, about 10% decrease to about 25% decrease, about 10% decrease to about 20% decrease, about 10% decrease to about 15% decrease, about 15% decrease to about 99% decrease, an about 15% decrease to about 95% decrease, about 15% decrease to about 90% decrease, about 15% decrease to about 85% decrease, about 15% decrease to about 80% decrease, about 15% decrease to about 75% decrease, about 15% to about 70% decrease, about 15% decrease to about 65% decrease, about 15% decrease to about 60% decrease, about 15% decrease to about 55% decrease, about 15% decrease to about 50% decrease, about 15% decrease to about 45% decrease, about 15% decrease to about 40% decrease, about 15% decrease to about 35% decrease, about 15% decrease to about 30% decrease, about 15% decrease to about 25% decrease, about 15% decrease to about 20% decrease, about 20% decrease to about 99% decrease, an about 20% decrease to about 95% decrease, about 20% decrease to about 90% decrease, about 20% decrease to about 85% decrease, about 20% decrease to about 80% decrease, about 20% decrease to about 75% decrease, about 20% to about 70% decrease, about 20% decrease to about 65% decrease, about 20% decrease to about 60% decrease, about 20% decrease to about 55% decrease, about 20% decrease to about 50% decrease, about 20% decrease to about 45% decrease, about 20% decrease to about 40% decrease, about 20% decrease to about 35% decrease, about 20% decrease to about 30% decrease, about 20% decrease to about 25% decrease, about 25% decrease to about 99% decrease, an about 25% decrease to about 95% decrease, about 25% decrease to about 90% decrease, about 25% decrease to about 85% decrease, about 25% decrease to about 80% decrease, about 25% decrease to about 75% decrease, about 25% to about 70% decrease, about 25% decrease to about 65% decrease, about 25% decrease to about 60% decrease, about 25% decrease to about 55% decrease, about 25% decrease to about 50% decrease, about 25% decrease to about 45% decrease, about 25% decrease to about 40% decrease, about 25% decrease to about 35% decrease, about 25% decrease to about 30% decrease, about 30% decrease to about 99% decrease, an about 30% decrease to about 95% decrease, about 30% decrease to about 90% decrease, about 30% decrease to about 85% decrease, about 30% decrease to about 80% decrease, about 30% decrease to about 75% decrease, about 30% to about 70% decrease, about 30% decrease to about 65% decrease, about 30% decrease to about 60% decrease, about 30% decrease to about 55% decrease, about 30% decrease to about 50% decrease, about 30% decrease to about 45% decrease, about 30% decrease to about 40% decrease, about 30% decrease to about 35% decrease, about 35% decrease to about 99% decrease, an about 35% decrease to about 95% decrease, about 35% decrease to about 90% decrease, about 35% decrease to about 85% decrease, about 35% decrease to about 80% decrease, about 35% decrease to about 75% decrease, about 35% to about 70% decrease, about 35% decrease to about 65% decrease, about 35% decrease to about 60% decrease, about 35% decrease to about 55% decrease, about 35% decrease to about 50% decrease, about 35% decrease to about 45% decrease, about 35% decrease to about 40% decrease, about 40% decrease to about 99% decrease, an about 40% decrease to about 95% decrease, about 40% decrease to about 90% decrease, about 40% decrease to about 85% decrease, about 40% decrease to about 80% decrease, about 40% decrease to about 75% decrease, about 40% to about 70% decrease, about 40% decrease to about 65% decrease, about 40% decrease to about 60% decrease, about 40% decrease to about 55% decrease, about 40% decrease to about 50% decrease, about 40% decrease to about 45% decrease, about 45% decrease to about 99% decrease, an about 45% decrease to about 95% decrease, about 45% decrease to about 90% decrease, about 45% decrease to about 85% decrease, about 45% decrease to about 80% decrease, about 45% decrease to about 75% decrease, about 45% to about 70% decrease, about 45% decrease to about 65% decrease, about 45% decrease to about 60% decrease, about 45% decrease to about 55% decrease, about 45% decrease to about 50% decrease, about 50% decrease to about 99% decrease, an about 50% decrease to about 95% decrease, about 50% decrease to about 90% decrease, about 50% decrease to about 85% decrease, about 50% decrease to about 80% decrease, about 50% decrease to about 75% decrease, about 50% to about 70% decrease, about 50% decrease to about 65% decrease, about 50% decrease to about 60% decrease, about 50% decrease to about 55% decrease, about 55% decrease to about 99% decrease, an about 55% decrease to about 95% decrease, about 55% decrease to about 90% decrease, about 55% decrease to about 85% decrease, about 55% decrease to about 80% decrease, about 55% decrease to about 75% decrease, about 55% to about 70% decrease, about 55% decrease to about 65% decrease, about 55% decrease to about 60% decrease, about 60% decrease to about 99% decrease, an about 60% decrease to about 95% decrease, about 60% decrease to about 90% decrease, about 60% decrease to about 85% decrease, about 60% decrease to about 80% decrease, about 60% decrease to about 75% decrease, about 60% to about 70% decrease, about 60% decrease to about 65% decrease, about 65% decrease to about 99% decrease, an about 65% decrease to about 95% decrease, about 65% decrease to about 90% decrease, about 65% decrease to about 85% decrease, about 65% decrease to about 80% decrease, about 65% decrease to about 75% decrease, about 65% to about 70% decrease, about 70% decrease to about 99% decrease, an about 70% decrease to about 95% decrease, about 70% decrease to about 90% decrease, about 70% decrease to about 85% decrease, about 70% decrease to about 80% decrease, about 70% decrease to about 75% decrease, about 75% decrease to about 99% decrease, an about 75% decrease to about 95% decrease, about 75% decrease to about 90% decrease, about 75% decrease to about 85% decrease, about 75% decrease to about 80% decrease, about 80% decrease to about 99% decrease, an about 80% decrease to about 95% decrease, about 80% decrease to about 90% decrease, about 80% decrease to about 85% decrease, about 85% decrease to about 99% decrease, an about 85% decrease to about 95% decrease, about 85% decrease to about 90% decrease, about 90% decrease to about 99% decrease, an about 90% decrease to about 95% decrease, or about 95% decrease to about 99% decrease) in the number of senescent cells in the subject (e.g., a decrease in the number of senescent cells in one or more specific tissues involved and/or implicated in the aging-related disease or disorder in the subject), e.g., as compared to the number of senescent cells in the subject prior to treatment.

In some examples of these methods, the subject has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus. In some embodiments, these methods can result in a decrease in the infectious titer (e.g., viral titer) in a subject (e.g., as compared to the infectious titer in the subject prior to treatment). In some embodiments, these methods can result in a reduction in the number, severity, or frequency of one or more symptoms of the infectious disease (e.g., viral infection) in the subject (e.g., as compared to the number, severity, or frequency of the one or more symptoms of the infectious disease in the subject prior to treatment).

The term "subject" refers to any mammal. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine or primate animals) may be employed.

Methods of Killing a Cancer Cell, an Infected Cell, or a Senescent Cell

Also provided herein are methods of killing a cancer cell (e.g. any of the exemplary types of cancer described herein or known in the art), an infected cell (e.g., a cell infected with any of the exemplary viruses described herein or known in the art), or a senescent cell (e.g., a senescent cancer cell, a senescent fibroblast, or a senescent endothelial cell) in a subject in need thereof (e.g., any of the exemplary subjects described herein or known in the art) that include administering to the subject a therapeutically effective amount of any of NK cells produced by any of the methods described herein or any of the compositions (e.g., pharmaceutical compositions) described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. Non-limiting examples of an infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Senescent Cells

Senescence is a form of irreversible growth arrest accompanied by phenotypic changes, resistance to apoptosis and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence the tissue hemostasis, disease and aging through their secretory phenotype. Senescence is considered as a physiologic process and is important in promoting wound healing, tissue homeostasis, regeneration, and fibrosis regulation. For instance, transient induction of senescent cells is observed during would healing and contributes to wound resolution. Perhaps one of the most important roles of senescence is its role in tumor suppression. However, the accumulation of senescent cells also drives aging and aging-related diseases and conditions. The senescent phenotype also can trigger chronic inflammatory responses and consequently augment chronic inflammatory conditions to promote tumor growth. The connection between senescence and aging was initially based on observations that senescent cells accumulate in aged tissue. The use of transgenic models has enabled the detection of senescent cells systematically in many age-related pathologies. Strategies to selectively eliminate senescent cells have demonstrated that senescent cells can indeed play a causal role in aging and related pathologies.

Senescent cells display important and unique properties which include changes in morphology, chromatin organization, gene expression, and metabolism. There are several biochemical and functional properties associated with cellular senescence, such as (i) increased expression of $p16^{INK4a}$ and $p21^{CIP1}$, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-β), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer and aging-related diseases.

The secretion profile of senescent cells are context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD+/NADH ratio activated AMPK signaling which induced MiDAS through the activation of p53. As a result, p53 inhibited NF-κB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression $p16^{INK4a}$ and $p21^{CIP1}$ induced the senescent phenotype in human fibroblasts without an inflammatory SASP indicating that the growth arrest itself did not stimulate SASP.

One of the most defining characteristics of senescence is stable growth arrest. This is achieved by two important pathways, the $p16^{INK4a}$/Rb and the p53/$p21^{CIP1}$, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of $p16^{INK4a}$ and ARF (both encoded by CDKN2A) and $P15^{INK4b}$ (encoded by CDKN2B): p53 induces transcription of cyclin-dependent kinase inhibitor ($p21^{CIP1}$) and along with both $p16^{INK4a}$ and $p15^{INK4b}$ block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya, *J Clin Invest.* 128(4):1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for Natural Killer (NK) cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv, Oncogene 32(15): 1971-1977, 2013), hepatocellular carcinoma (Iannello, *J Exp Med* 210(10): 2057-2069, 2013), multiple myeloma (Soriani, *Blood* 113 (15): 3503-3511, 2009), and glioma cells stressed by dysfunction of the mevalonate pathway (Ciaglia, *Int J Cancer* 142(1): 176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton, *Elife* 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80+ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky, *Cell* 134(4): 657-667, 2008). Studies have described various models to study senescence including liver fibrosis (Krizhanovsky, *Cell* 134(4): 657-667, 2008), osteoarthritis (Xu, *J Gerontol A Blot Sci Med Sci* 72(6): 780-785, 2017), and Parkinson's disease (Chinta, *Cell Rep* 22(4): 930-940, 2018). Animal models for studying senescent cells are described in: Krizhanovsky, *Cell* 134(4): 657-667, 2008; Baker, *Nature* 479(7372): 232-236, 2011; Farr, *Nat Med* 23(9): 1072-1079, 2017; Bourgeois, *FEBS Lett* 592(12): 2083-2097, 2018; Xu, *Nat Med* 24(8): 1246-1256, 2018).

Methods of Increasing Glucose Consumption of an NK Cell

Also provided herein are methods of increasing the glucose consumption of an NK cell that include: (a) contacting a natural killer cell in a liquid culture medium (e.g., any of the liquid culture media described herein) including an effective amount of a first multi-chain chimeric polypeptide comprising a first chimeric polypeptide and a second chimeric polypeptide for a first period of time under conditions that allow for the differentiation of the natural killer cell; and (b) contacting the natural killer cell in a liquid culture medium comprising an effective amount of (i) a second multi-chain chimeric polypeptide comprising a first chimeric polypeptide and a second chimeric polypeptide, and (ii) an IgG1 antibody construct that includes at least one antigen-binding domain that binds specifically to the linker domain (e.g., any of the exemplary IgG1 antibody constructs described herein), for a second period of time, under conditions that allow for glucose consumption in the NK cell.

In some embodiments of any of the methods described herein, the increase in glucose consumption is compared to the level of glucose consumption in a similar NK cell not contacted with any of the multi-chain chimeric polypeptides described herein.

Non-limiting assays that can be used to detect glucose consumption include, e.g., assays that include the use of radiolabeled 3-O-methylglucose or radiolabeled 2-deoxyglucose, or an enzymatic, fluorometric assay for detecting 2-deoxyglucose. Additional examples of assays that can be used to detect glucose consumption are described in, e.g., Yamamoto et al., *Curr. Protoc. Pharmacol., Chapter* 12, Unit 12.14.1-22, December 2011; Zou et al., *J. Biochem. Biophys. Methods* 64(3):207-215, September 2005; and MacKrell et al., *Diabetes* p. 1-9, published online on Mar. 13, 2012.

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the second multi-chain chimeric polypeptide, and the IgG1 antibody construct at a molar ratio of about 0.5:1 to about 2:1 (e.g., about 0.8:1 to about 1.2:1).

In some examples of these methods, the NK cell was previously obtained from a subject. Some embodiments of these methods further include obtaining the NK cell from the subject prior to the contacting step. In some embodiments of these methods, the NK cell has previously been genetically modified to express a chimeric antigen receptor or a recombinant T-cell receptor. Some embodiments of these methods further include, after the contacting step, introducing into the NK cell a nucleic acid encoding a chimeric antigen-receptor or a recombinant T-cell receptor. Some embodiments of these methods further include, before the contacting step, introducing into the NK cell a nucleic acid encoding a chimeric antigen-receptor or a recombinant T-cell receptor. Some embodiments of these methods further include, after the contacting step, isolating the NK cell. Some embodiments of these methods further include, after the contacting step, administering the NK cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Also provided herein are activated NK cells produced by any of the methods described herein. Also provided herein are pharmaceutical compositions that include any of the activated NK cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated NK cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Oxidative Phosphorylation of an NK Cell

Also provided herein are methods of increasing the oxidative phosphorylation of an NK cell that include: (a) contacting a natural killer cell in a liquid culture medium (e.g., any of the liquid culture media described herein) including an effective amount of any of the first multi-chain chimeric polypeptides described herein for a first period of time under conditions that allow for the differentiation of the natural killer cell; and (b) contacting the natural killer cell in a liquid culture medium comprising an effective amount of (i) any of the second multi-chain chimeric polypeptides described herein, and (ii) an IgG1 antibody construct that includes at least one antigen-binding domain that binds specifically to the linker domain (e.g., any of the exemplary IgG1 antibody constructs described herein), for a second period of time, under conditions that allow for oxidative phosphorylation in the natural killer cell.

In some embodiments of any of the methods described herein, the increase in oxidative phosphorylation is compared to the level of oxidative phosphorylation in a similar NK cell not contacted with any of the multi-chain chimeric polypeptides described herein.

Non-limiting assays that can be used to detect oxidative phosphorylation include, e.g., immunofluorescent assays and colorimetric assays. A non-limiting commercial assay that can be used to determine the level of oxidative phosphorylation is MitoTox™ Complete OXPHOS Activity Assay (Abcam). Additional examples of assays that can be used to detect oxidative phosphorylation are described in, e.g., Chance et al., *Nature* 175:1120-1121, 1955; Pullman et al., Science 123(3208):1105-1107, 1956; Van Bergen et al., *Mitochondrion* 15:24-33, 2014; and Rocha et al., *Sci. Rep.* 5:15037, 2015.

In some examples of these methods, the IgG1 antibody construct is a monoclonal IgG1 antibody, where both of the antigen-binding domains in the monoclonal IgG1 antibody bind specifically to the linker domain. In some examples of these methods, the IgG1 antibody construct is a bispecific IgG1 antibody, where one of the two antigen-binding domains in the bispecific IgG1 antibody binds specifically to the linker domain.

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the second multi-chain chimeric polypeptide and the IgG1 antibody construct at a molar ratio of about 0.5:0.5:1 to about 2:2:1 (e.g., about 0.8:0.8:1 to about 1.2:1.2:1).

In some examples of these methods, the NK cell was previously obtained from a subject. Some embodiments of these methods further include obtaining the NK cell from the subject prior to the contacting step. In some embodiments of these methods, the NK cell has previously been genetically modified to express a chimeric antigen receptor or a recombinant T-cell receptor. Some embodiments of these methods further include, after the contacting step, introducing into the NK cell a nucleic acid encoding a chimeric antigen-receptor or a recombinant T-cell receptor. Some embodiments of these methods further include, before the contacting step, introducing into the NK cell a nucleic acid encoding a chimeric antigen-receptor or a recombinant T-cell receptor. Some embodiments of these methods further include, after the contacting step, isolating the NK cell. Some embodiments of these methods further include, after the contacting step, administering the NK cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Also provided herein are activated NK cells produced by any of these methods. Also provided herein are pharmaceutical compositions that include any of the activated NK cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated NK cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated NK cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Aerobic Glycolysis of an Immune Cell

Also provided herein are methods of increasing the aerobic glycolysis of an immune cell that include: (a) contacting a natural killer cell in a liquid culture medium (e.g., any of the liquid culture media described herein) including an effective amount of any of the first multi-chain chimeric polypeptides described herein for a first period of time under conditions that allow for the differentiation of the natural killer cell; and (b) contacting the natural killer cell in a liquid culture medium comprising an effective amount of (i) any of the second multi-chain chimeric polypeptides described herein for a second period of time, under conditions that allow for aerobic glycolysis in the natural killer cell.

In some embodiments of any of the methods described herein, the increase in aerobic glycolysis is compared to the level of aerobic glycolysis in a similar NK cell not contacted with any of the multi-chain chimeric polypeptides described herein.

Non-limiting assays that can be used to detect aerobic glycolysis include, e.g., detection of ATP and/or $CO_2$ production, e.g., using gas chromatography/mass spectrometry, or extracellular acidification rate. Additional examples of assays that can be used to detect aerobic glycolysis are described in, e.g., Zhang et al., *Bone* 114:150-160, 2018; Zhao et al., *J. Breast Cancer* 21(2):112-123, 2018; Li et al., *Cell Comm. Signal.* 16(1):26, 2018; Cai et al., *J. Exp. Clin. Cancer Res.* 37(1):104, 2018; and Zhang et al., *Oncol. Rep.* 40(2):1156-1164, 2018.

In some examples of these methods, the IgG1 antibody construct is a monoclonal IgG1 antibody, where both of the antigen-binding domains in the monoclonal IgG1 antibody bind specifically to the linker domain. In some examples of these methods, the IgG1 antibody construct is a bispecific IgG1 antibody, where one of the two antigen-binding domains in the bispecific IgG1 antibody binds specifically to the linker domain.

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the second multi-chain chimeric polypeptide and the IgG1 antibody construct at a molar ratio of about 0.5:0.5:1 to about 2:2:1 (e.g., about 0.8:0.8:1 to about 1.2:1.2:1).

In some examples of these methods, the NK cell was previously obtained from a subject. Some embodiments of these methods further include obtaining the NK cell from the subject prior to the contacting step. In some embodiments of these methods, the NK cell has previously been genetically modified to express a chimeric antigen receptor or a recombinant T-cell receptor. Some embodiments of these methods further include, after the contacting step, introducing into the NK cell a nucleic acid encoding a chimeric antigen-receptor or a recombinant T-cell receptor. Some embodiments of these methods further include, before the contacting step, introducing into the NK cell a nucleic acid encoding a chimeric antigen-receptor or a recombinant T-cell receptor. Some embodiments of these methods further include, after the contacting step, isolating the NK cell. Some embodiments of these methods further include, after the contacting step, administering the NK cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated NK cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Extracellular Acidification Rate (ECAR) of an Immune Cell

Also provided herein are method of increasing the extracellular acidification rate (ECAR) of a NK cell that include: (a) contacting a natural killer cell in a liquid culture medium (e.g., any of the liquid culture media described herein) including an effective amount of any of the first multi-chain chimeric polypeptides described herein for a first period of time under conditions that allow for the differentiation of the natural killer cell; and (b) contacting the natural killer cell in a liquid culture medium comprising an effective amount of any of the second multi-chain chimeric polypeptides described herein and any of the IgG1 antibody constructs described herein for a second period of time, under conditions that allow for extracellular acidification by the natural killer cell.

In some embodiments of any of the methods described herein, the increase in extracellular acidification rate (ECAR) is compared to the level of extracellular acidification rate (ECAR) in a similar NK cell not contacted with any of the multi-chain chimeric polypeptide and/or the IgG1 antibody construct that includes at least one antigen-binding domain that binds specifically to the linker domain.

Non-limiting commercial assays that can be used to detect extracellular acidification rate (ECAR) include, e.g., Glycolysis Assay (Extracellular Acidification Kit) (ab197244 or ab197245) (Abcam), MITO-ID® Extracellular pH Sensor Kit (ENZ-51048) (Enzo Life Sciences), and pH-Xtra™-Glycolysis Assay (Extracellular Acidification). Additional examples of assays that can be used to detect extracellular acidification rate (ECAR) are described in, e.g., Owicki et al., *Biosens. Bioelectron.* 7(4):255-272, 1992; Hynes et al., *Analytical Biochem.* 390(1):21-28, 2009; Trevani et al., *J. Immunol.* 162(8):4849-4857, 1999; and Mookerjee et al., *J. Vis. Exp.* 106:53464, 2015.

In some examples of these methods, the IgG1 antibody construct is a monoclonal IgG1 antibody, where both of the antigen-binding domains in the monoclonal IgG1 antibody bind specifically to the linker domain. In some examples of these methods, the IgG1 antibody construct is a bispecific IgG1 antibody, where one of the two antigen-binding domains in the bispecific IgG1 antibody binds specifically to the linker domain.

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the second multi-chain chimeric polypeptide and the IgG1 antibody construct at a molar ratio of about 0.5:0.5:1 to about 2:2:1 (e.g., about 0.8:0.8:1 to about 1.2:1.2:1).

In some examples of these methods, the NK cell was previously obtained from a subject. Some embodiments of these methods further include obtaining the NK cell from the subject prior to the contacting step. In some embodiments of these methods, the NK cell has previously been genetically modified to express a chimeric antigen receptor or a recombinant T-cell receptor. Some embodiments of these methods further include, after the contacting step, introducing into the NK cell a nucleic acid encoding a chimeric antigen-receptor or a recombinant T-cell receptor. Some embodiments of these methods further include, before the contacting step, introducing into the NK cell a nucleic acid encoding a chimeric antigen-receptor or a recombinant T-cell receptor. Some embodiments of these methods further include, after the contacting step, isolating the NK cell. Some embodiments of these methods further include, after the contacting step, administering the NK cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated NK cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated NK cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Mitochondrial Oxygen Consumption Rate of an Immune Cell

Also provided herein are methods of increasing the mitochondrial oxygen consumption rate of a natural killer cell that include: (a) contacting a natural killer cell in a liquid culture medium (e.g., any of the liquid culture media described herein) including an effective amount of any of the first multi-chain chimeric polypeptides described herein; and (b) contacting the natural killer cell in a liquid culture medium comprising an effective amount of any of the second multi-chain chimeric polypeptides described herein and any of the IgG1 antibody constructs described herein for a second period of time, under conditions that allow for mitochondrial oxygen consumption rate by the natural killer cell.

In some embodiments of any of the methods described herein, the increase in mitochondrial oxygen consumption rate is compared to the level of mitochondrial oxygen consumption rate in a similar NK cell not contacted with any of the multi-chain chimeric polypeptides described herein.

Non-limiting commercial assays that can be used to detect mitochondrial oxygen consumption rate include, e.g., assays that include the use of an electrode or a commercially available kit, e.g., Oxygen Consumption Rate Assay Kit (Cayman Chemical), the Seahorse assay (as described in Sakamuri et al., *Geroscience* 40(3):347-356, 2018). Additional examples of assays that can be used to detect mitochondrial oxygen consumption rate are described in, e.g., Li et al., *Mitochondrial Disorders*, pp. 63-72, December 2011; Kumagi et al., *Synapse* e22067, August 2018; Takahashi et al., *J. Physiol. Sci.* 67(6):731-737, 2017; and Iihoshi et al., *Toxicol. Lett.* 277:109-114, 2017.

In some examples of these methods, the IgG1 antibody construct is a monoclonal IgG1 antibody, where both of the antigen-binding domains in the monoclonal IgG1 antibody bind specifically to the linker domain. In some examples of these methods, the IgG1 antibody construct is a bispecific IgG1 antibody, where one of the two antigen-binding domains in the bispecific IgG1 antibody binds specifically to the linker domain.

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the second multi-chain chimeric polypeptide and the IgG1 antibody construct at a molar ratio of about 0.5:0.5:1 to about 2:2:1 (e.g., about 0.8:0.8:1 to about 1.2:1.2:1).

In some examples of these methods, the NK cell was previously obtained from a subject. Some embodiments of these methods further include obtaining the NK cell from the subject prior to the contacting step. In some embodiments of these methods, the NK cell has previously been genetically modified to express a chimeric antigen receptor or a recombinant T-cell receptor. Some embodiments of these methods further include, after the contacting step, introducing into the NK cell a nucleic acid encoding a chimeric antigen-receptor or a recombinant T-cell receptor. Some embodiments of these methods further include, before the contacting step, introducing into the NK cell a nucleic acid encoding a chimeric antigen-receptor or a recombinant T-cell receptor. Some embodiments of these methods further include, after the contacting step, isolating the NK cell. Some embodiments of these methods further include, after the contacting step, administering the NK cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Expression of Activating Receptors in a NK Cell

Also provided herein are methods of increasing expression of activating receptors in a natural killer cell (e.g., any of the exemplary activating receptors of a natural killer cell described herein) that include: (a) contacting a natural killer cell in a liquid culture medium (e.g., any of the liquid culture media described herein) including an effective amount of any of the first multi-chain chimeric polypeptides described herein; and (b) contacting the natural killer cell in a liquid culture medium comprising an effective amount of any of the second multi-chain chimeric polypeptides described herein and any of the IgG1 antibody constructs described herein for a second period of time, under conditions that allow for mitochondrial oxygen consumption rate by the natural killer cell.

In some examples of these methods, the IgG1 antibody construct is a monoclonal IgG1 antibody, where both of the antigen-binding domains in the monoclonal IgG1 antibody bind specifically to the linker domain. In some examples of these methods, the IgG1 antibody construct is a bispecific IgG1 antibody, where one of the two antigen-binding domains in the bispecific IgG1 antibody binds specifically to the linker domain.

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the second multi-chain chimeric polypeptide and the IgG1 antibody construct at a molar ratio of about 0.5:0.5:1 to about 2:2:1 (e.g., about 0.8:0.8:1 to about 1.2:1.2:1).

In some examples of these methods, the NK cell was previously obtained from a subject. Some embodiments of these methods further include obtaining the NK cell from the subject prior to the contacting step. In some embodiments of these methods, the NK cell has previously been genetically modified to express a chimeric antigen receptor or a recombinant T-cell receptor. Some embodiments of these methods further include, after the contacting step, introducing into the NK cell a nucleic acid encoding a chimeric antigen-receptor or a recombinant T-cell receptor. Some embodiments of these methods further include, before the contacting step, introducing into the NK cell a nucleic acid encoding a chimeric antigen-receptor or a recombinant T-cell receptor. Some embodiments of these methods further include, after the contacting step, isolating the NK cell. Some embodiments of these methods further include, after the contacting step, administering the NK cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Persistence of a NK Cell Upon Administration to a Subject

Also provided herein are methods of increasing persistence of a natural killer cell (e.g., any of the exemplary activating receptors of a natural killer cell described herein) upon administration to a subject that include, prior to administration of the NK cell to the subject: (a) contacting the natural killer cell in a liquid culture medium (e.g., any of the liquid culture media described herein) including an effective amount of any of the first multi-chain chimeric polypeptides described herein; and (b) contacting the natural killer cell in a liquid culture medium comprising an effective amount of any of the second multi-chain chimeric polypeptides described herein and any of the IgG1 antibody constructs described herein for a second period of time, under conditions that allow for mitochondrial oxygen consumption rate by the natural killer cell.

In some examples of these methods, the IgG1 antibody construct is a monoclonal IgG1 antibody, where both of the antigen-binding domains in the monoclonal IgG1 antibody bind specifically to the linker domain. In some examples of these methods, the IgG1 antibody construct is a bispecific IgG1 antibody, where one of the two antigen-binding domains in the bispecific IgG1 antibody binds specifically to the linker domain.

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the second multi-chain chimeric polypeptide and the IgG1 antibody construct at a molar ratio of about 0.5:0.5:1 to about 2:2:1 (e.g., about 0.8:0.8:1 to about 1.2:1.2:1).

In some examples of these methods, the NK cell was previously obtained from a subject. Some embodiments of these methods further include obtaining the NK cell from the subject prior to the contacting step. In some embodiments of these methods, the NK cell has previously been genetically modified to express a chimeric antigen receptor or a recombinant T-cell receptor. Some embodiments of these methods further include, after the contacting step, introducing into the NK cell a nucleic acid encoding a chimeric antigen-receptor or a recombinant T-cell receptor. Some embodiments of these methods further include, before the contacting step, introducing into the NK cell a nucleic acid encoding a chimeric antigen-receptor or a recombinant T-cell receptor. Some embodiments of these methods further include, after the contacting step, isolating the NK cell. Some embodiments of these methods further include, after the contacting step, administering the NK cell to a subject in need thereof.

In some examples of these methods, the subject has been identified or diagnosed as having an age-related disease or condition. In some examples of these methods, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Additional Therapeutic Agents

Some embodiments of any of the methods described herein can further include administering to a subject (e.g., any of the subjects described herein) a therapeutically effective amount of one or more additional therapeutic agents. The one or more additional therapeutic agents can be administered to the subject at substantially the same time as a single-chain chimeric polypeptide (e.g., any of the single-chain chimeric polypeptides described herein), multi-chain chimeric polypeptides (e.g., any of the multi-chain chimeric polypeptides described herein), or an activated immune cell (e.g., an activated NK cell or an activated T cell) (e.g., administered as a single formulation or two or more formulations to the subject). In some embodiments, one or more additional therapeutic agents can be administered to the subject prior to administration of a single-chain chimeric polypeptide (e.g., any of the single-chain chimeric polypeptides described herein), multi-chain chimeric polypeptides (e.g., any of the multi-chain chimeric polypeptides described herein), or an activated immune cell (e.g., an activated NK cell or an activated T cell). In some embodiments, one or more additional therapeutic agents can be administered to the subject after administration of a single-chain chimeric polypeptide (e.g., any of the single-chain chimeric polypeptides described herein), multi-chain chimeric polypeptides (e.g., any of the multi-chain chimeric polypeptides described herein), or an activated immune cell (e.g., an activated NK cell or an activated T cell) to the subject.

Non-limiting examples of additional therapeutic agents include: anti-cancer drugs, activating receptor agonists, immune checkpoint inhibitors, agents for blocking HLA-specific inhibitory receptors, Glucogen Synthase Kinase (GSK) 3 inhibitors, and antibodies.

Non-limiting examples of anticancer drugs include antimetabolic drugs (e.g., 5-fluorouracil (5-FU), 6-mercaptopurine (6-MP), capecitabine, cytarabine, floxuridine, fludarabine, gemcitabine, hydroxycarbamide, methotrexate, 6-thioguanine, cladribine, nelarabine, pentostatin, or pemetrexed), plant alkaloids (e.g., vinblastine, vincristine, vindesine, camptothecin, 9-methoxycamptothecin, coronaridine, taxol, naucleaorals, diprenylated indole alkaloid, montamine, schischkiniin, protoberberine, berberine, sanguinarine, chelerythrine, chelidonine, liriodenine, clivorine, β-carboline, antofine, tylophorine, cryptolepine, neocryptolepine, corynoline, sampangine, carbazole, crinamine, montanine, ellipticine, paclitaxel, docetaxel, etoposide, tenisopide, irinotecan, topotecan, or acridone alkaloids), proteasome inhibitors (e.g., lactacystin, disulfiram, epigallocatechin-3-gallate, marizomib (salinosporamide A), oprozomib (ONX-0912), delanzomib (CEP-18770), epoxomicin, MG132, beta-hydroxy beta-methylbutyrate, bortezomib, carfilzomib, or ixazomib), antitumor antibiotics (e.g., doxorubicin, daunorubicin, epirubicin, mitoxantrone, idarubicin, actinomycin, plicamycin, mitomycin, or bleomycin), histone deacetylase inhibitors (e.g., vorinostat, panobinostat, belinostat, givinostat, abexinostat, depsipeptide, entinostat, phenyl butyrate, valproic acid, trichostatin A, dacinostat, mocetinostat, pracinostat, nicotinamide, cambinol, tenovin 1, tenovin 6, sirtinol, ricolinostat, tefinostat, kevetrin, quisinostat, resminostat, tacedinaline, chidamide, or selisistat), tyrosine kinase inhibitors (e.g., axitinib, dasatinib, encorafinib, erlotinib, imatinib, nilotinib, pazopanib, and sunitinib), and chemotherapeutic agents (e.g., all-trans retinoic acid, azacitidine, azathioprine, doxifluridine, epothilone, hydroxyurea, imatinib, teniposide, tioguanine, valrubicin, vemurafenib, and lenalidomide). Additional examples of chemotherapeutic agents include alkylating agents, e.g., mechlorethamine, cyclophosphamide, chlorambucil, melphalan, ifosfamide, thiotepa, hexamethylmelamine, busulfan, altretamine, procarbazine, dacarbazine, temozolomide, carmustine, lumustine, streptozocin, carboplatin, cisplatin, and oxaliplatin.

Non-limiting examples of activating receptor agonists include any agonists for activating receptors which activate and enhance the cytotoxicity of NK cells, including anti-CD16 antibodies (e.g., anti-CD16/CD30 bispecific monoclonal antibody (BiMAb)) and Fc-based fusion proteins. Non-limiting examples of checkpoint inhibitors include anti-PD-1 antibodies (e.g., MEDI0680), anti-PD-L1 antibodies (e.g., BCD-135, BGB-A333, CBT-502, CK-301, CS1001, FAZ053, KN035, MDX-1105, MSB2311, SHR-1316, anti-PD-L1/CTLA-4 bispecific antibody KN046, anti-PD-L1/TGFβRII fusion protein M7824, anti-PD-L1/TIM-3 bispecific antibody LY3415244, atezolizumab, or avelumab), anti-TIM3 antibodies (e.g., TSR-022, Sym023, or MBG453) and anti-CTLA-4 antibodies (e.g., AGEN1884, MK-1308, or an anti-CTLA-4/OX40 bispecific antibody ATOR-1015). Non-limiting examples of agents for blocking HLA-specific inhibitory receptors include monalizumab (e.g., an anti-HLA-E NKG2A inhibitory receptor monoclonal antibody). Non-limiting examples of GSK3 inhibitor include tideglusib or CHIR99021. Non-limiting examples of antibodies that can be used as additional therapeutic agents include anti-CD26 antibodies (e.g., YS110), anti-CD36 antibodies, and any other antibody or antibody construct that can bind to and activate an Fc receptor (e.g., CD16) on a NK cell. In some embodiments, an additional therapeutic agent can be insulin or metformin.

EXAMPLES

The invention is further described in the following examples, which do not limit the scope of the invention described in the claims.

Example 1: Creation of an IL-12/IL-15RαSu DNA Construct

In a non-limiting example, an IL-12/IL-15RαSu DNA construct was created (see FIG. 1) The human IL-12 subunit sequences, human IL-15RαSu sequence, human IL-15 sequence, human tissue factor 219 sequence, and human IL-18 sequence were obtained from the UniProt website and DNA for these sequences was synthesized by Genewiz. A DNA construct was made linking the IL-12 subunit beta (p40) to IL-12 subunit alpha (p35) with a GS (3) linker to generate a single chain version of IL-12 and then directly linking the IL-12 sequence to the IL-15RαSu sequence. The final IL-12/IL-15RαSu DNA construct sequence was synthesized by Genewiz.

The nucleic acid sequence of the IL12/IL-15RαSu construct (including signal peptide sequence) is as follows (SEQ ID NO: 59):

```
(Signal peptide)
ATGAAATGGGTGACCTTTATTTCTTTACTGTTCCTCTTTA

GCAGCGCCTACTCC

(Human IL-12 subunit beta (p40))
ATTTGGGAACTGAAGAAGGACGTCTACGTGGTCGAACTGG

ACTGGTATCCCGATGCTCCCGGCGAAATGGTGGTGCTCAC

TTGTGACACCCCCGAAGAAGACGGCATCACTTGGACCCTC

GATCAGAGCAGCGAGGTGCTGGGCTCCGGAAAGACCCTCA

CAATCCAAGTTAAGGAGTTCGGAGACGCTGGCCAATACAC

ATGCCACAAGGGAGGCGAGGTGCTCAGCCATTCCTTATTA

TTATTACACAAGAAGGAAGACGGAATCTGGTCCACCGACA

TTTTAAAAGATCAGAAGGAGCCCAAGAATAAGACCTTTTT

AAGGTGTGAGGCCAAAAACTACAGCGGTCGTTTCACTTGT

TGGTGGCTGACCACCATTTCCACCGATTTAACCTTCTCCG

TGAAAAGCAGCCGGGGAAGCTCCGACCCTCAAGGTGTGAC

ATGTGGAGCCGCTACCCTCAGCGCTGAGAGGGTTCGTGGC

GATAACAAGGAATACGAGTACAGCGTGGAGTGCCAAGAAG

ATAGCGCTTGTCCCGCTGCCGAAGAATCTTTACCCATTGA

GGTGATGGTGGACGCCGTGCACAAACTCAAGTACGAGAAC

TACACCTCCTCCTTCTTTATCCGGGACATCATTAAGCCCG

ATCCTCCTAAGAATTTACAGCTGAAGCCTCTCAAAAATAG

CCGGCAAGTTGAGGTCTCTTGGGAATATCCCGACACTTGG

AGCACACCCCACAGCTACTTCTCTTTAACCTTTTGTGTGC

AAGTTCAAGGTAAAAGCAAGCGGGAGAAGAAAGACCGGGT

GTTTACCGACAAAACCAGCGCCACCGTCATCTGTCGGAAG

AACGCCTCCATCAGCGTGAGGGCTCAAGATCGTTATTACT

CCAGCAGCTGGTCCGAGTGGGCCAGCGTGCCTTGTTCC

(Linker)
GGCGGTGGAGGATCCGGAGGAGGTGGCTCCGGCGGCGGAG

GATCT

(Human IL-12 subunit alpha (p35))
CGTAACCTCCCCGTGGCTACCCCCGATCCCGGAATGTTCC

CTTGTTTACACCACAGCCAGAATTTACTGAGGGCCGTGAG

CAACATGCTGCAGAAAGCTAGGCAGACTTTAGAATTTTAC

CCTTGCACCAGCGAGGAGATCGACCATGAAGATATCACCA

AGGACAAGACATCCACCGTGGAGGCTTGTTTACCTCTGGA

GCTGACAAAGAACGAGTCTTGTCTCAACTCTCGTGAAACC

AGCTTCATCACAAATGGCTCTTGTTTAGCTTCCCGGAAGA

CCTCCTTTATGATGGCTTTATGCCTCAGCTCCATCTACGA

GGATTTAAAGATGTACCAAGTGGAGTTCAAGACCATGAAC
```

-continued

```
GCCAAGCTGCTCATGGACCCTAAACGGCAGATCTTTTTAG

ACCAGAACATGCTGGCTGTGATTGATGAGCTGATGCAAGC

TTTAAACTTCAACTCCGAGACCGTCCCTCAGAAGTCCTCC

CTCGAGGAGCCCGATTTTTACAAGACAAAGATCAAACTGT

GCATTTTACTCCACGCCTTTAGGATCCGGGCCGTGACCAT

TGACCGGGTCATGAGCTATTTAAACGCCAGC

(Human IL-15R a sushi domain)
ATTACATGCCCCCCTCCCATGAGCGTGGAGCACGCCGACA

TCTGGGTGAAGAGCTATAGCCTCTACAGCCGGGAGAGGTA

TATCTGTAACAGCGGCTTCAAGAGGAAGGCCGGCACCAGC

AGCCTCACCGAGTGCGTGCTGAATAAGGCTACCAACGTGG

CTCACTGGACAACACCCTCTTTAAAGTGCATCCGG
```

Example 2: Creation of an IL-18/TF/IL-15 DNA Construct

In a non-limiting example, an IL-18/TF/IL-15 construct was made (see FIG. 2) linking the IL-18 sequence to the N-terminus coding region of tissue factor 219, and further linking the IL-18/TF construct with the N-terminus coding region of IL-15. The nucleic acid sequence of the IL-18/TF/IL-15 construct (including leader sequence), synthesized by Genewiz, is as follows (SEQ ID NO: 60):

```
(Signal peptide)
ATGAAGTGGGTCACATTTATCTCTTTACTGTTCCTCTTCT

CCAGCGCCTACAGC

(Human IL-18)
TACTTCGGCAAACTGGAATCCAAGCTGAGCGTGATCCGGA

ATTTAAACGACCAAGTTCTGTTTATCGATCAAGGTAACCG

GCCTCTGTTCGAGGACATGACCGACTCCGATTGCCGGGAC

AATGCCCCCCGGACCATCTTCATTATCTCCATGTACAAGG

ACAGCCAGCCCCGGGGCATGGCTGTGACAATTAGCGTGAA

GTGTGAGAAAATCAGCACTTTATCTTGTGAGAACAAGATC

ATCTCCTTTAAGGAAATGAACCCCCCCGATAACATCAAGG

ACACCAAGTCCGATATCATCTTCTTCCAGCGGTCCGTGCC

CGGTCACGATAACAAGATGCAGTTCGAATCCTCCTCCTAC

GAGGGCTACTTTTTAGCTTGTGAAAAGGAGAGGGATTTAT

TCAAGCTGATCCTCAAGAAGGAGGACGAGCTGGGCGATCG

TTCCATCATGTTCACCGTCCAAAACGAGGAT

(Human Tissue Factor 219)
AGCGGCACAACCAACACAGTCGCTGCCTATAACCTCACTT

GGAAGAGCACCAACTTCAAAACCATCCTCGAATGGGAACC

CAAACCCGTTAACCAAGTTTACACCGTGCAGATCAGCACC

AAGTCCGGCGACTGGAAGTCCAAATGTTTCTATACCACCG

ACACCGAGTGCGATCTCACCGATGAGATCGTGAAAGATGT

GAAACAGACCTACCTCGCCCGGGTGTTTAGCTACCCCGCC
```

-continued

```
GGCAATGTGGAGAGCACTGGTTCCGCTGGCGAGCCTTTAT
ACGAGAACAGCCCCGAATTTACCCCTTACCTCGAGACCAA
TTTAGGACAGCCCACCATCCAAAGCTTTGAGCAAGTTGGC
ACAAAGGTGAATGTGACAGTGGAGGACGAGCGGACTTTAG
TGCGGCGGAACAACACCTTTCTCAGCCTCCGGGATGTGTT
CGGCAAAGATTTAATCTACACACTGTATTACTGGAAGTCC
TCTTCCTCCGGCAAGAAGACAGCTAAAACCAACACAAACG
AGTTTTTAATCGACGTGGATAAAGGCGAAAACTACTGTTT
CAGCGTGCAAGCTGTGATCCCCTCCCGGACCGTGAATAGG
AAAAGCACCGATAGCCCCGTTGAGTGCATGGGCCAAGAAA
AGGGCGAGTTCCGGGAG

(Human IL-15)
AACTGGGTGAACGTCATCAGCGATTTAAAGAAGATCGAAG
ATTTAATTCAGTCCATGCATATCGACGCCACTTTATACAC
AGAATCCGACGTGCACCCCTCTTGTAAGGTGACCGCCATG
AAATGTTTTTTACTGGAGCTGCAAGTTATCTCTTTAGAGA
GCGGAGACGCTAGCATCCACGACACCGTGGAGAATTTAAT
CATTTTAGCCAATAACTCTTTATCCAGCAACGGCAACGTG
ACAGAGTCCGGCTGCAAGGAGTGCGAAGAGCTGGAGGAGA
AGAACATCAAGGAGTTTCTGCAATCCTTTGTGCACATTGT
CCAGATGTTCATCAATACCTCC
```

Example 3: Secretion of IL-12/IL-15RαSu and IL-18/TF/IL-15 Fusion Proteins

The IL-12/IL-15RαSu and IL-18/TF/IL-15 DNA constructs were cloned into a pMSGV-1 modified retrovirus expression vector (as described by Hughes, Hum Gene Ther 16:457-72, 2005, hereby incorporated by reference), and the expression vector was transfected into CHO-K1 cells. Co-expression of the two constructs in CHO-K1 cells allowed for formation and secretion of a soluble IL-18/TF/IL-15:IL-12/IL-15RαSu protein complex (referred to as 18t15-12s; see FIGS. 3 and 4). The 18t15-12s protein was purified from CHO-K1 cell culture supernatant using anti-TF antibody (hOAT) affinity chromatography and size exclusion chromatography resulting in soluble (non-aggregated) protein complexes consisting of IL-12/IL-15RαSu and IL-18/TF/IL-15 fusion proteins.

The amino acid sequence of the IL12/IL-15RαSu fusion protein (including signal peptide sequence) is as follows (SEQ ID NO: 61):

```
(Signal peptide)
MKWVTFISLLFLFSSAYS

(Human IL-12 subunit beta (p40))
IWELKKDVYVVELDWYPDAPGEMVVLTCDTPEEDGITWTL
DQSSEVLGSGKTLTIQVKEFGDAGQYTCHKGGEVLSHSLL
LLHKKEDGIWSTDILKDQKEPKNKTFLRCEAKNYSGRFTC
```

-continued

```
WWLTTISTDLTFSVKSSRGSSDPQGVTCGAATLSAERVRG
DNKEYEYSVECQEDSACPAAEESLPIEVMVDAVHKLKYEN
YTSSFFIRDIIKPDPPKNLQLKPLKNSRQVEVSWEYPDTW
STPHSYFSLTFCVQVQGKSKREKKDRVFTDKTSATVICRK
NASISVRAQDRYYSSSWSEWASVPCS

(Linker)
GGGGSGGGGSGGGGS

(Human IL-12 subunit alpha (p35))
RNLPVATPDPGMFPCLHHSQNLLRAVSNMLQKARQTLEFY
PCTSEEIDHEDITKDKTSTVEACLPLELTKNESCLNSRET
SFITNGSCLASRKTSFMMALCLSSIYEDLKMYQVEFKTMN
AKLLMDPKRQIFLDQNMLAVIDELMQALNFNSETVPQKSS
LEEPDFYKTKIKLCILLHAFRIRAVTIDRVMSYLNAS(Hu
manIL-15Rasushidomain)ITCPPPMSVEHADIWVKS
YSLYSRERYICNSGFKRKAGTSSLTECVLNKATNVAHWTT
PSLKCIR
```

The amino acid sequence of the IL-18/TF/IL-15 fusion protein (including signal peptide sequence) is as follows (SEQ ID NO: 62):

```
(Signal peptide)
MKWVTFISLLFLFSSAYS

(Human IL-18)
YFGKLESKLSVIRNLNDQVLFIDQGNRPLFEDMTDSDCRD
NAPRTIFIISMYKDSQPRGMAVTISVKCEKISTLSCENKI
ISFKEMNPPDNIKDTKSDIIFFQRSVPGHDNKMQFESSSY
EGYFLACEKERDLFKLILKKEDELGDRSIMFTVQNED

(Human Tissue Factor 219)
SGTTNTVAAYNLTWKSTNFKTILEWEPKPVNQVYTVQIST
KSGDWKSKCFYTTDTECDLTDEIVKDVKQTYLARVFSYPA
GNVESTGSAGEPLYENSPEFTPYLETNLGQPTIQSFEQVG
TKVNVTVEDERTLVRRNNTFLSLRDVFGKDLIYTLYYWKS
SSSGKKTAKTNTNEFLIDVDKGENYCFSVQAVIPSRTVNR
KSTDSPVECMGQEKGEFRE

(Human IL-15)
NWVNVISDLKKIEDLIQSMHIDATLYTESDVHPSCKVTAM
KCFLLELQVISLESGDASIHDTVENLIILANNSLSSNGNV
TESGCKECEELEEKNIKEFLQSFVHIVQMFINTS
```

In some cases, the leader (signal sequence) peptide is cleaved from the intact polypeptide to generate the mature form that may be soluble or secreted.

Example 3: Creation of an IL-7/IL-15RαSu DNA Construct

Figure 1:
FIG. 1 shows a schematic diagram of an exemplary IL-12/IL-15RαSu DNA construct.
Figure 2:
FIG. 2 shows a schematic diagram of an exemplary IL-18/TF/IL-15 DNA construct.
Figure 3:
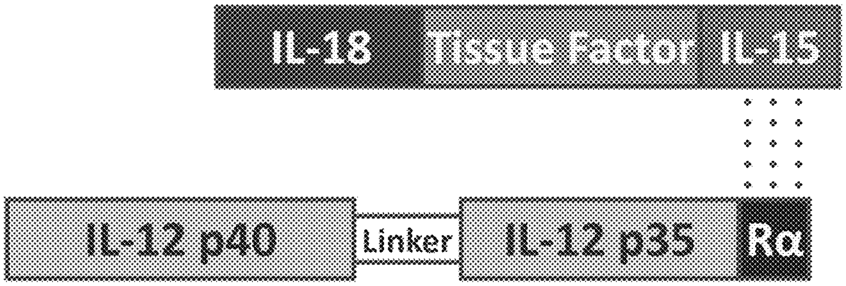
FIG. 3 shows a schematic diagram of the interaction between the exemplary IL-12/IL-15RαSu and IL-18/TF/IL-15 DNA constructs.
Figure 4:
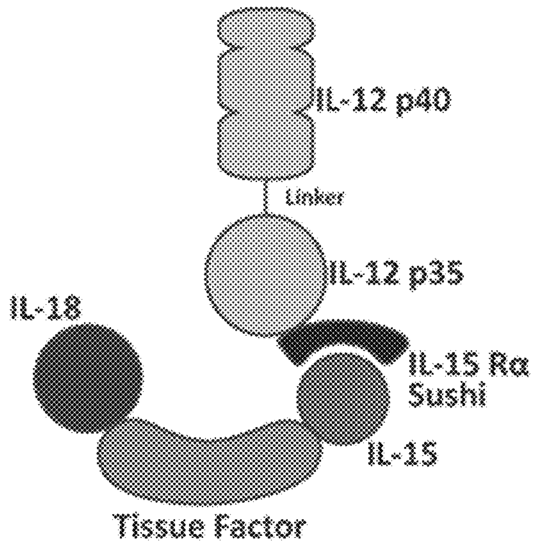
FIG. 4 shows a schematic diagram of the interaction between the exemplary IL-12/IL-15RαSu and IL-18/TF/IL-15 fusion proteins resulting in IL-18/TF/IL-15:IL-12/IL-15RαSu complex (18t15-12s).
Figure 5:
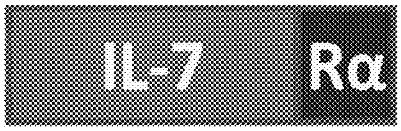
FIG. 5 shows a schematic diagram of an exemplary IL-7/IL-15RαSu DNA construct.
Figure 6:
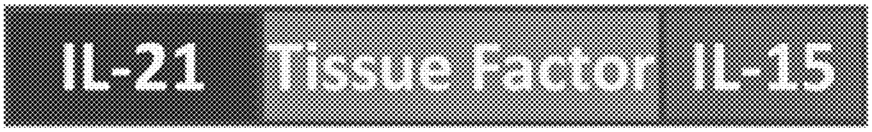
FIG. 6 shows a schematic diagram of an exemplary IL-21/TF/IL-15 DNA construct.
Figure 7:
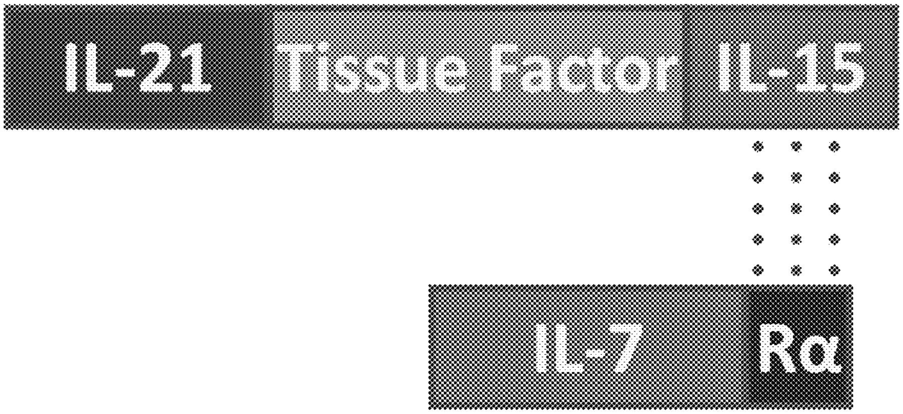
FIG. 7 shows a schematic diagram of the interaction between the exemplary IL-7/IL-15RαSu and IL-21/TF/IL-15 DNA constructs.
Figure 8:
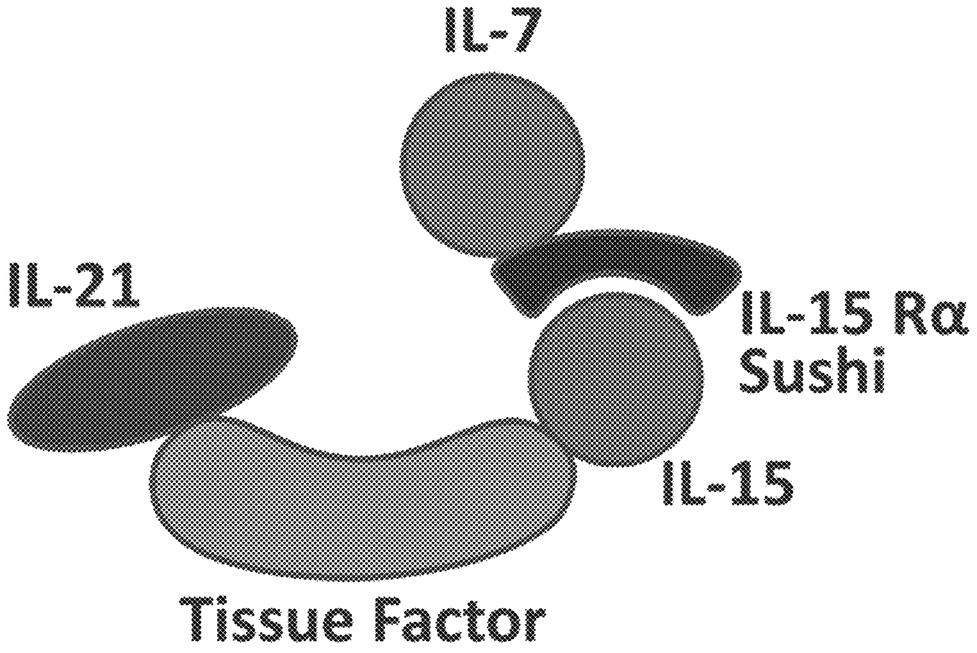
FIG. 8 shows a schematic diagram of the interaction between the exemplary IL-7/IL-15RαSu and IL-21/TF/IL-15 fusion proteins resulting in an IL-21/TF/IL-15: IL-7/IL-complex (21t15-7s).
Figure 9:
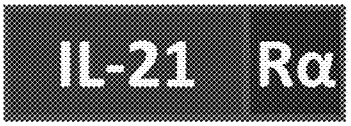
FIG. 9 shows a schematic diagram of an exemplary IL-21/IL-15RαSu DNA construct.
Figure 10:
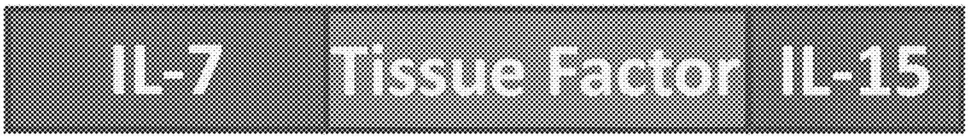
FIG. 10 shows a schematic diagram of an exemplary IL-7/TF/IL-15 DNA construct.

In a non-limiting example, an IL-7/IL-15RαSu DNA construct was created (see FIG. 5). The human IL-7 sequence, human IL-15RαSu sequence, human IL-15 sequence, and human tissue factor 219 sequence were obtained from the UniProt website and DNA for these sequences was synthesized by Genewiz. A DNA construct was made linking the IL-7 sequence to the IL-15RαSu sequence. The final IL-7/IL-15RαSu DNA construct sequence was synthesized by Genewiz.

Example 4: Creation of an IL-21/TF/IL-15 DNA Construct

In a non-limiting example, an IL-21/TF/IL-15 construct was made (see FIG. 6) by linking the IL-21 sequence to the N-terminus coding region of tissue factor 219, and further linking the IL-21/TF construct with the N-terminus coding region of IL-15.

Example 5: Secretion of IL-7/IL-15RαSu and IL-21/TF/IL-15 Fusion Proteins

The IL-7/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:IL-7/IL-15RαSu protein complex (referred to as 21t15-7s, see FIGS. 7 and 8). The 21t15-7s protein was purified from CHO-K1 cell culture supernatant using anti-TF antibody affinity chromatography and size exclusion chromatography resulting in soluble (non-aggregated) protein complexes consisting of IL-7/IL-15RαSu and IL-21/TF/IL-15 fusion proteins.

In some cases, the leader (signal sequence) peptide is cleaved from the intact polypeptide to generate the mature form that may be soluble or secreted.

Example 6: Creation of an IL-21/IL-15RαSu DNA Construct

In a non-limiting example, an IL-21/IL-15RαSu DNA construct was created. The human IL-21 sequence and human IL-15RαSu sequence were obtained from the UniProt website and DNA for these sequences was synthesized by Genewiz. A DNA construct was made linking the IL-21 sequence to the IL-15RαSu sequence. The final IL-21/IL-DNA construct sequence was synthesized by Genewiz. See FIG. 9.

Example 7: Creation of an IL-7/TF/IL-15 DNA Construct

In a non-limiting example, an IL-7/TF/IL-15 construct was made by linking the IL-7 sequence to the N-terminus coding region of tissue factor 219, and further linking the IL-7/TF construct with the N-terminus coding region of IL-15. See FIG. 10.

Example 8: Secretion of IL-21/IL-15RαSu and IL-7/TF/IL-15 Fusion Proteins

Figure 11:
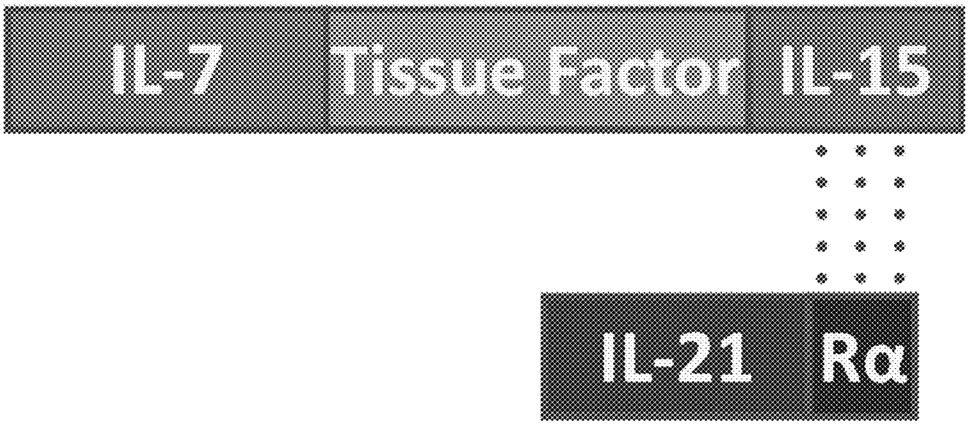
FIG. 11 shows a schematic diagram of the interaction between the exemplary IL-21/IL-15RαSu and IL-7/TF/IL-15 DNA constructs.
Figure 12:
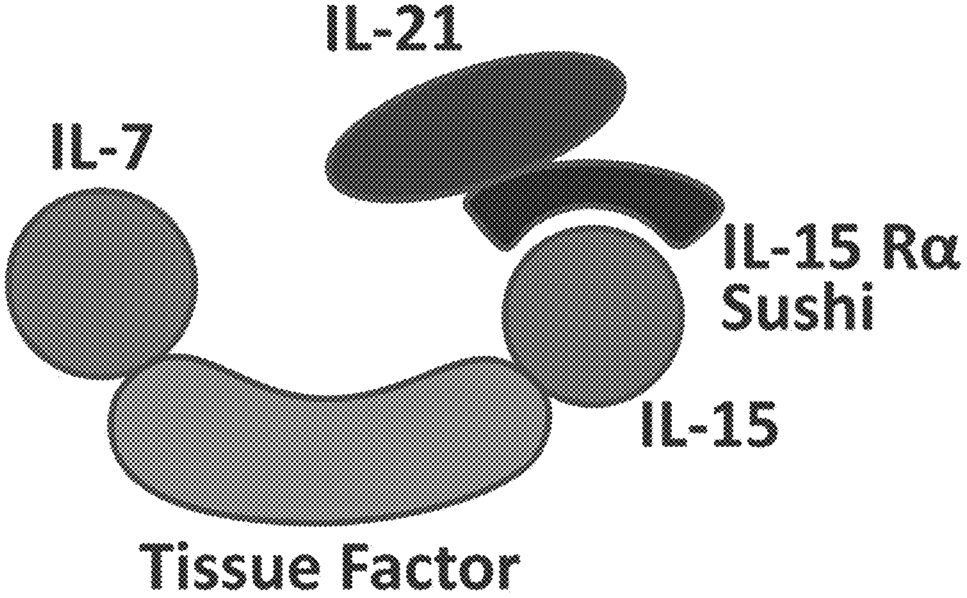
FIG. 12 shows a schematic diagram of the interaction between the exemplary IL-21/IL-15RαSu and IL-7/TF/IL-15 fusion proteins resulting in an IL-7/TF/IL-15:IL-21/IL-15RαSU complex (7t15-21s).

The IL-21/IL-15RαSu and IL-7/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-7/TF/IL-15:IL-21/IL-15RαSu protein complex (referred to as 7t15-21s) (FIGS. 11 and 12). The 7t15-21s protein was purified from CHO-K1 cell culture supernatant using anti-TF antibody (IgG1) affinity chromatography and size exclusion chromatography resulting in soluble (non-aggregated) protein complexes consisting of IL-21/IL-15RαSu and IL-7/TF/IL-15 fusion proteins.

Example 9: Measurement of Cytokine Signaling Via Downstream Protein Phosphorylation of STAT4 and STAT5

Figure 13:
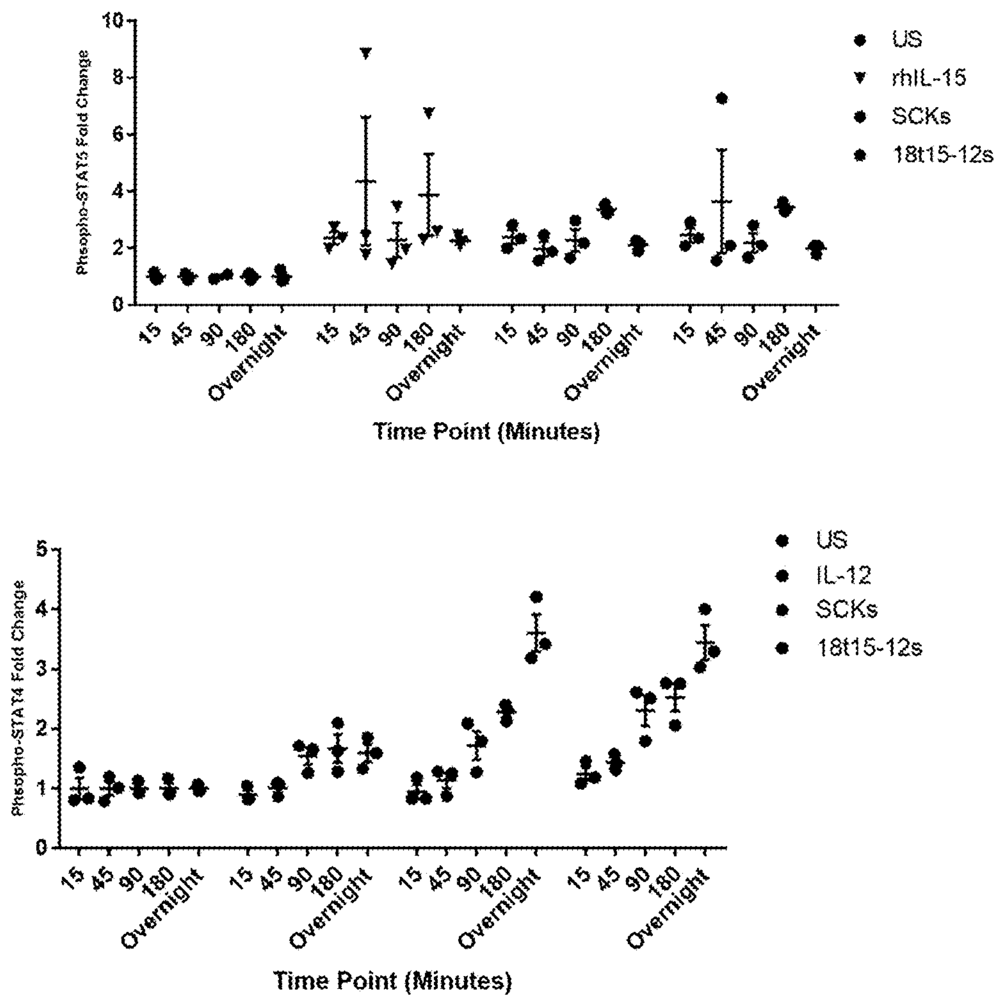
FIG. 13 shows a graph showing the fold-increase in STAT4 and STAT5 expression following in unstimulated NK cells (US) or NK cells contacted with a combination of an exemplary second multi-chain chimeric polypeptide and an exemplary IgG1 antibody construct (7t15-21s:anti-TF Ab), an exemplary first multi-chain chimeric polypeptide (18t15-12s), a combination of recombinant IL-12 and IL-18 (single cytokines), recombinant IL-12 (IL-12), or recombinant IL-18 (IL-18), for 5 minutes, 15 minutes, 30 minutes, 60 minutes, or overnight.

A set of experiments was performed to determine the effect of a first multi-chain chimeric polypeptide (IL-12/IL-15RαSu and IL-18/IL-15: 18t15-12s) on cytokine signaling on purified NK cells (FIG. 13).

In these experiments, fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, CD69-APCFire750 (BioLegend). Cells were counted and resuspended in $0.5\times10^6$/mL in 96 wells flat bottom plate in 0.1 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). Cells were stimulated with hIL-12 (10 ng/mL) (Biolegend) and hIL-15 (50 ng/mL) (NCI) or either mix-cytokines of hIL-12 (10 ng/mL) (Biolegend), hIL-18 (50 ng/mL)(R&D Systems) and hIL-15 (50 ng/mL) (NCI) or IL-12/IL-15RαSu and IL-18/IL-15 multi-chain chimeric polypeptide 100 nM for 15, 45, 90, 180 minutes or overnight at 37° C., 5% CO2. Cells were harvested at different points and fixed in Paraformaldehyde (Sigma) to a final concentration of 1.6%. Plates were incubated in dark in room temperature for 10 minutes. 100 mL of FACS buffer (1×PBS (Hyclone) with 0.5% BSA (EMD Millipore) and 0.001% Sodium Azide (Sigma) was added in Cells and transferred to 96 wells "V" bottom plate. Cells were washed for 1500 RPM for 5 minutes at room temperature. Cell pellet was mixed in 100 mL chilled methanol and pipetting up and down gently and incubate for 30 minutes at 4° C. Cells were mixed with 100 mL of FACS buffer and washed and centrifuged for 1500 RPM for 5 minutes at room temperature. Cell pellets were mixed with 50 mL of FACS buffer containing 4 mL of pSTAT4 (BD Bioscience) and pSTAT5 (BD Bioscience) and incubated for 30 minutes at room temp in the dark. Cells were mixed with 100 mL of FACS buffer, washed and centrifuged for 1500 RPM for 5 minutes at room temperature. Cell pellets were mixed with 50 mL of FACS buffer and analyzed by Flow Cytometry (Celesta-BD Bioscience).

The data show that cytokine signaling is elevated (STAT4 and STAT5) following contact with the IL-12/IL-15RαSu and IL-18/IL-15) multi-chain chimeric polypeptide compared to the controls (FIG. 13).

Example 10: Acute Stimulation of Immune Cells to Measure Extra Cellular Acidification Rate (ECAR) a Surrogate of Cellular Metabolism and Fitness A set of experiments was performed to determine the effect of a first multi-chain chimeric polypeptide (IL-12/IL-15RαSu and IL-18/IL-15: 18t15-12s) on ECAR on purified NK cells (FIG. 14).

In these experiments, fresh human leukocytes were obtained from the blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APCFire750 (BioLegend). Cells were counted and resuspended in $4\times10^6$/mL in 96 well, 50 μL/well, were seeded in Cell-Tak-coated Seahorse Bioanalyzer XFe96 culture plates in Seahorse XF RPMI medium, pH 7.4 supplemented with 2 mM L-glutamine. The cells were allowed to attach to the plate for 30 mins at 37° C. Additional 130 μL of assay medium was added to each well of the plate (also the background wells). The plate was incubated in 37° C., non-$CO_2$ incubator for 1 hr. For Calibration plate, the 10× solution of Glucose/oligomycin/2DG were prepared in Seahorse assay media. 20 μL volume of Glucose/oligomycin/2DG were added to ports B, C and D of the extracellular flux plate that was calibrated overnight. For the acute experiment hIL-12 (10 ng/mL) (Biolegend) and hIL-15 (50 ng/mL) (NCI) or either mix-cytokines of hIL-12 (10 ng/mL) (Biolegend), hIL-18 (50 ng/mL)(R&D Systems) and hIL-15 (50 ng/mL) (NCI) or 100 nM of IL-12/IL-15RαSu and IL-18/IL-chimeric polypeptide were added directly to the port A of the calibration plate. Extracellular acidification rate (ECAR) was measured using an XFe96 Extracellular Flux Analyzer. Complete ECAR analysis consisted of four stages: basal (without drugs), glycolysis induction (10 mM glucose), maximal glycolysis induction (2 μM oligomycin), and glycolysis inhibition (100 mM 2-DG). (Experiment representation of one donor out of 9).

Figure 14:
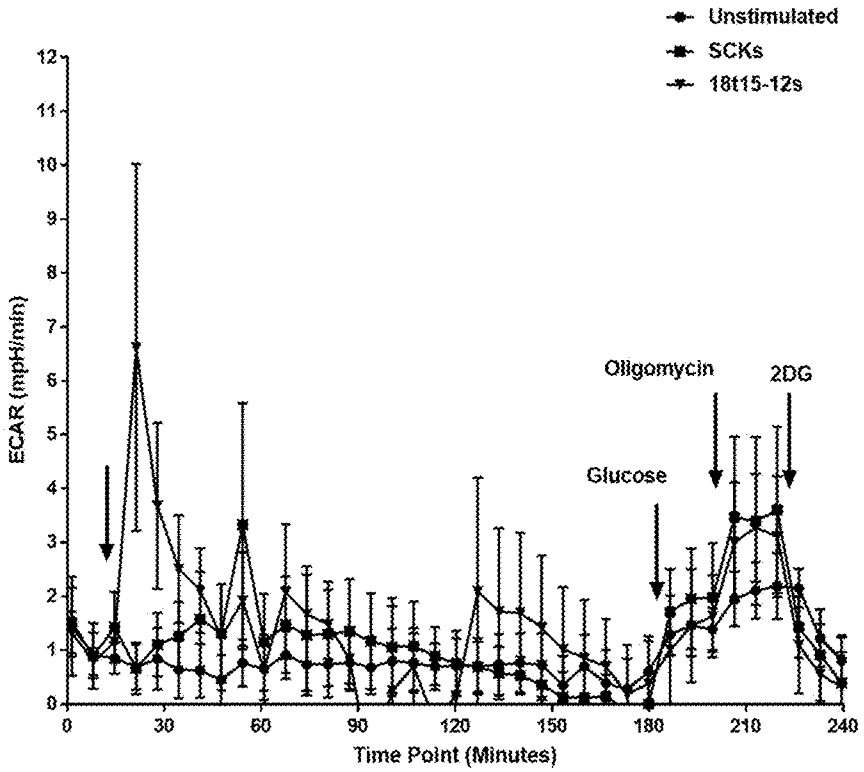
FIG. 14 is graph showing the extracellular acidification rate (ECAR) in unstimulated NK cells and NK cells contacted with an exemplary first multi-chain chimeric polypeptide (18t15-12s) at 10 nM or 100 nM, or with a combination of recombinant cytokines (IL-12, IL-15, and IL18) for 0 to 4 hours. The NK cells were obtained from three different donors.

The data show that ECAR is elevated following contact with an IL-12/IL-15RαSu and IL-18/IL-15) multi-chain chimeric polypeptide compared to the controls (FIG. 14).

Example 11: Acute Stimulation of Immune Cells to Measure Extra Cellular Acidification Rate (ECAR) in the Presence of Glucose A set of experiments was performed to determine the effect of the first multi-chain chimeric polypeptide (IL-12/IL-15RαSu and IL-18/IL-15: 18t15-12s) on ECAR on purified NK cells when in the presence of glucose (FIG. 15).

In these experiments, fresh human leukocytes were obtained from the blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APCFire750 (BioLegend). Cells were counted and resuspended in $4\times10^6$/mL in 96 well, 50 μL/well, were seeded in Cell-Tak-coated Seahorse Bioanalyzer XFe96 culture plates in Seahorse XF RPMI medium, pH 7.4 supplemented with 2 mM L-glutamine. The cells were allowed to attach to the plate for 30 mins at 37° C. Additional 130 μL of assay medium was added to each well of the plate (also the background wells). The plate was incubated in 37° C., non-$CO_2$ incubator for 1 hr. For Calibration plate: the 10× solution of oligomycin/2DG were prepared in Seahorse assay media. 20 μL volume of oligomycin/2DG were added to port B and C of the extracellular flux plate that was calibrated overnight. Cells were stimulated with Glucose (10 mM) mixed with single cytokines or (IL-12/IL-15RαSu and IL-18/IL-15) multi-chain polypeptide or media alone were added directly to the port A of the calibration plate. Extracellular acidification rate (ECAR) was measured using an XFe96 Extracellular Flux Analyzer. Complete ECAR analysis consisted of four stages: basal (without drugs), glycolysis induction (10 mM glucose), maximal glycolysis induction (2 μM oligomycin), and glycolysis inhibition (100 mM 2-DG). (Experiment representation of one donor out of 4).

Figure 15:
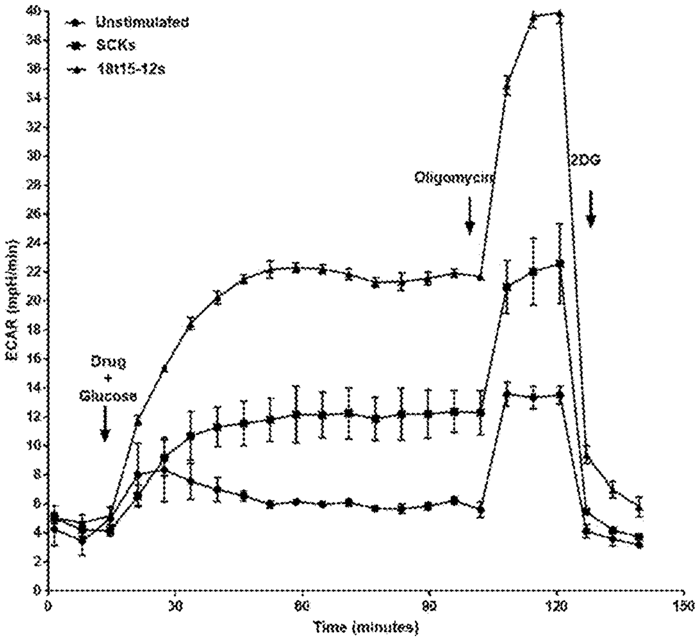
FIG. 15 is graph showing the extracellular acidification rate (ECAR) in unstimulated NK cells and NK cells contacted with an exemplary first multi-chain chimeric polypeptide (18t15-12s) or with a combination of recombinant cytokines (IL-12, IL-15, and IL18) for 0 to 3 hours. The NK cells were obtained from three different donors. The NK cells were further contacted with an addition of glucose, oligomycin, and 2-deoxyglucose where indicated.

The data show that ECAR is elevated following contact with an IL-12/IL-15RαSu and IL-18/IL-15: 18t15-12s multi-chain chimeric polypeptide and in the presence of glucose compared to the controls (FIG. 15).

Example 12: Acute Stimulation of Immune Cells to Measure Extra Cellular Acidification Rate (ECAR) with Addition (Spike) of Glucose to Show Increased Glycolysis and Glycolytic Capacity A set of experiments was performed to determine the effect of a first multi-chain chimeric polypeptide (IL-12/IL-15RαSu and IL-18/IL-15: 18t15-12s) on ECAR on NK cells when glucose was spiked in after the addition of the fusion protein (FIG. 16).

In these experiments, fresh human leukocytes were obtained from the blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APCFire750 (BioLegend). Cells were counted and resuspended in $4\times10^6$/mL in 96 well, 50 μL/well, were seeded in Cell-Tak-coated Seahorse Bioanalyzer XFe96 culture plates in Seahorse XF RPMI medium, pH 7.4 supplemented with 2 mM L-glutamine. The cells were allowed to attach to the plate for 30 mins at 37° C. Additional 130 μL of assay medium was added to each well of the plate (also the background wells). The plate was incubated in 37° C., non-CO2 incubator for 1 hr. For Calibration plate: The 10× solution of Glucose/oligomycin/2DG were prepared in Seahorse assay media. 20 μL volume of Glucose/oligomycin/2DG were added to port B, C and D of the extracellular flux plate that was calibrated overnight. For the acute experiment hIL-12 (10 ng/mL) (Biolegend) and hIL-15 (50 ng/mL) (NCI) or either mix-cytokines of hIL-12 (10 ng/mL) (Biolegend), hIL-18 (50 ng/mL)(R&D Systems) and hIL-15 (50 ng/mL) (NCI) or 100 nM of IL-12/IL-15RαSu and IL-18/IL-15 were added directly to the port A. Cells were stimulated with Glucose (10 mM) after 3 reading of acute stimulation with mixture of single cytokine or IL-12/IL-15RαSu and IL-18/IL-15 multi-chain chimeric polypeptide or media alone. Extracellular acidification rate (ECAR) was measured using an XFe96 Extracellular Flux Analyzer. Complete ECAR analysis consisted of four stages: basal (without drugs), glycolysis induction (10 mM glucose), maximal glycolysis induction (2 μM oligomycin), and glycolysis inhibition (100 mM 2-DG). (Experiment representation of one donor out of 4).

Figure 16:
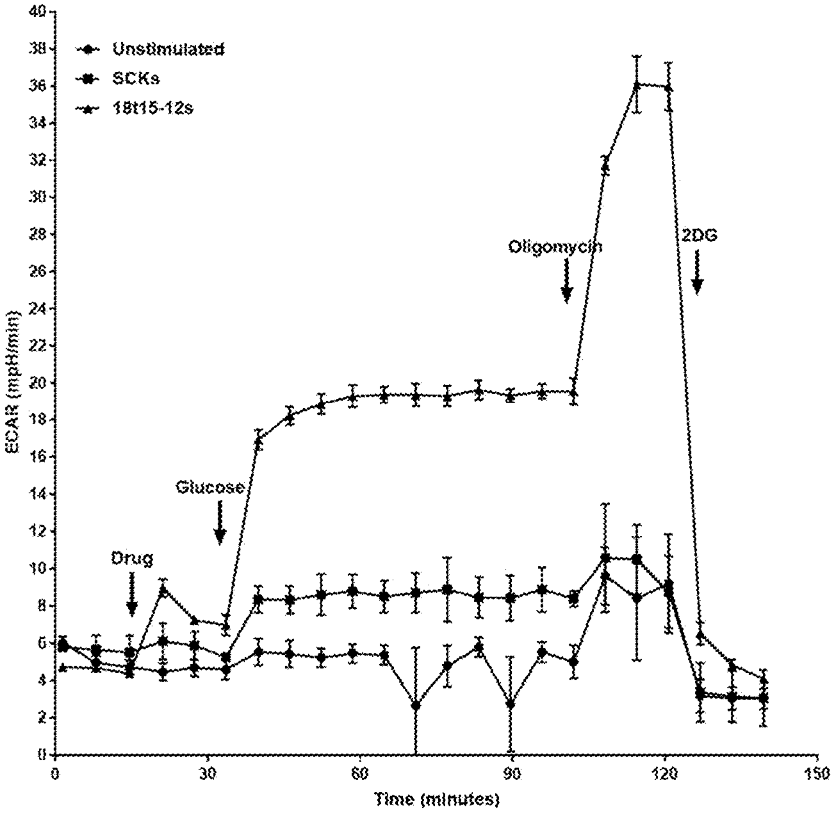
FIG. 16 is a graph of the fold-change in gene expression of mTORC1, MYC and SREBP in unstimulated NK cells or NK cells contacted with a combination of recombinant cytokines (IL-12, IL-15, and IL-18), an exemplary first multi-chain chimeric polypeptide (18t15-12s), or a control multi-chain chimeric polypeptide (7t15-21s) for 1 hour or 3 hours.

The data show that ECAR is elevated following contact with the IL-12/IL-15RαSu and IL-18/IL-15: 18t15-12s) multi-chain chimeric polypeptide and when the glucose is spiked in after the addition of the fusion protein compared to the controls (FIG. 16).

Example 13: Gene Expression Analysis of mTOR, MYC and SREBP after Stimulation with IL-12/IL-15RαSu and IL-18/IL-15 Multi-Chain Chimeric Polypeptide Showing Speed of Drug Effects on Cellular Gene Programing A set of experiments was performed to determine the effect of a first multi-chain chimeric polypeptide (IL-12/IL-15RαSu and IL-18/IL-15) on gene expression in NK cells (FIG. 17).

In these experiments, fresh human leukocytes were obtained from the blood bank and CD56+NK cells were isolated with the RosetteSep/human NK cell reagent (Stem-Cell Technologies). The purity of NK cells was >70% and confirmed by staining with CD56-BV421, CD16-BV510, CD25-PE, CD69-APCFire750 (BioLegend). Cells were counted and resuspended in $2\times10^6$/mL in 24 wells flat bottom plate in 1 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). Cells were stimulated with hIL-12 (10 ng/mL) (Biolegend) and hIL-15 (50 ng/mL) (NCI) or either mix-cytokines of hIL-12 (10 ng/mL) (Biolegend), hIL-18 (50 ng/mL)(R&D Systems) and hIL-15 (50 ng/mL) (NCI) or IL-12/IL-15RαSu and IL-18/IL-15 multi-chain chimeric polypeptide complex 100 nM for 60 and 180 minutes at 37°, 5% $CO_2$. Cells were harvested at different points and proceed for gene expression analysis. RNA extraction, cDNA synthesis and real-time PCR: Total RNA was extracted using RNeasy Mini Kit (Qiagen #74106) according to the manufacturer's instructions. 1 μg of total RNA was used for cDNA synthesis using the QuantiTect Reverse Transcription Kit (Qiagen). Real-time PCR was carried out with CFX96 Detection System (Bio-Rad) using FAM labeled predesigned primers for human specific genes mTORC, Myc, SREBP and 18S were purchased from Thermo Scientific. Reactions were run in triplicate in three independent experiments. The housekeeping gene 18S ribosomal RNA was used as an internal control to normalize the variability in expression levels. The expression of each target mRNA relative to 18S rRNA was calculated based on Ct as $2^{-\Delta(\Delta Ct)}$, in which $\Delta Ct=Ct_{target}-Ct_{18S}$. The data is presented as fold change as compared to no treatment control.

Figure 17:
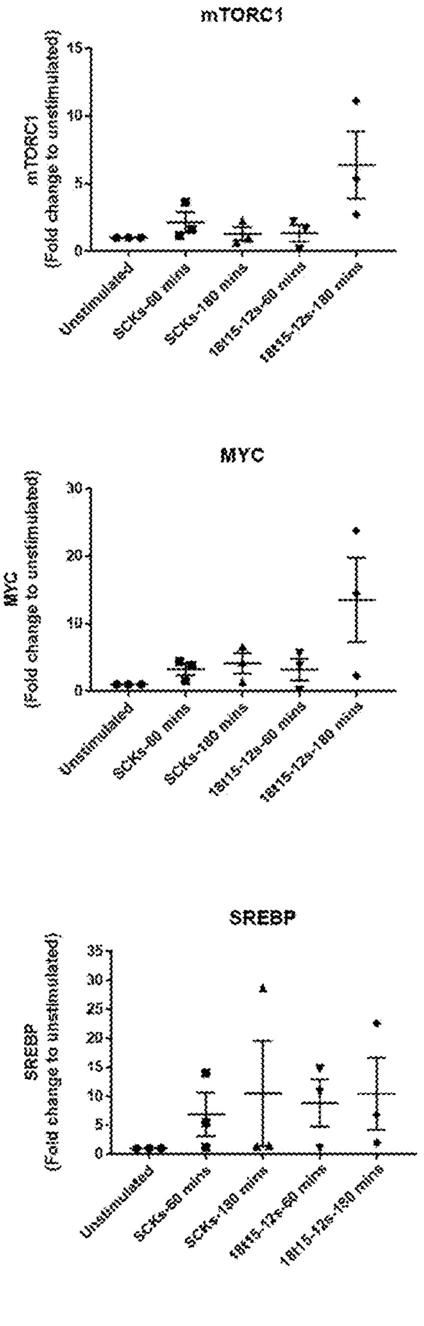
FIG. 17 is a graph showing the expression of exemplary activation markers, mTORC1, MYC, and SREBP, in NK cells that were unstimulated or contacted with a combination of recombinant cytokines (IL-12, IL-15, and IL-18) or 100 nM of an exemplary first multi-chain chimeric polypeptide (18t15-12s) for 30 minutes to 3 hours.

The data show that gene expression is elevated following contact with the IL-12/IL-15RαSu and IL-18/IL-15) multi-chain chimeric polypeptide compared to the controls (FIG. 17).

Example 14: Increase in Activation and Intracellular Markers after Stimulation with IL-12/IL-15RαSu and IL-18/IL-15 Multi-Chain Chimeric Polypeptide A set of experiments was performed to determine the effect of a first multi-chain chimeric polypeptide (IL-12/IL-15RαSu and IL-18/IL-15) on activation in NK cells (FIG. 18).

In these experiments, fresh human leukocytes were obtained from the blood bank and CD56+ NK cells were isolated with the RosetteSep/human NK cell reagent (Stem-Cell Technologies). The purity of NK cells was >70% and confirmed by staining with CD56-BV421, CD16-BV510, CD25-PE, CD69-APCFire750 (BioLegend). Cells were counted and resuspended in 0.2×106/mL in 96 well flat bottom plate in 0.2 mL of complete media (Cells were cultured in RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-12 (10 ng/mL) (Biolegend), hIL-18 (50 ng/mL)(R&D) and hIL-15 (50 ng/mL) (NCI) or 100 nM of IL-12/IL-15RαSu and IL-18/IL-15 multi-chain chimeric polypeptide for 30, 60, 90 and 180 minutes at 37 □, 5% CO2. Next day cells were treated with 10 μg/mL of Brefeldin A (Sigma) and 1× of Monensin (eBioscience) for 4 hrs. Cells were harvested and surface stained for CD56-BV421, CD16-BV510, CD25-APC, CD69-APCFire750, CD62L-PeCy7 for 30 minutes. After surface staining, cells were washed (1500 RPM for 5 minutes in room temperature) in FACS buffer (1×PBS (Hyclone) with 0.5% BSA (EMD Millipore) and 0.001% Sodium Azide (Sigma)) and fixed for 10 minutes at room temperature. After fixation steps, cells were washed (1500 RPM for 5 minutes in room temperature) in 1× Permeabilized Buffer (eBioscience) and stained for intracellular staining of IFN-γ-PE (Biolegend) for 30 minutes at room temperature. Cells were washed once again with 1× Permeabilized Buffer and then washed with FACS buffer. Cell pellets were resuspended in 300 μL of FACS Buffer for analysis by Flow Cytometry (Celesta-BD Bioscience).

Figure 18:
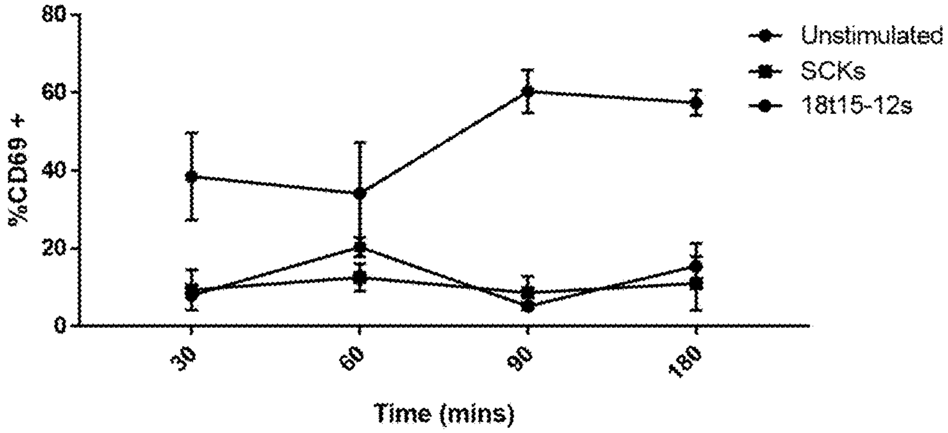
FIG. 18 shows the percentage of CD69 positive and interferon-gamma positive NK cells following NK cell following no stimulation or stimulation with a mixture of recombinant cytokines (IL-12, IL-15, and IL-18) or an exemplary first multi-chain chimeric polypeptide (18t15-12s) for 3 hours or overnight.
Figure 18:
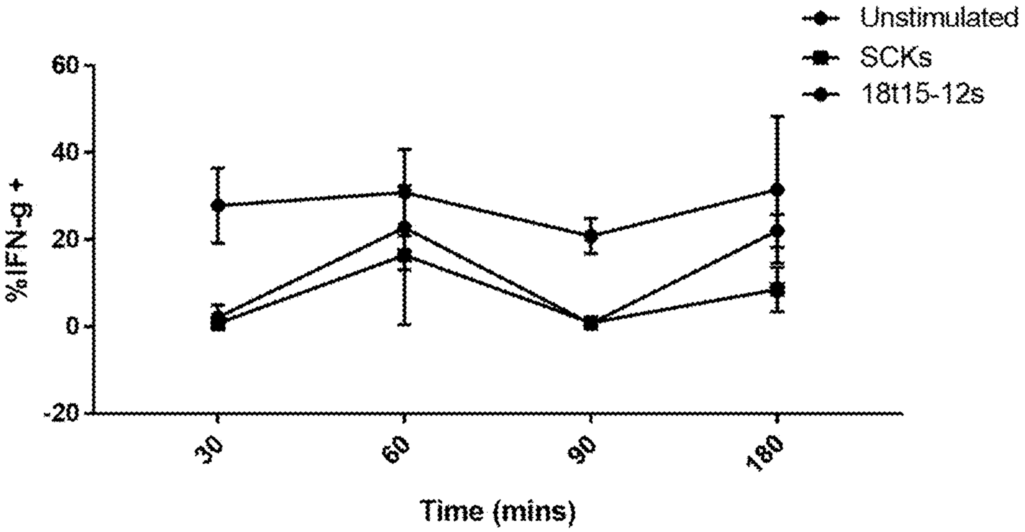

The data show that NK activation is elevated following contact with the IL-12/IL-15RαSu and IL-18/IL-15) multi-chain chimeric polypeptide compared to the controls (FIG. 18).

Example 15: Increase in 41BB and IL21R Markers after Stimulation with an IL-12/IL-15RαSu and IL-18/IL-15 Multi-Chain Chimeric Polypeptide Comparing Short Term Vs Overnight Showing Cells are Primed to Respond to Activating Stimuli A set of experiments was performed to determine the effect of a first multi-chain chimeric polypeptide (IL-12/IL-15RαSu and IL-18/IL-15) on activation in NK cells (FIG. 19).

In these experiments, fresh human leukocytes were obtained from the blood bank and $CD56^+$ NK cells were isolated with the RosetteSep/human NK cell reagent (Stem-Cell Technologies). The purity of NK cells was >70% and confirmed by staining with CD56-BV421, CD16-BV510, CD25-PE, CD69-APCFire750 (BioLegend). Cells were counted and resuspended in $0.2\times10^6$/mL in 96 wells flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-12 (10 ng/mL) (Biolegend), hIL-18 (50 ng/mL)(R&D Systems) and hIL-15 (50 ng/mL) (NCI) or 100 nM of IL-12/IL-15RαSu and IL-18/IL-15 multi-chain chimeric polypeptide for either 180 minutes or overnight at 37° C., 5% $CO_2$. Cells were harvested, and surface stained for CD56-BV421, CD16-BV510, IL21r-PE, 41BB-APC.Cy7 (BioLegend) for 30 minutes. After surface staining, cells were washed (1500 RPM for 5 minutes at room temperature) in FACS buffer (1×PBS (Hyclone) with 0.5% BSA (EMD Millipore) and 0.001% Sodium Azide (Sigma)). After two washes, cells were analyzed by Flow Cytometry (Celesta-BD Bioscience).

Figure 19:
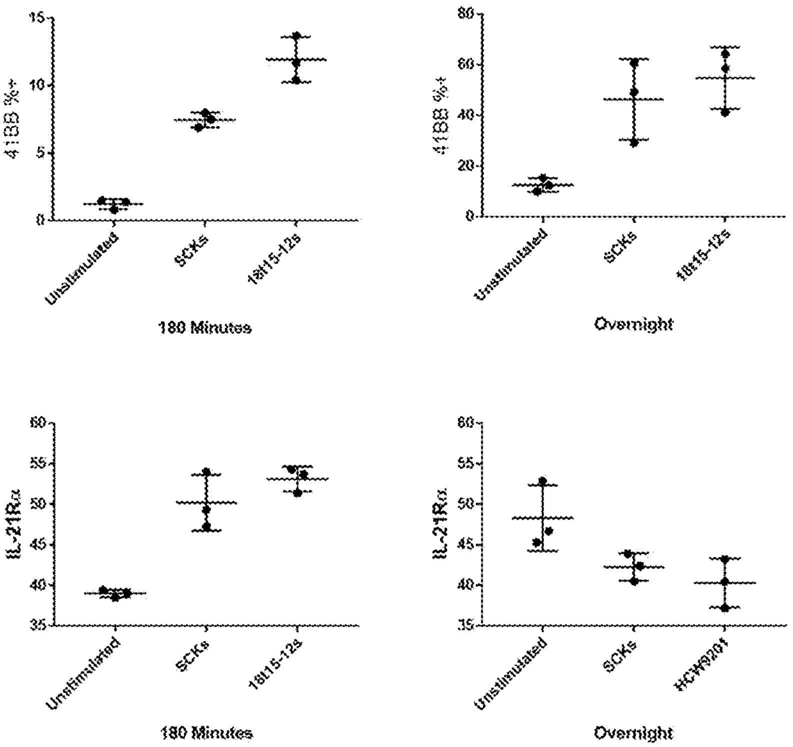
FIG. 19 shows the percentage of 41BB positive and IL-21 receptor α-positive NK cells following NK cell following no stimulation or stimulation with a mixture of recombinant cytokines (IL-12, IL-15 and IL-18) or an exemplary first multi-chain chimeric polypeptide (18t15-12s) for 3 hours or overnight.

The data show that NK activation is elevated following contact with the IL-12/IL-15RαSu and IL-18/IL-15) multi-chain chimeric polypeptide compared to the controls (FIG. 19).

Figure 20:
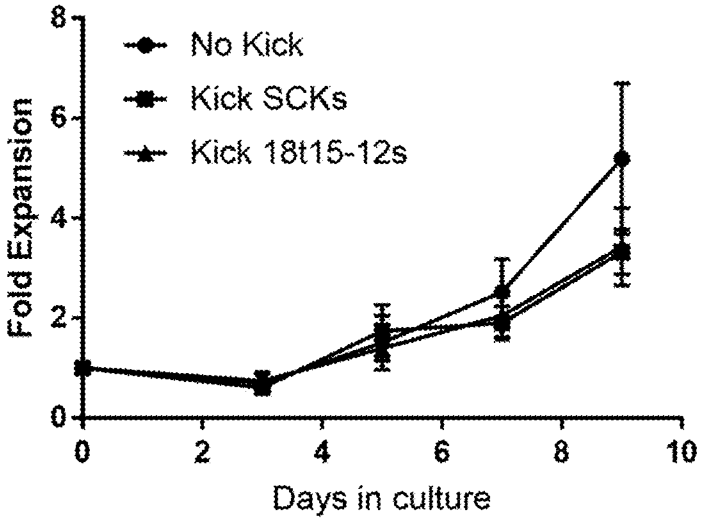
FIG. 20 is a graph showing the fold expansion of NK cells over time that received the following treatments: (i) received no initial stimulation and subsequently contacted with a combination of an exemplary second multi-chain chimeric polypeptide (7t15-21s) and an exemplary IgG1 antibody construct (18t15-12s); (ii) initial stimulation with a combination of recombinant cytokines (IL-12, IL-15, and IL-18) and subsequently contacted with a combination of an exemplary second multi-chain chimeric polypeptide (7t15-21s) and an exemplary IgG1 antibody construct (18t15-12s); or (iii) initial stimulation with an exemplary first multi-chain chimeric polypeptide and subsequently contacted with a combination of an exemplary second multi-chain chimeric polypeptide (7t15-21s) and an exemplary IgG1 antibody construct (18t15-12s).

Example 16: Expansion of NK Cells by IL-7/IL-15RαSu and IL-21/IL-15 Multi-Chain Chimeric Polypeptide and IgG1 Antibody Construct after Short Stimulations (180 Minutes) with IL-12/IL-15RαSu and IL-18/IL-15 Multi-Chain Chimeric Polypeptide or Media Alone A set of experiments was performed to determine the effect of a first multi-chain chimeric polypeptide (IL-12/IL- 15RαSu and IL-18/IL-15), the second multi-chain chimeric polypeptide (IL-7/IL-15RαSu and IL-21/IL-15), the IgG1 antibody construct on expansion of NK cells (FIG. 20).

In these experiments, fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, CD69-APCFire750 (BioLegend). Cells were counted and resuspended in $1\times10^8$/mL in 96 wells flat bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-12 (10 ng/mL) (Biolegend), hIL-18 (50 ng/mL)(R&D Systems) and hIL-15 (50 ng/mL) (NCI) or 100 nM of IL-12/IL-15RαSu and IL-18/IL-15 multi-chain chimeric polypeptide for 180 minutes. Cells were diluted from $1\times10^8$/mL to $2\times10^6$/mL with 100 nM of IL-7/IL-15RαSu and IL-21/IL-15 and 50 nM of IgG1 antibody construct in 24 wells plate at 37°, 5% $CO_2$. Cells were maintained at $2\times10^6$/mL with fresh complete containing 100 nM of IL-7/IL-15RαSu and IL-21/IL-15 and 50 nM of IgG1 antibody construct. Cell expansion was measured in fold expansion (3 Donors).

The data show that NK expand following treatment with the first multi-chain chimeric polypeptide (IL-12/IL-15RαSu and IL-18/IL-15), the second chimeric polypeptides (IL-7/IL-15RαSu and IL-21/IL-15) and the IgG1 antibody construct.

Example 17: Increase in Degranulation Markers after Stimulation with an Exemplary First Multi-Chain Chimeric Polypeptide and Expansion with an Exemplary Second Multi-Chain Chimeric Polypeptide A set of experiments was performed to determine the effect of a first multi-chain chimeric polypeptide (IL-12/IL-15RαSu and IL-18/IL-15), a second multi-chain chimeric polypeptide (IL-7/IL-15RαSu and IL-21/IL-15), and a IgG1 antibody construct on degranulation of NK cells (FIG. 11).

In these experiments, fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, CD69-APCFire750 (BioLegend). Cells were counted and resuspended in $1\times10^8$/mL in 96 wells flat bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-12 (10 ng/mL) (Biolegend), hIL-18 (50 ng/mL)(R&D Systems) and hIL-15 (50 ng/mL) (NCI) or 100 nM of IL-12/IL-15RαSu and IL-18/IL-15 multi-chain chimeric polypeptide for 180 minutes. Cells were diluted from $1\times10^8$/mL to $2\times10^6$/mL with 100 nM of IL-7/IL-15RαSu and IL-21/IL-15 multi-chain chimeric polypeptide and 50 nM of IgG1 antibody construct in 24 wells plate at 37° C. with 5% $CO_2$. Cells were maintained at $2\times10^6$/mL with fresh complete containing 100 nM of IL-7/IL-15RαSu and IL-21/IL-15 and 50 nM of IgG1 antibody construct or 1 ng/mL of rhIL-15 up to day 11. Cells were harvested and resuspended in 2:1 (effector:target) ratio with K562 cell lines (target) with 4 μls of CD107-FITC (Biolegend) at 37°, 5% $CO_2$. After four hours of incubation cells were harvested and surface stained for CD56-BV421, CD16-BV510 for 30 minutes. After surface staining, cells were washed (1500 RPM for 5 minutes in room temperature) in FACS buffer (1×PBS (Hyclone) with 0.5% BSA (EMD Millipore) and 0.001% Sodium Azide (Sigma). Cell pellets were resuspended in 50 μL of FACS Buffer for Flow Cytometry analysis (Celesta-BD Bioscience).

Figure 21:
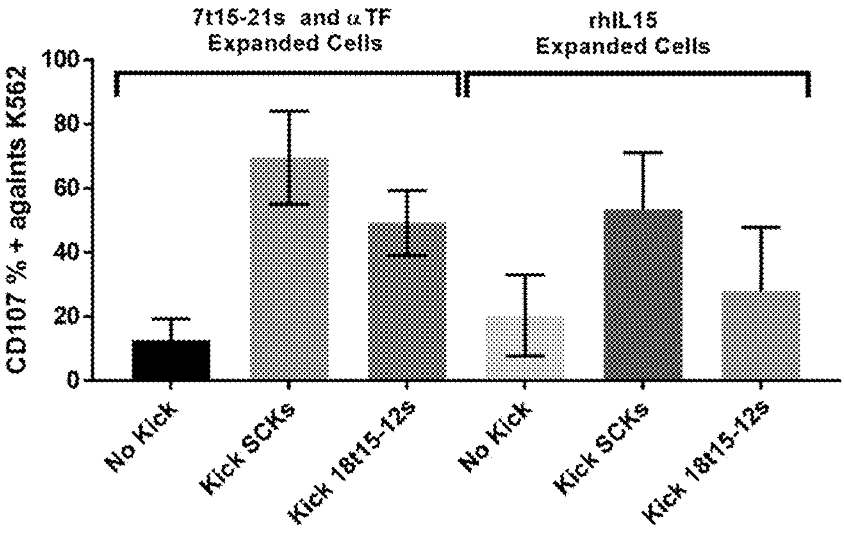
FIG. 21 is a graph showing the percentage of CD107a positive cells that received the following treatments: (i) no initial stimulation and subsequent treatment with a combination of an exemplary second multi-chain chimeric polypeptide (7t15-21s) and an exemplary IgG1 antibody construct (αTF Ab); (ii) initial stimulation with a combination of cytokines (IL-12, IL-15, and IL-18) and subsequent treatment with a combination of an exemplary second multi-chain chimeric polypeptide (7t15-21s) and an exemplary IgG1 antibody construct (αTF Ab); (iii) initial stimulation with an exemplary first multi-chain chimeric polypeptide (18t15-12s) and subsequent treatment with combination of an exemplary second multi-chain chimeric polypeptide (7t15-21s) and an exemplary IgG1 antibody construct (αTF Ab); (iv) no initial stimulation and subsequent treatment with recombinant IL-15; (v) initial stimulation with a combination of cytokines (IL-12, IL-15 and IL-18) and subsequent treatment with recombinant IL-15; or (vi) initial stimulation with an exemplary first multi-chain chimeric polypeptide.

The data show the NK cells exhibit enhanced cytotoxicity against target cells after treatment with a first multi-chain chimeric polypeptide (IL-12/IL-15RαSu and IL-18/IL-15$^{(D8N)}$), a second multi-chain chimeric polypeptides (IL-7/IL-15RαSu and IL-21/IL-15$^{(D8N)}$), and a IgG1 antibody construct (FIG. 21).

Example 18: Oxygen Consumption Rate (OCR)

Fresh human leukocytes were obtained from the blood bank and $CD56^+$ NK cells were isolated with the RosetteSep/human NK cell reagent (StemCell Technologies) and CD69-APCFire750 (BioLegend). Cells were counted and resuspended in $1\times10^8$/mL in a 96-well flat-bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone). Cells were stimulated with either a mixture of cytokines (SCKs) [hIL-12 (10 ng/mL) (BioLegend), hIL-18 (50 ng/mL) (R&D Systems), and hIL-15 (50 ng/mL) (NCI)] or 100 nM of 18t15-12s for 180 minutes (Kick) or with media only (not stimulated). Cells were diluted from $1\times10^8$/mL to $2\times10^6$/mL and expanded with 100 nM of 7t15-21s and 50 nM of anti-tissue factor antibody (IgG1) (αTF Ab) in a 24-well plate at 37° C., 5% $CO_2$. Cells were maintained at $2\times10^6$/mL with fresh complete media containing 100 nM of 7t15-21s and nM of αTF Ab or 50 ng/mL of recombinant human IL-15 for 14 days. Cells were harvested on day 14, counted and resuspended in $4\times10^6$/mL in a 96-well plate, 50 μL/well, and were seeded in Cell-Tak-coated Seahorse Bioanalyzer XFe96 culture plates in Seahorse XF RPMI medium, pH 7.4 supplemented with 10 mM glucose and 2 mM L-glutamine. The cells were allowed to attach to the plate for 30 mins at 37° C. Additionally, 130 μL of the assay medium was added to each well of the plate (also the background wells). The plate was incubated in 37° C., non-$CO_2$ incubator for 1 hour. For Calibration plate: The 10× solution of oligomycin/FCCP/rotenone were prepared in Seahorse assay media. 20 μL of oligomycin, FCCP and rotenone was added to each of the ports of the extracellular flux plate that was calibrated overnight. Oxygen Consumption Rate (OCR) was measured using an XFe96 Extracellular Flux Analyzer. Complete OCR analysis consisted of four stages: basal respiration (without drugs), ATP-linked respiration/proton leak (1.5 μM oligomycin), maximal respiration (2 μM FCCP), and spare respiration (0.5 μM rotenone). The OCR graph is a combined representation of three donors.

Figure 22:
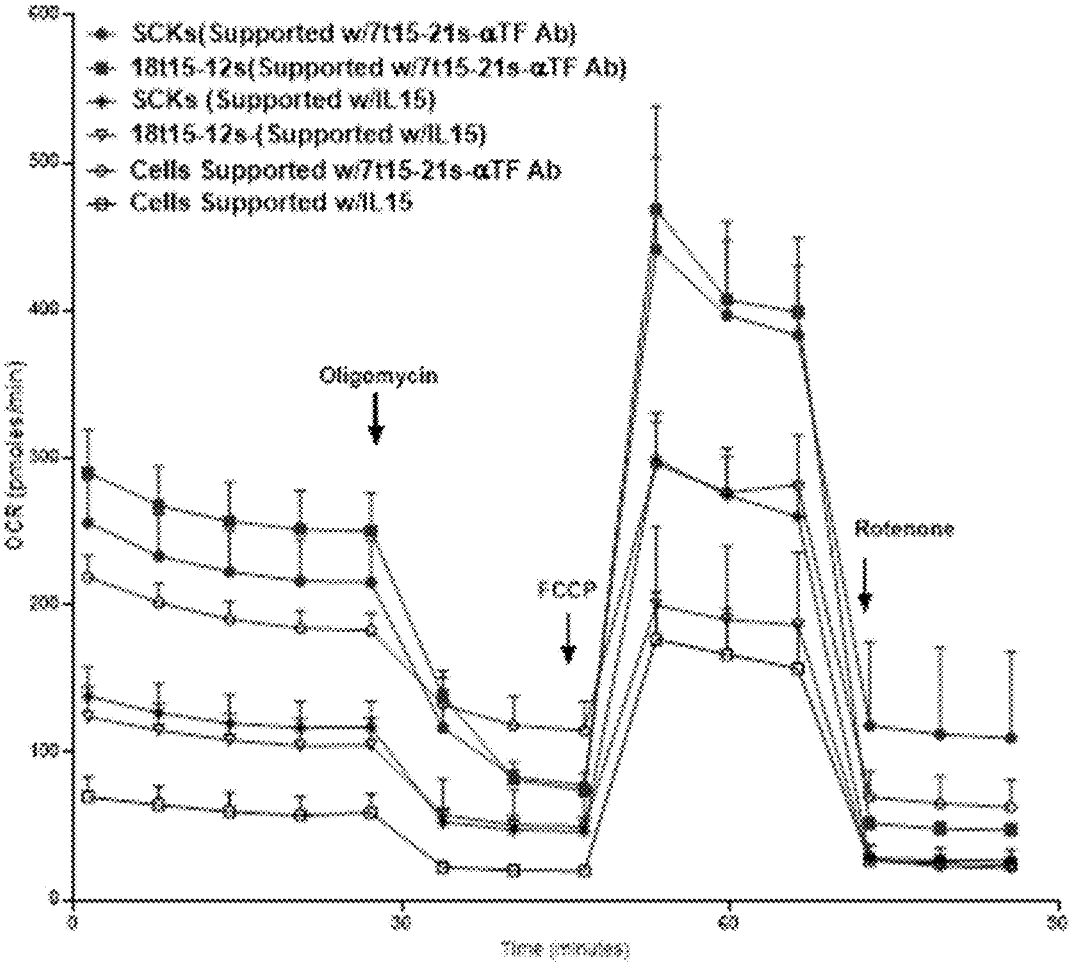
FIG. 22 is a graph showing the oxygen consumption rate (OCR) analysis of stimulated human NK cells, where the OCR analysis consists of four stages: basal respiration (without drugs), ATP-linked respiration/proton leak (1.5 μM oligomycin), maximal respiration (2 μM FCCP), and spare respiration (0.5 μM rotenone). The OCR graph is a combined representation of NK cells obtained three donors. The NK cells were stimulated as shown and as described in the corresponding Example.

The data show that NK cells stimulated with either a mixture of cytokines (SCKs) or with 18t15-12s and then supported for expansion with 7t15-21s and anti-tissue factor antibody (αTF Ab) resulted in increased oxygen consumption rate (OCR). Addition of carbonyl cyanide-4 (trifluoromethoxy) phenylhydrazone (FCCP) further enhanced the oxygen consumption rate (OCR) capacity. The data also show that the unstimulated cells, cells stimulated with mixture of cytokines (SCKs) or with 18t15-12s and supported for expansion with 7t15-21s and anti-tissue factor antibody ($\alpha$TF Ab) also resulted in an increase in the OCR. However, NK cells treated overnight with mixture of cytokines (SCKs) or with 18t15-12s and then supported with a low dose of IL-15 did not show much increase in the OCR. Overall, NK cells stimulated (Kick) with 18t15-12s and then expanded with 7t15-21s and anti-tissue factor antibody ($\alpha$TF Ab) are more metabolically fit as compared to NK cells stimulated with 18t15-12s and then expanded with a low dose of IL-15 (FIG. 22).

Example 19: Gene Expression Analysis of IFN-$\gamma$ and NKG2D after Stimulation with 18t15-12s Fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, and CD69-APC-Fire750 (BioLegend). Cells were counted and resuspended in $1\times10^8$/mL in 96-well flat bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). Cells were divided into a short-term activation (180 mins) or long-term activation group (overnight stimulation for 12-16 hours), or were not stimulated. Cells were stimulated (Kick) with either a mixture of cytokines (SCKs) [hIL-12 (10 ng/mL) (BioLegend), hIL-18 (50 ng/mL) (R&D Systems) and hIL-15 (50 ng/mL) (NCI)] or 100 nM of 18t15-12s for 180 minutes or for 12-16 hours. Cells were diluted from $1\times10^8$/mL to $2\times10^6$/mL and expanded with 100 nM of 7t15-21s and 50 nM of anti-tissue factor antibody ($\alpha$TF Ab) in a 24-well plate at 37° C., 5% $CO_2$. Cells were maintained at $2\times10^6$/mL with fresh complete media containing 100 nM of 7t15-21s and 50 nM of $\alpha$TF Ab for 14 days. Every other day cells were stimulated with fresh media and 100 nM of 7t15-21s and 50 nM of $\alpha$TF Ab up to 14 days. Cells were harvested on day 14, at different points, and then evaluated for gene expression analysis. RNA extraction, cDNA synthesis, and real-time PCR were performed. Total RNA was extracted using RNeasy Mini Kit (Qiagen #74106) according to the manufacturer's instructions. One µg of total RNA was used for cDNA synthesis using the QuantiTect Reverse Transcription Kit (Qiagen). Real-time PCR was carried out with CFX96 Detection System (Bio-Rad) using FAM labeled predesigned primers purchased for IFN$\gamma$ and NKG2D from Thermo Scientific. Reactions were run in triplicate in three independent experiments. The housekeeping gene 18S ribosomal RNA was used as an internal control to normalize the variability in expression levels. The expression of each target mRNA relative to 18S rRNA was calculated based on Ct as $2^{-\Delta(\Delta Ct)}$, in which $\Delta Ct=Ct_{target}-Ct_{18S}$. The data is presented as fold-change as compared to no treatment control.

Figure 23:
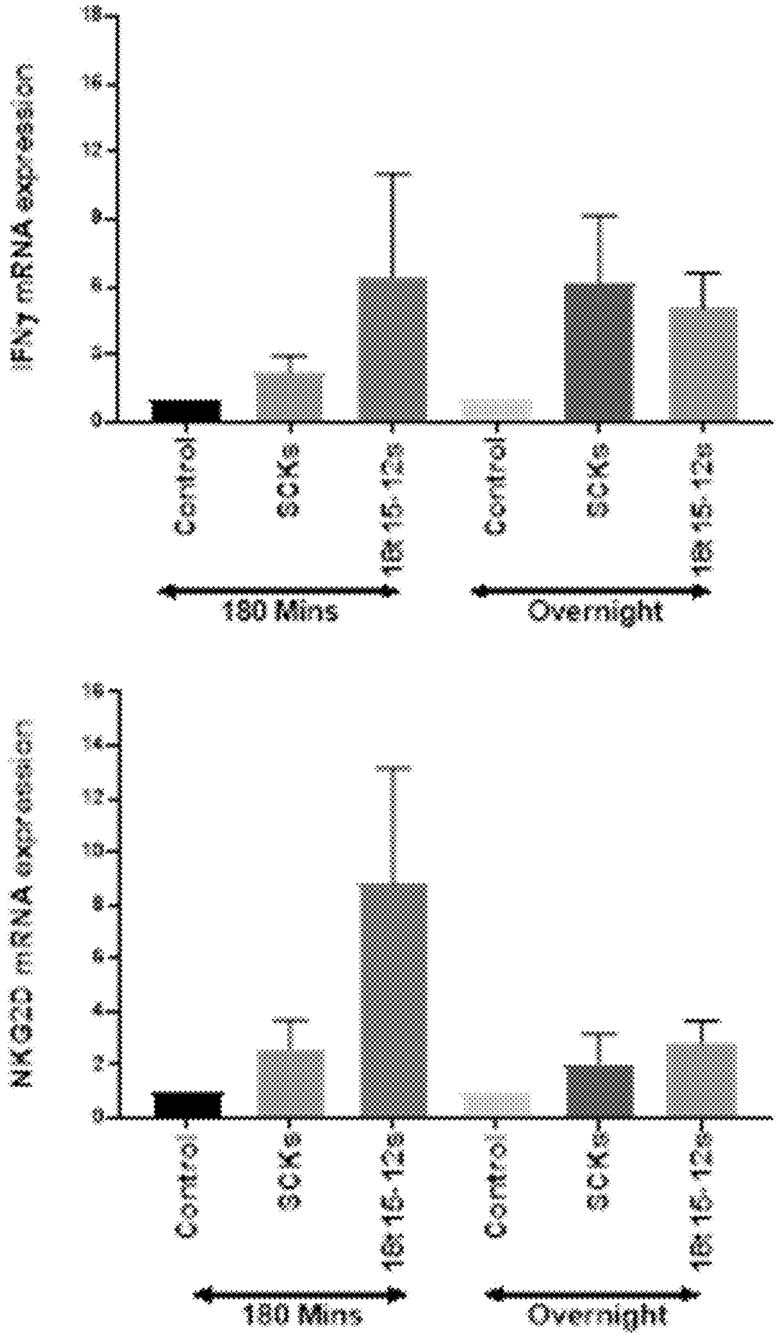
FIG. 23 is a graph showing IFN-γ mRNA and NKG2D mRNA levels after stimulation with 18t15-12s or a combination of individual cytokines, where cells were divided into a short-term activation (180 mins) or long-term activation (overnight stimulation for 12-16 hours) groups, or were not stimulated.

The data show that NK cells stimulated with 18t15-12s for 180 minutes and then expanded with 7t15-21s and anti-tissue factor antibody ($\alpha$TF Ab) were able to increase IFN-$\gamma$ and NKG2D gene expression compared to NK cells stimulated with a mixture of cytokines (SCKs) and then expanded with 7t15-21s and anti-tissue factor antibody ($\alpha$TF Ab). There was no difference in the IFN-$\gamma$ and NKG2D gene expression in overnight stimulated NK cells with a mixture of cytokines (SCKs) or 18t15-12s and then expanded with 7t15-21s and anti-tissue factor antibody ($\alpha$TF Ab). This implies that short-term stimulation with 18t15-12s, and then expansion with 7t15-21s and anti-tissue factor antibody ($\alpha$TF Ab) is enough to upregulate memory-like markers on NK cells (FIG. 23).

Example 20: Persistence of Adoptively Transferred NK Cells, Activated with 18t15-12s and Expanded with 7t15-21s and $\alpha$TF IgG1 in an NSG Mouse Model Fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, and CD69-APC-Fire750 (BioLegend). Cells were counted and resuspended in $1\times10^8$/mL in a 96-well flat bottom plate in complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone). Cells were either unstimulated with media as a control or stimulated (Kick) with 100 nM of 18t15-12s for either 180 minutes or for 12-16 hours (overnight). Cells were diluted from $1\times10^8$/mL to $2\times10^6$/mL with 100 nM of 7t15-21s and 50 nM of anti-tissue factor antibody ($\alpha$TF Ab) in a 24-well plate at 37° C., 5% $CO_2$. Cells were maintained at $2\times10^6$/mL with fresh complete media containing 100 nM of 7t15-21s and nM of $\alpha$TF Ab for 21 days. Cells were maintained at $2\times10^6$/mL with fresh complete media containing 100 nM of 7t15-21s and 50 nM of $\alpha$TF Ab and as the volume increased, the cells were transferred to higher volume flasks. Cells were harvested on day 21 and counted using trypan blue to access the fold-expansion. Expanded cells were washed three times in warm HBSS Buffer (Hyclone) at 1000 RPM for 10 minutes at room temperature. Cells were resuspended in $10\times10^6$/0.2 mL HBSS buffer and injected intravenously in tail-vein of NSG mouse (NOD scid gamma mouse) (Jackson Laboratories). Cells were supported with Proleukin (rhIL2) (5000 IU) by subcutaneous injection every 48 hours, up to Day 12. Engraftment of cells were measured every week in blood staining for hCD45, mCD45, hCD56, hCD3 and hCD16 by flow cytometry (Celesta-BD Bioscience). (Data represent 5 mice per group).

Figure 24:
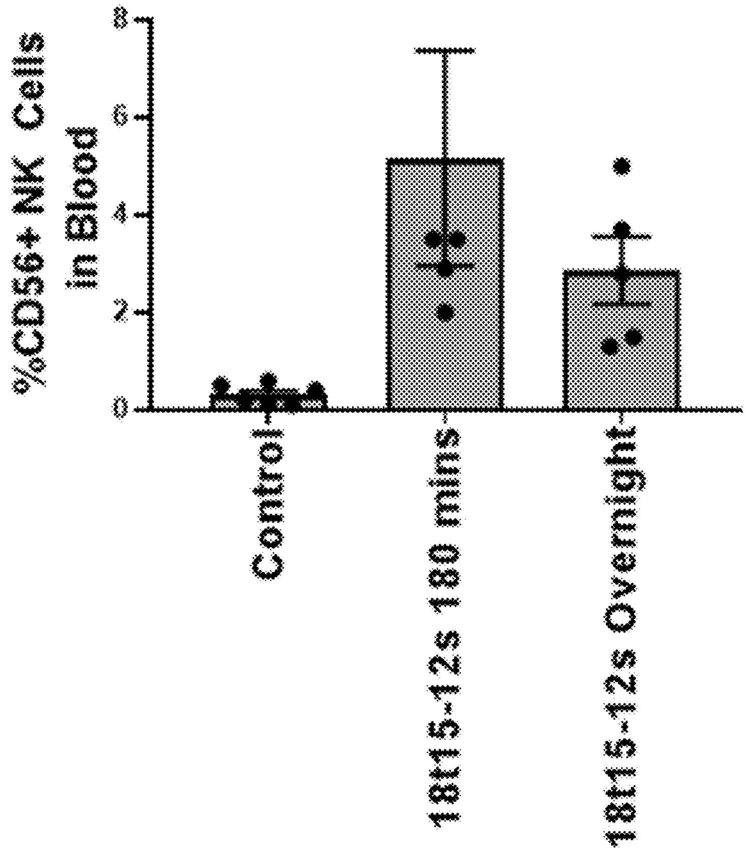
FIG. 24 is a graph showing persistence of adoptively transferred NK cells ($CD56^+$ cells) that were expanded with 7t15-21s-αTF Ab in an NSG mouse model, where prior to the expansion, the cells were either unstimulated with media as a control or stimulated (Kick) with 100 nM of 18t15-12s for either 180 minutes or for 12-16 hours (overnight).

The data show that NK cells stimulated with 18t15-12s for either 180 minutes or overnight and supported for expansion with 7t15-21s and anti-tissue factor antibody ($\alpha$TF Ab) are able to persist in vivo for up to 12 days after infusion in NSG mouse compared to NK cells without the stimulation with 18t15-12s (FIG. 24).

Example 21: Epigenetic Analysis of DNA Methylation of IFN$\gamma$-CNS-1 CpG Region Fresh human leukocytes were obtained from the blood bank and $CD56^+$ NK cells were isolated with the RosetteSep/human NK cell reagent (StemCell Technologies). The purity of NK cells was >85% and confirmed by staining with CD56-BV421, CD16-BV510, CD25-PE, and CD69-APC-Fire750 (BioLegend). Cells were counted and resuspended at a density of $2\times10^6$ cells/mL in RPMI 1640 medium (Gibco) supplemented with 2 mM L-glutamine (Thermo Life Technologies), antibiotics (penicillin, 10,000 units/mL; streptomycin, 10,000 µg/mL; Thermo Life Technologies), and 10% FBS (Hyclone). Cells (1 mL) were transferred in a 24-well flat bottom plate, and subjected to either: no treatment, or stimulated with a mixture of single cytokines (SCKs) [hIL-12 (10 ng/mL) (BioLegend), hIL-18 (50 ng/mL) (R&D Systems) and hIL-15 (50 ng/mL) (NCI)] or 18t15-12s (100 nM) for a short-term exposure of either 180 minutes or 12-16 hours (Overnight) at 37° C. under an atmosphere of 5% $CO_2$. Then, the NK cells were washed and resuspended in complete RPMI 1640 medium supplemented with 7t15-21s plus the anti-tissue factor antibody (αTF Ab, 50 nM) and incubated for 14 days (Long-term). Cells were replenished with 7t15-21s plus αTF Ab (50 nM) to keep the cell density at approximately $1\times10^6$ cells/mL.

Treatment of NK cells with single cytokines followed by a low dose of IL-15 has been shown to promote memory-like NK cells differentiation and was used as comparative controls for memory-like NK-cell epigenetics. Unexposed/untreated NK cells from donors to treatment groups were used as positive controls for full DNA methylation levels. Genomic DNA (nDNA) was extracted from NK cells (0.2-$1.0\times10^6$) using the QIAamp UCP DNA Micro Kit (Qiagen). Purified nDNA (500 ng) was subjected to sodium bisulfate treatment using the EZ DNA Methylation-Direct kit (Zymo Research) according to the manufacturer's protocol. Bisulfite treatment introduces methylation-dependent changes in the DNA with demethylated cytosines being converted into uracil, whereas methylated cytosines remain unchanged. The bisulfate-treated nDNA (10-50 ng) was used as template to PCR amplify a 247-bp region of the IFNγ distal promoter conserved noncoding sequence 1 (CNS-1) enhancer region containing six characterized CpG sites (located at positions −4399, −4377, −4360 −4325, −4293, and −4278 relative to the transcription start site). This CNS-1 region has been found to be important in T-cell and NK cells differentiation and is epigenetically regulated by DNA methylation (Dong et al., *Eur. J. Immunol.* 43:793-804, 2013). The PCR were performed using the Pyromark PCR kit (Qiagen) with the forward primer IFNG-CNS1F (5'-AGAAAAGGGGGGATTTA-3') (SEQ ID NO: 81) and the biotinylated reverse primer IFNG-CNS1R-bio (5'-TAACACTCACAACCAAATTATC-3') (SEQ ID NO: 82) (GENEWIZ). The PCR conditions were 15 min at 95° C., 50 cycles of 35 sec at 95° C., sec at 55° C., 40 sec at 72° C. followed by 5 min at 72° C. The integrity and quality of the 247-bp PCR amplified products were visualized on a 1.2% TAE agarose gel. The DNA methylation status of the six CpG sites was determined by pyrosequencing, which is the gold standard technique to quantitatively measure DNA methylation at single CpG-site. Pyrosequencing reactions were performed at Johns Hopkins University Genetic Resources Core Facility using the DNA sequencing primers C4399-CNS1F (5'-GGGGATTTAGAAAAAT-3' (SEQ ID NO: 83), specific to the CpG sites −4399, −4377, −4360, and −4325), and C4293-CNS1F (5'-TGTATGATGTTAG-GAGTTT-3' (SEQ ID NO: 84), specific to the CpG sites −4293, −4278, and −4227). For DNA methylation controls, human non-methylated and methylated genomic DNA were used (Zymo Research). The methylation percentages of the six IFNγ CNS-1 CpG sites were averaged for each treatment.

Figure 25:
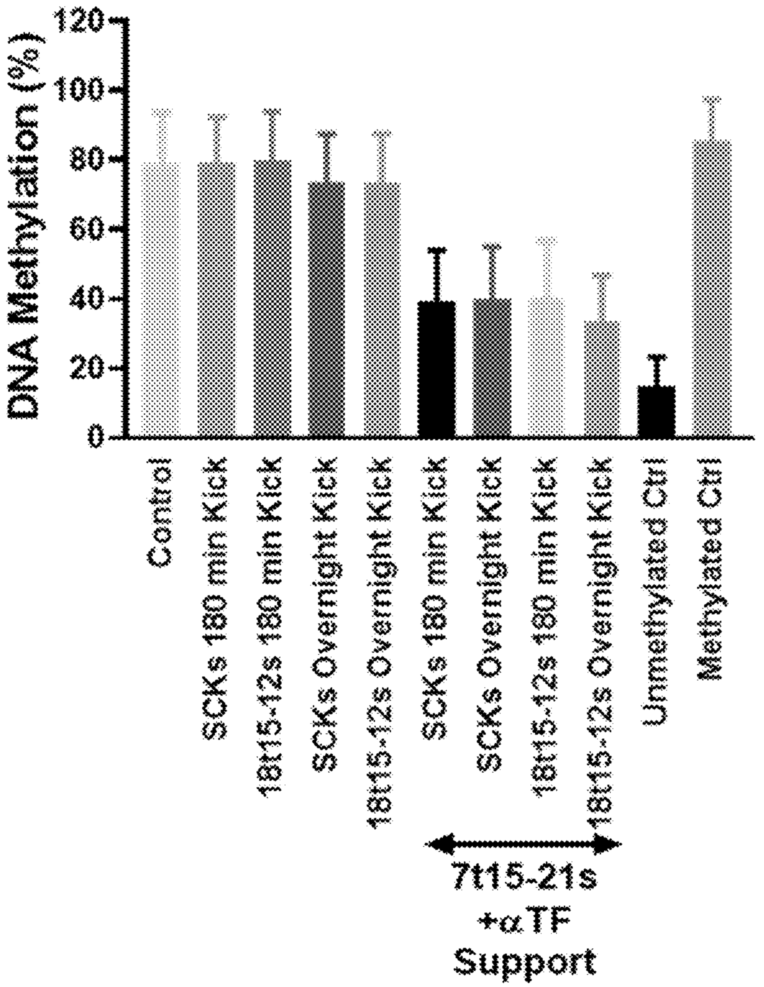
FIG. 25 is a graph showing epigenetic analysis of "Kick and Expansion" on DNA methylation of IFNγ CNS-1 CpG region, where cells were transferred in a 24 well flat bottom plate, and subjected to either: no treatment, or stimulation with a mixture of single cytokines or 18t15-12s for a short-term exposure of either 180 minutes or 12-16 hours (overnight). Then, the NK cells were washed and resuspended in complete RPMI 1640 medium supplemented with 7t15-21s plus the anti-tissue factor antibody (αTF Ab) and incubated for 14 days (long-term). DNA isolated from the cells was subjected to pyrosequencing analysis of DNA methylation of CpG sites located within the IFNγ CNS-1 region.

Analysis of the DNA methylation status of these six IFNγ CNS-1 CpG sites revealed higher levels of DNA demethylation in NK cells stimulated (kick) for 180 minutes or 12-16 hours (Overnight) with either a mixture of single cytokines (SCKs) or 18t15-12s and supported for 14 days (Long-term) in culture by 7t15-21s (50 nM) plus αTF Ab (50 nM) compared to unexposed (Control) or NK cells stimulated (kick) for 180 minutes or Overnight (Short-term) with either a mixture of single cytokines (IL12+IL18+IL15) or 18t15-12s. Indeed, the 7t15-21s+αTF Ab supported NK cells exhibited 33.80%±13.20 to 40.72%±15.96 DNA methylation compared to 79.50%±14.21 for unexposed (Control), 79.25%±13.14 to 79.97%±14.13 for 180 minutes stimulated (kick), and 73.51%±14.08 to 73.66%±14.01 for overnight stimulated (kick) NK cells. Taken together, these results suggest that long-term exposure of NK cells to 7t15-21s+αTF Ab induces significant DNA demethylation of the CpG sites within the CNS-1 region, leading to epigenetic remodeling of IFNγ gene expression and interconversion of NK cells into innate immune memory NK cells (FIG. 25).

Example 22: Epigenetic Analysis of Memory-Like NK Cells In Vivo

Fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, and CD69-APC-Fire750 (BioLegend). Cells were counted and resuspended at a density of $2\times10^6$ cells/mL in RPMI 1640 medium (Gibco) supplemented with 2 mM L-glutamine (Thermo Life Technologies), antibiotics (penicillin, 10,000 units/mL; streptomycin, 10,000 pg/mL; Thermo Life Technologies), and 10% FBS (Hyclone). Cells (1 mL) were transferred in 24 wells flat bottom plate, and subjected to either: stimulated with mixture of-single cytokines (labeled SCKs) [hIL-12 (10 ng/mL) (BioLegend), hIL-18 (50 ng/mL) (R&D Systems), and hIL-15 (50 ng/mL) (NCI)] or 18t15-12s (100 nM) for 12-16 hours at 37° C. under an atmosphere of 5% $CO_2$. Then, the NK cells were washed and resuspended in complete RPMI 1640 medium supplemented with 7t15-21s+anti-tissue factor antibody (αTF Ab), and incubated for 14 days, with medium frequently replenished with fresh 7t15-21s+αTF Ab to keep the cell density at approximately $1\times10^6$ cells/mL. After 14 days of expansion, the activated NK cells were either processed for pyrosequencing analysis (pre-infusion samples) or infused in NSG mice (five groups, five mice per group). At day 9 post-infusion, the spleen of each mice was collected, and NK cells purified and combined for each group (five group, five mice per groups). The samples (post-infusion) were subjected to pyrosequencing analysis of DNA methylation of CpG sites located within the IFNγ CNS-1 region as described below.

Genomic DNA (nDNA) was extracted from NK cells (0.2-$1.0\times10^6$) using the QIAamp UCP DNA Micro Kit (Qiagen). Purified nDNA (500 ng) was subjected to sodium bisulfite treatment using the EZ DNA Methylation-Direct kit (Zymo Research) according to the manufacturer's protocol. Bisulfite treatment introduces methylation-dependent changes in the DNA with demethylated cytosines being converted into uracil, whereas methylated cytosines remain unchanged. The bisulfite-treated nDNA (10-50 ng) was used as template to PCR amplify a 247-bp region of the IFNγ distal promoter conserved noncoding sequence 1 (CNS-1) enhancer region containing six characterized CpG sites (located at positions −4399, −4377, −4360 −4325, −4293, and −4278 relative to the transcription start site). This CNS-1 region has been found to be important in T-cell and NK cells differentiation and is epigenetically regulated by DNA methylation (Dong et al., *Eur. J. Immunol.* 43:793-804, 2013). The PCR were performed using the Pyromark PCR kit (Qiagen) with the forward primer IFNG-CNS1F (5'-AGAAAAGGGGGGATTTA-3'; SEQ ID NO: 81) and the biotinylated reverse primer IFNG-CNS1R-bio (5'-TAACACTCACAACCAAATTATC-3'; SEQ ID NO: 82) (GENEWIZ). The PCR conditions were 15 min at 95° C., 50 cycles of 35 sec at 95° C., 35 sec at 55° C., 40 sec at 72° C. followed by 5 min at 72° C. The integrity and quality of the 247-bp PCR amplified products were visualized on a 1.2%

TAE agarose gel. The DNA methylation status of the six CpG sites was determined by pyrosequencing, which is the gold standard technique to quantitatively measure DNA methylation at single CpG-site. Pyrosequencing reactions were performed at Johns Hopkins University Genetic Resources Core Facility using the DNA sequencing primers C4399-CNS1F (5'-GGGGATTTAGAAAAAT-3' (SEQ ID NO: 83), specific to the CpG sites −4399, −4377, −4360, and −4325), and C4293-CNS1F (5'-TGTATGATGTTAG-GAGTTT-3' (SEQ ID NO: 84), specific to the CpG sites −4293, −4278, and −4227). For DNA methylation controls, human non-methylated and methylated genomic DNA were used (Zymo Research). The methylation percentages of the six IFNγ CNS-1 CpG sites were averaged for each treatment.

Figure 26:
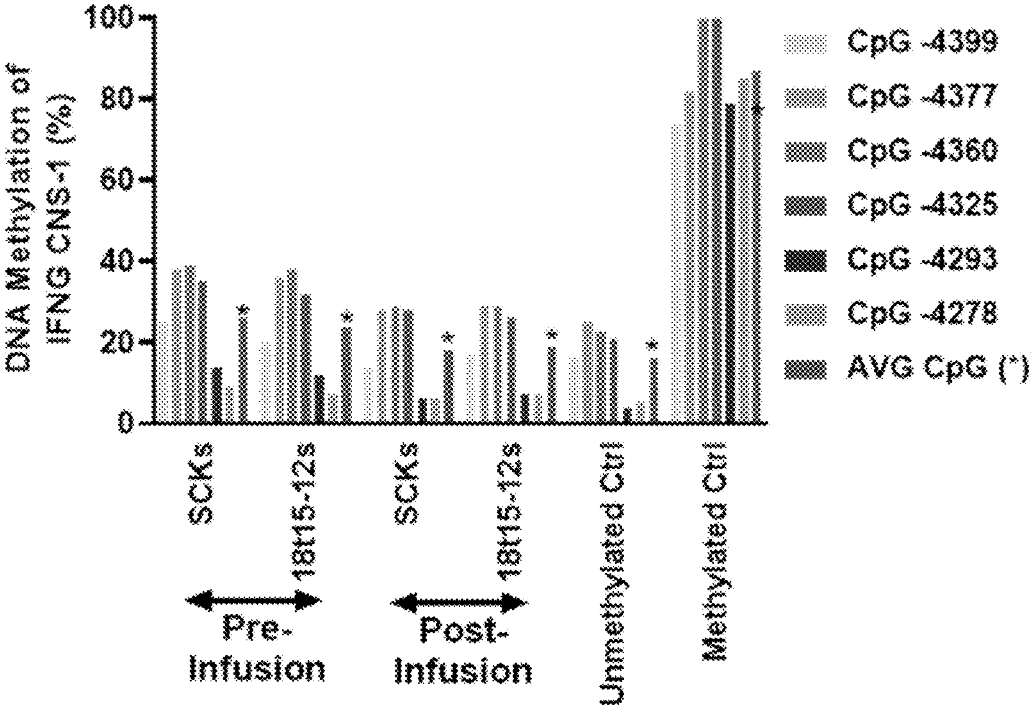
FIG. 26 is a graph showing epigenetic analysis of memory-like NK cells in vivo, where cells were subjected to either: stimulation with mixture of-single cytokines or 18t15-12s for 12-16 hours. Then, the NK cells were washed and resuspended in complete RPMI 1640 medium supplemented with 7t15-21s+anti-tissue factor antibody (αTF Ab), and incubated for 14 days. After 14 days of expansion, the activated NK cells were either processed for pyrosequencing analysis (pre-infusion samples) or infused in NSG mice (five groups, five mice per group). At day 9 post-infusion, the spleen of each mice was collected, and NK cells purified and combined for each group (five group, five mice per groups). The samples (post-infusion) were subjected to pyrosequencing analysis of DNA methylation of CpG sites located within the IFNγ CNS-1 region.

Analysis of the DNA methylation status of these six IFNγ CNS-1 CpG sites revealed higher levels of DNA demethylation in pre-infused activated NK cells stimulated overnight with either a mixture of single cytokines (IL12+IL18+IL15) or 18t15-12s and supported for 14 days in culture by 7t15-21s (50 nM) plus αTF Ab (50 nM) compared to methylated DNA controls. Indeed, the single cytokines and the 18t15-12s stimulated NK cells exhibited 26.99%±12.85 and 24.58%±13.22 DNA methylation, respectively, versus 87.09%±10.65 for methylated DNA controls. More important, post-infused NK cells isolated from NSG mice at day 9 also exhibited very low levels of DNA methylation with 18.97%±11.17 and 19.57%±10.22 DNA methylation for single cytokines and 18t15-12s treated NK cells, respectively. Taken together, these results suggest that the memory-like phenotype of activated NK cells in maintained in vivo for up 9 days, and that once the epigenetic remodeling mechanism is established, it is fixed in subsequent NK cell progeny and persist in vivo (FIG. 26).

Example 23: Expansion of NK Cells by IL-7/IL-21/IL-15 and Anti-TF IgG1

Figure 27:
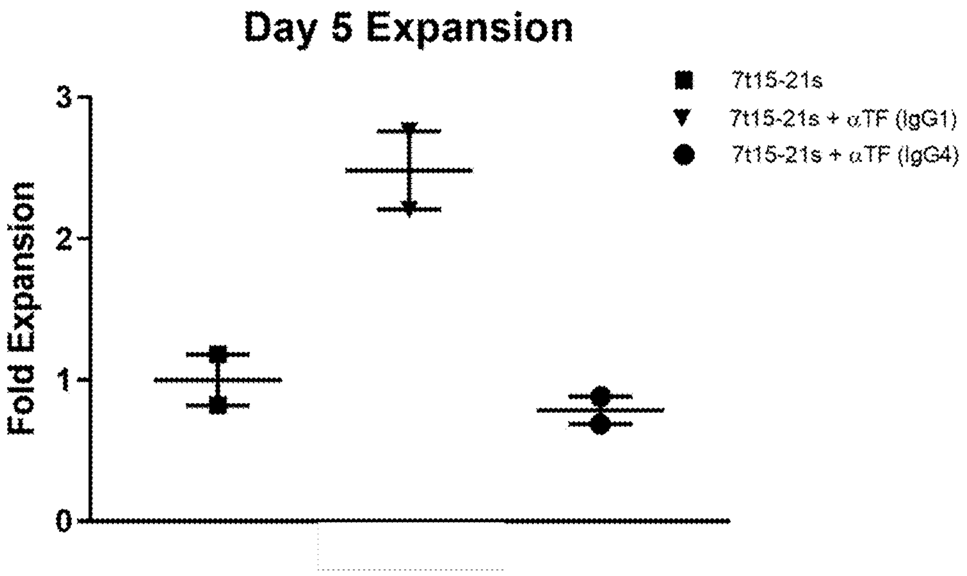
FIG. 27 is a graph showing the fold expansion of NK cells on day 5 of expansion, where the data shows that NK cells require IgG1 signal for expansion.
Figure 28:
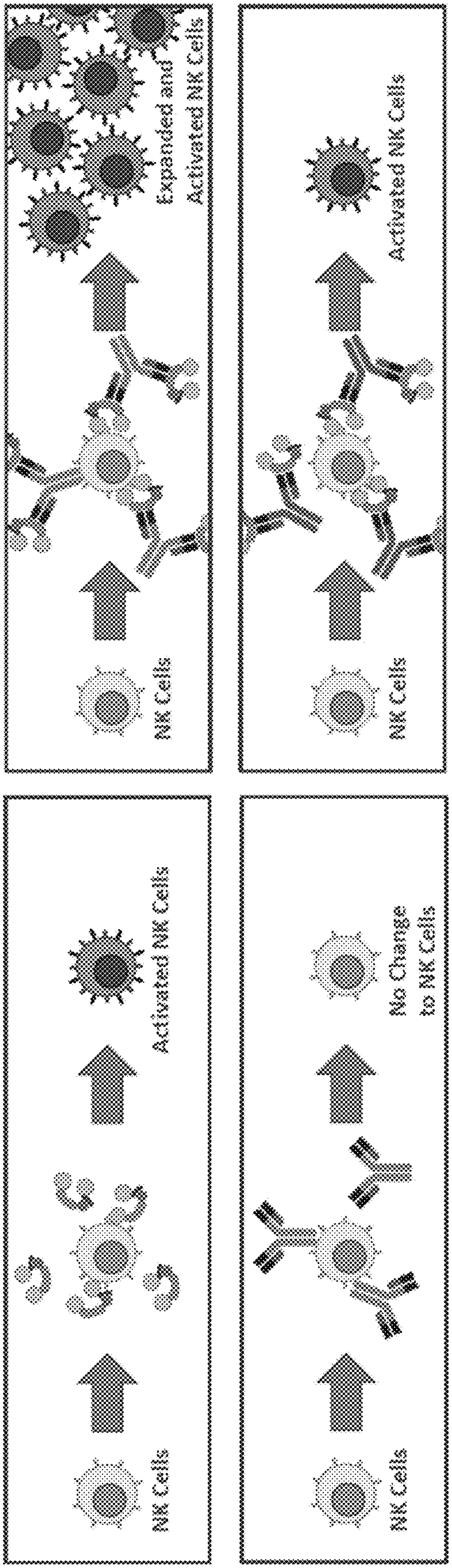
FIG. 28 is an exemplary embodiment of the presently claimed methods.

In a non-limiting example, a set of experiments was performed to determine the effect of 7t15-21s alone or 7t15-21s in combination with either anti-TF IgG1 or anti-TF IgG4 on expansion of NK cells (assessed at 5 days of expansion). The data show that NK cells require IgG1 signal for expansion (FIG. 27). A schematic diagram depicting NK cell expansion and activation is shown in FIG. 28.

Example 24: Expansion of Primary NK Cells with 7t15-21s+αTF Ab

Figure 29:
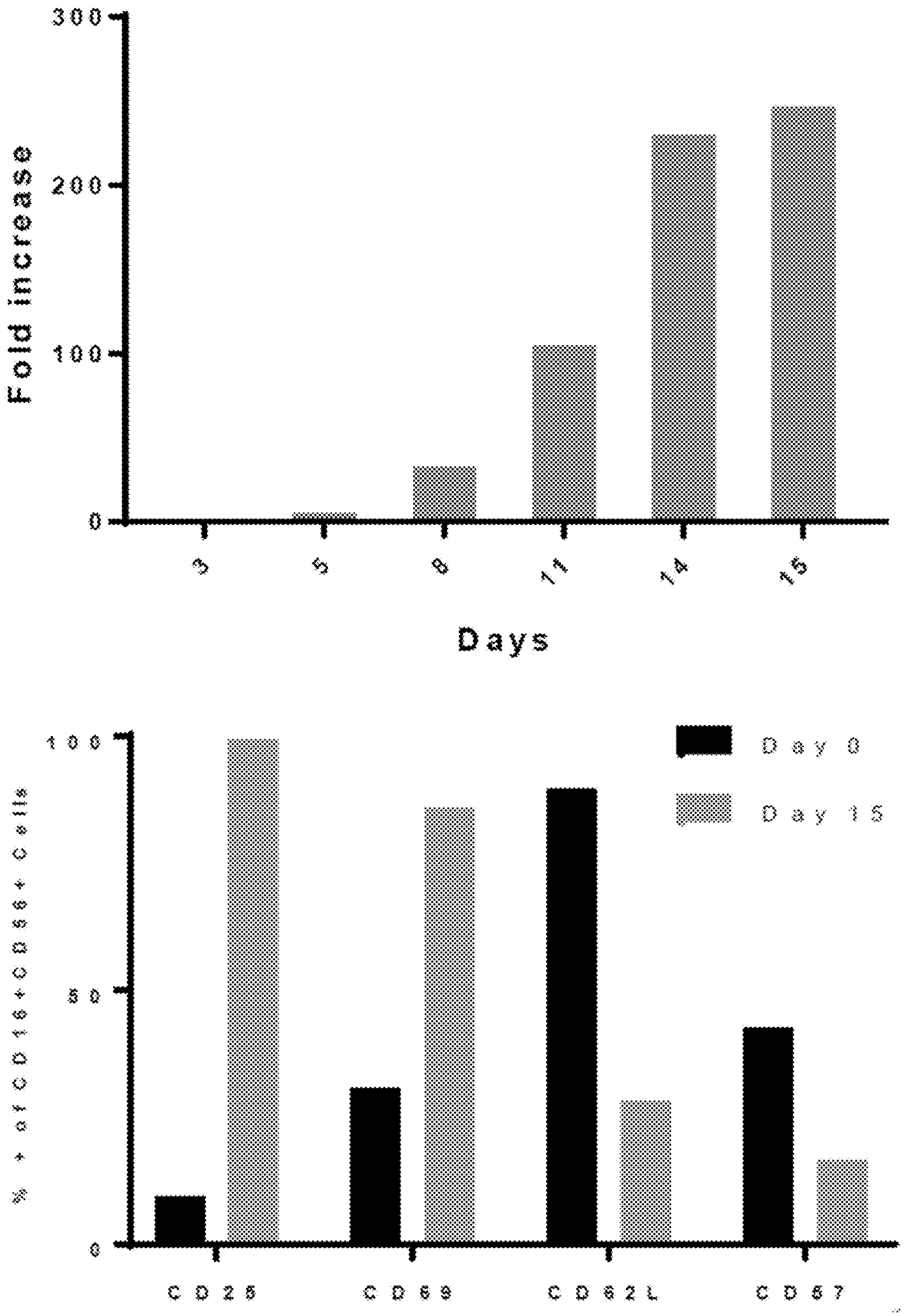
FIG. 29 is a set of graphs showing expansion of primary NK cells using the methods described herein.

In a non-limiting example, a set of experiments was performed to determine the effect of 7t15-21s and anti-TF IgG1 on expansion of primary NK cells over a time period of 15 days. The data shows NK cells expanded over the 15-day period and had increased expression of surface markers CD25 and CD69, and decreased expression of CD62L and CD57 (FIG. 29).

Example 25: Expansion Strategy after Short Term Activation

Figure 33:
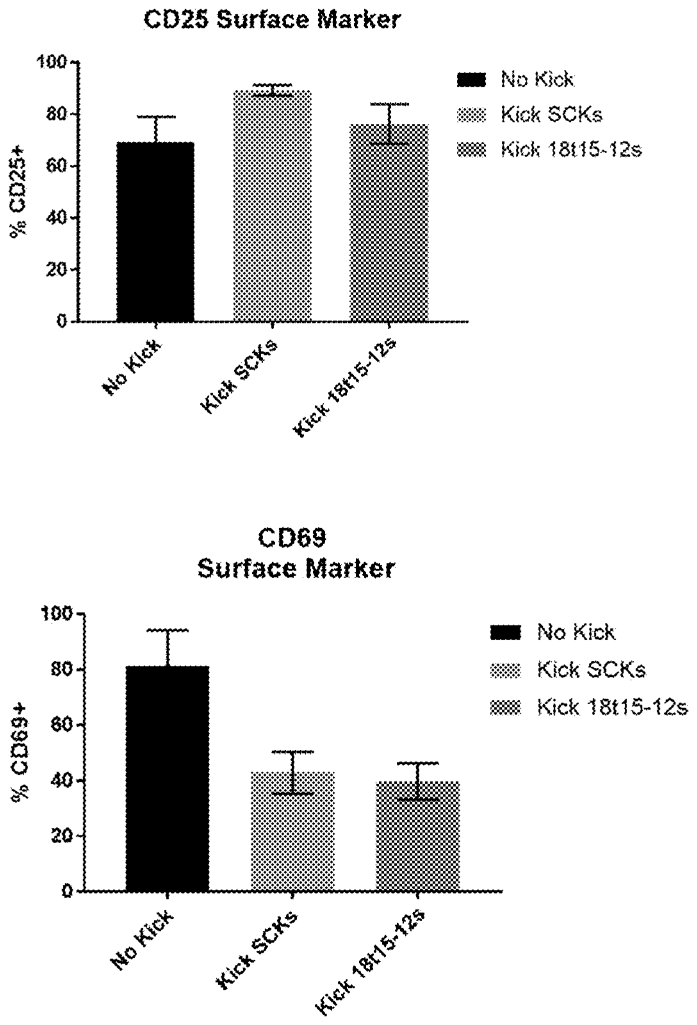
FIG. 33 is a set of graphs showing the percentage of surface markers CD25 (upper panel) and CD26 (lower panel) after day 10.
Figure 34:
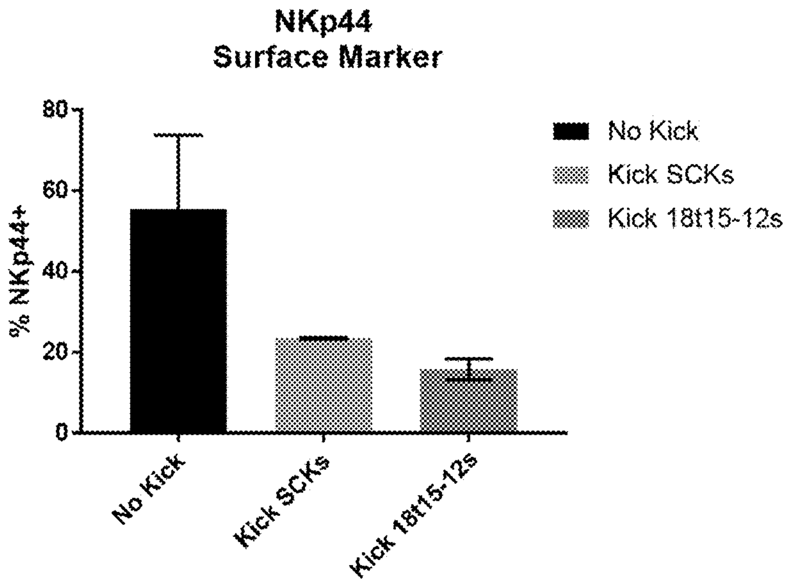
FIG. 34 is a set of graphs showing the percentage of surface markers NKp44 (upper panel) and NKp30 (lower panel) after day 10.
Figure 34:
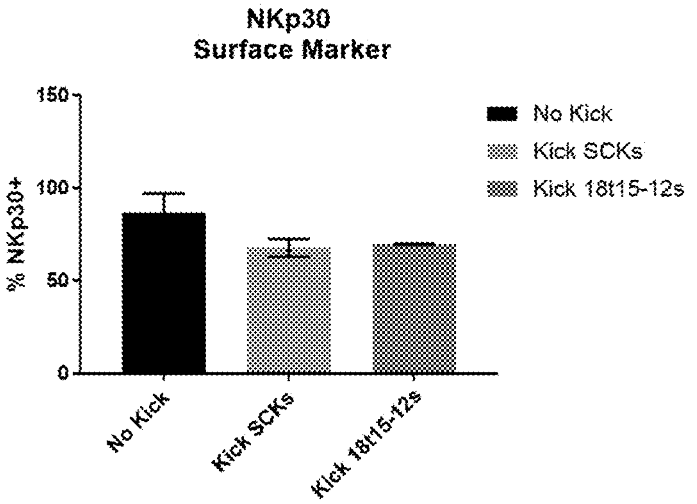
Figure 35:
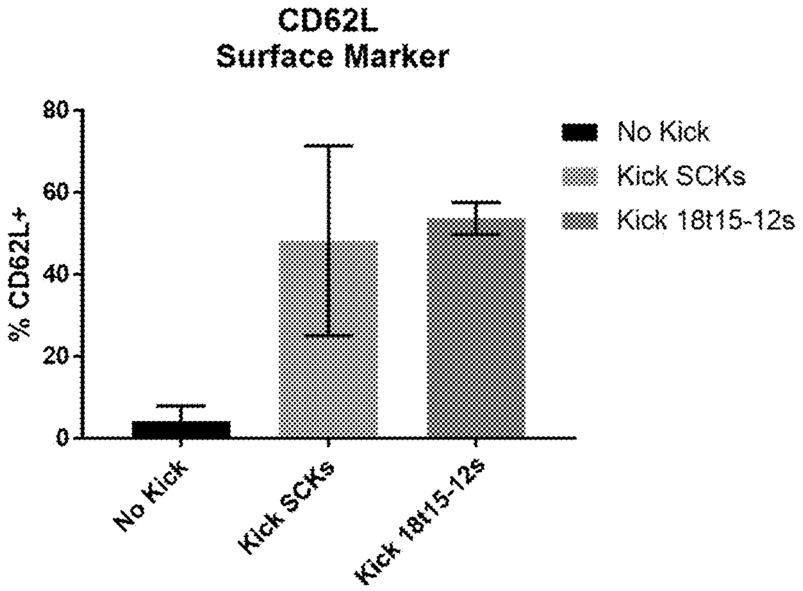
FIG. 35 is a set of graphs showing the percentage of surface markers CD62L (upper panel) and CD16 (lower panel) after day 10. The data show that activation with 18t15-12s and expansion with 7t15-21s and anti-tissue factor IgG1 antibody resulted in an increase in expression of CD62L.
Figure 35:
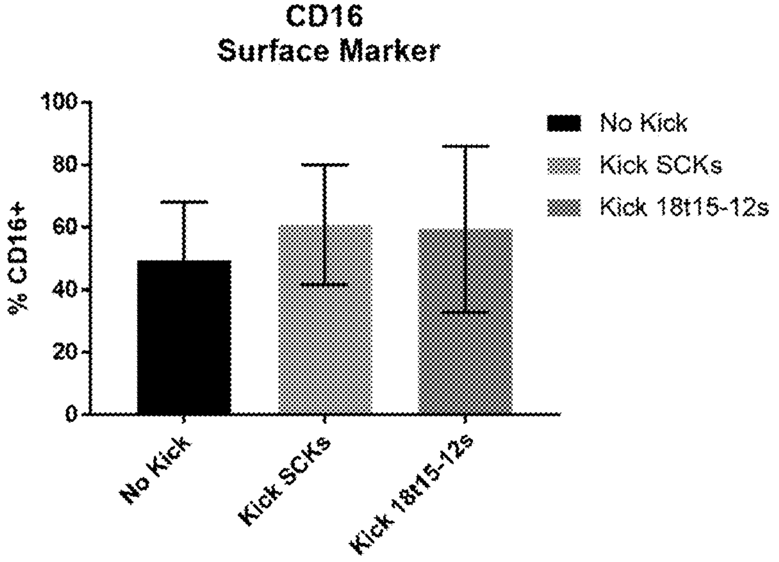
Figure 36:
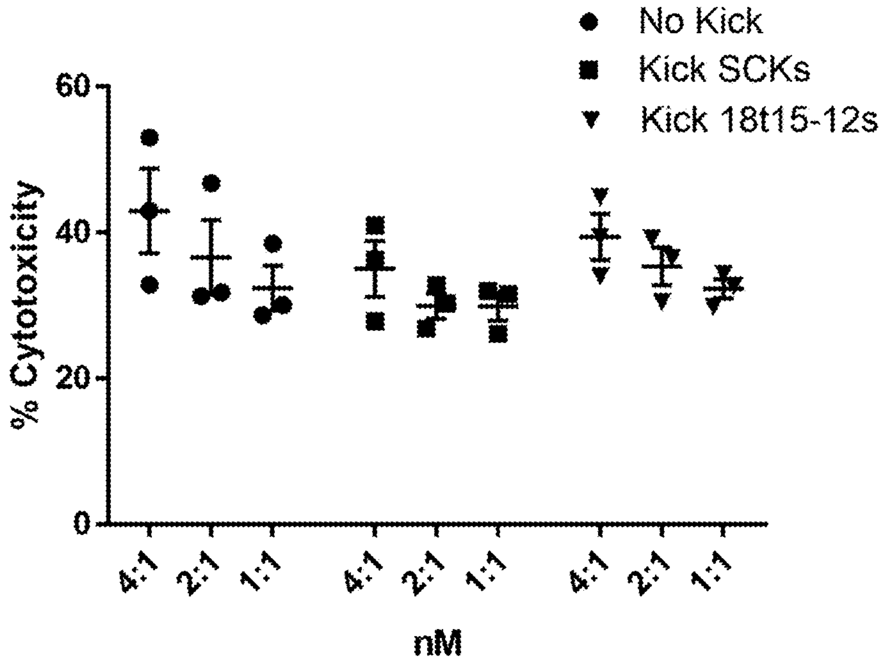
FIG. 36 is a graph showing the cytotoxicity in cells following no stimulation or stimulation with a mixture of recombinant cytokines (IL-12, IL-15, and IL-18) or an exemplary first multi-chain chimeric polypeptide (18t15-12s).

In a non-limiting example, NK cells were activated for a short term of 1-3 hours with 18t15-12s to induce memory-like NK cells. After a short-term kick, the NK cells were expanded with 7t15-21s and anti-TF IgG1 for 14-21 days. The expansion of memory-like NK cells were characterized by measuring the percentage of surface markers (e.g., CD25, CD69, NKp44, NKp30, CD62L, and CD16) expression in the kicked and expanded NK cells (FIGS. 33-35). The data also shows the cytotoxicity of NK cells following no stimulation or stimulation with a mixture of recombinant cytokines (IL-12, IL-15, and IL-18) or 18t15-12s (FIG. 36).

Example 26. Kick and Expansion of Cord Blood-Derived NK Cells

Fresh human $CD34^-$ cord blood were obtained (OrganaBio) and $CD56^+$ NK cells were isolated with the $CD56^+CD16^+$ NK cell isolation kit (Miltenyi Biotec). The purity of NK cells was >50% and confirmed by staining with CD56-BV421, CD16-BV510, CD4-BV488, CD14-APC, CD8 PerCP Cy5.5, CD3 APC CY7 (BioLegend). Cells were counted and resuspended at a density of $1\times10^6$ cells/mL in PBS. 2 μM of final concentration of Cell-Trace Violet Dye (CTV) (Life Technologies) were added to the cells and incubated for 20 minutes at 37° C. under an atmosphere of 5% $CO_2$. Cells were resuspended at five times volume in fresh pre-warmed RPMI 1640 medium (Gibco) supplemented with 2 mM L-glutamine (Thermo Life Technologies), antibiotics (penicillin, 10,000 units/mL; streptomycin, 10,000 μg/mL; Thermo Life Technologies), and 10% FBS (Hyclone) for 5 minutes at room temperature. Cells were washed 2 times at 1000 rpm for 10 minutes at counted and resuspended at a density of $2\times10^6$ cells/mL in RPMI 1640 medium (Gibco) supplemented with 2 mM L-glutamine (Thermo Life Technologies), antibiotics (penicillin, 10,000 units/mL; streptomycin, 10,000 μg/mL; Thermo Life Technologies), and 10% FBS (Hyclone). Cells (0.1 mL) were transferred in a 96-well flat-bottom plate, and subjected to either: no treatment (media), or stimulated with 18t15-12s (250 nM) for a short-term exposure of either 180 minutes (kick) or 12-16 hours (overnight kick) at 37° C. under an atmosphere of 5% $CO_2$. Then, all conditions of NK cells were washed and resuspended in complete RPMI 1640 medium supplemented with 7t15-21s (200 nM) plus the anti-tissue factor antibody (αTF Ab, 100 nM) and incubated for 7 days (long-term). Cells were replenished with 7t15-21s (200 nM) plus αTF Ab (100 nM) to keep the cell density at approximately $2\times10^6$ cells/mL every 48 to 72 hrs. To assess cell proliferation, NK cells were harvested and surface stained for CD56 for 30 minutes. After surface staining, cells were washed (1500 RPM for 5 minutes at room temperature) in FACS buffer (1×PBS (Hyclone) with 0.5% BSA (EMD Millipore) and 0.001% Sodium Azide (Sigma)). After two washes, cells were analyzed by Flow Cytometry (Celesta-BD Bioscience).

Figure 37A:
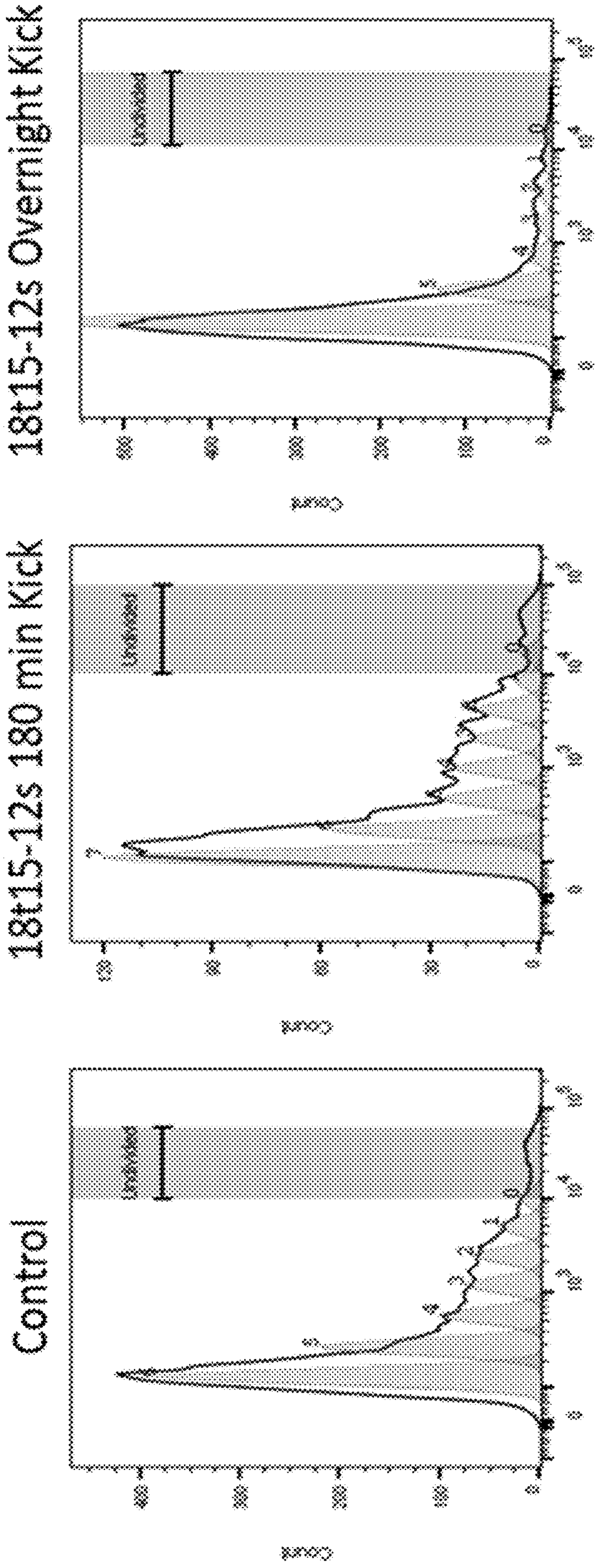
FIG. 37A is a set of histograms showing the expansion of cord blood-derived NK cells without treatment or following stimulation for 180 minutes or 12-16 hours with 18t15-12s (250 nM), then expanded using 7t15-21s (200 nM) with anti-tissue factor antibody (αTF Ab, 100 nM) for 7 days.
Figure 37B:
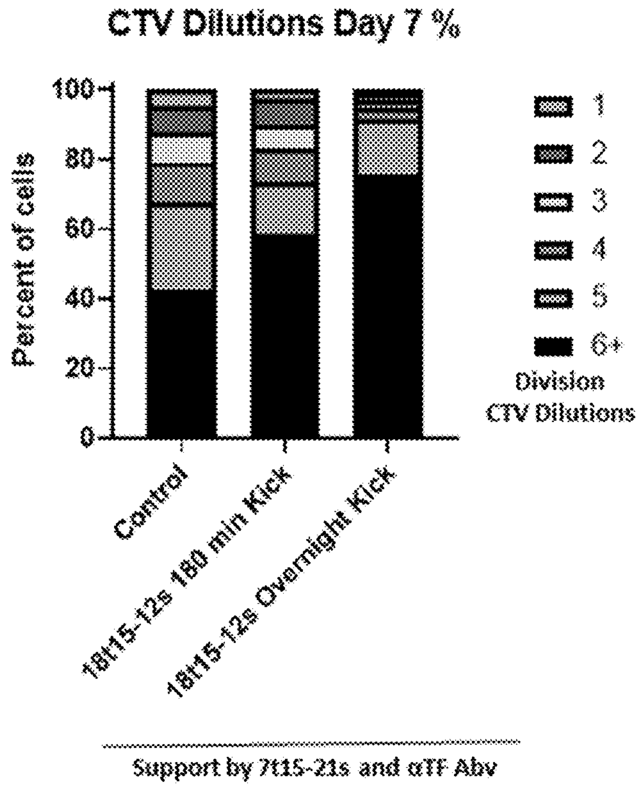
FIG. 37B is a graph showing the percentage of cell proliferation of cord blood-derived NK cells without treatment or following stimulation for 180 minutes or 12-16 hours with 18t15-12s (250 nM), then expanded using 7t15-21s (200 nM) with anti-tissue factor antibody (αTF Ab, 100 nM) for 7 days.

Analysis of the cell proliferation of NK cells stimulated (kick) for 180 minutes or 12-16 hours (Overnight) with 18t15-12s and supported for 7 days in culture by 7t15-21s (200 nM) plus αTF Ab (100 nM) increased proliferative capacity compared to unstimulated cells supported with 7t15-21s (200 nM) plus αTF Ab (100 nM). As shown in FIG. 37A, compared to the control, which are unstimulated cells supported with 7t15-21s (200 nM) plus αTF Ab (100 nM), the treatment group stimulated with cytokines (kick and overnight kick) shows increased proliferation of NK cells (number of divisions). The control group shows dividing cells in different stages of divisions compared to few terminal divisions in NK cells stimulated for 180 minutes (kick) or 12-16 hours (overnight kick) with 18t15-12s and supported for 7 days in culture by 7t15-21s (200 nM) plus αTF Ab (100 nM). FIG. 37B represents the percentage of cell proliferation.

Taken together, this result suggests that NK cells derived from cord blood, stimulated 18t15-12s and supported by 7t15-21s plus αTF Ab has increased proliferative capacity.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of enhancing cytotoxicity of a NK cell comprising the following steps:

(a) contacting a natural killer cell in a liquid culture medium comprising an effective amount of a first multi-chain chimeric polypeptide for 15 minutes to one day under conditions that allow for differentiation of the natural killer (NK) cell; and (b) contacting the natural killer cell in a liquid culture medium comprising an effective amount of (i) a second multi-chain chimeric polypeptide and (ii) an IgG1 antibody construct, for 1 day to 30 days under conditions that allow for the activation and proliferation of the natural killer cell, wherein the first multi-chain chimeric polypeptide comprises:

a first chimeric polypeptide comprising a first target-binding domain, a soluble tissue factor domain comprising a sequence that is at least 90% identical to SEQ ID NO: 5, and a first domain of a pair of affinity domains comprising a sequence that is at least 90% identical to SEQ ID NO: 26; and a second chimeric polypeptide comprising a second domain of a pair of affinity domains comprising a sequence that is at least 90% identical to SEQ ID NO: 24 and a second target-binding domain, wherein the first chimeric polypeptide and the second chimeric polypeptide in the first multi-chain chimeric polypeptide associate through the binding of the first domain and the second domain of the pair of affinity domains in the first multi-chain chimeric polypeptide;

wherein (A) the first target-binding domain in the first multi-chain chimeric polypeptide comprises a sequence at least 90% identical to SEQ ID NO: 20 and the second target-binding domain in the first multi-chain chimeric polypeptide comprises a first sequence that is at least 90% identical to SEQ ID NO: 14 and a second sequence that is at least 90% identical to SEQ ID NO: 16, or (B) the first target-binding domain in the first multi-chain chimeric polypeptide comprises a first sequence that is at least 90% identical to SEQ ID NO: 14 and a second sequence that is at least 90% identical to SEQ ID NO: 16, and the second target-binding domain in the first multi-chain chimeric polypeptide comprises a sequence at least 90% identical to SEQ ID NO: 20; and wherein the second multi-chain chimeric polypeptide comprises:

a first chimeric polypeptide comprising a first target-binding domain, a soluble tissue factor domain comprising a sequence that is at least 90% identical to SEQ ID NO: 5, a first domain of a pair of affinity domains comprising a sequence that is at least 90% identical to SEQ ID NO: 26, and a second chimeric polypeptide comprising a second domain of a pair of affinity domains comprising a sequence that is at least 90% identical to SEQ ID NO: 24, and a second target-binding domain, wherein the first chimeric polypeptide and the second chimeric polypeptide in the second multi-chain chimeric polypeptide associate through the binding of the first domain and the second domain of the pair of affinity domains in the second multi-chain chimeric polypeptide;

wherein (A) the first target-binding domain in the second multi-chain chimeric polypeptide comprises a sequence that is at least 90% identical to SEQ ID NO: 23 and the second target-binding domain in the second multi-chain chimeric polypeptide comprises a sequence that is at least 90% identical to SEQ ID NO: 22, or (B) the first target-binding domain in the second multi-chain chimeric polypeptide comprises a sequence that is at least 90% identical to SEQ ID NO: 22 and the second target-binding domain in the second multi-chain chimeric polypeptide comprises a sequence that is at least 90% identical to SEQ ID NO: 23; and wherein the IgG1 antibody construct comprises at least one antigen-binding domain that binds specifically to the soluble tissue factor domain.

2. The method of claim 1, wherein the first target-binding domain and the soluble tissue factor domain directly abut each other in the first chimeric polypeptide in the first multi-chain chimeric polypeptide.

3. The method of claim 1, wherein the first chimeric polypeptide in the first multi-chain chimeric polypeptide further comprises a linker sequence between the first target-binding domain and the soluble tissue factor domain in the first chimeric polypeptide.

4. The method of claim 1, wherein the soluble tissue factor domain and the first domain of the pair of affinity domains in the first chimeric polypeptide in the first multi-chain chimeric polypeptide directly abut each other in the first chimeric polypeptide.

5. The method of claim 1, wherein the first chimeric polypeptide in the first multi-chain chimeric polypeptide further comprises a linker sequence between the soluble tissue factor domain and the first domain of the pair of affinity domains in the first chimeric polypeptide.

6. The method of claim 1, wherein the second domain of the pair of affinity domains and the second target-binding domain in the second chimeric polypeptide in the first multi-chain chimeric polypeptide directly abut each other in the second chimeric polypeptide.

7. The method of claim 1, wherein the second chimeric polypeptide in the first multi-chain chimeric polypeptide further comprises a linker sequence between the second domain of the pair of affinity domains and the second target-binding domain in the second chimeric polypeptide.

8. The method of claim 1, wherein the soluble tissue factor domain is a soluble human tissue factor domain.

9. The method of claim 8, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

10. The method of claim 1, wherein the first multi-chain chimeric polypeptide and the second multi-chain chimeric polypeptide do not stimulate coagulation in a mammal.

11. The method of claim 1, wherein the first target-binding domain and the linker domain in the first chimeric polypeptide in the second multi-chain chimeric polypeptide directly abut each other in the first chimeric polypeptide.

12. The method of claim 1, wherein the first chimeric polypeptide in the second multi-chain chimeric polypeptide further comprises a linker sequence between the first target-binding domain and the linker domain in the first chimeric polypeptide.

13. The method of claim 1, wherein the linker domain and the first domain of the pair of affinity domains directly abut each other in the first chimeric polypeptide in the second multi-chain chimeric polypeptide.

14. The method of claim 1, wherein the first chimeric polypeptide in the second multi-chain chimeric polypeptide further comprises a linker sequence between the linker domain and the first domain of the pair of affinity domains in the first chimeric polypeptide.

15. The method of claim 1, wherein the second domain of the pair of affinity domains and the second target-binding domain in the second chimeric polypeptide of the second multi-chain chimeric polypeptide directly abut each other in the second chimeric polypeptide.

16. The method of claim 1, wherein the second chimeric polypeptide in the second multi-chain chimeric polypeptide further comprises a linker sequence between the second domain of the pair of affinity domains and the second target-binding domain in the second chimeric polypeptide.

17. The method of claim 1, wherein the IgG1 antibody construct is a monoclonal IgG1 antibody, where both antigen-binding domains in the monoclonal IgG1 antibody bind specifically to the soluble tissue factor domain.

18. The method of claim 1, wherein the first period of time is 15 minutes to 4 hours.

19. The method of claim 1, wherein the liquid culture medium in step (b) comprises the second multi-chain chimeric polypeptide and the IgG1 antibody construct at a molar ratio of 0.5:1 to 2:1.

20. The method of claim 1, wherein the NK cell was previously obtained from a subject.

21. The method of claim 20, wherein the method further comprises obtaining the NK cell from the subject prior to step (a).

22. The method of claim 1, wherein the NK cell has previously been genetically modified to express a chimeric antigen receptor or a recombinant T-cell receptor.

23. The method of claim 1, wherein the method further comprises, after step (b), isolating the NK cell.

24. The method of claim 23, wherein the method further comprises, administering the NK cell to a subject identified or diagnosed as having a cancer.

25. The method of claim 1, wherein:

the first chimeric polypeptide in the first multi-chain chimeric polypeptide comprises a sequence that is at least 90% identical to SEQ ID NO: 63;

the second chimeric polypeptide in the first multi-chain chimeric polypeptide comprises a sequence that is at least 90% identical to SEQ ID NO: 65;

the first chimeric polypeptide in the second multi-chain chimeric polypeptide comprises a sequence that is at least 90% identical to SEQ ID NO: 67; and the second chimeric polypeptide in the second multi-chain chimeric polypeptide comprises a sequence that is at least 90% identical to SEQ ID NO: 69.

26. The method of claim 1, wherein:

the first chimeric polypeptide in the first multi-chain chimeric polypeptide comprises a sequence that is at least 95% identical to SEQ ID NO: 63;

the second chimeric polypeptide in the first multi-chain chimeric polypeptide comprises a sequence that is at least 95% identical to SEQ ID NO: 65;

the first chimeric polypeptide in the second multi-chain chimeric polypeptide comprises a sequence that is at least 95% identical to SEQ ID NO: 67; and the second chimeric polypeptide in the second multi-chain chimeric polypeptide comprises a sequence that is at least 95% identical to SEQ ID NO: 69.

27. The method of claim 1, wherein:

the first chimeric polypeptide in the first multi-chain chimeric polypeptide comprises SEQ ID NO: 63;

the second chimeric polypeptide in the first multi-chain chimeric polypeptide comprises SEQ ID NO: 65;

the first chimeric polypeptide in the second multi-chain chimeric polypeptide comprises SEQ ID NO: 67; and the second chimeric polypeptide in the second multi-chain chimeric polypeptide comprises SEQ ID NO: 69.

28. The method of claim 1, wherein:

the first chimeric polypeptide in the first multi-chain chimeric polypeptide comprises SEQ ID NO: 64;

the second chimeric polypeptide in the first multi-chain chimeric polypeptide comprises SEQ ID NO: 66;

the first chimeric polypeptide in the second multi-chain chimeric polypeptide comprises SEQ ID NO: 68; and the second chimeric polypeptide in the second multi-chain chimeric polypeptide comprises SEQ ID NO: 70.

29. The method of claim 1, wherein:

the first chimeric polypeptide in the first multi-chain chimeric polypeptide comprises a sequence that is at least 90% identical to SEQ ID NO: 63;

the second chimeric polypeptide in the first multi-chain chimeric polypeptide comprises a sequence that is at least 90% identical to SEQ ID NO: 65;

the first chimeric polypeptide in the second multi-chain chimeric polypeptide comprises a sequence that is at least 90% identical to SEQ ID NO: 71; and the second chimeric polypeptide in the second multi-chain chimeric polypeptide comprises a sequence that is at least 90% identical to SEQ ID NO: 73.

30. The method of claim 1, wherein:

the first chimeric polypeptide in the first multi-chain chimeric polypeptide comprises a sequence that is at least 95% identical to SEQ ID NO: 63;

the second chimeric polypeptide in the first multi-chain chimeric polypeptide comprises a sequence that is at least 95% identical to SEQ ID NO: 65;

the first chimeric polypeptide in the second multi-chain chimeric polypeptide comprises a sequence that is at least 95% identical to SEQ ID NO: 71; and the second chimeric polypeptide in the second multi-chain chimeric polypeptide comprises a sequence that is at least 95% identical to SEQ ID NO: 73.

31. The method of claim 1, wherein:

the first chimeric polypeptide in the first multi-chain chimeric polypeptide comprises SEQ ID NO: 63;

the second chimeric polypeptide in the first multi-chain chimeric polypeptide comprises SEQ ID NO: 65;

the first chimeric polypeptide in the second multi-chain chimeric polypeptide comprises SEQ ID NO: 71; and the second chimeric polypeptide in the second multi-chain chimeric polypeptide comprises SEQ ID NO: 73.

32. The method of claim 1, wherein:

the first chimeric polypeptide in the first multi-chain chimeric polypeptide comprises SEQ ID NO: 64;

the second chimeric polypeptide in the first multi-chain chimeric polypeptide comprises SEQ ID NO: 66;

the first chimeric polypeptide in the second multi-chain chimeric polypeptide comprises SEQ ID NO: 72; and the second chimeric polypeptide in the second multi-chain chimeric polypeptide comprises SEQ ID NO: 74.

33. The method of claim 1, wherein:

the first target-binding domain of the first multi-chain chimeric polypeptide comprises a sequence that is at least 90% identical to SEQ ID NO: 20;

the second target-binding domain of the first multi-chain chimeric polypeptide comprises a first sequence that is at least 90% identical to SEQ ID NO: 14 and a second sequence that is at least 90% identical to SEQ ID NO: 16;

the first target-binding domain of the second multi-chain chimeric polypeptide comprises a sequence that is at least 90% identical to SEQ ID NO: 23; and the second target-binding domain of the second multi-chain chimeric polypeptide comprises a sequence that is at least 90% identical to SEQ ID NO: 22.

34. The method of claim 1, wherein:

the first target-binding domain of the first multi-chain chimeric polypeptide comprises a sequence that is at least 95% identical to SEQ ID NO: 20;

the soluble tissue factor domain of the first multi-chain chimeric polypeptide comprises a sequence that is at least 95% identical to SEQ ID NO: 5;

the first domain of the pair of affinity domains of the first multi-chain chimeric polypeptide comprises a sequence that is at least 95% identical to SEQ ID NO: 26;

the second target-binding domain of the first multi-chain chimeric polypeptide comprises a first sequence that is at least 95% identical to SEQ ID NO: 14 and a second sequence that is at least 95% identical to SEQ ID NO: 16;

the second domain of the pair of affinity domains of the first multi-chain chimeric polypeptide comprises a sequence that is at least 95% identical to SEQ ID NO: 24;

the first target-binding domain of the second multi-chain chimeric polypeptide comprises a sequence that is at least 95% identical to SEQ ID NO: 23;

the soluble tissue factor domain of the second multi-chain chimeric polypeptide comprises a sequence that is at least 95% identical to SEQ ID NO: 5;

the first domain of the pair of affinity domains of the second multi-chain chimeric polypeptide comprises a sequence that is at least 95% identical to SEQ ID NO: 26;

the second target-binding domain of the second multi-chain chimeric polypeptide comprises a sequence that is at least 95% identical to SEQ ID NO: 22; and the second domain of the pair of affinity domains of the second multi-chain chimeric polypeptide comprises a sequence that is at least 95% identical to SEQ ID NO: 24.

35. The method of claim 1, wherein:

the first target-binding domain of the first multi-chain chimeric polypeptide comprises SEQ ID NO: 20;

the soluble tissue factor domain of the first multi-chain chimeric polypeptide comprises SEQ ID NO: 5;

the first domain of the pair of affinity domains of the first multi-chain chimeric polypeptide comprises SEQ ID NO: 26;

the second target-binding domain of the first multi-chain chimeric polypeptide comprises a first sequence of SEQ ID NO: 14 and a second sequence of SEQ ID NO: 16;

the second domain of the pair of affinity domains of the first multi-chain chimeric polypeptide comprises SEQ ID NO: 24;

the first target-binding domain of the second multi-chain chimeric polypeptide comprises SEQ ID NO: 23;

the soluble tissue factor domain of the second multi-chain chimeric polypeptide comprises SEQ ID NO: 5;

the first domain of the pair of affinity domains of the second multi-chain chimeric polypeptide comprises SEQ ID NO: 26;

the second target-binding domain of the second multi-chain chimeric polypeptide comprises SEQ ID NO: 22; and the second domain of the pair of affinity domains of the second multi-chain chimeric polypeptide comprises SEQ ID NO: 24.

36. The method of claim 1, wherein:

the first target-binding domain of the first multi-chain chimeric polypeptide comprises a sequence that is at least 90% identical to SEQ ID NO: 20;

the second target-binding domain of the first multi-chain chimeric polypeptide comprises a first sequence that is at least 90% identical to SEQ ID NO: 14 and a second sequence that is at least 90% identical to SEQ ID NO: 16;

the first target-binding domain of the second multi-chain chimeric polypeptide comprises a sequence that is at least 90% identical to SEQ ID NO: 22; and the second target-binding domain of the second multi-chain chimeric polypeptide comprises a sequence that is at least 90% identical to SEQ ID NO: 23.

37. The method of claim 1, wherein:

the first target-binding domain of the first multi-chain chimeric polypeptide comprises a sequence that is at least 95% identical to SEQ ID NO: 20;

the soluble tissue factor domain of the first multi-chain chimeric polypeptide comprises a sequence that is at least 95% identical to SEQ ID NO: 5;

the first domain of the pair of affinity domains of the first multi-chain chimeric polypeptide comprises a sequence that is at least 95% identical to SEQ ID NO: 26;

the second target-binding domain of the first multi-chain chimeric polypeptide comprises a first sequence that is at least 95% identical to SEQ ID NO: 14 and a second sequence that is at least 95% identical to SEQ ID NO: 16;

the second domain of the pair of affinity domains of the first multi-chain chimeric polypeptide comprises a sequence that is at least 95% identical to SEQ ID NO: 24;

the first target-binding domain of the second multi-chain chimeric polypeptide comprises a sequence that is at least 95% identical to SEQ ID NO: 22;

the soluble tissue factor domain of the second multi-chain chimeric polypeptide comprises a sequence that is at least 95% identical to SEQ ID NO: 5;

the first domain of the pair of affinity domains of the second multi-chain chimeric polypeptide comprises a sequence that is at least 95% identical to SEQ ID NO: 26;

the second target-binding domain of the second multi-chain chimeric polypeptide comprises a sequence that is at least 95% identical to SEQ ID NO: 23; and the second domain of the pair of affinity domains of the second multi-chain chimeric polypeptide comprises a sequence that is at least 95% identical to SEQ ID NO: 24.

38. The method of claim 1, wherein:

the first target-binding domain of the first multi-chain chimeric polypeptide comprises SEQ ID NO: 20;

the soluble tissue factor domain of the first multi-chain chimeric polypeptide comprises SEQ ID NO: 5;

the first domain of the pair of affinity domains of the first multi-chain chimeric polypeptide comprises SEQ ID NO: 26;

the second target-binding domain of the first multi-chain chimeric polypeptide comprises a first sequence of SEQ ID NO: 14 and a second sequence of SEQ ID NO: 16;

the second domain of the pair of affinity domains of the first multi-chain chimeric polypeptide comprises SEQ ID NO: 24;

the first target-binding domain of the second multi-chain chimeric polypeptide comprises SEQ ID NO: 22;

the soluble tissue factor domain of the second multi-chain chimeric polypeptide comprises SEQ ID NO: 5;

the first domain of the pair of affinity domains of the second multi-chain chimeric polypeptide comprises SEQ ID NO: 26;

the second target-binding domain of the second multi-chain chimeric polypeptide comprises SEQ ID NO: 23; and the second domain of the pair of affinity domains of the second multi-chain chimeric polypeptide comprises SEQ ID NO: 24.

* * * * *